United States Patent
Meyers et al.

(10) Patent No.: US 7,494,793 B2
(45) Date of Patent: Feb. 24, 2009

(54) 21686, DEHYDROGENASE

(75) Inventors: Rachel Meyers, Newton, MA (US);
William James Cook, Natick, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 286 days.

(21) Appl. No.: 11/335,810

(22) Filed: Jan. 19, 2006

(65) Prior Publication Data

US 2006/0166326 A1 Jul. 27, 2006

Related U.S. Application Data

(63) Continuation of application No. 10/664,506, filed on Sep. 17, 2003, now Pat. No. 7,045,325, which is a continuation of application No. 09/838,561, filed on Apr. 18, 2001, now Pat. No. 6,627,423, which is a continuation-in-part of application No. 09/816,760, filed on Mar. 23, 2001, now Pat. No. 6,613,555, which is a continuation-in-part of application No. 09/634,955, filed on Aug. 8, 2000, now Pat. No. 6,511,834.

(60) Provisional application No. 60/192,002, filed on Mar. 24, 2000.

(51) Int. Cl.
C12N 9/04 (2006.01)
C12N 15/00 (2006.01)
C12Q 1/00 (2006.01)
C12Q 1/68 (2006.01)
C12P 21/04 (2006.01)
C07H 21/04 (2006.01)

(52) U.S. Cl. .................. 435/190; 435/4; 435/6; 435/69.1; 435/71.1; 435/440; 536/23.2; 536/23.4

(58) Field of Classification Search .................. None
See application file for complete search history.

(56) References Cited

U.S. PATENT DOCUMENTS

| 5,750,873 | A | 5/1998 | Dellaporta |
| 5,928,923 | A | 7/1999 | Lal et al. |
| 6,046,001 | A | 4/2000 | Bandman et al. |

FOREIGN PATENT DOCUMENTS

| EP | 1033401 | 9/2000 |
| WO | WO 98/39448 | 9/1998 |
| WO | WO 99/14328 | 3/1999 |
| WO | WO 99/33982 | 7/1999 |
| WO | WO 99/38972 | 8/1999 |
| WO | WO 00/00621 | 1/2000 |
| WO | WO 00/17222 | 3/2000 |
| WO | WO 00/15796 | 4/2000 |
| WO | WO 00/18916 | 4/2000 |
| WO | WO 00/20604 | 4/2000 |
| WO | WO 00/53757 | 9/2000 |
| WO | WO 00/55174 | 10/2000 |
| WO | WO 00/58496 | 10/2000 |
| WO | WO 00/77023 | 12/2000 |
| WO | WO 01/02568 | 1/2001 |

OTHER PUBLICATIONS

Branden et al. Introduction to Protein Structure, Garland Publishing Inc., New York, p. 247, 1991.*
Akbar S. K., et al. Int. J. Exp. Pathol. 79(5):279-291 (1998).
Akbar, S. M. F., et al., Eur. J. Clin. Invest. 29(9):786-792 (1999).
Almond, N. et al., Immunol. Lett. 66(1-3):167-170 (1999).
Andersson, B. et al., Anal. Biochem. 236(1):107-113 (1996).
Babinet, C. et al., Science 230(4730):1160-1163 (1985).
Blasco, R. et al., J. Virol. 65(9):4598-4608 (1991).
Bocher, W. O. et al., Hepatology 31(2):480-487 (2000).
Brown, J. J., et al., Hepatology 31(1):173-181 (2000).
Butel, J. S., Carcinogenesis 21(3):405-426 (2000).
Cavanaugh, V. J., et al., J. Virol. 72(4):2630-2637 (1998).
Cavanaugh, V. J., et al., J. Virol. 71(4):3236-3243 (1997).
Chou, C. K., et al., Hepatology 16(1):13-18 (1992).
Cote, P. et al., Hepatology 31(1):190-200 (2000).
Das, A. K., et al., J. Biol. Chem. 275(32):24333-24340 (2000).
Douglas, N. J., et al., J. Gen. Virol. 77(pt. 12):3113-3120 (1996).
Farza, H. et al., Proc. Natl. Acad. Sci U.S.A.84(5):1187-1191 (1987).
Fenner, F., FEMS Microbiol. Rev. 24(2):123-133 (2000).
Gripon, P. et al., J. Med. Virol. 28(3):193-199 (1989).
LeGuerhier, F. et al., Antimicrob. Agents Chemother. 44(1):111-122 (2000).
Guidotti, L. G., et al., J. Virol. 69(10):6158-6169 (1995).
Hayashi, Y. et al., Biochim . Biophys. Acta. 1352(2):145-150 (1997).
Hayashi, K. et al., Pathol. Int. 50(2):85-97 (2000).
Heise, Y. et al., J. Virol. 73(1):474-481 (1999).
Hsu, L. et al., Gene 174(2):319-322 (1996).
Ilan, E. et al., Hepatology 29(2): 553-562 (1999).
Kisseljov, F. L., Biochemistry 65(1):68-77 (2000).
Korba, B. E. et al., Hepatology 31(5):1165-1175 (2000).
Koziel, M. J., Antivir. Ther. 3(Suppl 3):13-24 (1998).
Lai, C. H., et al., Genome Res. 10(5):703-713 (2000).
Larkin, J. et al., Nat. Med. 5(8):907-912 (1999).

(Continued)

Primary Examiner—Yong D Pak

(57) ABSTRACT

The invention provides isolated nucleic acids molecules, designated DHDR nucleic acid molecules, which encode novel DHDR-related dehydrogenase molecules. The invention also provides antisense nucleic acid molecules, recombinant expression vectors containing DHDR nucleic acid molecules, host cells into which the expression vectors have been introduced, and nonhuman transgenic animals in which a DHDR gene has been introduced or disrupted. The invention still further provides isolated DHDR proteins, fusion proteins, antigenic peptides and anti-DHDR antibodies. Diagnostic methods utilizing compositions of the invention are also provided.

10 Claims, 43 Drawing Sheets

OTHER PUBLICATIONS

Madden, C. R., et al., *J. Virol.* 74(11):5266-5272 (2000).
Niewiesk, S., *Immunol. Lett.* 65(1-2):47-50 (1999).
Ohashi, K. et al., *Nat. Med.* 6(3):327-331 (2000).
Pasquinelli, C. et al., *Hepatology* 25(3):719-727 (1997).
Renard, C. A., et al., *Res. Virol.* 149(3):133-143 (1998).
Sakai, N. et al., *FEBS Lett.* 350(2-3):309-313 (1994).
Schat, K. A., et al., *Dev. Comp. Immunol.* 24(2-3):201-221 (2000).
Schwarz, M. et al., *J. Clin. Invest.* 106(9):1175-1184 (2000).
Seeger, C. et al., *Microbiol. Mol. Biol. Rev.* 64(1):51-68 (2000).
Senkevich, T. G. et al., *Science* 273(5276):813-816 (1996).
Shimoda, N. et al., *Genomics* 58(3):219-232 (1999).
Torresi, J. et al., *Gastroenterology* 118(2 Suppl 1):S83-103 (2000).
Tur-Kaspa, R. et al., *Proc. Natl. Acad. Sci. U.S.A.* 83(6):1627-1631 (1986).
Vickery, K. et al., *J. Med. Virol.* 58(1):19-25 (1999).
Virgin, H. W. et al., *Curr. Opin. Immunol.* 11(4):371-379 (1999).
Wieland, S. F. et al., *J. Virol.* 74(9):4165-4173 (2000).
Wiemann, S. et al., *Genome Res.* 11(3):422-435 (2001).
Zhang, J. et al., *Biochim. Biophys. Acta.* 1435(1-2):184-190 (1999).
Zhao, H. F. et al., *FEBS Lett.* 259(1):153-157 (1989).
Results of BLASTN search of nucleic acid patent database using DHDR-4 nucleotide sequence.
Results of BLASTN search of nucleic acid patent database using DHDR-1 nucleotide sequence.
Results of BLASTN search of GenBank database (dbEST) using DHDR-2 nucleotide sequence.
Results of BLASTN search of nucleic acid patent database (FastAlert_N) using DHDR-2 nucleotide sequence.
Results of BLASTN search of GenBank database (nucleic acid) using DHDR-2 nucleotide sequence.
Results of BLASTN search of nucleic acid patent database (PatentDbPreviewNuc) using DHDR-2 nucleotide sequence.
Results of BLASTN search of GenBank database (dbEST) using DHDR-4 nucleotide sequence.
Results of BLASTN search of GenBank database (nucleic acid) using DHDR-4 nucleotide sequence.
Results of BLASTX search of GenBank database (protein) using DHDR-4 predicted polypeptide sequence.
Results of BLASTN search of nucleic acid patent database (PatentDbPreviewNuc) using DHDR-4 nucleotide sequence.
Results of BLASTN search of GenBank database (dbEST) using DHDR-4 nucleotide sequence.
Results of BLASTN search of nucleic acid patent database (FastAlert_N) using DHDR-3 nucleotide sequence.
Results of BLASTX search of protein patent database (FastAlert_P) using DHDR-3 predicted polypeptide sequence.
Results of BLASTN search of GenBank database (nucleic acid) using DHDR-3 nucleotide sequence.
Results of BLASTN search of nucleic acid patent database (PAtentDbPreviewNuc) using DHDR-3 nucleotide sequence.
Results of BLASTX search of protein patent database using DHDR-3 predicted polypeptide sequence.
Results of BLASTN search of GenBank database (dbEST) using DHDR-1 nucleotide sequence.
Results of BLASTN search nucleic acid patent database (FastAlert_N) using DHDR-1 nucleotide sequence.
Results of BLASTN search of GenBank database (nucleic acid) using DHDR-1 nucleotide sequence.
GenSeq Accession No. C09039 for Human secreted protein 5' EST, Seq Id No. 13114.
GenSeq Accession No. X98422 for Human cancer cell derived cDNA #148.
GenSeq Accession No. X99042 for Human validated cancer cell derived cDNA #364.
GenBank Accession No. AI091419 for ow62e03.x1 Soares_NSF_F8_9W_OT_PA_P_S1 *Homo sapiens* cDNA clone Image:1651420 3' similar to WP: T25G12.7 CE07544 Dehydrogenase; contains TAR1.t3 MER22 repetitive element; mRNA sequence.
GenBank Accession No. AI741629 for wg28f07.x1 Soares_NSF_F8_9W_OT_PA_P_S1 *Homo sapiens* cDNA clone Image:2366437 3' similar to WP: T25G12.7 CE07544 Dehydrogenase; contains TAR1.t3 MER22 repetitive element; mRNA sequence.
GenBank Accession No. AI741640 for wg28g07.x1 Soares_NSF_F8_9W_OT_PA_P_S1 *Homo sapiens* cDNA clone Image:2366460 3' similar to WP: T25G12.7 CE07544 Dehydrogenase; contains TAR1.t3 MER22 repetitive element; mRNA sequence.
GenBank Accession No. AI458236 for tj53e07.x1 Soares_NSF_F8_9W_OT_PA_P_S1 *Homo sapiens* cDNA clone Image:2145252 3' similar to WP: T25G12.7 CE07544 Dehydrogenase; contains TAR1.t3 MER22 repetitive element; mRNA sequence.
GenBank Accession No. AI222126 for qh02g04.x1 Soares_NSF_F8_9W_OT_PA_P_S1 *Homo sapiens* cDNA clone Image:184542 3' similar to WP: T25G12.7 CE07544 Dehydrogenase; contains TAR1.t3 MER22 repetitive element; mRNA sequence.
GenBank Accession No. AA953672 for oo02e08.s1 Soares_NSF_F8_9W_OT_PA_P_S1 *Homo sapiens* cDNA clone Image:1565030 3' similar to WP: T25G12.7 CE07544 Dehydrogenase; contains TAR1.t3 MER22 repetitive element; mRNA sequence.
GenBank Accession No. AI376903 for tc27f05.x1 Soares_NSF_F8_9W_OT_PA_P_S1 *Homo sapiens* cDNA clone Image:2065857 3' similar to WP: T25G12.7 CE07544 Dehydrogenase; contains TAR1.t3 MER22 repetitive element; mRNA sequence.
GenBank Accession No. AI141463 for qa67d12.x1 Soares_NSF_F8_9W_OT_PA_P_S1 *Homo sapiens* cDNA clone Image:1691831 3' similar to WP: T25G12.7 CE07544 Dehydrogenase; contains TAR1.t3 MER22 repetitive element; mRNA sequence.
GenBank Accession No. AI022337 for ow95a11.x1 Soares_NSF_F8_9W_OT_PA_P_S1 *Homo sapiens* cDNA clone Image:1654556 3' similar to WP: T25G12.7 CE07544 Dehydrogenase; contains TAR1.t3 MER22 repetitive element; mRNA sequence.
GenBank Accession No. AI168267 for oo10c10.x1 Soares_NSF_F8_9W_OT_PA_P_S1 *Homo sapiens* cDNA clone Image:1565778 3' similar to WP: T25G12.7 CE07544 Dehydrogenase; contains TAR1.t3 MER22 repetitive element; mRNA sequence.
GenBank Accession No. AF151851 for *Homo sapiens* CG1-93 protein mRNA, complete cds.
GenBank Accession No. AL117567 for *Homo sapiens* mRNA; cDNA DKFZp566O084 (from clone DKFZp566o084); complete cds.
GenBank Accession No. G41333 for Z1176 Zebrafish AB Danio rerio STS genomic, sequence tagged site.
GenBank Accession No. AV652436 for AV652436 GLC *Homo sapiens* cDNA clone GLCDAD01 3', mRNA sequence.
GenBank Accession No. AI765848 for wi85c03.x1 NCI_CGAP_Kid12 *Homo sapiens* cDNA clone Image:2400100 3' similar to TR: Q42232 Q42232 Tropinone Reductase Homologue ; MRNA sequence.
GenBank Accession No. BE220231 for hv69f02.x1 NCI_CGAP_Lu24 *Homo sapiens* cDNA clone Image:3178683 3' similar to TR: Q9ZW14 Q9ZW14 Putative Tropinone Reductase; MRNA sequence.
GenBank Accession No. BF108369 for 7n62f05.x1 NCI_CGAP_Lu24 *Homo sapiens* cDNA clone Image:3569408 3' similar to TR: Q9WVK3 Q9WVK3 Putative Short-Chain Dehydrogenase/Reductase mRNA Complete CDS.
GenBank Accession No. BE550902 for 7b65g01.x1 NCI_CGAP_Lu24 *Homo sapiens* cDNA clone Image:3233136 3' similar to SW: YKUF_BACSU O34717 Hypothetical Oxidoreductase in Chev-Moba Intergenic Region.
GenBank Accession No. AI435448 for th94e11.x1 Soares_NSF_F8_9W_OT_PA_P _S1 *Homo sapiens* cDNA clone Image:2126348 3' similar to SW: FABG_MYCTU Q48930 3-Oxoacyl-[ACYL-Carrier Protein] Reductase.

GenBank Accession No. BE300277 for 600944051T1 NIH_MGC_17 *Homo sapiens* cDNA clone Image:2960244 3', MRNA sequence.
GenBank Accession No. BE280956 for 601155875F1 NIH_MGC_21 *Homo sapiens* cDNA clone Image:3139219 5', MRNA sequence.
GenBank Accession No. BE382385 for 601815316F2 NIH_MGC_17 *Homo sapiens* cDNA clone Image:4049499 5', MRNA sequence.
GenBank Accession No. BF726019 for bx23a05.y1 Human Iris cDNA (Un-normalized, unamplified): BX *Homo sapiens* cDNA clone bx23a05 5', MRNA sequence.
GenBank Accession No. AF232009 for *Homo sapiens* peroxisomal trans 2-enoyl CoA reductase mRNA, complete cds.
GenBank Accession No. AJ250303 for *Homo sapiens* mRNA for putative short chain alcohol dehydrogenase.
GenBank Accession No. AF119841 for *Homo sapiens* PRO 1004 mRNA, complete cds.
GenBank Accession No. AF232010 for *Cavia* sp. peroxisomal trans 2-enoyl CoA reductase mRNA, complete cds.
GenBank Accession No. AF099742 for *Rattus norvegicus* putative short-chain dehydrogenase/reductase mRNA, complete cds.
GenBank Accession No. AF021854 for *Rattus norvegicus* peroxisomal trans 2-enoyl CoA reductase px-2, 4-DCR#1 mRNA, complete cds.
GenBank Accession No. AF232011 for *Mus musculus* peroxisomal trans 2-enoyl CoA reductase mRNA, complete cds.
GenBank Accession No. AR007559 for Sequence 2 from Patent US 5750873.
GenBank Accession No. BF569876 for 602185823F1 NIH_MGC_45 *Homo sapiens* cDNA clone Image:4310212 5', mRNA sequence.
GenBank Accession No. BF569788 for 602185723F1 NIH_MGC_45 *Homo sapiens* cDNA clone Image:4310213 5', mRNA sequence.
GenBank Accession No. BF337229 for 602035036F1 NIH_CGAP_Brn64 *Homo sapiens* cDNA clone Image:4182969 5', mRNA sequence.
GenBank Accession No. BE389320 for 601286201F1 NIH_MGC_44 *Homo sapiens* cDNA clone Image:3612936 5', mRNA sequence.
GenBank Accession No. BE393409 for 601308354F1 NIH_MGC_44 *Homo sapiens* cDNA clone Image:3626629 5', mRNA sequence.
GenBank Accession No. BF533271 for 602073726F1 NIH_CGAP_Li9 *Mus musculus* cDNA clone Image:4210518 5', mRNA sequence.
GenBank Accession No. BF535721 for 602051225F1 NIH_CGAP_SG2 *Mus musculus* cDNA clone Image:4190478 5', mRNA sequence.
GenBank Accession No. BF532852 for 602074958F1 NIH_CGAP_Li9 *Mus musculus* cDNA clone Image:4211726 5', mRNA sequence.
GenBank Accession No. BF236705 for 602028695F1 NIH_CGAP_Li9 *Mus musculus* cDNA clone Image:4163927 5', mRNA sequence.
GenBank Accession No. BE808024 for 213133 MARC 2BOV *Bos Taurus* cDNA 5', mRNA sequence.
GenBank Accession No. AF277719 for *Homo sapiens* 3 beta-hydroxy-delta 5-C27-steroid oxidoreductase mRNA, complete cds.
GenBank Accession No. AF277718 for *Mus musculus sapiens* 3 beta-hydroxy-delta 5-C27-steroid oxidoreductase mRNA, complete cds.
GenBank Accession No. AB000199 for *Rattus norveginicus* ccca2 mRNA, complete cds.
GenBank Accession No. S72665 for Ig V-D-J region (RM)—human (fragment).
GenBank Accession No. AF232699 for *Sus scrofa* 3 beta-hydroxysteroid dehydrogenase/delta-5-delta-4 isomerase (3b-HSD) mRNA, 3b-HSD-1 allele, complete cds.
GenBank Accession No. X17614 for Bovine mRNA for 3 beta hydroxy-5-ene steroid dehydrogenase/delta-5-delta-4 isomerase (EC 1.1.1.145, EC 5.3.3.1).
GenBank Accession No. U32426 for *Molluscum contagiosum* virus 3-beta hydroxy-5-ene steroid dehydrogenase (CX11) gene, complete cds.
GenBank Accession No. U86945 for *Mulluscum contagiosum* virus subtype 1 clone H-M ; H-N homolog of vaccinia A36R (H-M-N-1), hypothetical protein (H-M-N-2), putative CC chemokine (H-M-N-3), homolog of vaccinia A37R (H-M-N-4), hypothetical protein (H-M-N-5), hypothetical protein (H-M-N-6) and homolog of vaccinia A44L (H-M-N-7) genes, complete cds, and hypothetical protein (H-M-N-8_gene, partial cds.
GenBank Accession No. U60315 for *Molluscum contagiosum* virus subtype 1, complete genome.
GenBank Accession No. M72474 for *Vaccinia* virus gene ORF2, ORF3, ORF4, ORF5, ORF6, and ORF7 complete cds ; ORF1, 5' end ; ORF8, 3' end.
GenBank Accession No. AI863355 for tz47c11.x1 NCI_CGAP_Brn52 *Homo sapiens* cDNA clone Image:2291732 3' similar to TR :O50217 O50217 Phenylace-Taldehyde Dehydrogenase ; mRNA sequence.
GenBank Accession No. AI863364 for tz47d11.x1 NCI_CGAP_Brn52 *Homo sapiens* cDNA clone Image:2291733 3' similar to SW:YDCW_*Ecoli* P77674 Putative Betaine Aldehyde Dehydrogenase; mRNA sequence.
GenBank Accession No. BE048206 for tz47c11.y1 NCI_CGAP_Brn52 *Homo sapiens* cDNA clone Image:2291732 5' similar to SW:FEAB_*Ecoli* P80668 Phenylacetaldehyde Dehydrogenase; mRNA sequence.
GenBank Accession No. AI674922 for wc73g08.x1 NCI_CGAP_Pan1 *Homo sapiens* cDNA clone Image:2324318 3' similar to TR:O50217 O50217 Phenylace-Taldehyde Dehydrogenase; mRNA sequence.
GenBank Accession No. BE048060 for tz47d11.y1 NCI_CGAP_Brn52 *Homo sapiens* cDNA clone Image:2291733 5' similar to SW:FEAB_*Ecoli* P80668 Phenylacetaldehyde Dehydrogenase; mRNA sequence.
GenBank Accession No. BE734592 for 601569937F1 NIH_MGC_21 *Homo sapiens* cDNA clone IMAGE:3844689 5', mRNA sequence.
GenBank Accession No. BE902065 for 601674824F NIH_MGC_21 *Homo sapiens* cDNA clone Image:3957749 5', mRNA sequence.
GenBank Accession No. BF189846 for 235590 MARC 2PIG *Sus Scrofa* cDNA 5', mRNA sequence.
GenBank Accession No. AI754389 for cr24e02.x1 Jia bone marrow stroma *Homo sapiens* cDNA clone HBMSC_cr24e02 3', mRNA sequence.
GenBank Accession No. BE235576 for 143113 MARC 1PIG *Sus scrofa* 5', mRNA sequence.
GenBank Accession No. AY00796 for *Homo sapiens* clone TCC-CIA00164 mRNA sequence.
GenBank Accession No. AX070214 for Sequence 686 from Patent WO0102568.
GenBank Accession No. AX072164 for Sequence 2636 from Patent WO0102568.
GenBank Accession No. AX070075 for Sequence 547 from Patent WO0102568.
GenBank Accession No. AK024182 for *Homo sapiens* cDNA FLJ14120 fis, clone MAMMA 1001956.
GenSeq Accession No. Z13403 for Human gene expression product cDNA sequence SEQ ID No. 872.
GenSeq Accession No. Z16204 for Human gene expression product cDNA sequence SEQ ID No. 3674.
GenSeq Accession No. A12992.

* cited by examiner

```
Input file Fbh32142FL.seq; Output File 32142.trans
Sequence length 2660

M   A   A   T        4
CCTTTNTNRCCACGCGTCCGAGAGCGCCCCGCAGTCTTCGCGGAAAGCGTTCGGGGTAGGCG   ATG GCT GCG ACG       12

R   A   G   P   R   A   R   E   I   F   T   S   L   E   Y   G   P   V   P   E        24
CGT GCA GGG CCC CGC GCC CGC GAG ATC TTC ACC TCG CTG GAG TAC GGA CCG GTG CCG GAG        72

S   H   A   C   A   L   W   L   D   T   Q   D   R   C   L   G   H   Y   V             44
AGC CAC GCA TGC GCA CTG GCC TGG CTG GAC ACC CAG GAC CGG TGC TTG GGC CAC TAT GTG       132

N   G   K   W   L   K   P   E   H   R   N   S   V   P   C   Q   D   P   I   T        64
AAT GGG AAG TGG TTA AAG CCT GAA CAC AGA AAT TCA GTG CCT TGC CAG GAT CCC ATC ACA       192

G   E   N   L   A   S   C   L   Q   A   Q   A   E   D   V   A   A   A   V   E        84
GGA GAG AAC TTG GCC AGT TGC CTG CAG GCA CAG GCC GAG GAT GTG GCT GCA GCC GTG GAG       252

A   A   R   M   A   F   K   G   W   S   A   H   P   G   V   V   R   A   Q   H       104
GCA GCC AGG ATG GCA TTT AAG GGC TGG AGT GCG CAC CCC GGC GTC GTC CGG GCC CAG CAC       312

L   T   R   L   A   E   V   I   Q   K   H   Q   R   L   L   W   T   L   E   S       124
CTG ACC AGG CTG GCC GAG GTG ATC CAG AAG CAC CAG CGG CTG CTG TGG ACC CTG GAA TCC       372

L   V   T   G   R   A   V   R   E   V   R   D   G   D   V   Q   L   A   Q   Q       144
CTG GTG ACT GGG CGG GCT GTT CGA GAG GTT CGA GAC GGG GAC GTC CAG CTG GCC CAG CAG       432

L   L   H   Y   H   A   I   Q   A   S   T   Q   E   E   A   L   A   G   W   E       164
CTG CTC CAC TAC CAT GCA ATC CAG GCA TCC ACC CAG GAG GAG GCA CTG GCA GGC TGG GAG       492

P   M   G   V   I   G   L   I   L   P   P   T   F   S   F   L   E   M   M   W       184
CCC ATG GGA GTA ATT GGC CTC ATC CTG CCA CCC ACA TTC TCC TTC CTT GAG ATG ATG TGG       552

R   I   C   P   A   L   A   V   G   C   T   V   V   A   L   V   P   P   A   S       204
AGG ATT TGC CCT GCC CTG GCT GTG GGC TGC ACC GTG GTG GCC CTC GTG CCC CCG GCC TCC       612

P   A   P   L   L   L   A   Q   L   A   G   E   L   G   P   F   P   G   I   L       224
CCG GCG CCC CTC CTC CTG GCC CAG CTG GCG GGG GAG CTG GGC CCC TTC CCG GGA ATC CTG       672

N   V   V   S   G   P   A   S   L   V   P   I   L   A   S   Q   P   G   I   R       244
AAT GTC GTC AGT GGC CCT GCG TCC CTG GTG CCC ATC CTG GCC TCC CAG CCT GGA ATC CGG       732

K   V   A   F   C   G   A   P   E   E   G   R   A   L   R   R   S   L   A   G       264
AAG GTG GCC TTC TGC GGA GCC CCG GAG GAA GGG CGT GCC CTT CGA CGG AGC CTG GCG GGA       792

E   C   A   E   L   G   L   A   L   G   T   E   S   L   L   L   L   T   D   T       284
GAG TGT GCG GAG CTG GGC CTG GCG CTG GGG ACG GAG TCG CTG CTG CTG CTG ACG GAC ACG       852
```

Fig. 1A

```
  A   D   V   D   S   A   V   E   G   V   V   D   A   A   W   S   D   R   G   P    304
GCG GAC GTA GAC TCG GCC GTG GAG GGT GTC GTG GAC GCC GCC TGG TCC GAC CGC GGC CCG    912

G   G   L   R   L   L   I   Q   E   S   V   W   D   E   A   M   R   R   L   Q    324
GGT GGC CTC AGG CTC CTC ATC CAG GAG TCT GTG TGG GAT GAA GCC ATG AGA CGG CTG CAG    972

E   R   M   G   R   L   R   S   G   R   G   L   D   G   A   V   D   M   G   A    344
GAG CGG ATG GGG CGG CTT CGG AGT GGC CGA GGG CTG GAT GGG GCC GTG GAC ATG GGG GCC   1032

R   G   A   A   A   C   D   L   V   Q   R   F   V   R   E   A   Q   S   Q   G    364
CGG GGG GCT GCC GCA TGT GAC CTG GTC CAG CGC TTT GTG CGT GAG GCC CAG AGC CAG GGT   1092

A   Q   V   F   Q   A   G   D   V   P   S   E   R   P   F   Y   P   P   T   L    384
GCA CAG GTG TTC CAG GCT GGT GAT GTG CCT TCG GAA CGC CCA TTC TAT CCC CCA ACC TTG   1152

V   S   N   L   P   P   A   S   P   C   A   Q   V   E   V   P   W   P   V   V    404
GTC TCC AAC CTG CCC CCA GCC TCC CCA TGT GCC CAG GTG GAG GTG CCG TGG CCT GTG GTC   1212

V   A   S   P   F   R   T   A   K   E   A   L   L   V   A   N   G   T   P   R    424
GTG GCC TCC CCC TTC CGC ACA GCC AAG GAG GCA CTG TTG GTG GCC AAC GGG ACG CCC CGC   1272

G   G   S   A   S   V   W   S   E   R   L   G   Q   A   L   E   L   G   Y   G    444
GGG GGC AGC GCC AGT GTG TGG AGC GAG AGG CTG GGG CAG GCG CTG GAG CTG GGC TAT GGG   1332

L   Q   V   G   T   V   W   I   N   A   H   G   L   R   D   P   S   V   P   T    464
CTC CAG GTG GGC ACT GTC TGG ATC AAC GCC CAC GGC CTC AGA GAC CCT TCG GTG CCC ACA   1392

G   G   C   K   E   S   G   C   S   W   H   G   G   P   D   G   L   Y   E   Y    484
GGC GGC TGC AAG GAG AGT GGG TGT TCC TGG CAC GGG GGC CCA GAC GGG CTG TAT GAG TAT   1452

L   R   P   S   G   T   P   A   R   L   S   C   L   S   K   N   L   N   Y   D    504
CTG CGG CCC TCA GGG ACC CCT GCC CGG CTG TCC TGC CTC TCC AAG AAC CTG AAC TAT GAC   1512

T   F   G   L   A   V   P   S   T   L   P   A   G   P   E   I   G   P   S   P    524
ACC TTT GGC CTC GCT GTG CCC TCA ACC CTG CCG GCT GGG CCT GAA ATA GGG CCC AGC CCA   1572

A   P   P   Y   G   L   F   V   G   G   R   F   Q   A   P   G   A   R   S   S    544
GCA CCC CCC TAT GGG CTC TTC GTT GGG GGC CGT TTC CAG GCT CCT GGG GCC CGA AGC TCC   1632

R   P   I   R   D   S   S   G   N   L   H   G   Y   V   A   E   G   G   A   K    564
AGG CCC ATC CGG GAT TCG TCT GGC AAT CTC CAT GGC TAC GTG GCT GAG GGT GGA GCC AAG   1692

D   I   R   G   A   V   E   A   A   H   Q   A   F   P   G   W   A   G   Q   S    584
GAC ATC CGA GGT GCT GTG GAG GCC GCT CAC CAG GCT TTC CCT GGC TGG GCG GGC CAG TCC   1752

P   G   A   R   A   A   L   L   W   A   L   A   A   A   L   E   R   R   K   S    604
CCA GGA GCC CGG GCA GCC CTG CTG TGG GCC CTG GCG GCT GCA CTG GAG CGC CGG AAG TCT   1812
```

Fig. 1B

```
 T   L   A   S   R   L   E   R   Q   G   A   E   L   K   A   A   E   A   E   V    624
ACC CTG GCC TCA AGG CTG GAG AGG CAG GGA GCG GAG CTC AAG GCT GCG GAG GCG GAG GTG   1872

E   L   S   A   R   R   L   R   A   W   G   A   R   V   Q   A   Q   G   H   T    644
GAG CTG AGC GCA AGA CGA CTT CGG GCG TGG GGG GCC CGG GTG CAG GCC CAA GGC CAC ACC   1932

L   Q   V   A   G   L   R   G   P   V   L   R   L   R   E   P   L   G   V   L    664
CTG CAG GTA GCC GGG CTG AGA GGC CCT GTG CTG CGC CTG CGG GAG CCG CTG GGT GTG CTG   1992

A   V   V   C   P   D   E   W   P   L   L   A   F   V   S   L   L   A   P   A    684
GCT GTG GTG TGT CCG GAC GAG TGG CCC CTG CTT GCC TTC GTG TCC CTG CTG GCT CCC GCC   2052

L   A   Y   G   N   T   V   V   M   V   P   S   A   A   C   P   L   L   A   L    704
CTG GCC TAC GGC AAC ACT GTG GTC ATG GTG CCC AGT GCG GCC TGT CCT CTG CTG GCC CTG   2112

E   V   C   Q   D   M   A   T   V   F   P   A   G   L   A   N   V   V   T   G    724
GAG GTC TGC CAG GAC ATG GCC ACC GTG TTC CCA GCA GGC CTG GCC AAC GTG GTG ACA GGA   2172

D   R   D   H   L   T   R   C   L   A   L   H   Q   D   V   Q   A   M   W   Y    744
GAC CGG GAC CAT CTG ACC CGC TGC CTG GCC TTG CAC CAA GAC GTC CAG GCC ATG TGG TAT   2232

F   G   S   A   Q   G   S   Q   F   V   E   W   A   S   A   G   N   L   K   P    764
TTC GGA TCA GCC CAG GGT TCC CAG TTT GTC GAG TGG GCC TCG GCA GGA AAC CTC AAA CCG   2292

V   W   A   S   R   G   C   P   R   A   W   D   Q   E   A   E   G   A   G   P    784
GTG TGG GCG AGC AGG GGC TGC CCG CGG GCC TGG GAC CAG GAG GCC GAG GGG GCA GGC CCA   2352

E   L   G   L   R   V   A   R   T   K   A   L   W   L   P   M   G   D   *        803
GAG CTG GGG CTG CGA GTG GCG CGG ACC AAG GCC CTG TGG CTG CCT ATG GGG GAC TGA       2409

TGCCTGAGCGCCACCTACTGCATTTTGGACACCTCACACCAAGGGGAGATGCACCCCACAGACACCTGGGACTTTCCCC

TTCTGGTTCCTGTGTCTCCCAATAAACTCTCTGACCAACCCTAAAAAAAAAAAAAAAAAAAAAAAAAAAARWARMAACTTC

TGGCAGATATGAGGCTTTTTTCTTTTTTTTT
```

Fig. 1C

Transmembrane Segments Predicted by MEMSAT

| Start | End | Orient | Score |
|---|---|---|---|
| 159 | 175 | ins-->out | 0.1 |

>32142
MAATRAGPRAREIFTSLEYGPVPESHACALAWLDTQDRCLGHYVNGKWLKPEHRNSVPCQ
DPITGENLASCLQAQAEDVAAAVEAARMAFKGWSAHPGVVRAQHLTRLAEVIQKHQRLLW
TLESLVTGRAVREVRDGDVQLAQQLLHYHAIQASTQEEALAGWEPMGVIGLILPPTFSFL
EMMWRICPALAVGCTVVALVPPASPAPLLLAQLAGELGPFPGILNVVSGPASLVPILASQ
PGIRKVAFCGAPEEGRALRRSLAGECAELGLALGTESLLLLTDTADVDSAVEGVVDAAWS
DRGPGGLRLLIQESVWDEAMRRLQERMGRLRSGRGLDGAVDMGARGAAACDLVQRFVREA
QSQGAQVFQAGDVPSERPFYPPTLVSNLPPASPCAQVEVPWPVVVASPFRTAKEALLVAN
GTPRGGSASVWSERLGQALELGYGLQVGTVWINAHGLRDPSVPTGGCKESGCSWHGGPDG
LYEYLRPSGTPARLSCLSKNLNYDTFGLAVPSTLPAGPEIGPSPAPPYGLFVGGRFQAPG
ARSSRPIRDSSGNLHGYVAEGGAKDIRGAVEAAHQAFPGWAGQSPGARAALLWALAAALE
RRKSTLASRLERQGAELKAAEAEVELSARRLRAWGARVQAQGHTLQVAGLRGPVLRLREP
LGVLAVVCPDEWPLLAFVSLLAPALAYGNTVVMVPSAACPLLALEVCQDMATVFPAGLAN
VVTGDRDHLTRCLALHQDVQAMWYFGSAQGSQFVEWASAGNLKPVWASRGCPRAWDQEAE
GAGPELGLRVARTKALWLPMGD

Fig. 3

Protein Family / Domain Matches, HMMer Version 2

```
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - - -
HMM file:                /prod/ddm/seqanal/PFAM/pfam5.0/Pfam
Sequence file:           /prod/ddm/wspace/orfanal/oa-script.9519.seq
- - - - - - - - - - - - - - - - - - - - - - - - - - - - - - - - - - - - -
    Query: 32142

Scores for sequence family classification (score includes all domains):
Model      Description                                     Score      E-value   N
--------   -----------                                     -----      -------  ---
aldedh     Aldehyde dehydrogenase family                   149.8      4.7e-41   1

Parsed for domains:
Model      Domain   seq-f,seq-t    hmm-f hmm-t       score  E-value
--------   ------   ----- -----    ----- -----       -----  -------
aldedh       1/1       47   494 ..     1   492 []    149.8  4.7e-41

Alignments of top-scoring domains:
aldedh: domain 1 of 1, from 47 to 494: score 149.8, E = 4.7e-41
                   *->ewvdsasgktfevvNPankgevigrvpeataeDvdaAVkAAkeAfks
                      +w +++   +  +++ +P + ge +++    +a+aeDv aAV AA+ Afk+
         32142   47  KWLWPEHRNSVPCQDPIT-GENLASCLQAQAEDVAAAVEAARMAFKG   92

GpwWakvpaseRariLrkladlieeredeLaaletlDlGKplaeAkgDte
                      W++ p     Ra+ L +la+ i+ ++ +L   le+l +G  ++e+  + +
         32142   93  ---WSAHPGVVRAQHLTRLAEVIQKHQRLLWTLESLVTGRAVREVRDG-D   138 vgraideiryyagwarklmgerrvipslatdgdeelnytrrePlGVvgvI
                      v+ a + ++y a +a+                t+   e ++  +eP GV+g I
         32142  139  VQLAQQLLHYHAIQAS------------TQ---EEALAGWEPMGVIGLI   172 sPWNFPlllalwklapALAaGNTVVlKPSEqTPlt...alllaelieeaGa
                      P  F +l ++w ++pALA G+TVV   +    P+++   llla l   e G
         32142  172  LPPTFSFLEMMWRICPALAVGCTVV---ALVPPASpaPLLLAQLAGELG-   218 nnlPkGVvnvvpGfGaevGqaLlshpdidkisFTGSteVGklimeaAAak
                      +G +nvv G +a+ +   L+s+p+i+k++F G +e G+ + ++ A +
         32142  219  --PFPGILNVVSG-PASLVPILASQPGIRKVAFCGAPEEGRALRRSLAGE   265 nlkkVtLELGGKsPvIVfdDADLdkAverivfgaFgnaGQvCiApsRllv
                      +    L LG  s     d AD d Ave++v  +a       G    ++ Rll+
         32142  266  -CAELGLALGTESLLLLTDTADVDSAVEGVVDAAWSDRG---PGGLRLLI   311 hesiydeFveklkervkklkliGdpldsdtniyGPlIseqqfdrvlsyIe
                      +es+ de +  +l+er+ +l+    G +ld  +   + G+    +++ d v +++
         32142  312  QESVWDEAMRRLQERMGRLR-SGRGLDGAVDM-GAR-GAAACDLVQRFVR   358 dgkeeGAkvlcGGerdeskeylggGyyvqPTiftdVtpdMkImkEEIFGP
                      ++++ +GA+v + G ++ +        + ++  PT+++++  p +++++ E+    P
         32142  359  EAQSQGAQVFQAGDVPSE---RP---FYPPTLVSNLPPASPCAQVEVPWP   402

VlpiikfkdldEAIelaNdteYGLAayvFTkdilarafrvakaleaGiVw
                      V++  f++    EA+  aN t+ G +a+v+++   l   a     +l++G+Vw
         32142  403  VVVASPFRTAKEALLVANGTPRGGSASVWSER-LGQALELGYGLQVGTVW   451 vNDvcvhaaaepqlPFGGvHqSSGiGrehgGkygleeYteiKtVtirl<-*
                      +N    ++  +p++P GG  K+  SG +  ++ G++gl  eY++    + rl
         32142  452  IN--AHGLRDPSVPTGGCKE-SGCSWHG-GPDGLYEYLRPSGTPARL     494
```

Fig. 4

ProDom Matches

| ProdomId | Start | End | Description | Score |
|---|---|---|---|---|
| View Prodom 135 [Boxer ▼] [Showing match ▼] [Go!] | 101 | 770 | p99.2 (229) DHAL(10) DHAB(10) DHAM(7) // DEHYDROGENASE OXIDOREDUCTASE ALDEHYDE NAD PROTEIN CLASS SEMIALDEHYDE PRECURSOR TRANSIT PEPTIDE | 280 |
| ProdomId | Start | End | Description | Score |

View Prodom 135 [Boxer ▼] [Showing match ▼] [Go!]

>135 p99.2 (229) DHAL(10) DHAB(10) DHAM(7)  // DEHYDROGENASE OXIDOREDUCTASE
    ALDEHYDE NAD PROTEIN CLASS SEMIALDEHYDE PRECURSOR TRANSIT PEPTIDE
    Length = 494

Score = 280 (103.6 bits), Expect = 7.8e-22, P = 7.8e-22
Identities = 87/289 (30%), Positives = 142/289 (49%)

Query:  216 ELGPFPGILNVVSG--PASLVPILASQPGIRKVAFCGAPEEGRALRRSXXXXXXXXXXXX 273
            E G   PG++NVV+G    A +    L S P I K++F G+ E G+A+ ++
Sbjct:  194 EAGLPPGVINVVTGFGGAEVGEALVSHPDIDKISFTGSTEVGKAIMKAAAEKNLKPVTLE 253

Query:  274 XXXXX--XXXXDTADVDSAVEGVVDAAWSDRGP---GGLRLLIQESVWDEAMRRLQERMG 328
                      D  D+D AVE VV  A+ + G         R+ +QES++DE + +L ER+
Sbjct:  254 LGGKNPVIVFEDADDLDKAVESVVFGAFFNSGQVCTAASRIFVQESIYDEFVEKLVERVK 313

Query:  329 RL-RSGRG--LDGAVDMGAR-GAAACDLVQRFVREAQSQGAQVFQAGD---VPSERPFY- 380
            +L + G    LD  DMG      + +Q ++ EA+++GA++    G+    E ++
Sbjct:  314 KLLKVGEDDPLDPDTDMGPLINEEQYEKIQSYIEEAKAEGAKLVCGGERRKAGDEGGYFI 373

Query:  381 PPTLVSNLPPASPCAQVEVPWPVVVASPFRT-AKEALLVANGTPRGGSASVWSERLGQAL 439
             PT+++++      Q E+   PV+     F+     EA+ +AN  T  G  +A V++  + +A
Sbjct:  374 QPTILTDVTEDMRIMQEEIFGPVLPVIKFKDDLDEAIELANDTEYGLAAGVFTRDIERAQ 433

Query:  440 ELGYGLQVGTVWINA---HGLRDPSVPTGGCKESGCSWH-GGPDGLYEY 484
            +    L+ GTVW+N    H +     P GG K+SG    GG  GL EY
Sbjct:  434 RVAERLEAGTVWVNDNIYHVSAEAQAPFGGYKQSGIGGREGGKYGLEEY 482

Score = 262 (97.3 bits), Expect = 8.2e-20, P = 8.2e-20
Identities = 86/301 (28%), Positives = 140/301 (46%)

Query:  101 RAQHLTRLAEVIQKHQRLLWTLESLVTGRAVREVRDGDVQLAQQLLHYHA---------- 150
            RA+ L +LA+++++++   L LE+L TG+ + E +  +V   A   L Y+A
Sbjct:   61 RARILRKLADLLEENKDELAALETLETGKPLAEAKVAEVARAVDYLRYYAGMAEKLMGEE 120

Query:  151 -IQASTQEE----ALAGWEPMGVIGLILPPTFSFLEMMWRICPALAVGVTXX---XXXXX 202
             I   S  E          EP+GV+  I P   F +   +W+I PALA  G T
Sbjct:  121 TIPTSLSESPGSMSYTMREPLGVVAAITPWNFPLMMAVWKIAPALAAGNTVVLKPSEQTP 180

Query:  203 XXXXXXXXXXXGELGPFPGILNVVSG--PASLVPILASQPGIRKVAFCGAPEEGRALRR 260
                       E G   PG++NVV+G    A +    L S P I K++F G+ E G+A+ +
Sbjct:  181 LTALLLAELIKEAEAGLPPGVINVVTGFGGAEVGEALVSHPDIDKISFTGSTEVGKAIMK 240

Query:  261 SXXXXXXXXXXXXXXXXX--XXXXDTADVDSAVEGVVDAAWSDPGP---GGLRLLIQESV 315
            +                       D  D+D AVE VV  A+ + G         R+ +QES+
Sbjct:  241 AAAEKNLKPVTLELGGKNPVIVFEDADDLDKAVESVVFGAFFNSGQVCTAASRIFVQESI 300

Query:  316 WDEAMRRLQERMGRL-RSGRG--LDGAVDMGAR-GAAACDLVQRFVREAQSQGAQVFQAG 371
            +DE + +L ER+ +L + G    LD  DMG      + +Q ++ EA+++GA++    G
Sbjct:  301 YDEFVEKLVERVKKLLKVGEDDPLDPDTDMGPLINEEQYEKIQSYIEEAKAEGAKLVCGG 360

Query:  372 D 372
            +
Sbjct:  361 E 361

Fig. 5A

Score = 219 (82.2 bits), Expect = 4.9e-15, P = 4.9e-15
Identities = 75/236 (31%), Positives = 105/236 (44%)

```
Query:   550 SSGNLHGYVAEGGAKDIRGAVEAAHQAFPG--WAGQSP-GXXXXXXXXXXXXXXERRKSTL 606
             ++G +    V E   +D+ AVEAA +AF G  W   SP                E K  L
Sbjct:    20 TNGEVIAQVPEATKEDVDKAVEAAREAFKGGEWGKTSPLSERARILRKLADLLEENKDEL  79

Query:   607 AS--RLERQGXXXXXXXXXXXXXXXXRRLRAW-GARVQAQGH-TLQVAGLRGP---VLRLRE 659
             A+   LE                   LR + G    + G  T+  +    P       +RE
Sbjct:    80 AALETLETGKPLAEAKVAEVARAVDYLRYYAGMAEKLMGEETIPTSLSESPGSMSYTMRE  139

Query:   660 PLGVLAVVCPDEWPLLAFVSLLAPALATGNTVVMVPSAACPLLAL---EVCQDMATVFPA 716
             PLGV+A + P +PL+ V +APALA GNTVV+ PS   PL AL     E+  ++      P
Sbjct:   140 PLGVVAAITPWNFPLMMAVWKIAPALAAGNTVVLKPSEQTPLTALLLAELIKEAEAGLPP 199

Query:   717 GLANVVTG-DRDHLTRCLALHQDVQAMWYFGSAQ-GSQFVEWASAGNLKPVWASRG 770
             G+ NVVTG     +  L  D+ + + GS + G   ++ A+ NLKPV      G
Sbjct:   200 GVINVVTGFGGAEVGEALVSHPDIDKISFTGSTEVGKAIMKAAAEKNLKPVTLELG 255
```

Fig. 5B

Input file Fbh21481FL.seq; Output File 21481.trans
Sequence length 1379

TTTGGCCCTCGAGGCCAAGAATTCGGCACGAGGAGCAAGTGGCCTTAACACATGGATTTTCTTCCAAAAATGCAGACCC

ATTTTAATTAAGTTTGTAATTAACCACTGGGGAGGGCAGGCCCCCTGGATTCGGTCTGCTTTCGGAGACACTGTGAGTA

ACTTCCTATTTGTTGAACATTTGGGGATTAGCACGCCCACTGGGTGTTCAGCTTGGAGGCTTGCACAGAGCTGAGCTCC

CTGCAGCCTTGGGCCTCCCCCTGCCCTGGGAGTCCTGATCAGCGTCTCTTTGCAAAGCCAATCCCCTTTTACTCCGTTG

```
                    M   G   V   M   A   M   L   M   L   P   L   L   L   L   G   I    16
TCCCCCAGAACAAG ATG GGA GTC ATG GCC ATG CTG ATG CTC CCC CTG CTG CTG CTG GGA ATC     48

S   G   L   L   F   I   Y   Q   E   V   S   R   L   W   S   K   S   A   V   Q    36
AGC GGC CTC CTC TTC ATT TAC CAA GAG GTG TCC AGG CTG TGG TCA AAG TCA GCT GTG CAG   108

N   K   V   V   V   I   T   D   A   I   S   G   L   G   K   E   C   A   R   V    56
AAC AAA GTG GTG GTG ATC ACC GAT GCC ATC TCA GGA CTG GGC AAG GAG TGT GCT CGG GTG   168

F   H   T   G   G   A   R   L   V   L   C   G   K   N   W   E   R   L   E   N    76
TTC CAC ACA GGT GGG GCA AGG CTG GTG CTG TGT GGA AAG AAC TGG GAG AGG CTA GAG AAC   228

L   Y   D   A   L   I   S   V   A   D   P   S   K   T   F   T   P   K   L   V    96
CTA TAT GAT GCC TTG ATC AGC GTG GCT GAC CCC AGC AAG ACA TTC ACC CCA AAG CTG GTC   288

L   L   D   L   S   D   I   S   C   V   P   D   V   A   K   E   V   L   D   C   116
CTG TTG GAC CTC TCA GAC ATC AGC TGT GTC CCA GAT GTG GCA AAA GAA GTC CTG GAT TGC   348

Y   G   C   V   D   I   L   I   N   N   A   S   V   K   V   K   G   P   A   H   136
TAT GGC TGT GTG GAC ATC CTC ATC AAC AAT GCC AGT GTG AAG GTG AAG GGG CCT GCC CAT   408

K   I   S   L   E   L   D   K   K   I   M   D   A   N   Y   F   G   P   I   T   156
AAG ATT TCT CTG GAG CTC GAC AAA AAG ATC ATG GAT GCC AAT TAC TTT GGC CCC ATC ACA   468

L   T   K   A   L   L   P   N   M   I   S   R   R   T   G   Q   I   V   L   V   176
TTG ACG AAA GCC CTG CTT CCC AAC ATG ATC TCC CGG AGA ACA GGC CAA ATC GTG TTA GTG   528

N   N   I   Q   G   K   F   G   I   P   F   R   T   T   Y   A   A   S   K   H   196
AAT AAT ATC CAA GGG AAG TTT GGA ATC CCG TTC CGT ACG ACT TAC GCT GCC TCC AAG CAC   588
```

Fig. 6A

```
A   A   L   G   F   F   D   C   L   R   A   E   V   E   E   Y   D   V   V   I   216
GCA GCC CTG GGC TTC TTT GAC TGC CTC CGA GCC GAA GTG GAG GAA TAC GAT GTT GTC ATC 648

S   T   V   S   P   T   F   I   R   S   Y   H   V   Y   P   E   Q   G   N   W   236
AGC ACC GTG AGC CCG ACT TTC ATC CGG TCG TAC CAC GTG TAT CCA GAG CAA GGA AAC TGG 708

E   A   S   I   W   K   F   F   F   R   K   L   T   Y   G   V   H   P   V   E   256
GAA GCT TCC ATT TGG AAA TTC TTT TTC AGG AAG CTG ACC TAC GGC GTG CAC CCA GTA GAG 768

V   A   E   E   V   M   R   T   V   R   R   K   K   Q   E   V   F   M   A   N   276
GTG GCG GAG GAG GTG ATG CGC ACC GTG CGG AGG AAG AAG CAA GAG GTG TTT ATG GCC AAC 828

P   I   P   K   A   A   V   Y   V   R   T   F   F   P   E   F   F   F   A   V   296
CCC ATC CCC AAG GCC GCC GTG TAC GTC CGC ACC TTC TTC CCG GAG TTC TTT TTC GCC GTG 888

V   A   C   G   V   K   E   K   L   N   V   P   E   E   G   *                   312
GTG GCC TGT GGG GTG AAG GAG AAG CTC AAT GTC CCG GAG GAG GGG TAA                 936

CTGCAGGAGGCCAAATGGGCCACCCCTTGGAAATAAAGGTTTTTCTGGCAAAAAAAAAAAAAAAAAAAAAANTTTGCGGC

CGCAAGCTTATTCCCTTTAGGGAGGGTTAATTTT
```

Fig. 6B

Signal Peptide Predictions for 21481

| Method | Predict | Score | Mat@ |
|---|---|---|---|
| SignalP (eukaryote) | YES | | 19 |

Note: amino-terminal 70aa used for signal peptide prediction

Transmembrane Segments Predicted by MEMSAT

| Start | End | Orient | Score |
|---|---|---|---|
| 7 | 23 | ins-->out | 4.5 |

>21481
MGVMAMLMLPLLLLGISGLLFIYQEVSRLWSKSAVQNKVVVITDAISGLGKECARVFHTG
GARLVLCGKNWERLENLYDALISVADPSKTFTPKLVLLDLSDISCVPDVAKEVLDCYGCV
DILINNASVKVKGPAHKISLELDKKIMDANYFGPITLTKALLPNMISRRTGQIVLVNNIQ
GKFGIPFRTTYAASKHAALGFFDCLRAEVEEYDVVISTVSPTFIRSYHVYPEQGNWEASI
WKFFFRKLTYGVHPVEVAEEVMRTVRRKKQEVFMANPIPKAAVYVRTFFPEFFFAVVACG
VKEKLNVPEEG

Transmembrane Segments for Presumed Mature Peptide

| Start | End | Orient | Score |
|---|---|---|---|
| 265 | 283 | ins-->out | 0.2 |

>21481 mature
LLFIYQEVSRLWSKSAVQNKVVVITDAISGLGKECARVFHTGGARLVLCGKNWERLENLY
DALISVADPSKTFTPKLVLLDLSDISCVPDVAKEVLDCYGCVDILINNASVKVKGPAHKI
SLELDKKIMDANYFGPITLTKALLPNMISRRTGQIVLVNNIQGKFGIPFRTTYAASKHAA
LGFFDCLRAEVEEYDVVISTVSPTFIRSYHVYPEQGNWEASIWKFFFRKLTYGVHPVEVA
EEVMRTVRRKKQEVFMANPIPKAAVYVRTFFPEFFFAVVACGVKEKLNVPEEG

Fig. 8

Protein Family / Domain Matches, HMMer Version 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - -
HMM file:            /prod/ddm/seqanal/PFAM/pfam5.0/Pfam
Sequence file:       /prod/ddm/wspace/orfanal/oa-script.9650.seq
- - - - - - - - - - - - - - - - - - - - - - - - - - - - - - - - - - - -
Query: 21481

Scores for sequence family classification (score includes all domains):
Model       Description                                    Score    E-value   N
--------    -----------                                    -----    -------  ---
adh_short   short chain dehydrogenase                      120.0    4.5e-32   1
A2M         Alpha-2-macroglobulin family                     0.5        7.1   1

Parsed for domains:
Model       Domain   seq-f  seq-t   hmm-f  hmm-t       score   E-value
--------    ------   -----  -----   -----  -----       -----   -------
adh_short   1/1         38    227 ..     1    203 []    120.0   4.5e-32
A2M         1/1        278    291 ..     1     14 [.      0.5       7.1

Alignments of top-scoring domains:
adh_short: domain 1 of 1, from 38 to 227: score 120.0, E = 4.5e-32
                   *->KvaLvTGassGIGlaiAkrLakeGakVvvadrneeklekGavakelk
                      Kv+++T a sG+G+++A+ +++ Ga++v+++ n e+le+   ++l
         21481  38    KVVVITDAISGLGKECARVFHTGGARLVLCGKNWERLEN--LYDALI  82 elGgnd..kdralaiqlDvtdeesv.aaveqaverlGrlDvLVNNAGgii
                   +++++    + 1D++d + v++++++++++ +G +D+L+NNA   +
         21481  83  SV-ADPskTFTPKLVLLDLSDISCVpDVAKEVLDCYGCVDILINNAS--V 129 llrpgpfaelsrtmeedwdrvidvNltgvflltravlplmamkkrggGrI
                      gp+++++s    +e+ ++++d N++g++ lt+a+lp    m+ r+ G I
         21481  130 -KVKGPAHKIS---LELDKKIMDANYFGPITLTKALLP--NMISRRTGQI 173 vNiSSvaGrkegglvgvpggsaYsASKaAvigltrsLAlElaphgIrVna
                   v + + G    + g p+++ Y+ASK+A g+ ++L+ E+ ++ + ++
         21481  174 VLVNNIQG-----KFGIPFRTTYAASKHAALGFFDCLRAEVEEYDVVIST 218

VAPGgvdTd<-*
                   v+P +++
         21481  219 VSPTFIRSY    227

A2M: domain 1 of 1, from 278 to 291: score 0.5, E = 7.1
                   *->idedditiRSyFPE<-*
                      i+   + +R++FPE
         21481  278    IPKAAVYVRTFFPE    291

Fig. 9

ProDom Matches

| ProdomId | Start | End | Description | Score |
|---|---|---|---|---|
| View Prodom 11 [Boxer ▼] [Showing match ▼][Go!] | 99 | 219 | p99.2 (1078) ADH(34) GALE(20) FABG(13)// OXIDOREDUCTASE PROTEIN DEHYDROGENASE NAD REDUCTASE NADP BIOSYNTHESIS SYNTHASE ALCOHOL PUTATIVE | 113 |
| ProdomId | Start | End | Description | Score |

```
View Prodom 11  [Boxer ▼] [Showing match ▼] [Go!]

>11 p99.2 (1078) ADH(34) GALE(20) FABG(13)   // OXIDOREDUCTASE PROTEIN
    DEHYDROGENASE NAD REDUCTASE NADP BIOSYNTHESIS SYNTHASE ALCOHOL PUTATIVE
    Length = 269

Score = 113 (44.8 bits), Expect = 0.00016, P = 0.00016
Identities = 41/138 (29%), Positives = 63/138 (45%)

Query:    99 DLSDIS-CVPDVAKEVLDCYGCVDILINNASVKV-KGPAHKISLELD-----RKIMDANY 151
             D+ D+    V   V +E   +G +D+L+NNA V  K  A  ++ E       +++++ N
Sbjct:    87 DVEDVEKLVETVVEEFSGIHGKIDVLVNNAGVMAPKAVAESMTEETSDDEEWEEVIEVNV 146

Query:   152 FGPITLTKALLPNMIS--------RRTGQIVLVNNIQGK-FGIP-FRTTYAASKHAALGF 201
             G    LT+A LP M          R  G IV V ++ G   GP   +  Y+ASK A   F
Sbjct:   147 TGTFNLTQAALPAMKKFSDAAAKKRFVGTIVNVASVAGSTMGSPGSQAAYSASKAAVESF 206

Query:   202 FDCLRAEVEEYDVVISTV 219
             L  E+  Y   ++ V
Sbjct:   207 TKSLAMELSPYSASVAMV 224
```

Fig. 10

Input file Fbh25964F1.seq; Output File 25964.trans
Sequence length 1725

GAGAAGGAGGAGCCAGCGGAAGGACGGTGTGCGGGCCGGCCAGCCCTGGACGAAAGAAGAGGGCCCCTCCAGGCCAGTC

TGGGCACCCTGGGATAGCGGCTGCAGCCATCAGCAGGGGCAGACGGCAGGTGGCCTGGTTGCTGCAGCTCCCAGGATCA

GCTCTGCCCTCCCCGCAAACGCCAGCCTCGTCACCGCTCCAGGGCACCTCCAGCAGTAACAGGTGGTTGCAGCAGGTGG

```
                                                  M   A   D   S   A   Q   A   Q   K     9
CAGCCAGCCCCTGGATGAGCCAAGGTCTCTTCCCCAGCCAGGC ATG GCC GAC TCT GCA CAG GCC CAG AAG    27

L   V   Y   L   V   T   G   G   C   G   F   L   G   E   H   V   V   R   M   L     29
CTG GTG TAC CTG GTC ACA GGG GGC TGT GGC TTC CTG GGA GAG CAC GTG GTG CGA ATG CTG    87

L   Q   R   E   P   R   L   G   E   L   R   V   F   D   Q   H   L   G   P   W     49
CTG CAG CGG GAG CCC CGG CTC GGG GAG CTG CGG GTC TTT GAC CAA CAC CTG GGT CCC TGG   147

L   E   E   L   K   T   G   P   V   R   V   T   A   I   Q   G   D   V   T   Q     69
CTG GAG GAG CTG AAG ACA GGG CCT GTG AGG GTG ACT GCC ATC CAG GGG GAC GTG ACC CAG   207

A   H   E   V   A   A   A   V   A   G   A   H   V   V   I   H   T   A   G   L     89
GCC CAT GAG GTG GCA GCA GCT GTG GCC GGA GCC CAT GTG GTC ATC CAC ACG GCT GGG CTG   267

V   D   V   F   G   R   A   S   P   K   T   I   H   E   V   N   V   Q   G   T    109
GTA GAC GTG TTT GGC AGG GCC AGT CCC AAG ACC ATC CAT GAG GTC AAC GTG CAG GGT ACC   327

R   N   V   I   E   A   C   V   Q   T   G   T   R   F   L   V   Y   T   S   S    129
CGG AAC GTG ATC GAG GCT TGT GTG CAG ACC GGA ACA CGG TTC CTG GTC TAC ACC AGC AGC   387

M   E   V   V   G   P   N   T   K   G   H   P   F   Y   R   G   N   E   D   T    149
ATG GAA GTT GTG GGG CCT AAC ACC AAA GGT CAC CCC TTC TAC AGG GGC AAC GAA GAC ACC   447

P   Y   E   A   V   H   R   H   P   Y   P   C   S   K   A   L   A   E   W   L    169
CCA TAC GAA GCA GTG CAC AGG CAC CCC TAT CCT TGC AGC AAG GCC CTG GCC GAG TGG CTG   507

V   L   E   A   N   G   R   K   V   R   G   G   L   P   L   V   T   C   A   L    189
GTC CTG GAG GCC AAC GGG AGG AAG GTC CGT GGG GGG CTG CCC CTG GTG ACG TGT GCC CTT   567

R   P   T   G   I   Y   G   E   G   H   Q   I   M   R   D   F   Y   R   Q   G    209
CGT CCC ACG GGC ATC TAC GGT GAA GGC CAC CAG ATC ATG AGG GAC TTC TAC CGC CAG GGC   627

L   R   L   G   G   W   L   F   R   A   I   P   A   S   V   E   H   G   R   V    229
CTG CGC CTG GGA GGT TGG CTC TTC CGG GCC ATC CCG GCC TCT GTG GAG CAT GGC CGG GTC   687
```

Fig. 11A

```
      Y   V   G   N   V   A   W   M   H   V   L   A   A   R   E   L   E   Q   R   A   249
     TAT GTG GGC AAT GTT GCC TGG ATG CAC GTG CTG GCA GCC CGG GAG CTG GAG CAG CGG GCA   747

A   L   M   G   G   Q   V   Y   F   C   Y   D   G   S   P   Y   R   S   Y   E   269
     GCC CTG ATG GGC GGC CAG GTA TAC TTC TGC TAC GAT GGA TCA CCC TAC AGG AGC TAC GAG   807

D   F   N   M   E   F   L   G   P   C   G   L   R   L   V   G   A   R   P   L   289
     GAT TTC AAC ATG GAG TTC CTG GGC CCC TGC GGA CTG CGG CTG GTG GGC GCC CGC CCA TTG   867

L   P   Y   W   L   L   V   F   L   A   A   L   N   A   L   L   Q   W   L   L   309
     CTG CCC TAC TGG CTG CTG GTG TTC CTG GCT GCC CTC AAT GCC CTG CTG CAG TGG CTG CTG   927

R   P   L   V   L   Y   A   P   L   L   N   P   Y   T   L   A   V   A   N   T   329
     CGG CCA CTG GTG CTC TAC GCA CCC CTG CTG AAC CCC TAC ACG CTG GCC GTG GCC AAC ACC   987

T   F   T   V   S   T   D   K   A   Q   R   H   F   G   Y   E   P   L   F   S   349
     ACC TTC ACC GTC AGC ACC GAC AAG GCT CAG CGC CAT TTC GGC TAT GAG CCC CTG TTC TCG  1047

W   E   D   S   R   T   R   T   I   L   W   V   Q   A   A   T   G   S   A   Q   369
     TGG GAG GAT AGC CGG ACC CGC ACC ATT CTC TGG GTA CAG GCC GCT ACG GGT TCA GCC CAG  1107

*                                                                                370
     TGA                                                                               1110
    CGGTGGGGCTGGGGCCTGGAGGCCCAGATACAGCACATCCACCCAGGTCCCGAGCCCTCACACCCTGGACGGGAAGGGA

CAGCTGCATTCCAGAGCAGGAGGCAGGGCTGTGGGGCCAGAATGGCTGTCCTTGTCGTAGAGCCCTCCACATTTTCTTT

TTCTTTTTTGAGACAGGGTCTTGCTCTGTCACCCAGACTGGAATGCAAGTGGTGTGANTCATAAGCTCACTNGMACCCT

YAANCCTTCTGGGTTCAAGCAATCCTTNCTNGCCTYAANCCTTCTNGAACAAGCTTGGGANCCACAGGTGCACGCCANC

CACANCCTGGCTTTTTTTT
```

Fig. 11B

Transmembrane Segments Predicted by MEMSAT

| Start | End | Orient | Score |
|---|---|---|---|
| 10 | 26 | out-->ins | 1.0 |
| 73 | 90 | ins-->out | 2.0 |
| 289 | 305 | out-->ins | 3.0 |
| 312 | 333 | ins-->out | 1.2 |

>25964
MADSAQAQKLVYLVTGGCGFLGEHVVRMLLQREPRLGELRVFDQHLGPWLEELKTGPVRV
TAIQGDVTQAHEVAAAVAGAHVVIHTAGLVDVFGRASPKTIHEVNVQGTRNVIEACVQTG
TRFLVYTSSMEVVGPNTKGHPFYRGNEDTPYEAVHRHPYPCSKALAEWLVLEANGRKVRG
GLPLVTCALRPTGIYGEGHQIMRDFYRQGLRLGGWLFRAIPASVEHGRVYVGNVAWMHVL
AARELEQRAALMGGQVYFCYDGSPYRSYEDFNMEFLGPCGLRLVGARPLLPYWLLVFLAA
LNALLQWLLRPLVLYAPLLNPYTLAVANTTFTVSTDKAQRHFGYEPLFSWEDSRTRTILW
VQAATGSAQ

Fig. 13

Protein Family / Domain Matches, HMMer Version 2
```
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - -
HMM file:              /prod/ddm/seqanal/PFAM/pfam5.0/Pfam
Sequence file:         /prod/ddm/wspace/orfanal/oa-script.9289.seq
- - - - - - - - - - - - - - - - - - - - - - - - - - - - - - - - - - - -
Query:  25964

Scores for sequence family classification (score includes all domains):
Model            Description                                Score    E-value   N
--------         -----------                                -----    -------  ---
3Beta_HSD        3-beta hydroxysteroid dehydrogenase/iso    676.9    1e-199    1
S-AdoMet_synt    S-adenosylmethionine synthetase              1.8     0.78     1
adh_short        short chain dehydrogenase                  -48.6     0.022    1
Epimerase        NAD dependent epimerase/dehydratase fam   -148.0     0.0016   1

Parsed for domains:
Model            Domain  seq-f  seq-t     hmm-f  hmm-t      score   E-value
--------         ------  -----  -----     -----  -----      -----   -------
adh_short        1/1       10    197  ..     1    203  []    -48.6    0.022
S-AdoMet_synt    1/1      341    351  ..   365    376  .]      1.8    0.78
3Beta_HSD        1/1        1    365  [.     1    425  []    676.9    1e-199
Epimerase        1/1       12    365  ..     1    359  []   -148.0    0.0016

Alignments of top-scoring domains:
adh_short: domain 1 of 1, from 10 to 197: score -48.6, E = 0.022
                   *->KvaLvTGassGIGlaiAkrLakeGakVvvadrneeklekGavalelk
                      v LvTG+++ +G +++ L+ +    ++ ++  +   G +++elk
          25964  10     LVYLVTGGCGFLGEHVVRMLLQR--EPRLGELRVFDQHLGPWLEELK 54 elGgndkdralaiqlDvtdeesv.aaveqaverlGrlDvLVNNAGgiill
                    +    r+ aiq+Dvt++ +v aav+ a        +v++ AG +
          25964  55   TGPV----RVTAIQGDVTQAHEVaAAVAGA-------HVVIHTAG--L-- 89 rpgpfaelsrtmeedwdrvidvNltgvflltravlplmamkkrggGrIvN
                     +  f + s   ++   +++vN+ g    tr v++ a ++ g    v
          25964  90   -VDVFGRAS---PK---TIHEVNVQG----TRNVIE--ACVQTGTRFLVY 126 iSSvaGrke...............g.glvgvpggsaYsASKaAvigltrs
                   +SS     +e  ++++++++  +++ +   ++ +Y +SKa   l++
          25964 127  TSS----MEvvgpntkghpfyrgnEdTPYEAVHRHPYPCSKA----LAEW 168

LAlElaphgIr......VnavaPGgvdTd<-*
                   L lE  +++r++ +    a P g++ +
          25964 169  LVLEANGRKVRgglplvTCALRPTGIYGE     197

S-AdoMet_synt: domain 1 of 1, from 341 to 351: score 1.8, E = 0.78
                   *->HFGreevdFpWE<-*
                      HFG e  F+WE
          25964 341    HFGYEP-LFSWE     351
```

Fig. 14A

```
3Beta_HSD: domain 1 of 1, from 1 to 365: score 676.9, E = 1e-199
              *->elseseldmaglsclVTGGgGFlGrhIVreLlregeslqevRvfDlrf
                 +++s++    l++lVTGG+GFlG+h Vr+Ll+++++l e+RvfD +
      25964   1    -MADSAQAQKLVYLVTGGCGFLGEHVVRMLLQREPRLGELRVFDQHL  46 spelde.dssklqvitkikyieGDvtDkqdlaaAlqgiSCCTLLDmTLmD
              +p+l+e +++++ v+    +i+GDvt+++++aaA++g+
      25964  47   GPWLEElKTGPVRVT----AIQGDVTQAHEVAAAVAGA-----------  80 dvvIHtAaiiDvfGelrvsGSDLSFGVTVLFLAVTEGSYVVFYmGATDLR
              +vvIHtA+++DvfG
      25964  81   HVVIHTAGLVDVFG------------------------------------  94 kasrdrimkVNVkGTqnvldACveaGVrvlVYTSSmeVVGpNsrGqpivN
              as+  +i++VNV+GT+nv++ACv++G+r+lVYTSSmeVVGpN +G+p+++
      25964  95   RASPKTIHEVNVQGTRNVIEACVQTGTRFLVYTSSMEVVGPNTKGHPFYR 144

GdEttpYestDDhqdaYpeSKalAEklVLkANGsmlknGgrLyTCALRPa
              G+E+tpYe++  h+++Yp+SKalAE lVL+ANG+ +++G L+TCALRP+
      25964 145   GNEDTPYEAV--HRHPYPCSKALAEWLVLEANGRKVRGGLPLVTCALRPT 192 gIfGeGdqflvpflrqlvknGlakfriGdknalsdrVYVgNVAwAHILAA
              gI+GeG q + +f+rq +++G+ +fr   ++ + rVYVgNCAw+H+LAA
      25964 193   GIYGEGHQIMRDFYRQGLRLGGWLFRAIPASVEHGRVYVGNVAWMHVLAA 242 raLqdpkkGREGassiaGqaYFIsDdsPvnSYddFnrtllkalGlrlpst
              r+L+++     a+ + Gq+YF++D+sP++SY+dFn+++l ++Glrl +
      25964 243   RELEQR------AALMGGQVYFCYDGSPYRSYEDFNMEFLGPCGLRLVGA 286 w.rlPlpllyvlaylnellswLLrklalrYtPllnpytvtlanttFtfst
              ++lP++ll++la+ln+ll+wLLr+l + Y Pllnpyt+++anttFt+st
      25964 287   RpLLPYWLLVFLAALNALLQWLLRPL-VLYAPLLNPYTLAVANTTFTVST 335 nKAkkdLGYePlvtwEEarakTieWiqele<-*
              +KA++++GYePl++wE +r +Ti+W+q+
      25964 336   DKAQRHFGYEPLFSWEDSRTRTILWVQAAT      365
```

Fig. 14B-1

```
Epimerase: domain 1 of 1, from 12 to 365: score -148.0, E = 0.0016
              *->ILVTGGAGFIGShlvreLlnn...ygddkVvvLDnLtdyYqyagnea
                 +LVTGG GF G h+vr Li+ +++ g   +V    +      + +
     25964  12  YLVTGGCGFLGEHVVRMLLQReprLGELRV-----FD----QHLGPW  49 rlevvegnprytFvkGDIcDrdlldkvfaehqpDaViHfAAeshV.drSi
                ++e + g  r+t ++GD+  +  ++a     +ViH A++  V +r
     25964  50  LEELKTGPVRVTAIQGDVTQAHEVAAAVAGA--HVVIHTAGLVDVfGR--  95 ekPlayidtNvvGTltLLEaaRnYWsaLdetkagvkkfvfsSTdeVYGdl
                 P +   + Nv GT + +Ea+        g   +v+ S+ eV G +
     25964  96  ASPKTIHEVNVQGTRNVIEACV---------QTGTRFLVYTSSMEVVGPN 136 esiPisaF...tEdtPynPs..SPYgaSKassEllvrayhraygLpaiiL
                ++  +   F ++ EdtPy   ++ PY   SKa  E lv     +
     25964 137  TKGHP--FyrgNEDTPYEAVhrHPYPCSKALAEWLVLEAN---------- 174

RyFNvYGpyqsgriGedpngfpekLIPliiqnalgkgeplpvYGdDYpTp
                        G+   g+            +Pl+ + al    p  +YG
     25964 175  ------GRKVRGG-----------LPLV-TCALR---PTGIYG------ 196

DGtqv.RDw....................ihVeDharANhllaltkg
                +G q+ RD+ +++ + ++    +  + + +++++V ++a   h+la +++
     25964 197  EGHQImRDFyrqglrlggwlfraipasvehgrVYVGNVAWM-HVLAAREL 245

.........................................raGkgsevYNiGg
                +++    +++        ++++ ++ ++ + +  ++ + + +G
     25964 246  eqraalmggqvyfcydgspyrsyedfnmeflgpcqlrLVG---------- 285 gneysnlEvVeaIekllgelaPekphvkakedpatfvddRpGddarya..
                 + + + +++++l+ 1       + ++ +++       ++++a
     25964 286  -ARPLLPYWLLVFLAALNALLQWL-----LRPLVLYAPLLN--PYTLAva 327

.....aDasKikreLGWkPevtnleeGladTvnWylene<-*
                +++ +++ +K++I  G++P +   e+  +T+ W  +
     25964 328  ntttftVSTDKAQRHFGYEPLFS-WEDSRTRTILWVQAAT        365
```

Fig 14B-2

| ProdomId | Start | End | Description | Score |
|---|---|---|---|---|
| View Prodom 1280 [Boxer ▼] [Showing match ▼] [Go!] | 11 | 362 | p99 2 (39) 3BHS(5) 3BH1(4) 3BH2(3) // DEHYDROGENASE STEROID BETA-HYDROXYSTEROID 3BETA-HSD DEHYDROGENASE/DELTA 5-->4-ISOMERASE INCLUDES: PROGESTERONE 3-BETA-HYDROXY-DELTA5-STEROID 3-BETA-HYDROXY-5-ENE | 395 |
| ProdomId | Start | End | Description | Score |

```
View Prodom 1280 [Boxer ▼] [Showing match ▼] [Go!]
>1280 p99.2 (39) 3BHS(5) 3BH1(4) 3BH2(3)  // DEHYDROGENASE STEROID
     BETA-HYDROXYSTEROID 3BETA-HSD DEHYDROGENASE/DELTA 5-->4-ISOMERASE
     INCLUDES: PROGESTERONE 3-BETA-HYDROXY-DELTA5-STEROID 3-BETA-HYDROXY-5-ENE
     Length = 416

Score = 395 (144.1 bits), Expect = 3.2e-42, Sum P(2) = 3.2e-42
 Identities = 99/268 (36%), Positives = 134/268 (50%)

Query:    102 HEVNVQGTRNVIEACVQTGTRFLVYTSSMEVVGPNTKGHPFYRGNEDTPYEAVHRHPYPC 161
              ++ NVQGTRN+IE C     RF    MEV GPN+      G+E+   +E+   +PYP
Sbjct:    157 YKFNVQGTRNLIEKC-----RFF---GVMEVAGPNSYKEIILNGHEEEHHESTWPNPYPY 208

Query:    162 -SKALAEWLVLEANGRKVRGGLPLVTCALRPTGIYGEGHQIMRDFYRQGLRLGGWLFRAI 220
               SK +AE  VL ANG  ++ G  L TCALRP  IYGEG + +       Q L+ GG +FR
Sbjct:    209 YSKKMAEKAVLAANGSMLKNGGTLYTCALRPMYIYGEGDKFLSPMIVQALKNGGIMFRVG 268

Query:    221 PASVEHGRVYVGNVAWMHVXXXXXXXXXXXXX--MGGQVYFCYDGSPYRSYEDFNMEFLGP 278
                      VYVGNVAW H+             + GQ Y+  D +P++SY+D N
Sbjct:    269 GKFSVANPVYVGNVAWAHILAARGLQDPKKSPNIQGQFYYISDDTPHQSYDDLNYTLSKE 328

Query:    279 CGLRLVGARPLLP----YWXXXXXXXXXXXXXXXXXXXXXXXXXXNPYTLAVANTTFTVS 334
              GLRL  ++  LP    YW                          N +  + ++NTTFT S
Sbjct:    329 WGLRLDSSKWRLPLPLLYWLAFLLEMVSFLLRPISYNYQPPF---NRHLVTLSNTTFTFS 385

Query:    335 TDKAQRHFGYEPLFSWEDSRTRTILWVQ 362
                KAQR  GYEPL SWE+++  +T  W++
Sbjct:    386 YKKAQRDLGYEPLVSWEEAKQKTSEWIE 413

Score = 65 (27.9 bits), Expect = 3.2e-42, Sum P(2) = 3.2e-42
 Identities = 11/23 (47%), Positives = 17/23 (73%)

Query:     11 VYLVTGGCGFLGEHVVRMLLQRE 33
              VY VTGG  FLG ++V++L+   +
Sbjct:     14 VYAVTGGAEFLGRYIVKLLISAD 36
```

Fig. 15

```
                                                                  M   S   L   R    4
CCCACGCGTCCGCCCACGCGTCCGCGGACGCGTGGGCGGACGCGTGGGCGCCCGCCTCGA ATG TCC CTG AGA    12

P   R   R   A   C   A   Q   L   L   W   H   P   A   A   G   M   A   S   W   A   24
CCC AGA AGG GCT TGC GCT CAG CTG CTC TGG CAC CCC GCT GCA GGG ATG GCC TCC TGG GCT   72

K   G   R   S   Y   L   A   P   G   L   L   Q   G   Q   V   A   I   V   T   G   44
AAG GGC AGG AGC TAC CTG GCG CCT GGT TTG CTG CAG GGC CAA GTG GCC ATC GTC ACC GGC  132

G   A   T   G   I   G   K   A   I   V   K   E   L   L   E   L   G   S   N   V   64
GGG GCC ACG GGC ATC GGA AAA GCC ATC GTG AAG GAG CTC CTG GAG CTG GGG AGT AAT GTG  192

V   I   A   S   R   K   L   E   R   L   K   S   A   A   D   E   L   Q   A   N   84
GTC ATT GCA TCC CGT AAG TTG GAG AGA TTG AAG TCT GCG GCA GAT GAA CTG CAG GCC AAC  252

L   P   P   T   K   Q   A   R   V   I   P   I   Q   C   N   I   R   N   E   E  104
CTA CCT CCC ACA AAG CAG GCA CGA GTC ATT CCC ATA CAA TGC AAC ATC CGG AAT GAG GAG  312

E   V   N   N   L   V   K   S   T   L   D   T   F   G   K   I   N   F   L   V  124
GAG GTG AAT AAT TTG GTC AAA TCT ACC TTA GAT ACT TTT GGT AAG ATC AAT TTC TTG GTG  372

N   N   G   G   Q   F   L   S   P   A   E   H   I   S   S   K   G   W   H  144
AAC AAT GGA GGA GGC CAG TTT CTT TCC CCT GCT GAA CAC ATC AGT TCT AAG GGA TGG CAC  432

A   V   L   E   T   N   L   T   G   T   F   Y   M   C   K   A   V   Y   S   S  164
GCT GTG CTT GAG ACC AAC CTG ACG GGT ACC TTC TAC ATG TGC AAA GCA GTT TAC AGC TCC  492

W   M   K   E   H   G   G   S   I   V   N   I   I   V   P   T   K   A   G   F  184
TGG ATG AAA GAG CAT GGA GGA TCT ATC GTC AAT ATC ATT GTC CCT ACT AAA GCT GGA TTT  552

P   L   A   V   H   S   G   A   A   R   A   G   V   Y   N   L   T   K   S   L  204
CCA TTA GCT GTG CAT TCT GGA GCT GCA AGA GCA GGT GTT TAC AAC CTC ACC AAA TCT TTA  612

A   L   E   W   A   C   S   G   I   R   I   N   C   V   A   P   G   V   I   Y  224
GCT TTG GAA TGG GCC TGC AGT GGA ATA CGG ATC AAT TGT GTT GCC CCT GGA GTT ATT TAT  672

S   Q   T   A   V   E   N   Y   G   S   W   G   Q   S   F   F   E   G   S   F  244
TCC CAG ACT GCT GTG GAG AAC TAT GGT TCC TGG GGA CAA AGC TTC TTT GAA GGG TCT TTT  732

Q   K   I   P   A   K   R   I   G   V   P   E   E   V   S   S   V   V   C   F  264
CAG AAA ATC CCC GCT AAA CGA ATT GGT GTT CCT GAG GAG GTC TCC TCT GTG GTC TGC TTC  792

L   L   S   P   A   A   S   F   I   T   G   Q   S   V   D   V   D   G   G   R  284
CTA CTG TCT CCT GCA GCT TCC TTC ATC ACT GGA CAG TCG GTG GAT GTG GAT GGG GGC CGG  852

S   L   Y   T   H   S   Y   E   V   P   D   H   D   N   W   P   K   G   A   G  304
AGT CTC TAT ACT CAC TCG TAT GAG GTA CCA GAT CAT GAC AAC TGG CCC AAG GGA GCA GGG  912

D   L   S   V   V   K   K   M   K   E   T   L   K   E   K   A   K   L   *      323
GAC CTT TCT GTT GTC AAA AAG ATG AAG GAG ACC TTA AAG GAG AAA GCT AAG CTC TGA     969

GCTGAGGAAACAAGGTGTCCTCCATCCCCAGTGCCTTCACATCTTGAGGATATGCTTCTGTACTTTTTAAAAGCTTATA

GTTGGTATGGAAAACATTTTTCTTATTTTTAAGTGTTATTAATTATATCTATGGAAAAACTATTCCTGAAATATATACA

GTCTTATGTCCCAAAAAAAAAA
```

Fig. 16

CLUSTAL W (1.74) multiple sequence alignment

5052204_SDR_rat    -------------------MGSWKSGQSYLAAGLLQNQVAVVTGGATGIGKAISRELLHL
21686              MSLRPRRACAQLLWHPAAGMASWAKGRSYLAPGLLQGQVAIVTGGATGIGKAIVKELLEL
                                      *.** .*:**..*:************ :*.*

5052204_SDR_rat    GCNVVIASRKLDRLTAAVDELRASQPPSSSTQVTAIQCNIRKEEEVNNLVKSTLAKYGKI
21686              GSNVVIASRKLERLKSAADELQANLPPTKQARVIPIQCNIRNEEEVNNLVKSTLDTFGKI
                   *.*******:..:*.***:*. **:..::* .***:******** .:*

5052204_SDR_rat    NFLVNNAGGQFMAPAEDITAKGWQAVIETNLTGTFYMCKAVYNSWMKDHGGSIVNIIVLL
21686              NFLVNNGGGQFLSPAEHISSKGWHAVLETNLTGTFYMCKAVYSSWMKEHGGSIVNIIVPT
                   ****.::*:***.*::**********.:*******

5052204_SDR_rat    NNGFPTAAHSGAARAGVYNLTKTMALTWASSGVRINCVAPGTIYSQTAVDNYGELGQTMF
21686              KAGFPLAVHSGAARAGVYNLTKSLALEWACSGIRINCVAPGVIYSQTAVENYGSWGQSFF
                   : *** *.************:: .:******.***:*. **::*

5052204_SDR_rat    EMAFENIPAKRVGLPEEISPLVCFLLSPAASFITCQLINVDGGQALYTRNFTIPDHDNWP
21686              EGSFQKIPAKRIGVPEEVSSVVCFLLSPAASFITGQSVDVDGGRSLYTHSYEVPDHDNWP
                   * :*::*****:*:***:*:.***********  ::::*:.:. :*******

5052204_SDR_rat    VGAGDSSFIKKVKESLKKQARL
21686              KGAGDLSVVKKMKETLKEKAKL
                   ****  *.:::**::*:*

Fig. 17

Signal Peptide Predictions for 21686

| Method | Predict | Score | Mat@ |
|---|---|---|---|
| Signal (eukaryote) | MAYBE | | 20 |

Note: amino-terminal 70aa used for signal peptide prediction

Transmembrane Segments Predicted by MEMSAT

| Start | End | Orient | Score |
|---|---|---|---|
| 29 | 50 | ins-->out | 0.9 |
| 170 | 188 | out-->ins | 0.2 |
| 208 | 224 | ins-->out | 0.6 |
| 258 | 275 | out-->ins | 2.6 |

>21686
MSLRPRRACAQLLWHPAAGMASWAKGRAYLAPGLLQGQVAIVTGGATGIGKAIVKELLEL
GSNVVIASRKLERLKSAADELQANLPPTKQARVIPIQCNIRNEEEVNNLVKSTLDTFGKI
NFLVNNGGGQFLSPAEHISSKGWHAVLETNLTGTFYMCKAVYSSWMKEHGGSIVNIIVPT
KAGFPLAVHSGAARAGVYNLTKSLALEWACSGIRINCVAPGVIYSQTAVENYGSWGQSFF
EGSFQKIPAKRIGVPEEVSSVVCFLLSPAASFITGQSVDVDGGRSLYTHSYEVPDHDNWP
KGAGDLSVVKKMKETLKEKAKL

Transmembrane Segments for Presumed Mature Peptide

| Start | End | Orient | Score |
|---|---|---|---|
| 10 | 31 | ins-->out | 0.9 |
| 151 | 169 | out-->ins | 0.2 |
| 189 | 205 | ins-->out | 0.6 |
| 239 | 256 | out-->ins | 2.6 |

>21686_mature
MASWAKGRSYLAPGLLQGQVAIVTGGATGIGKAIVKELLELGSNVVIASRKLERLKSAAD
ELQANLPPTKQARVIPIQCNIRNEEEVNNLVKSTLDTFGKINFLVNNGGGQFLSPAEHIS
SKGWHAVLETNLTGTFYMCKAVYSSWMKEHGGSIVNIIVPTKAGFPLAVHSGAARAGNYN
LTKSLALEWACSGIRINCVAPGVIYSQTAVENYGSWGQSFFEGSFQKIPAKRIGVPEEVS
SVVCFLLSPAASFITGQSVDVDGGRSLYTHSYEVPDHDNWPKGAGDLSVVKKMKETLKEK
AKL

Fig. 19

Protein Family / Domain Matches, HMMer Version 2

```
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - -
HMM file:                 /prod/ddm/seqanal/PFAM/pfam4.4/Pfam
Sequence file:            /prod/ddm/wspace/orfanal/oa-script.19160.seq
- - - - - - - - - - - - - - - - - - - - - - - - - - - - - - - - - - -
Query:   21686

Scores for sequence family classification (score includes all domains):
Model          Description                                Score      E-value   N
--------       -----------                                -----      -------  ---
adh_short      short chain dehydrogenase                  162.5      7.3e-45   1
adh_short_C2   short chain dehydrogenase/reductase C-te    47.2      3.7e-10   1

Parsed for domains:
Model          Domain   seq-f  seq-t    hmm-f hmm-t      score   E-value
--------       -------  -----  -----    ----- -----      -----   -------
adh_short      1/1       38    226  ..    1    203 []    162.5   7.3e-45
adh_short_C2   1/1      250    280  ..    1     31 []     47.2   3.7e-10

Alignments of top-scoring domains:
adh_short: domain 1 of 1, from 38 to 226:  score 162.5, E = 7.3e-45
                  *->KvaLvTGassGIGlaiAkrLakeGakVvvadrneeklekGavakelk
                     +va+vTG++ GIG+ai+k+L++ G +Vv+a r   e+l     ++++
        21686  38   QVAIVTGGATGIGKAIVKELLELGSNVVIASRKLERL-----KSAAD 79 elGgnd....kdralaiqlDvtdeesv.aaveqav rlGrlDvLVNNAGg
                  el +n+++++  r+++iq++++ ee+v+++v+  ++ +G+++ LVNN Gg
        21686  80  ELQANLpptkQARVIPIQCNIRNEEEVnNLVKSTLE FGKINFLVNNGGG 129

.iillrpgpfaelsrtmeedwdrvidvNltgvflltravlplmamkkrgg
                  +++     p++ +s   + w +v+++Nltg+f++++av      +k +g
        21686  130 qFL----SPAEHIS---SKGWHAVLETNLTGTFYMCKAVYS--SWMKEHG 170

GrIvNiSSvaGrkegglvgvpggsaYsASKaAvigltrsLAlElaphgIr
                  G+IvNi              + g+p ++ +A+ a+v  lt+sLAlE+a  gIr
        21686  171 GSIVNIIV-PT-----KAGFPLAVHSGAARAGVYNLTKSLALEWACSGIR 214

VnavaPGgvdTd<-*
                  +n+vaPG ++ +
        21686  215 INCVAPGVIYSQ    226 adh_short_C2: domain 1 of 1, from 250 to 280: score 47.2, E = 3.7e-10
                  *->gRlGePeEiAnavvFLASdaAsYiTGqtlvV<-*
                     +R G PeE++++v FL S+aAs+iTGq + V
        21686  250    KRIGVPEEVSSVVCFLLSPAASFITGQSVDV    280
```

Fig. 20

ProDom Matches

| ProdomId | Start | End | Description | Score |
|---|---|---|---|---|
| View Prodom 121622 [Boxer ▼] [Showing match ▼][Go!] | 29 | 82 | p99.2 (1) YSO5_CAEEL // HYPOTHETICAL 98.0 KD PROTEIN F56D1.5 IN CHROMOSOME II TRANSMEMBRANE | 70 |
| View Prodom 95301 [Boxer ▼] [Showing match ▼][Go!] | 35 | 82 | p99.2 (1) O27957_ARCFU // SHIKIMATE 5-DEHYDROGENASE AROE HYPOTHETICAL PROTEIN | 86 |
| View Prodom 11 [Boxer ▼] [Showing match ▼][Go!] | 37 | 231 | p99.2 (1078) ADH(34) GALE(20) FABG(13) // OXIDOREDUCTASE PROTEIN DEHYDROGENASE NAD REDUCTASE NADP BIOSYNTHESIS SYNTHASE ALCOHOL PUTATIVE | 157 |
| View Prodom 73753 [Boxer ▼] [Showing match ▼][Go!] | 237 | 286 | p99.2 (1) P71079_BACSU // UNIDENTIFIED DEHYDROGENASE | 84 |
| View Prodom 77223 [Boxer ▼] [Showing match ▼][Go!] | 243 | 287 | p99.2 (1) O07882_STAXY // GLUCOSE-1-DEHYDROGENASE | 92 |
| ProdomId | Start | End | Description | Score |

View Prodom 11 [Boxer ▼] [Showing match ▼][Go!]

```
>11 p99.2 (1078) ADH(34) GALE(20) FABG(13)   // OXIDOREDUCTASE PROTEIN
   DEHYDROGENASE NAD REDUCTASE NADP BIOSYNTHESIA SYNTHASE ALCOHOL PUTATIVE
   Length = 269

Score = 157 (60.3 bits), Expect = 1.2e-09, P = 1.2e-09
 Identities = 64/213 (30%), Positives = 106/213 (49%)

Query:   51 KAIVKELLELGSNVVIASRKLERLKSAADELQANLPPTKQA---RVIPIQCNIRNEEEVN 107
            K +V         S    AS+ E    + +A + T QA    V   + C++ +  E+V
Sbjct:   35 KVVVVSATSEESESTEASK--ESAMEVSKAVNAEVSATMQAVGVTVTKVTCDVADVEDVE 92

Query:  108 NLVKSTLDTF----GKINFLVNNGGGQFLSP---AEHISSKG-----WHAVLETNLTGTF 155
            LV++ ++   F     GKI+ LVNN G   ++P    AE ++  +       W  V+E N+TGTF
Sbjct:   93 KLVETVVEEFSGIHGKIDVLVNNAG--VMAPKAVAESMTEETSDDEEWEEVIEVNVTGTF 150

Query:  156 YMCKAVYSSWMK--------EHGGSIVNI--IVPTKAGFP--LAVHSGAARAGVYNLTKS 203
             + +A  + K          G+IVN+ +   + G P   A +S A++A V + TKS
Sbjct:  151 NLTQAALPAMKKFSDAAAKKRFVGTIVNVASVAGSTMGSPGSQAAYS-ASKAAVESFTKS 209

Query:  204 LALE---WACSG--IRINCVAPGVIYSQTAVEN 231
            LA+E    ++  S    +R+N VAPG + +  A+E+
Sbjct:  210 LAMELSPYSASVAMVRVNAVAPGYVETD-ALES 241

Score = 103 (41.3 bits), Expect = 0.0021, Sum P(2) = 0.0021
 Identities = 32/100 (32%), Positives = 54/100 (54%)

Query:   37 GQVAIVTGGA--TGIGKAIVKELLELGSNVVIASRKLERLKS--AADE-------LQAN 84
            G+ +VTGG+   +GIG AI ++L  E G+ VV+ S    E  +S    A+ E       + A
Sbjct:    7 GKTVLVTGGSGFSGIGLAIARQLAEEGAKVVVVSATSEESESTEASKESAMEVSKAVNAE 66

Query:   85 LPPTKQA---RVIPIQCNIRNEEEVNNLVKSTLDTFGKIN 121
            +   T QA   V  + C++ + E+V  LV++ ++  F  I+
Sbjct:   67 VSATMQAVGVTVTKVTCDVADVEDVEKLVETVVEEFSGIH 106

Score = 37 (18.1 bits), Expect = 0.0021, Sum P(2) = 0.0021
 Identities = 9/23 (39%), Positives = 13/23 (56%)

Query:  205 ALEWACSGIRINCVAPGVIYSQT 227
            ALE A +G+ +   V PG +   T
Sbjct:  238 ALESATNGLSVVTVRPGNVRVNT 260
```

Fig. 21A

View Prodom 77223 [Boxer|▼] [Showing match |▼] [Go!]

>77223 p99.2 (1) 007882_STAXY // GLUCOSE-1-DEHYDROGENASE
         Length = 67

Score = 92 (37.4 bits), Expect = 0.00031, P = 0.00031
 Identities = 19/45 (42%), Positives = 29/45 (64%)

Query:   243 SFQKIPAKRIGVPEEVSSVVCFLLSPAASFITGQSVDVDGGRSLY 287
             + + IPAK IG ++V++V  FL S  A +I G ++ VDGG + Y
Sbjct:    15 TLEMIPAKEIGFADQVANVARFLCSDLADYIHGTTIYVDGGMTNY 59

View Prodom 95301 [Boxer|▼] [Showing match |▼] [Go!]

>95301 p99.2 (1) 027957_ARCFU // SHIKIMATE 5-DEHYDROGENASE
AROE HYPOTHETICAL
         PROTEIN
         Length = 108

Score = 86 (35.3 bits), Expect = 0.0014, P = 0.0014
 Identities = 20/48 (41%), Positives = 31/48 (64%)

Query:    35 LQGQVAIVTGGATGIGKAIVKELLELGSNVVIASRKLERLKSAADELQ 82
             L G+ A+V G A G GKA   LL++GS V++A+R  E+ + A + L+
Sbjct:    10 LGGKTALVVG-AGGAGKAAALALLDMGSTVIVANRTEEKGREAVEMLR 56

View Prodom 73753 [Boxer|▼] [Showing match |▼] [Go!]

>73753 p99.2 (1) P71079_BACSU // UNIDENTFIED DEHYDROGENASE
         Length = 60

Score = 84 (34.6 bits), Expect = 0.0023, P = 0.0023
 Identities = 20/50 (40%), Positives = 29/50 (58%)

Query:   237 QSFFEGSFQKIPAKRIGVPEEVSSVVCFLLSPAASFITGQSVDVDGGRSL 286
             +   E + Q  PA R+    +++    V FL+S  A  I GQ++ VDGGRSL
Sbjct:     9 EDLLEDARQNTPAGRMVEIKDMVDTVEFLVSSKADMIRGQTIIVDGGRSL 58

View Prodom 121622 [Boxer|▼] [Showing match |▼] [Go!]

>121622 p99.2 (1) YSO5_CAEEL // HYPOTHETICAL 98.0 KD PROTEIN F56D1.5 IN
         CHROMOSOME II TRANSMEMBRANE
         Length = 194

Score = 70 (29.7 bits), Expect = 7.6, P = 1.0
 Identities = 20/57 (35%), Positives = 29/57 (50%)

Query:    29 YLAPG;;QGQV--AIVTGGATGIGKAIVKELLELG-SNVVIASRKLERLKSAADELQ 82
             + P L Q Q   +V+GG GIGKA  EL + G  V+  R  ++L S  E++
Sbjct:    62 FYKPNLEQYQHRWTVVSGGTDGIGKAYTLELAKRGLRKFVLIGRNPKKLDSVKSEIE 118

Fig. 21B

```
GGAATGGATGCTGTTGGCTTAAACCTCCCCCTGCCCTGGGGGTTGCAACCAGGGTCTCTG
CAAAGCCAATCCTTTGTCATCCCGCTGTCCTGCAGAGCAAGATGGGGCTCATGGCTGTCC
TGATGCTACCCCTGCTGCTGCTGGGAATCAGCGGCCTCCTCTTCATTTACCAGGAGGCAT
CCAGGCTGTGGTCGAAGTCTGCCGTGCAGAACAAAGTGGTGGTCATCACAGATGCCATCT
CAGGACTGGGAAAGGAGTGTGCTCGGGTGTTCCATGCAGGTGGGGCAAGGCTGGTGCTGT
GTGGAAAGAACTGGGAGGGACTGGAGAGCCTCTATGCCACCTTGACCAGTGTGGCTGACC
CCAGCAAGACATTCACCCCCAAGCTGGTCCTCCTGGATCTCTCAGACATTAGCTGTGTTC
AAGATGTGGCCAAAGAGGTCCTGGACTGCTACGGCTGTGTGGACATCCTCATCAACAATG
CCAGCGTGAAAGTGAAGGGGCCTGCCCACAAGATTTCCCTGGAGCTTGACAAAAAGATCA
TGGATGCCAACTACTTCGGACCCATCACTTTAACCAAAGTTCTGCTTCCCAACATGATCT
CCAGGAGAACAGGCCAGATTGTGTTAGTGAACAACATCCAAGCGAAGTTTGGAATCCCGT
TCCGCACAGCTTATGCAGCCTCTAAGCATGCCGTCATGGGCTTCTTTGACTGCCTCCGAG
CCGAGGTTGAGGAATACGATGTTGTGGTCAGCACCGTGAGCCCAACTTTCATCCGCTCCT
ACCGTGCTTCCCCTGAGCAAAGAAACTGGGAGACATCCATTTGTAAATTCTTCTGCAGGA
AGCTAGCCTATGGCGTGCACCCGGTGGAGGTGGCTGAGGAAGTGATGCGCACAGTACGGA
GGAAGAAGCAAGAGGTGTTCATGGCCAACCCGGTTCCTAAGGCTGCCGTGTTCATCCGCA
CCTTCTTCCCTGAGTTCTTCTTCGCTGTGGTGGCCTGTGGGGTGAAGGAGAAGCTCAATG
TCCCAGAAGAGGGTTAACCTCGTGGCCAAAGGGGTCACTCAAGGGGAATAAAGGCTTTCC
TAGAGAAAAAAAAAAAAAAAAAAAAAAAA
```

Fig. 31A

MGLMAVLMLPLLLLGISGLLFIYQEASRLWSKSAVQNKVVVITDAISGLGKECARVFHAG

GARLVLCGKNWEGLESLYATLTSVADPSKTFTPKLVLLDLSDISCVQDVAKEVLDCYGCV

DILINNASVKVKGPAHKISLELDKKIMDANYFGPITLTKVLLPNMISRRTGQIVLVNNIQ

AKFGIPFRTAYAASKHAVMGFFDCLRAEVEEYDVVVSTVSPTFIRSYRASPEQRNWETSI

CKFFCRKLAYGVHPVEVAEEVMRTVRRKKQEVFMANPVPKAAVFIRTFFPEFFFAVVACG

VKEKLNVPEEG.

Fig. 31B

GAP of: FrGcgManager_31_UFAHDJyG_  check: 516  from: 1  to: 936

M21481 ORF - Import - vector trimmed to: FrGcgManager_31_VFA0zr_19  check: 2871  from: 1  to: 933 h21481 ORF - Import - vector trimmed

Symbol comparison table: /ddm_local/gcg/gcg_9.1/gcgcore/data/rundata/
nwsgapdna.cmp
CompCheck: 8760

```
         Gap Weight:      12       Average Match:   10.000
      Length Weight:       4       Average Mismatch: 0.000

Quality:    8220              Length:      936
              Ratio:   8.810                Gaps:        0
  Percent Similarity: 88.103     Percent Identity:   88.103
```

Match display thresholds for the alignment(s):
    | = IDENTITY
    : = 5
    . = 1

FrGcgManager_31_UFAHDJyG_ x FrGcgManager_31_VFA0zr_19

```
  1 ATGGGGCTCATGGCTGTCCTGATGCTACCCCTGCTGCTGCTGGGAATCAG  50
    |||||  ||||||| | ||||||||| ||||||||||||||||||||||||
  1 atgggagtcatggccatgctgatgctcccccctgctgctgctgggaatcag  50

51 CGGCCTCCTCTTCATTTACCAGGAGGCATCCAGGCTGTGGTCGAAGTCTG 100
    ||||||||||||||||||||||| |||| |||||||||||||| ||||| |
 51 cggcctcctcttcatttaccaagaggtgtccaggctgtggtcaaagtcag 100

101 CCGTGCAGAACAAAGTGGTGGTCATCACAGATGCCATCTCAGGACTGGGA 150
    | ||||||||||||||||||||| |||| ||||||||||||||||||||
101 ctgtgcagaacaaagtggtggtgatcaccgatgccatctcaggactgggc 150

151 AAGGAGTGTGCTCGGGTGTTCCATGCAGGTGGGGCAAGGCTGGTGCTGTG 200
    |||||||||||||||||||||||| |||||||||||||||||||||||||
151 aaggagtgtgctcgggtgttccacacaggtggggcaaggctggtgctgtg 200

201 TGGAAAGAACTGGGAGGGACTGGAGAGCCTCTATGCCACCTTGACCAGTG 250
    ||||||||||||||||| | || |||| ||| ||| |||||| ||| | |
201 tggaaagaactgggagaggctagagaacctatatgatgccttgatcagcg 250

251 TGGCTGACCCCAGCAAGACATTCACCCCCAAGCTGGTCCTCCTGGATCTC 300
    |||||||||||||||||||||||||||| |||||||||||| |||| |||
251 tggctgacccagcaagacattcaccccaaagctggtcctgttggacctc 300
```

Fig. 32A

```
301 TCAGACATTAGCTGTGTTCAAGATGTGGCCAAAGAGGTCCTGGACTGCTA 350
    |||||||| |||||||| | |||||||||  |||||  |||||||||| |||||
301 tcagacatcagctgtgtcccagatgtggcaaaagaagtcctggattgcta 350

351 CGGCTGTGTGGACATCCTCATCAACAATGCCAGCGTGAAAGTGAAGGGGC 400
    |||||| |||||||||||||||||||||||||||| |||||| |||||||||
351 tggctgtgtggacatcctcatcaacaatgccagtgtgaaggtgaaggggc 400

401 CTGCCCACAAGATTTCCCTGGAGCTTGACAAAAAGATCATGGATGCCAAC 450
    ||||||  |||||||  ||||||||| ||||||||||||||||||||||||
401 ctgcccataagatttctctggagctcgacaaaaagatcatggatgccaat 450

451 TACTTCGGACCCATCACTTTAACCAAAGTTCTGCTTCCCAACATGATCTC 500
    |||| || ||||||||| || || ||||   ||||||||||||||||||||
451 tactttggccccatcacattgacgaaagccctgcttcccaacatgatctc 500

501 CAGGAGAACAGGCCAGATTGTGTTAGTGAACAACATCCAAGCGAAGTTTG 550
    | |||||||||||||||  || |||||||| || |||||||| |||||||
501 ccggagaacaggccaaatcgtgttagtgaataatatccaagggaagtttg 550

551 GAATCCCGTTCCGCACAGCTTATGCAGCCTCTAAGCATGCCGTCATGGGC 600
    |||||||||||| ||  |||| || |||| |||||  ||||| ||  ||||||
551 gaatcccgttccgtacgacttacgctgcctccaagcacgcagccctgggc 600

601 TTCTTTGACTGCCTCCGAGCCGAGGTTGACGAATACGATGTTGTGGTCAG 650
    ||||||||||||||||||||||||| || ||||||||||||||||  ||||
601 ttctttgactgcctccgagccgaagtggaggaatacgatgttgtcatcag 650

651 CACCGTGAGCCCAACTTTCATCCGCTCCTACCGTGCTTCCCCTGAGCAAA 700
    |||||||||||| |||||||||||| || |||| ||  || |||||||
651 caccgtgagcccgactttcatccggtcgtaccacgtgtatccagagcaag 700

701 GAAACTGGGAGACATCCATTTGTAAATTCTTCTGCAGGAAGCTAGCCTAT 750
    |||||||||||  | ||||||| ||||||||||| ||||||||| ||||
701 gaaactgggaagcttccatttggaaattcttttcaggaagctgacctac 750

751 GGCGTGCACCCGGTGGAGGTGGCTGAGGAAGTGATGCGCACAGTACGGAG 800
    |||||||||||| || ||||||||| ||||| |||||||||| || |||||
751 ggcgtgcacccagtagaggtggcggaggaggtgatgcgcaccgtgcggag 800

801 GAAGAAGCAAGAGGTGTTCATGGCCAACCCGGTTCCTAAGGCTGCCGTGT 850
    |||||||||||||||||| ||||||||||  | || |||| |||||||||
801 gaagaagcaagaggtgtttatggccaaccccatccccaaggccgccgtgt 850

851 TCATCCGCACCTTCTTCCCTGAGTTCTTCTTCGCTGTGGTGGCCTGTGGG 900
    | |||||||||||||||||  ||||||||||||||||||||||||||||||
851 acgtccgcaccttcttcccggagttcttttttcgccgtggtggcctgtggg 900

901 GTGAAGGAGAAGCTCAATGTCCCAGAAGAGGGTTAA 936
    ||||||||||||||||||||||||  || |||||
901 gtgaaggagaagctcaatgtcccggaggagggg... 933
```

Fig. 32B

```
GAP of: FrGcgManager_32_ZFA004eiD   check: 657   from: 1   to: 311 m21481 aa - Import - complete to: FrGcgManager_32_AGAjaPna_   check: 9949   from: 1   to: 311 h21481 aa - Import - complete

Symbol comparison table: /prod/ddm/seqanal/BLAST/matrix/aa/BLOSUM62
CompCheck: 1102
 Matrix made by matblas from blosum62.iij Gap Weight:        12       Average Match:     2.778
    Length Weight:         4       Average Mismatch: -2.248

Quality:      1467              Length:       311
            Ratio:     4.717                Gaps:         0
Percent Similarity:   92.926       Percent Identity:  91.318

Match display thresholds for the alignment(s):
                    | = IDENTITY
                    : = 2
                    . = 1

FrGcgManager 32_ZFA004eiD x FrGcgManager_32_AGAjaPna_ ..

1 MGLMAVLMLPLLLLGISGLLFIYQEASRLWSKSAVQNKVVVITDAISGLG  50
    ||.||.|||||||||||||||||| |||||||||||||||||||||||||
  1 MGVMAMLMLPLLLLGISGLLFIYQEVSRLWSKSAVQNKVVVITDAISGLG  50

51 KECARVFHAGGARLVLCGKNWEGLESLYATLTSVADPSKTFTPKLVLLDL 100
    |||||||| |||||||||||||| ||.||   | |||||||||||||||||
 51 KECARVFHTGGARLVLCGKNWERLENLYDALISVADPSKTFTPKLVLLDL 100

101 SDISCVQDVAKEVLDCYGCVDILINNASVKVKGPAHKISLELDKKIMDAN 150
    |||||| ||||||||||||||||||||||||||||||||||||||||||
101 SDISCVPDVAKEVLDCYGCVDILINNASVKVKGPAHKISLELDKKIMDAN 150

151 YFGPITLTKVLLPNMISRRTGQIVLVNNIQAKFGIPFRTAYAASKHAVMG 200
    ||||||||| |||||||||||||||||||| |||||||| |||||| :|
151 YFGPITLTKALLPNMISRRTGQIVLVNNIQGKFGIPFRTTYAASKHAALG 200

201 FFDCLRAEVEEYDVVVSTVSPTFIRSYRASPEQRNWETSICKFFCRKLAY 250
    |||||||||||||:||||||||||||| ||| ||| || ||| ||| |
201 FFDCLRAEVEEYDVVISTVSPTFIRSYHVYPEQGNWEASIWKFFFRKLTY 250

251 GVHPVEVAEEVMRTVRRKKQEVFMANPVPKAAVFIRTFFPEFFFAVVACG 300
    |||||||||||||||||||||||||||:|||||::|||||||||||||||
251 GVHPVEVAEEVMRTVRRKKQEVFMANPIPKAAVYVRTFFPEFFFAVVACG 300

301 VKEKLNVPEEG 311
    |||||||||||
301 VKEKLNVPEEG 311          Fig. 33
```

US 7,494,793 B2

21686, DEHYDROGENASE

RELATED APPLICATIONS

This application is a continuation of U.S. patent application Ser. No. 10/664,506, filed Sep. 17, 2003, now granted as U.S. Pat. No. 7,045,325; which is a continuation of U.S. patent application Ser. No. 09/838,561, filed Apr. 18, 2001, now granted as U.S. Pat. No. 6,627,423; which is a continuation-in-part of U.S. patent application Ser. No. 09/816,760, filed Mar. 23, 2001, now granted as U.S. Pat. No. 6,613,555; which is a continuation-in-part of U.S. patent application Ser. No. 09/634,955, filed Aug. 8, 2000, now granted as U.S. Pat. No. 6,511,834; which claims the benefit of U.S. Provisional Application Ser. No. 60/192,002, filed Mar. 24, 2000, now abandoned. The entire contents of all of the above-referenced applications are incorporated herein by this reference.

The contents of the Sequence Listing are submitted herewith on compact disc in duplicate. Each disc has a copy of the file "sequence listing.txt," which is incorporated herein by this reference. This file is 104 kilobytes and is a copy of the Supplemental Sequence Listing filed on Aug. 2, 2005 in U.S. patent application Ser. No. 10/664,506, filed Sep. 17, 2003. This file was copied onto compact disc on Jan. 17, 2006.

BACKGROUND OF THE INVENTION

The oxidation and reduction of molecules is of critical importance in most metabolic and catabolic pathways in cells. A large family of enzymes which facilitate these molecular alterations, termed dehydrogenases, have been identified. In the forward reaction, these enzymes catalyze the transfer of a hydride ion from the target substrate to the enzyme or a cofactor of the enzyme (e.g., $NAD^+$ or $NADP^+$), thereby forming a carbonyl group on the substrate. These enzymes are also able to participate in the reverse reaction, wherein a carbonyl group on the target molecule is reduced by the transfer of a hydride group from the enzyme. Members of the dehydrogenase family are found in nearly all organisms, from microbes to Drosophila to humans. Both between species and within the same species, dehydrogenases vary widely, and structural similarities between distant dehydrogenase family members are most frequently found in the cofactor binding site of the enzyme. Even within a particular subclass of dehydrogenase molecules, e.g., the short-chain dehydrogenase molecules, members typically display only 15-30% amino acid sequence identity, and this is limited to the cofactor binding site and the catalytic site (Jornvall et al. (1995) Biochemistry 34:6003-6013).

Different classes of dehydrogenases are specific for an array of biological and chemical substrates. For example, there exist dehydrogenases specific for alcohols, for aldehydes, for steroids, and for lipids, with particularly important classes of dehydrogenases including the short-chain dehydrogenase/reductases, the medium-chain dehydrogenases, the aldehyde dehydrogenases, the alcohol dehydrogenases, and the steroid dehydrogenases. Within each of these classes, each enzyme is specific for a particular substrate (e.g., ethanol or isopropanol, but not both with equivalent affinity). This exquisite specificity not only permits tight regulation of the metabolic and catabolic pathways in which these enzymes participate, without affecting similar but separate biochemical pathways in the same cell or tissue. The short-chain dehydrogenases, part of the alcohol oxidoreductase superfamily (Reid et al. (1994) Crit. Rev. Microbiol. 20:13-56), are $Zn^{++}$-independent enzymes with an N-terminal cofactor binding site and a C-terminal catalytic domain (Persson et al. (1995) Adv. Exp. Med. Biol. 372:383-395; Jornvall et al. (1995) supra), whereas the medium chain dehydrogenases are $Zn^{++}$-dependent enzymes with an N-terminal catalytic domain and a C-terminal coenzyme binding domain (Jornvall et al. (1995) supra; Jornvall et al. (1999) FEBS Lett. 445:261-264). The steroid dehydrogenases are a subclass of the short-chain dehydrogenases, and are known to be involved in a variety of biochemical pathways, affecting mammalian reproduction, hypertension, neoplasia, and digestion (Duax et al. (2000) Vitamins and Hormones 58:121-148). Aldehyde dehydrogenases show heterogeneity in the placement of these domains, and also heterogeneity in their substrates, which include toxic substances, retinoic acid, betaine, biogenic amine, and neurotransmitters (Hsu et al. (1997) Gene 189:89-94). It is common in higher organisms for different dehydrogenase molecules to be expressed in different tissues, according to the localization of the substrate for which the enzyme is specific. For example, different mammalian aldehyde dehydrogenases are localized to different tissues, e.g., salivary gland, stomach, and kidney (Hsu et al. (1997) supra).

Dehydrogenases play important roles in the production and breakdown of nearly all major metabolic intermediates, including amino acids, vitamins, energy molecules (e.g., glucose, sucrose, and their breakdown products), signal molecules (e.g., transcription factors and neurotransmitters), and nucleic acids. As such, their activity contributes to the ability of the cell to grow and differentiate, to proliferate, and to communicate and interact with other cells. Dehydrogenases also are important in the detoxification of compounds to which the organism is exposed, such as alcohols, toxins, carcinogens, and mutagens.

A dehydrogenase of the short-chain family, 11-beta-hydroxysteroid dehydrogenase, activates glucocorticoids in the liver. Glucocorticoids are known to induce transcription of hepatitis B virus (HBV) genes, probably by direct binding of the ligand-glucocorticoid receptor complex to an enhancer element in the HBV genome. There is also evidence that short chain dehydrogenases are transcriptional cofactors for retrovirus gene activation.

SUMMARY OF THE INVENTION

The present invention is based, at least in part, on the discovery of novel members of the family of dehydrogenase molecules, referred to herein as DHDR nucleic acid and protein molecules (e.g., DHDR-1, DHDR-2, DHDR-3, and DHDR-4). The DHDR nucleic acid and protein molecules of the present invention are useful as modulating agents in regulating a variety of cellular processes, e.g., viral infection, cellular proliferation, growth, differentiation, and/or migration. Accordingly, in one aspect, this invention provides isolated nucleic acid molecules encoding DHDR proteins or biologically active portions thereof, as well as nucleic acid fragments suitable as primers or hybridization probes for the detection of DHDR-encoding nucleic acids.

In one embodiment, a DHDR nucleic acid molecule of the invention is at least 50%, 55%, 60%, 65%, 70%, 75%, 80%, 82%, 85%, 89%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to the nucleotide sequence (e.g., to the entire length of the nucleotide sequence) shown in SEQ ID NO:1, 3, 4, 6, 7, 9, 10, 12, 14, or 16, or the nucleotide sequence of the DNA insert of the plasmid deposited with ATCC as Accession Number PTA-1845, or a complement thereof.

In a preferred embodiment, the isolated nucleic acid molecule includes the nucleotide sequence shown in SEQ ID NO:1, 3, 4, 6, 7, 9, 10, 12, 14, or 16, or a complement thereof. In another embodiment, the nucleic acid molecule includes SEQ ID NO:3 and nucleotides 1-62 of SEQ ID NO:1. In another embodiment, the nucleic acid molecule includes SEQ ID NO:6 and nucleotides 1-330 of SEQ ID NO:4. In yet another embodiment, the nucleic acid molecule includes SEQ ID NO:9 and nucleotides 1-280 of SEQ ID NO:7. In another embodiment, the nucleic acid molecule includes SEQ ID NO:12 and nucleotides 1-60 of SEQ ID NO:10. In another embodiment, the nucleic acid molecule includes SEQ ID NO:16 and nucleotides 1-101 of SEQ ID NO:14. In yet a further embodiment, the nucleic acid molecule includes SEQ ID NO:3 and nucleotides 2469-2660 of SEQ ID NO:1. In another embodiment, the nucleic acid molecule includes SEQ ID NO:6 and nucleotides 1264-1379 of SEQ ID NO:4. In another embodiment, the nucleic acid molecule includes SEQ ID NO:9 and nucleotides 1388-1725 of SEQ ID NO:7. In another embodiment, the nucleic acid molecule includes SEQ ID NO:12 and nucleotides 1027-1209 of SEQ ID NO:10. In still another embodiment, the nucleic acid molecule includes SEQ ID NO:16 and nucleotides 1035-1108 of SEQ ID NO:14. In another preferred embodiment, the nucleic acid molecule consists of the nucleotide sequence shown in SEQ ID NO:1, 3, 4, 6, 7, 9, 10, 12, 14, or 16.

In another embodiment, a DHDR nucleic acid molecule includes a nucleotide sequence encoding a protein having an amino acid sequence sufficiently identical to the amino acid sequence of SEQ ID NO:2, 5, 8, 11, or 15, or an amino acid sequence encoded by the DNA insert of the plasmid deposited with ATCC as Accession Number PTA-1845. In a preferred embodiment, a DHDR nucleic acid molecule includes a nucleotide sequence encoding a protein having an amino acid sequence at least 50%, 55%, 60%, 65%, 70%, 75%, 80%, 85%, 90%, 92%, 95%, 96%, 97%, 98%, 99%, 99.1%, 99.2%, 99.3%, 99.4%, 99.5%, 99.6%, 99.7%, 99.8%, 99.9%, 99.99% or more identical to the entire length of the amino acid sequence of SEQ ID NO:2, 5, 8, 11, or 15, or the amino acid sequence encoded by the DNA insert of the plasmid deposited with ATCC as Accession Number PTA-1845.

In another preferred embodiment, an isolated nucleic acid molecule encodes the amino acid sequence of human DHDR-1, DHDR-2, DHDR-3, or DHDR-4. In another preferred embodiment, an isolated nucleic acid molecule encodes the amino acid sequence of mouse DHDR-2. In yet another preferred embodiment, the nucleic acid molecule includes a nucleotide sequence encoding a protein having the amino acid sequence of SEQ ID NO:2, 5, 8, 11, or 15, or the amino acid sequence encoded by the DNA insert of the plasmid deposited with ATCC as Accession Number PTA-1845. In yet another preferred embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length. In a further preferred embodiment, the nucleic acid molecule is at least 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length and encodes a protein having a DHDR activity (as described herein).

Another embodiment of the invention features nucleic acid molecules, preferably DHDR nucleic acid molecules, which specifically detect DHDR nucleic acid molecules relative to nucleic acid molecules encoding non-DHDR proteins. For example, in one embodiment, such a nucleic acid molecule is at least 20, 30, 40, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more nucleotides in length and hybridizes under stringent conditions to a nucleic acid molecule comprising the nucleotide sequence shown in SEQ ID NO:1, 4, 7, 10, or 14, the nucleotide sequence of the DNA insert of the plasmid deposited with ATCC as Accession Number PTA-1845, or a complement thereof.

In preferred embodiments, the nucleic acid molecules are at least 15 (e.g., 15 contiguous) nucleotides in length and hybridize under stringent conditions to the nucleotide molecules set forth in SEQ ID NO:1, 4, 7, 10, or 14.

In other preferred embodiments, the nucleic acid molecule encodes a naturally occurring allelic variant of a polypeptide comprising the amino acid sequence of SEQ ID NO:2, 5, 8, 11, or 15, or an amino acid sequence encoded by the DNA insert of the plasmid deposited with ATCC as Accession Number PTA-1845, wherein the nucleic acid molecule hybridizes to a complement of a nucleic acid molecule comprising SEQ ID NO:1, 3, 4, 6, 7, 9, 10, 12, 14, or 16 under stringent conditions.

Another embodiment of the invention provides an isolated nucleic acid molecule which is antisense to a DHDR nucleic acid molecule, e.g., the coding strand of a DHDR nucleic acid molecule.

Another aspect of the invention provides a vector comprising a DHDR nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a DHDR protein, by culturing in a suitable medium, a host cell, e.g., a mammalian host cell such as a non-human mammalian cell, of the invention containing a recombinant expression vector, such that the protein is produced.

Another aspect of this invention features isolated or recombinant DHDR proteins and polypeptides. In one embodiment, an isolated DHDR protein includes at least one or more of the following domains: a transmembrane domain, a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, and/or a glucose-1-dehydrogenase domain.

In a preferred embodiment, a DHDR protein includes at least one or more of the following domains: a transmembrane domain, a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, and/or a glucose-1-dehydrogenase domain, and has an amino acid sequence at least about 50%, 55%, 60%, 65%, 67%, 68%, 70%, 75%, 80%, 85%, 90%, 92%, 95%, 96%, 97%, 98%, 99%, 99.1%, 99.2%, 99.3%, 99.4%, 99.5%, 99.6%, 99.7%, 99.8%, 99.9%, 99.99% or more identical to the amino acid sequence of SEQ ID NO:2, 5, 8, 11, or 15, or the amino acid sequence encoded by the DNA insert of the plasmid deposited with ATCC as Accession Number PTA-1845.

In another preferred embodiment, a DHDR protein includes at least one or more of the following domains: a transmembrane domain, a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, and/or a glucose-1-dehydrogenase domain, and has a DHDR activity (as described herein).

In yet another preferred embodiment, a DHDR protein includes at least one or more of the following domains: a transmembrane domain, a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, and/or a glucose-1-dehydrogenase domain, and is encoded by a nucleic acid molecule having a nucleotide sequence which hybridizes under stringent hybridization conditions to a complement of a nucleic acid molecule comprising the nucleotide sequence of SEQ ID NO:1, 3, 4, 6, 7, 9, 10, 12, 14, or 16.

In another embodiment, the invention features fragments of the protein having the amino acid sequence of SEQ ID NO:2, 5, 8, 11, or 15, wherein the fragment comprises at least 16 amino acids (e.g., contiguous amino acids) of the amino acid sequence of SEQ ID NO:2, 5, 8, 11, or 15, or an amino acid sequence encoded by the DNA insert of the plasmid deposited with the ATCC as Accession Number PTA-1845. In another embodiment, a DHDR protein has the amino acid sequence of SEQ ID NO:2, 5, 8, 11, or 15.

In another embodiment, the invention features a DHDR protein which is encoded by a nucleic acid molecule consisting of a nucleotide sequence at least about 50%, 55%, 60%, 65%, 70%, 75%, 80%, 85%, 89%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to a nucleotide sequence of SEQ ID NO:1, 3, 4, 6, 7, 9, 10, 12, 14, or 16, or a complement thereof. This invention further features a DHDR protein which is encoded by a nucleic acid molecule consisting of a nucleotide sequence which hybridizes under stringent hybridization conditions to a complement of a nucleic acid molecule comprising the nucleotide sequence of SEQ ID NO:1, 3, 4, 6, 7, 9, 10, 12, 14, or 16, or a complement thereof.

The proteins of the present invention or portions thereof, e.g., biologically active portions thereof, can be operatively linked to a non-DHDR polypeptide (e.g., heterologous amino acid sequences) to form fusion proteins. The invention further features antibodies, such as monoclonal or polyclonal antibodies, that specifically bind proteins of the invention, preferably DHDR proteins. In addition, the DHDR proteins or biologically active portions thereof can be incorporated into pharmaceutical compositions, which optionally include pharmaceutically acceptable carriers.

In another aspect, the present invention provides a method for detecting the presence of a DHDR nucleic acid molecule, protein, or polypeptide in a biological sample by contacting the biological sample with an agent capable of detecting a DHDR nucleic acid molecule, protein, or polypeptide such that the presence of a DHDR nucleic acid molecule, protein or polypeptide is detected in the biological sample.

In another aspect, the present invention provides a method for detecting the presence of DHDR activity in a biological sample by contacting the biological sample with an agent capable of detecting an indicator of DHDR activity such that the presence of DHDR activity is detected in the biological sample.

In another aspect, the invention provides a method for modulating DHDR activity comprising contacting a cell capable of expressing DHDR with an agent that modulates DHDR activity such that DHDR activity in the cell is modulated. In one embodiment, the agent inhibits DHDR activity. In another embodiment, the agent stimulates DHDR activity. In one embodiment, the agent is an antibody that specifically binds to a DHDR protein. In another embodiment, the agent modulates expression of DHDR by modulating transcription of a DHDR gene or translation of a DHDR mRNA. In yet another embodiment, the agent is a nucleic acid molecule having a nucleotide sequence that is antisense to the coding strand of a DHDR mRNA or a DHDR gene.

In one embodiment, the methods of the present invention are used to treat a subject having a disorder characterized by aberrant or unwanted DHDR protein or nucleic acid expression or activity by administering an agent which is a DHDR modulator to the subject. In one embodiment, the DHDR modulator is a DHDR protein. In another embodiment the DHDR modulator is a DHDR nucleic acid molecule. In yet another embodiment, the DHDR modulator is a peptide, peptidomimetic, or other small molecule. In a preferred embodiment, the disorder characterized by aberrant or unwanted DHDR protein or nucleic acid expression is a dehydrogenase-associated disorder, e.g., a viral disorder, a CNS disorder, a cardiovascular disorder, a muscular disorder, or a cell proliferation, growth, differentiation, or migration disorder.

The present invention also provides diagnostic assays for identifying the presence or absence of a genetic alteration characterized by at least one of (i) aberrant modification or mutation of a gene encoding a DHDR protein; (ii) mis-regulation of the gene; and (iii) aberrant post-translational modification of a DHDR protein, wherein a wild-type form of the gene encodes a protein with a DHDR activity.

In another aspect the invention provides methods for identifying a compound that binds to or modulates the activity of a DHDR protein, by providing an indicator composition comprising a DHDR protein having DHDR activity, contacting the indicator composition with a test compound, and determining the effect of the test compound on DHDR activity in the indicator composition to identify a compound that modulates the activity of a DHDR protein.

Other features and advantages of the invention will be apparent from the following detailed description and claims.

BRIEF DESCRIPTION OF THE DRAWINGS

FIGS. 1A-1C depict the cDNA sequence and predicted amino acid sequence of human DHDR-1 (clone FBH32142). The nucleotide sequence corresponds to nucleic acids 1 to 2660 of SEQ ID NO:1. The amino acid sequence corresponds to amino acids 1 to 802 of SEQ ID NO:2. The coding region without the 3' untranslated region of the human DHDR-1 gene is shown in SEQ ID NO:3.

FIG. 3 depicts the results of a search which was performed against the MEMSAT database and which resulted in the identification of one "transmembrane domains" in the human DHDR-1 protein (SEQ ID NO:2).

FIG. 4 depicts the results of a search which was performed against the HMM database and which resulted in the identification of an "aldehyde dehydrogenase family domain" in the human DHDR-1 protein. The aldehyde dehydrogenase family domain (SEQ ID NO:17) is aligned with DHDR-1 protein (32142, SEQ ID NO:2) residues.

FIGS. 5A-5B depict the results of a search which was performed against the ProDom database and which resulted in the identification of a "aldehyde dehydrogenase oxidoreductase domain" in the human DHDR-1 protein (SEQ ID NO:2). The aldehyde dehydrogenase oxidoreductase domain (SEQ ID NO:18) is aligned with DHDR-1 protein (Sbjct, SEQ ID NO:2) residues.

FIGS. 6A-6B depict the cDNA sequence and predicted amino acid sequence of human DHDR-2 (clone Fbh21481). The nucleotide sequence corresponds to nucleic acids 1379 of SEQ ID NO :4. The amino acid sequence corresponds to amino acids 1 to 311 of SEQ ID NO:5. The coding region without the 3' untranslated region of the human DHDR-2 gene is shown in SEQ ID NO:6.

FIG. 8 depicts the results of a signal peptide prediction and a search which was performed against the MEMSAT database and which resulted in the identification of a signal peptide and one "transmembrane domain"in the human DHDR-2 protein (SEQ ID NO:5). "21481 mature"peptide: a.a. 19-311 of SEO ID NO:5.

FIG. 9 depicts the results of a search which was performed against the HMM database and which resulted in the identification of a "short-chain dehydrogenase domain" in the human DHDR-2 protein. The short chain dehydrogenase domain (SEQ ID NO:19) is aligned with DHDR-2 protein (21481; SEQ ID NO:5) residues.

FIG. 10 depicts the results of a search which was performed against the ProDom database and which resulted in the identification of a "oxidoreductase protein dehydrogenase domain" in the human DHDR-2 protein (SEQ ID NO:5). The oxidoreductase protein dehydrogenase domain (SEQ ID NO:21) is aligned with DHDR-2 protein residues.

FIGS. 11A-11B depict the cDNA sequence and predicted amino acid sequence of human DHDR-3 (clone Fbh25964). The nucleotide sequence corresponds to nucleic acids 1 to 1725 of SEQ ID NO:7. The amino acid sequence corresponds to amino acids 1 to 369 of SEQ ID NO:8. The coding region without the 3' untranslated region of the human DHDR-3 gene is shown in SEQ ID NO:9.

FIG. 13 depicts the results of a search which was performed against the MEMSAT database and which resulted in the identification of four "transmembrane domains" in the human DHDR-3 protein (SEQ ID NO:8).

FIGS. 14A-14B depicts the results of a search which was performed against the HMM database and which resulted in the identification of a "3-beta hydroxysteroid dehydrogenase domain", a "short chain dehydrogenase domain", and a "NAD-dependent epimerase/dehydratase domain" in the human DHDR-3 protein. In FIG. 14A, the short chain dehydrogenase domain (SEQ ID NO:19) is aligned with DHDR-3 protein (25964; SEQ ID NO:8) residues. Also aligned is S-adenosylmethionine synthetase domain (SEQ ID NO:22) with DHDR-3 protein residues. FIG. 14B1 depicts an alignment of 3-betahydroxysteroid dehydrogenase domain (SEQ ID NO:23) with DHDR-3 protein residues. FIG. 14B2 depicts an alignment of NAD dependent epimerase/dehydratase domain (SEQ ID NO:24) with DHDR-3 protein residues.

FIG. 15 depicts the results of a search which was performed against the ProDom database and which resulted in the identification of a "3-beta hydroxysteroid dehydrogenase domain" in the human DHDR-3 protein (SEQ ID NO:8). The 3-beta hydroxysteroid dehydrogenase domain sequences (SEQ ID NO:25 and SEQ ID NO:26) are aligned with DHDR-3 (Subjct) protein residues.

FIG. 16 depicts the cDNA sequence and predicted amino acid sequence of human DHDR-4 (clone Fbh21686). The nucleotide sequence corresponds to nucleic acids 1 to 1209 of SEQ ID NO:10. The amino acid sequence corresponds to amino acids 1 to 322 of SEQ ID NO:11. The coding region without the 3' untranslated region of the human DHDR-4 gene is shown in SEQ ID NO:12.

FIG. 17 depicts an alignment of the human DHDR-4 amino acid sequence ("21686"; SEQ ID NO:11) with the amino acid sequence of Rattus norvegicus putative short-chain dehydrogenase/reductase ("5052204_SDR_rat"; GenBank Accession Number AF099742; SEQ ID NO:13) using the CLUSTAL W (1.74) multiple sequence alignment program. Identical amino acids are indicated by stars.

FIG. 19 depicts the results of a signal peptide prediction and a search which was performed against the MEMSAT database and which resulted in the identification of a "signal peptide"and four "transmembrane domains"in the human DHDR-4 protein (SEQ ID NO:11). "21686 mature"peptide: a.a. 20-322 of SEQ ID NO:11.

FIG. 20 depicts the results of a search which was performed against the HMM database and which resulted in the identification of a "short chain dehydrogenase domain" and a "short chain dehydrogenase/reductase domain" in the human DHDR-4 protein. The short chain dehydrogenase domain (SEQ ID NO:19) is aligned with DHDR-4 protein (21686; SEQ ID NO:11) residues. Also, short chain dehydrogenase/reductase C2 domain (SEQ ID NO:27) is aligned with DHDR-4 protein residues.

FIGS. 21A-21B depict the results of a search which was performed against the ProDom database and which resulted in the identification of a "oxidoreductase protein dehydrogenase domain" (SEQ ID NO:28, SEQ ID NO:29 and SEQ ID NO:30), a "shikimate 5-dehydrogenase domain" (SEQ ID NO:32), a "dehydrogenase domain" (SEQ ID NO:33), and a "glucose-1-dehydrogenase domain" (SEQ ID NO:31) in the human DHDR-4 protein (SEQ ID NO:11). Also depicted is an alignment of a hypothetical protein domain (SEQ ID NO:34 aligned with human DHDR-4 protein residues.

lung tumor; (34) lung—chronic obstructive pulmonary disease (COPD); (35) colon—inflammatory bowel disease (IBD); (36) normal liver; (37) liver—fibrosis; (38) dermal cells—fibroblasts; (39) normal tonsil; (40) lymph node; (41) small intestine; (42) skin—decubitus; (43) synovium; (44) bone marrow mononuclear cells (BM-MNC); (45) activated peripheral blood mononuclear cells (PBMCs).

Figure 23:
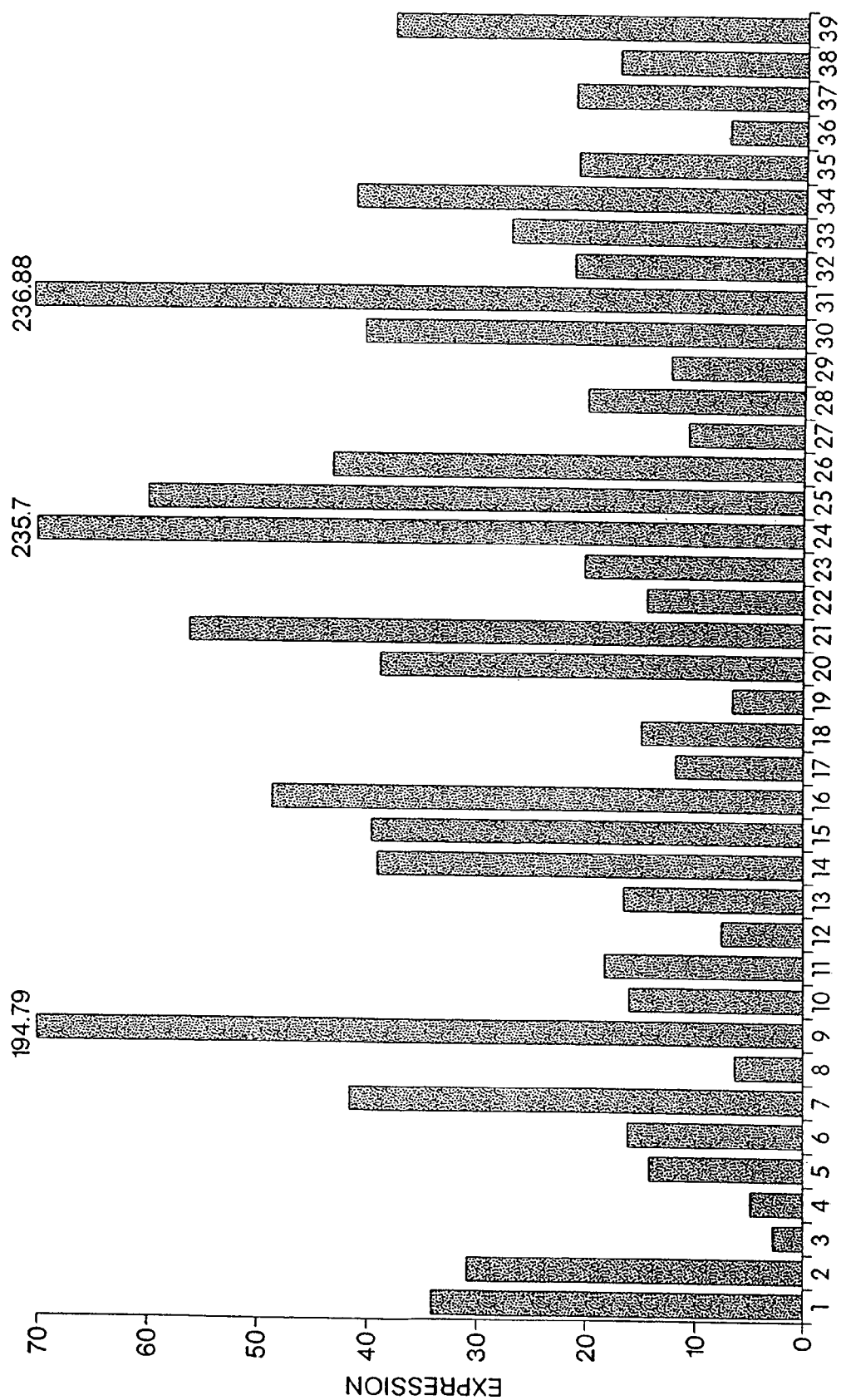

FIG. 23 depicts the expression levels of human DHDR-1 mRNA in various types of human tumors, as determined by Taqman analysis. Samples: (1-3) normal breast; (4) breast tumor—infiltrating ductal carcinoma (IDC); (5) breast tumor—infiltrating ductal carcinoma (MD-IDC); (6-8) breast tumor—infiltrating ductal carcinoma (IDC); (9) breast tumor; (10-11) normal ovary; (12-16) ovary tumor; (17-19) normal lung; (20) lung tumor—5 mC; (21-23) lung tumor—poorly differentiated non-small cell carcinoma of the lung (PDN-SCCL); (24) lung tumor—small cell carcinoma (SCC); (25) lung tumor—AC; (26) lung tumor—ACA; (27-29) normal colon; (30-31) colon tumor—MD; (32) colon tumor; (33) colon tumor—MD-PD; (34-35) colon tumor—liver metastasis; (36) normal liver (female); (37) hemangioma; (38) human microvascular endothelial cells (HMVECs)—arrested; (39) human microvascular endothelial cells (HMVECs)—proliferating.

Figure 24:
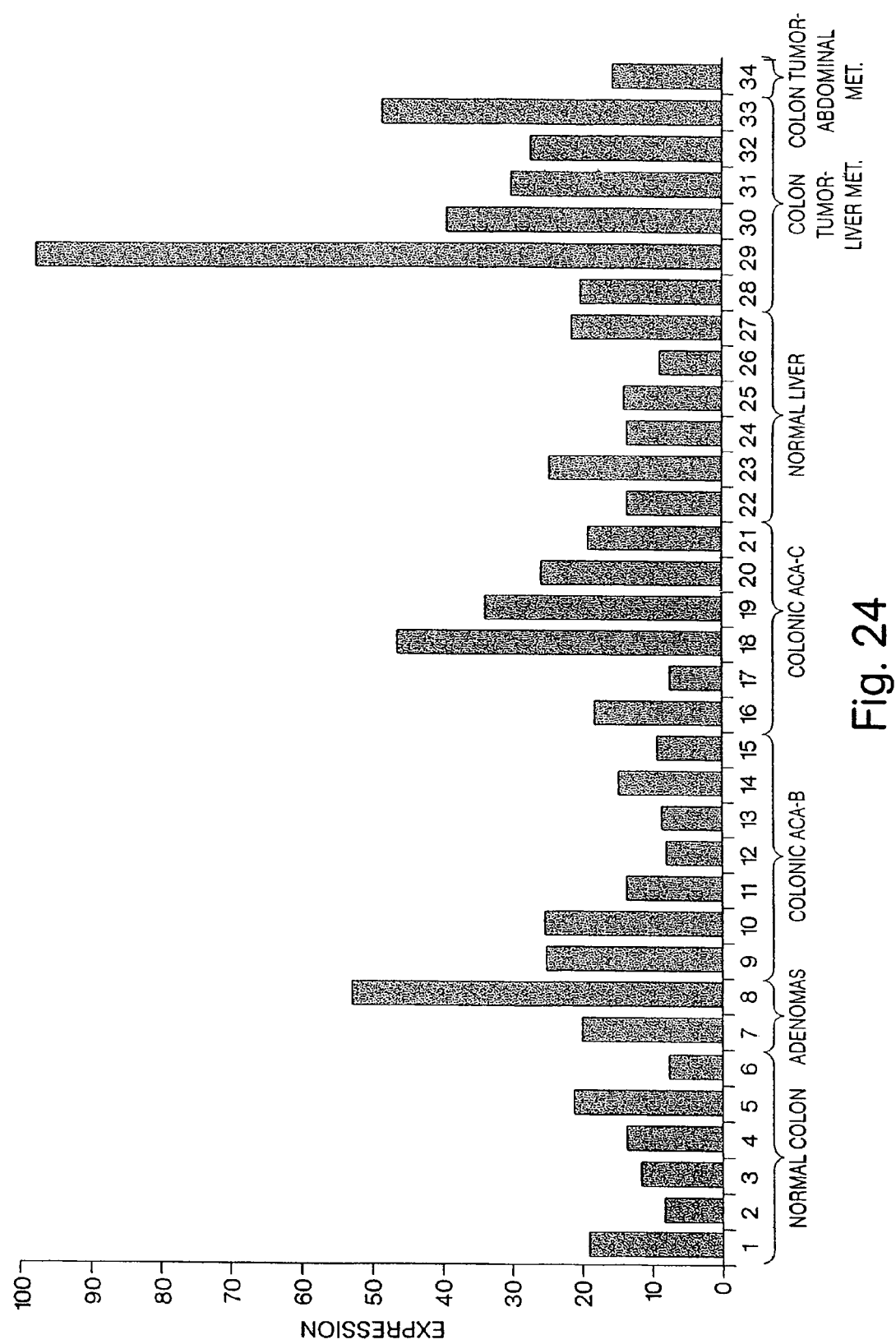

FIG. 24 depicts the expression levels of human DHDR-1 mRNA in various human colon tumor samples, as determined by Taqman analysis. Samples: (1-6) normal colon; (7-8) adenomas; (9-15) colonic ACA-B; (16-21); colonic ACA-C; (22-27) normal liver; (28-33) colon tumor—liver metastasis; (34) colon tumor—abdominal metastasis.

Figure 25:
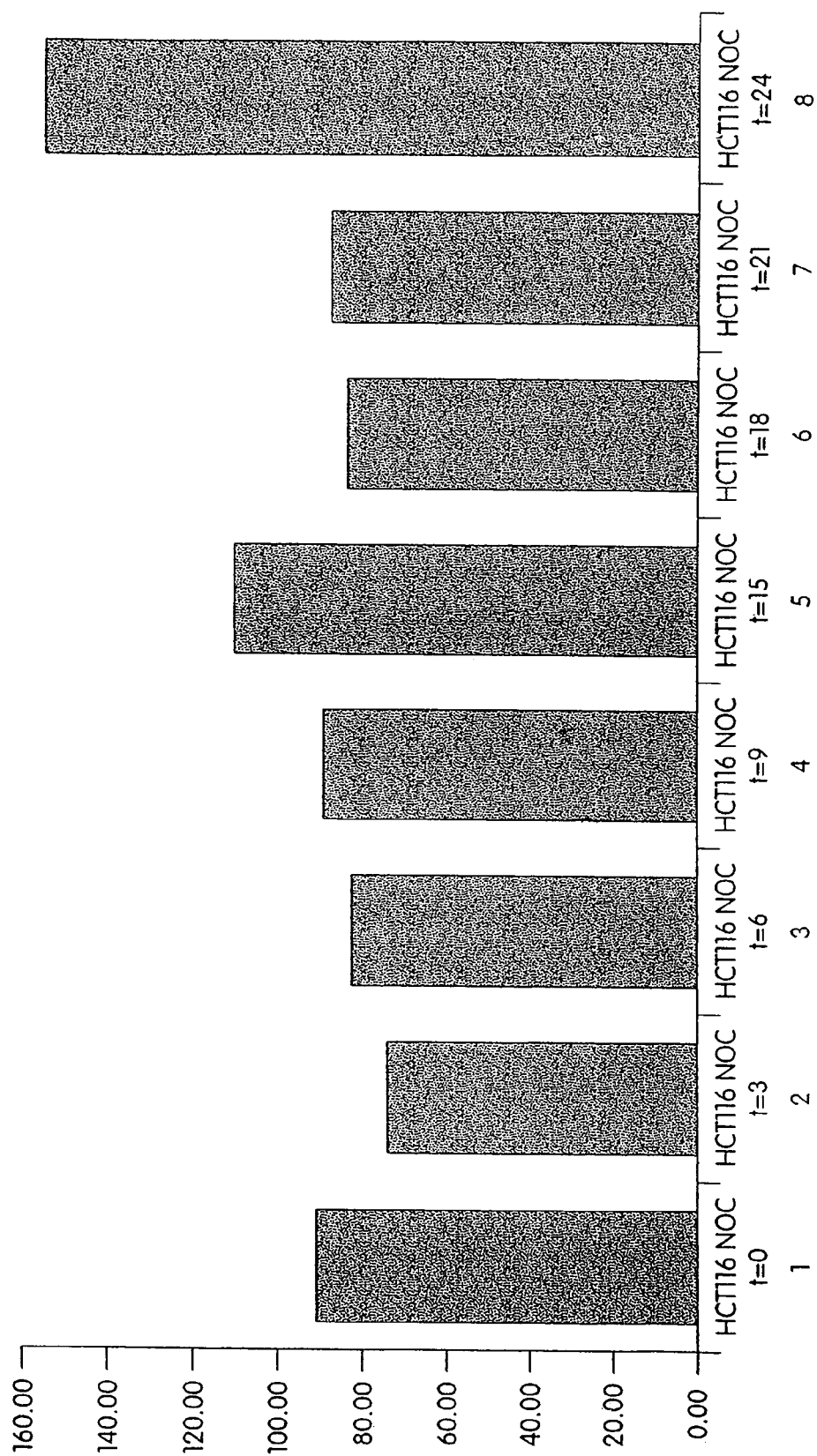

FIG. 25 depicts the expression levels of human DHDR-1 mRNA in NOC synchronized HCT116 cells at various time points after entry into the cell cycle, as determined by Taqman analysis. The time point t=0 signifies the G2/M border. Samples: (1) t=0; (2) t=3; (3) t=6; (4) t=9; (5) t=15; (6) t=18; (7) t=21; (8) t=24.

Figure 26:
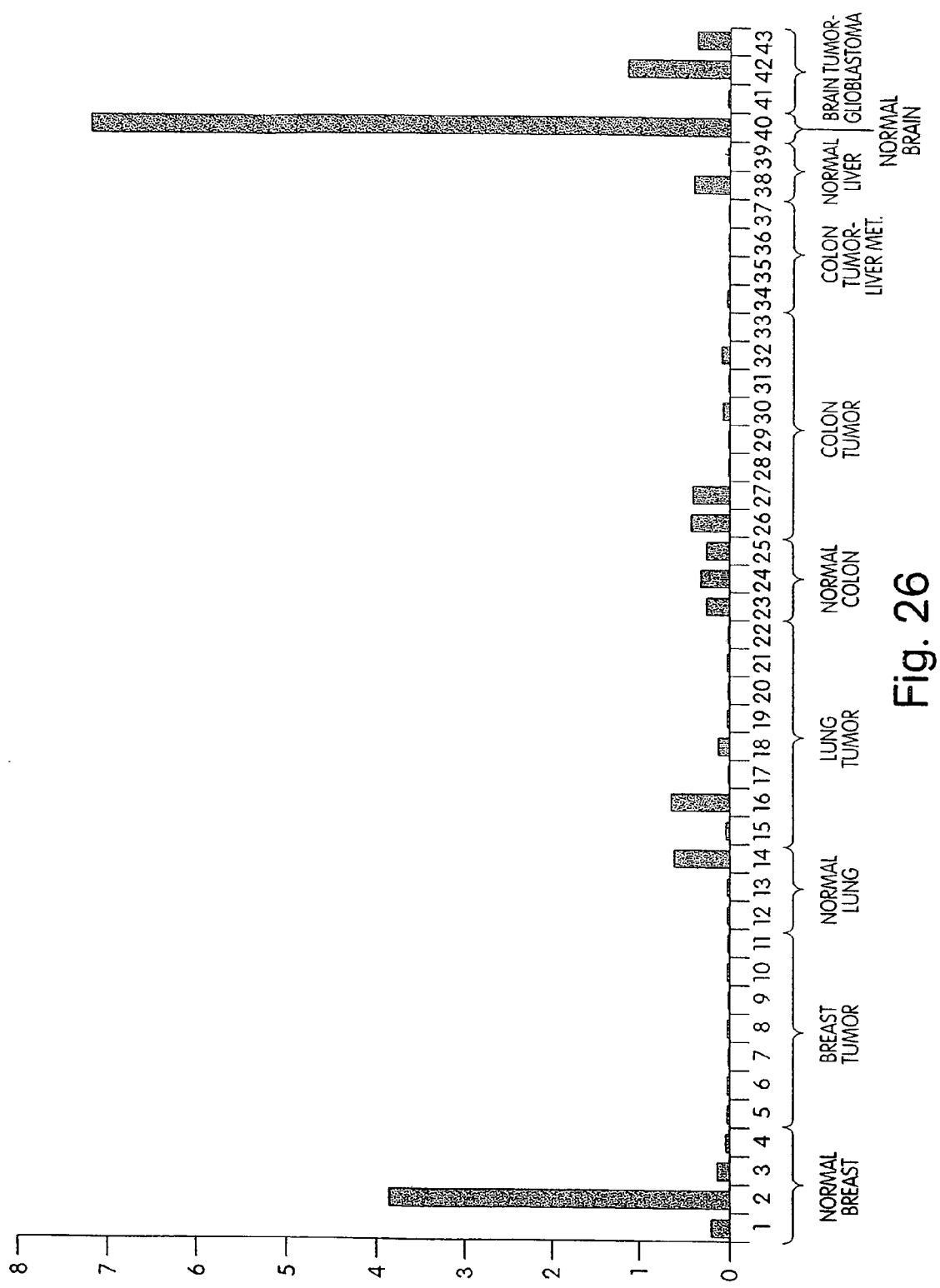

FIG. 26 depicts the expression levels of human DHDR-2 mRNA in various human clinical tumor samples, as determined by Taqman analysis. Samples: (1-4) normal breast; (5-11) breast tumor; (12-14) normal lung; (15-22) lung tumor; (23-25) normal colon; (26-33) colon tumor; (34-37) colon tumor—liver metastasis; (38-39) normal liver; (40) normal brain; (41-43) brain tumor—glioblastoma.

Figure 27:
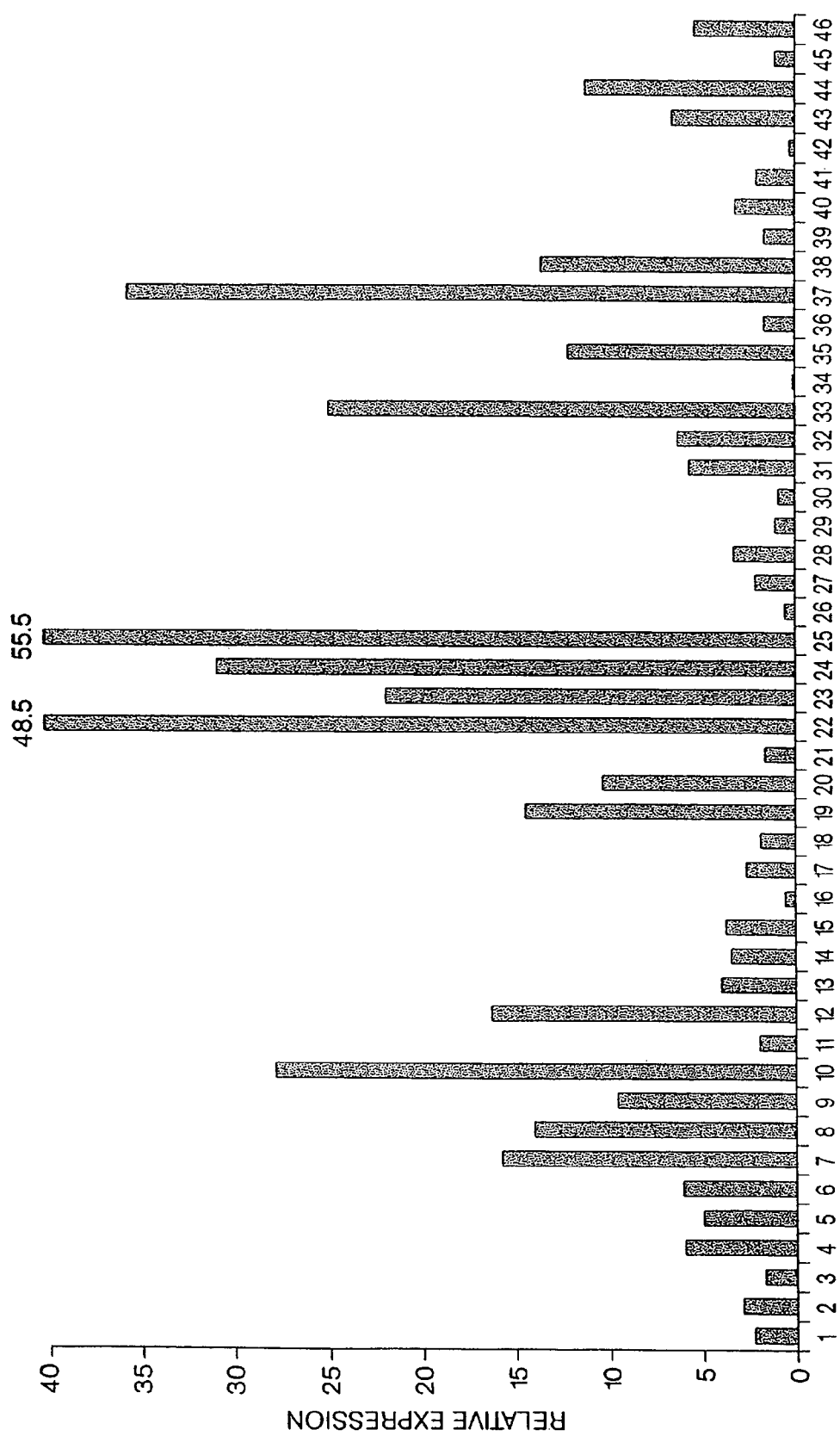

FIG. 27 depicts the expression levels of human DHDR-4 mRNA in various human cell types and tumors, as determined by Taqman analysis. Samples: (1) normal aorta; (2) normal fetal heart; (3) normal heart; (4) heart—congestive heart failure (CHF); (5) normal vein; (6) aortic smooth muscle cells; (7) normal spinal cord; (8) normal brain cortex; (9) brain—hypothalamus; (10) glial cells—astrocytes; (11) brain—glioblastoma; (12) normal breast; (13) breast tumor—infiltrating ductal carcinoma (IDC); (14) normal ovary; (15) ovary tumor; (16) pancreas; (17) normal prostate; (18) prostate tumor; (19) normal colon; (20) colon tumor; (21) colon—inflammatory bowel disease (IBD); (22) normal kidney; (23) normal liver; (24) liver—fibrosis; (25) normal fetal liver; (26) normal lung; (27) lung tumor; (28) lung—chronic obstructive pulmonary disease (COPD); (29) normal spleen; (30) normal tonsil; (31) normal lymph node; (32) normal thymus; (33) epithelial cells—prostate; (34) endothelial cells—aortic; (35) skeletal muscle; (36) dermal fibroblasts; (37) normal skin; (38) normal adipose tissue; (39) primary osteoblasts; (40) undifferentiated osteoblasts; (41) differentiated osteoblasts; (42) osteoclasts; (43) aortic smooth muscle cells (SMCs)—early; (44) aortic smooth muscle cells (SMCs)—late; (45) human umbilical vein endothelial cells (HUVECs)—shear; (46) human umbilical vein endothelial cells (HUVECs)—static.

Figure 28:
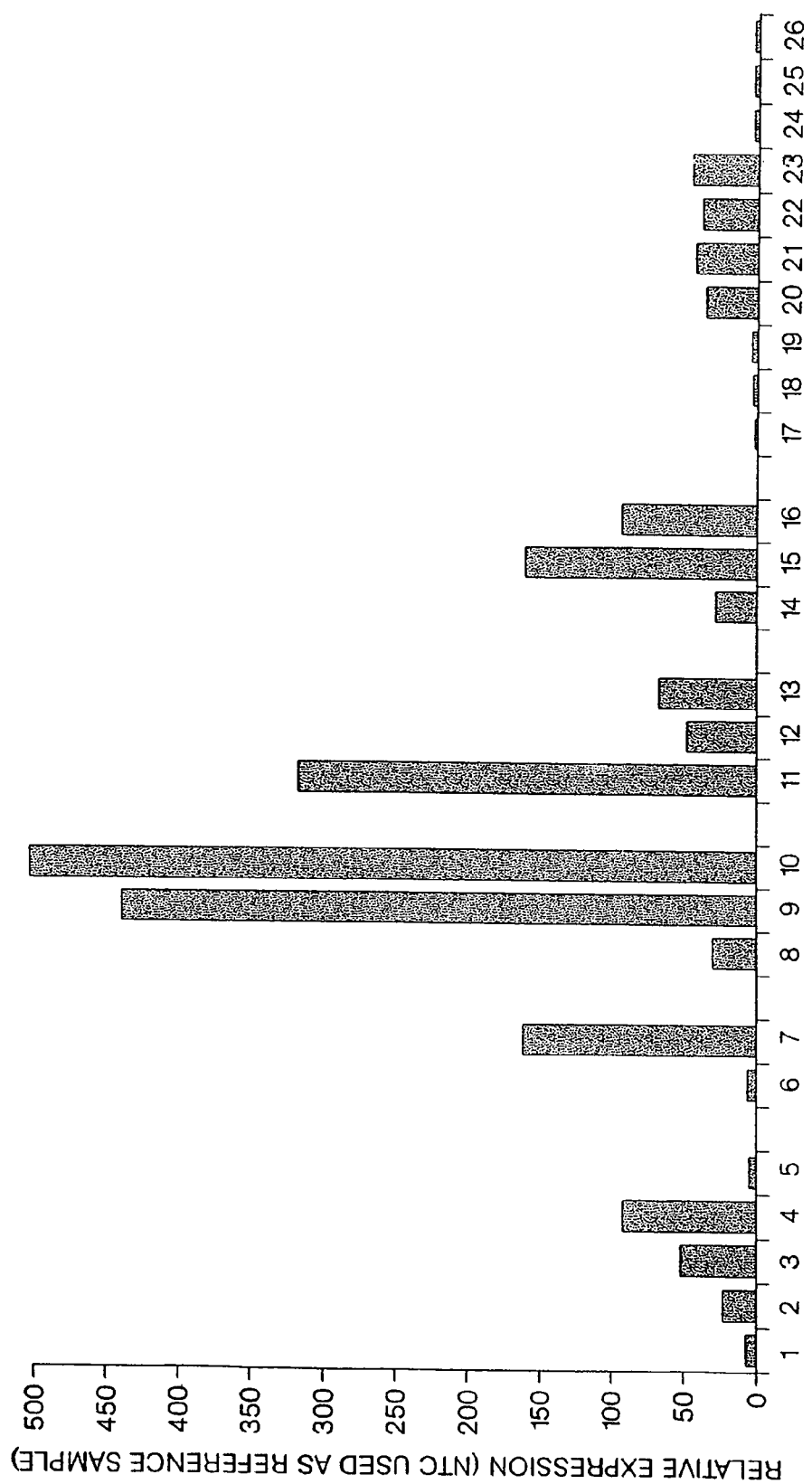

FIG. 28 depicts the expression levels of human DHDR-4 mRNA in various cell types and tissues, as determined by Taqman analysis. Samples: (1-2) normal liver; (3-4) HBV+ liver; (5) HCV+liver; (6) HepG2-B cells; (7) HepG2.2.15-B cells; (8) HepG2 cells (no treatment); (9) HepG2 cells—treated with Bayer compound (IC50); (10) HepG2 cells—treated with Bayer compound (IC100); (11) HepG2.2.15 cells (no treatment); (12) HepG2.2.15 cells—treated with Bayer compound (IC50); (13) HepG2.2.15 cells—treated with Bayer compound (IC100); (14) HepG2 control; (15) HepG2 cells transfected with the HBV-X gene; (16) HuH7 cells; (17-19) ganglia; (20) NT2/KOS—0 hr.; (21) NT2/KOS—2.5 hr.; (22) NT2/KOS—5 hr.; (23) NT2/KOS—7 hr.; (24) MRC/VZV—mock; (25) MRC/VZV—18 hr.; (26) MRC/VZV—72 hr.

Figure 29:
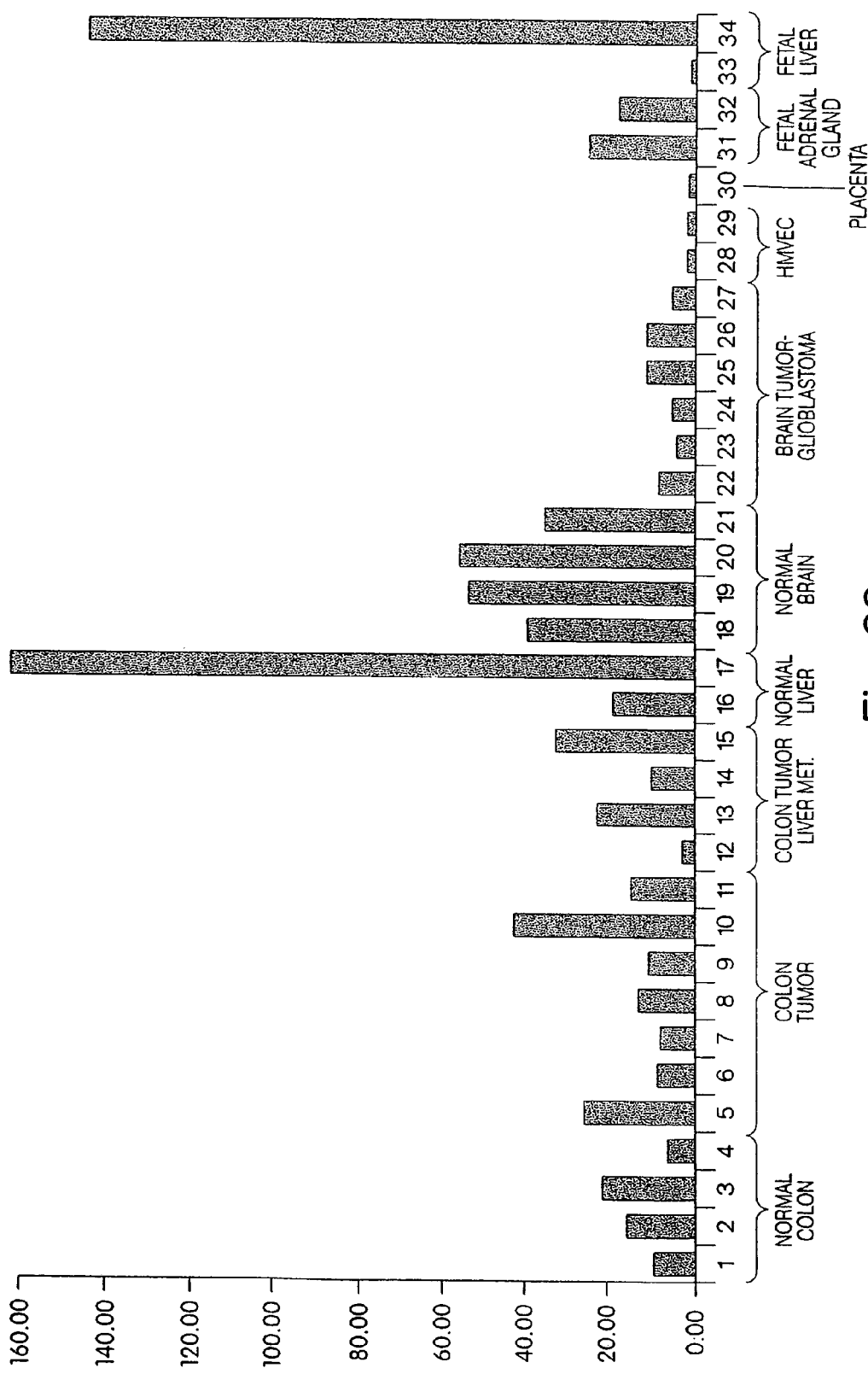

FIG. 29 depicts the expression levels of human DHDR-4 mRNA in various human tumor samples, as determined by Taqman analysis. Samples: (1-4) normal colon; (5-11) colon tumor; (12-15) colon tumor—liver metastasis; (16-17) normal liver; (18-21) normal brain; (22-27) brain tumor—glioblastoma; (28-29) human microvascular endothelial cells (HMVECs); (30) placenta; (31-32) fetal adrenal gland; (33-34) fetal liver.

Figure 30:
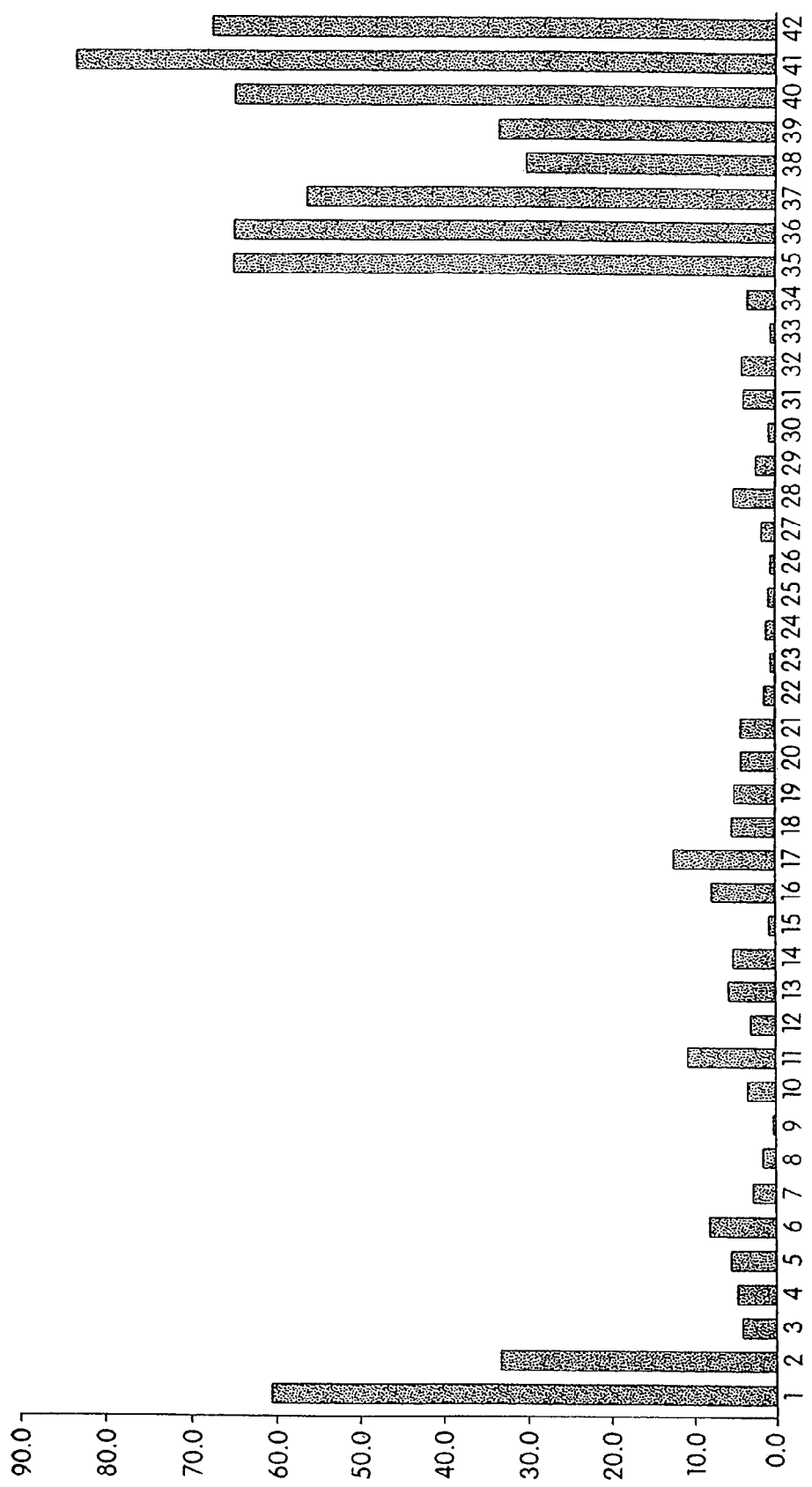

FIG. 30 depicts the expression levels of human DHDR-4 mRNA in various human tumors and synchronized A549 cells at various time points after entry into the cell cycle, as determined by Taqman analysis. The time point t=0 signifies the G2/M border. Samples: (1-4) normal breast; (5-10) breast tumor; (11-14) normal ovary; (15-22) ovary tumor; (23-26) normal lung; (27-34) lung tumor; (35-42) synchronized A549 cells: (35) t=0; (36) t=3 (RT); (37) t=3 (RT); (38) t=6; (39) t=9; (40) t=12 (RT); (41) t=18; (42) t=24.

FIGS. 31A-31B depict the cDNA sequence and predicted amino acid sequence of mouse DHDR-2 (clone m21481). The nucleotide sequence, corresponding to nucleic acids 1 to 1108 of SEQ ID NO:14, is shown in FIG. 31A. The coding region, corresponding to SEQ ID NO:16, is underlined. The amino acid sequence, corresponding to amino acids 1 to 311 of SEQ ID NO:15, is shown in FIG. 31B.

FIGS. 32A-32B depict an alignment of the mouse DHDR-2 nucleotide sequence ("M21484"; SEQ ID NO:14) with the human DHDR-2 nucleotide sequence ("h21484"; SEQ ID NO:4) using the GAP program in the GCG software package (nwsgapdna.cmp matrix) and a gap weight of 12 and a length weight of 4. As shown in the alignment, the mouse and human DHDR-2 nucleotide sequences are about 88.1% identical.

FIG. 33 depicts an alignment of the mouse DHDR-2 amino acid sequence ("m21484"; SEQ ID NO:15) with the human DHDR-2 amino acid sequence ("h21484"; SEQ ID NO:5) using the GAP program in the GCG software package (Blosum 62 matrix) and a gap weight of 12 and a length weight of 4. As shown in the alignment, the mouse and human DHDR-2 amino acid sequences are about 91.3% identical.

DETAILED DESCRIPTION OF THE INVENTION

The present invention is based, at least in part, on the discovery of novel molecules, referred to herein as "dehydrogenase" or "DHDR" nucleic acid and protein molecules, which are novel members of a family of enzymes possessing dehydrogenase activity. These novel molecules are capable of oxidizing or reducing biological molecules by catalyzing the transfer of a hydride moiety and, thus, play a role in or function in a variety of cellular processes, e.g., proliferation, growth, differentiation, migration, immune responses, hormonal responses, inter- or intra-cellular communication, and viral infection.

As used herein, the term "dehydrogenase" includes a molecule which is involved in the oxidation or reduction of a biochemical molecule (e.g., an amino acid, a vitamin, a steroid such as a glucocorticoid, or a nucleic acid), by catalyzing the transfer of a hydride ion to or from the biochemical molecule. Dehydrogenase molecules are involved in the metabolism and catabolism of biochemical molecules necessary for energy production or storage, for intra- or intercellular signaling, for metabolism or catabolism of metabolically important biomolecules, and for detoxification of potentially harmful compounds. Examples of dehydrogenases include alcohol dehydrogenases, aldehyde dehydrogenases, steroid dehydrogenases, and lipid dehydrogenases. Thus, the DHDR molecules of the present invention provide novel diagnostic targets and therapeutic agents to control dehydrogenase-associated disorders.

As used herein, a "dehydrogenase-associated disorder" includes a disorder, disease or condition which is caused or characterized by a misregulation (e.g., downregulation or upregulation) of dehydrogenase activity. Dehydrogenase-associated disorders can detrimentally affect cellular functions such as cellular proliferation, growth, differentiation, or migration, inter- or intra-cellular communication; tissue function, such as cardiac function or musculoskeletal function; systemic responses in an organism, such as nervous system responses, hormonal responses (e.g., insulin response), susceptibility to pathogenic infections (e.g., viral infections), or immune responses; and protection of cells from toxic compounds (e.g., carcinogens, toxins, or mutagens). Examples of dehydrogenase-associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of dehydrogenase-associated disorders include cardiac-related disorders. Cardiovascular system disorders in which the DHDR molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. DHDR-mediated or related disorders also include disorders of the musculoskeletal system such as paralysis and muscle weakness, e.g., ataxia, myotonia, and myokymia.

Dehydrogenase associated disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The DHDR molecules of the present invention are involved in signal transduction mechanisms, which are known to be involved in cellular growth, differentiation, and migration processes. Thus, the DHDR molecules may modulate cellular growth, differentiation, or migration, and may play a role in disorders characterized by aberrantly regulated growth, differentiation, or migration. Such disorders include cancer, e.g., carcinomas, sarcomas, leukemias, and lymphomas; tumor angiogenesis and metastasis; skeletal dysplasia; hepatic disorders; and hematopoietic and/or myeloproliferative disorders.

DHDR-associated or related disorders also include hormonal disorders, such as conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

DHDR-associated or related disorders also include immune disorders, such as autoimmune disorders or immune deficiency disorders, e.g., allergies, transplant rejection, responses to pathogenic infection (e.g., bacterial, viral, or parasitic infection), lupus, multiple sclerosis, congenital X-linked infantile hypogammaglobulinemia, transient hypogammaglobulinemia, common variable immunodeficiency, selective IgA deficiency, chronic mucocutaneous candidiasis, or severe combined immunodeficiency.

DHDR-associated or related disorders also include viral disorders, i.e., disorders affected or caused by infection by viruses (e.g., hepatitis A, hepatitis B, hepatitis delta, and other hepadnaviruses; Coxsackie B viruses; Epstein-Barr virus; adenovirus; rhinoviruses; human immunodeficiency virus (HIV); vaccinia virus; human T cell leukemia virus; RD114 virus; herpes simplex, herpes zoster, and other herpesviruses; Marek's disease virus; Yamaguchi sarcoma virus; human papillomaviruses; poliovirus; poxviruses; influenza virus; cytomegalovirus; encephalitis viruses; measles viruses; and ebola and other hemorrhagic viruses). Such disorders include, but are not limited to, hepatocellularcarcinoma, cirrhosis of the liver, cervical carcinoma, Burkitt's lymphoma, lymphoproliferative disease, Kaposi's sarcoma, T cell leukemia, B cell lymphoma, plasmablastic lymphoma, Rasmussen's syndrome, Marek's disease, warts (including common, genital, and plantar warts), genital herpes, common colds, acquired immune deficiency syndrome (AIDS), polymyositis, immunorestitution disease, chicken pox, shingles, ebola and other hemorrhagic fever diseases, cold sores, transient or acute hepatitis, chronic hepatitis, influenza, Reye syndrome, measles, Paget's disease, viral encephalitis, viral pneumonia, and viral meningitis.

Viral disorders also include disorders or conditions influenced by virus or viral activity. As used interchangeably herein, the terms "viral activity" and "virus activity" includes any activity known in the art to be characteristic of a virus and which can be detected by methods known in the art. For example, viral activity includes, but it not limited to, the ability of a virus to infect a cell or an organism (e.g., a human), the ability of a virus to replicate or reproduce in a cell or an organism (e.g., a human), the ability of a virus to induce an immune response in vitro or in vivo, the ability to induce expression of viral genes, and/or the ability to induce expression of host or exogenous genes not normally expressed by an uninfected cell.

DHDR-associated or related disorders also include disorders affecting tissues in which DHDR protein is expressed, e.g., liver, hepatocytes, hepatitis B-infected hepatocytes, HepG2 cells, hepatitis B-infected HepG2.2.15 cells, kidney, brain, primary osteoblasts, pituitary, CaCO cells, keratinocytes, aortic endothelial cells, fetal kidney, fetal lung, mammary epithelium, fetal spleen, fetal liver, umbilical smooth muscle, RAII Burkitt Lymphoma cells, lung, prostate, K53 red blood cells, fetal dorsal spinal cord, insulinoma cells, normal breast and ovarian epithelia, retina, HMC-1 mast cells, ovarian ascites, d8 dendritic cells, megakaryocytes, human mobilized bone morrow, mammary carcinoma, melanoma cells, lymph, vein, U937/A70p B cells, A549con cells, WT LN Cap testosterone cells, and esophagus.

As used herein, a "dehydrogenase-mediated activity" includes an activity which involves the oxidation or reduction of one or more biochemical molecules, e.g., biochemical molecules (e.g., glucocorticoids) in a neuronal cell, a liver cell, or a tumor cell associated with the regulation of one or more cellular processes. Dehydrogenase-mediated activities include the oxidation or reduction of biochemical molecules necessary for energy production or storage, for intra- or intercellular signaling, for metabolism or catabolism of metabolically important biomolecules, for viral infection, and for detoxification of potentially harmful compounds.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, the family of DHDR proteins comprises at least one "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) Annu. Rev. Neurosci. 19:235-263, the contents of which are incorporated herein by reference. Amino acid residues 159-175 of the native DHDR-1 protein are predicted to comprise a transmembrane domain (see FIG. 3). Amino acid residues 7-23 of the native DHDR-2 protein and residues 265-283 of the mature DHDR-2 protein are predicted to comprise a transmembrane domain (see FIG. 8). Amino acid residues 10-26, 73-90, 289-305, and 312-333 of the native DHDR-3 protein are predicted to comprise transmembrane domains (see FIG. 13). Amino acid residues 29-50, 170-188, 108-224, and 258-275 of the native DHDR-4 protein and residues 10-31, 151-169, 189-205, and 239-256 of the mature DHDR-4 protein are predicted to comprise transmembrane domains (see FIG. 19). Accordingly, DHDR proteins having at least 50-60% homology, preferably about 60-70%, more preferably about 70-80%, or about 80-90% homology with a transmembrane domain of human DHDR are within the scope of the invention.

In another embodiment of the invention, a DHDR protein of the present invention is identified based on the presence of a signal peptide. The prediction of such a signal peptide can be made, for example, utilizing the computer algorithm SignalP (Henrik et al. (1997) Prot. Eng. 10: 1-6). As used herein, a "signal sequence" or "signal peptide" includes a peptide containing about 15 or more amino acids which occurs at the N-terminus of secretory and membrane bound proteins and which contains a large number of hydrophobic amino acid residues. For example, a signal sequence contains at least about 10-30 amino acid residues, preferably about 15-25 amino acid residues, more preferably about 18-20 amino acid residues, and more preferably about 19 amino acid residues, and has at least about 35-65%, preferably about 38-50%, and more preferably about 40-45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer, and is cleaved in secreted and membrane bound proteins. A signal sequence was identified in the amino acid sequence of human DHDR-2 at about amino acids 1-18 of SEQ ID NO:5. A signal sequence was also identified in the amino acid sequence of human DHDR-4 at about amino acids 1-19 of SEQ ID NO:11.

In another embodiment, a DHDR molecule of the present invention is identified based on the presence of an "aldehyde dehydrogenase family domain" in the protein or corresponding nucleic acid molecule. As used herein, the term "aldehyde dehydrogenase family domain" includes a protein domain having an amino acid sequence of about 350-550 amino acid residues and a bit score of at least 149.8. Preferably, an aldehyde dehydrogenase family domain includes at least about 400-500, or more preferably about 448 amino acid residues, and a bit score of about 50, 60, 70, 80, 90, 100, 110, 120, 130, 140, 150, 160, 170, 180, 190, 200, 210, 220, 230, 240, or 250 or more. To identify the presence of an aldehyde dehydrogenase family domain in a DHDR protein, and make the determination that a protein of interest has a particular profile, the amino acid sequence of the protein is searched against a database of known protein domains (e.g., the HMM database). The aldehyde dehydrogenase family domain (HMM) has been assigned the PFAM Accession PF00171 (see the Pfam website, available online through Washington University in Saint Louis). A search was performed against the HMM database resulting in the identification of an aldehyde dehydrogenase family domain in the amino acid sequence of human DHDR-1 (SEQ ID NO:2) at about residues 47-494 of SEQ ID NO:2. The results of the search are set forth in FIG. 4.

In another embodiment, a DHDR molecule of the present invention is identified based on the presence of an "aldehyde dehydrogenase oxidoreductase domain" in the protein or corresponding nucleic acid molecule. As used herein, the term "aldehyde dehydrogenase oxidoreductase domain" includes a protein domain having an amino acid sequence of about 550-750 amino acid residues and having a bit score for the alignment of the sequence to the aldehyde dehydrogenase oxidoreductase domain of at least 280. Preferably, an aldehyde dehydrogenase oxidoreductase domain includes at least about 600-700, or more preferably about 670 amino acid residues, and has a bit score for the alignment of the sequence to the aldehyde dehydrogenase oxidoreductase domain of at least 125, 150, 175, 200, 225, 250, 275, 300, 325, 350, 375, 400 or higher. The aldehyde dehydrogenase oxidoreductase domain has been assigned ProDom entry 135. To identify the presence of an aldehyde dehydrogenase oxidoreductase domain in a DHDR protein, and to make the determination that a protein of interest has a particular profile, the amino acid sequence of the protein is searched against a database of known protein domains (e.g., the ProDom database) using the default parameters (available online through the ProDom website). A search was performed against the ProDom database resulting in the identification of an aldehyde dehydrogenase oxidoreductase domain in the amino acid sequence of human DHDR-1 (SEQ ID NO:2) at about residues 101-770 of SEQ ID NO:2. The results of the search are set forth in FIGS. 5A-5B.

In another embodiment, a DHDR molecule of the present invention is identified based on the presence of a "short chain dehydrogenase domain" in the protein or corresponding nucleic acid molecule. As used herein, the term "short chain dehydrogenase domain" includes a protein domain having an amino acid sequence of about 100-300 amino acid residues, and a bit score of at least 120.0-162.5. Preferably, a short chain dehydrogenase domain includes at least about 150-250, or more preferably about 187-195 amino acid residues, and has a bit score of at least 40, 50, 60, 70, 80, 90, 100, 110, 120, 130, 140, 150, 160, 170, 180, 190, 200, 210, 220, or more. To identify the presence of a short chain dehydrogenase domain in a DHDR protein, and make the determination that a protein of interest has a particular profile, the amino acid sequence of the protein is searched against a database of known protein domains (e.g., the HMM database). The short chain dehydrogenase domain (HMM) has been assigned the PFAM Accession PF00106 (see the Pfam website, available online through Washington University in Saint Louis). A search was performed against the HMM database resulting in the identification of a short chain dehydrogenase domain in the amino acid sequence of human DHDR-2 (SEQ ID NO:5) at about residues 38-227 of SEQ ID NO:5. The results of the search are set forth in FIG. 9. A search was also performed against the HMM database resulting in the identification of a short chain dehydrogenase domain in the amino acid sequence of human DHDR-3 (SEQ ID NO:8) at about residues 10-197 of SEQ ID NO:8. The results of this search are set forth in FIGS. 14A-14B. Another search performed against the HMM database resulted in the identification of a short chain dehydrogenase domain in the amino acid sequence of human DHDR-4 (SEQ ID NO:11) at about residues 38-226 of SEQ ID NO:11. The results of this search are set forth in FIG. 20.

In another embodiment, a DHDR molecule of the present invention is identified based on the presence of an "oxidoreductase protein dehydrogenase domain" in the protein or corresponding nucleic acid molecule. As used herein, the term "oxidoreductase protein dehydrogenase domain" includes a protein domain having an amino acid sequence of about 50-300 amino acid residues and having a bit score for the alignment of the sequence to the oxidoreductase protein dehydrogenase domain of at least 113. Preferably, an oxidoreductase protein dehydrogenase domain includes at least about 100-250, or more preferably about 120-200 amino acid residues, and has a bit score for the alignment of the sequence to the oxidoreductase protein dehydrogenase domain of at least 40, 50, 60, 70, 80, 90, 100, 110, 120, 130, 140, 150, 160, 170, 180, or higher. The oxidoreductase protein dehydrogenase domain has been assigned ProDom entry 11. To identify the presence of an oxidoreductase protein dehydrogenase domain in a DHDR protein, and to make the determination that a protein of interest has a particular profile, the amino acid sequence of the protein is searched against a database of known protein domains (e.g., the ProDom database) using the default parameters (available online through the ProDom website). A search was performed against the ProDom database resulting in the identification of an oxidoreductase protein dehydrogenase domain in the amino acid sequence of human DHDR-2 (SEQ ID NO:5) at about residues 99-219 of SEQ ID NO:5. The results of the search are set forth in FIG. 10. Another search was performed against the ProDom database, resulting in the identification of an oxidoreductase protein dehydrogenase domain in the amino acid sequence of human DHDR-4 (SEQ ID NO:11) at about residues 37-231 of SEQ ID NO:11. The results of this search are set forth in FIGS. 21A-21B.

In another embodiment, a DHDR molecule of the present invention is identified based on the presence of an "NAD-dependent epimerase/dehydratase domain" in the protein or corresponding nucleic acid molecule. As used herein, the term "NAD-dependent epimerase/dehydratase domain" includes a protein domain having an amino acid sequence of about 250-450 amino acid residues. Preferably, an NAD-dependent epimerase/dehydratase domain includes at least about 300-400, or more preferably about 354 amino acid residues. To identify the presence of an NAD-dependent epimerase/dehydratase domain in a DHDR protein, and to make the determination that a protein of interest has a particular profile, the amino acid sequence of the protein is searched against a database of known protein domains (e.g., the HMM database). The NAD-dependent epimerase/dehydratase domain (HMM) has been assigned the PFAM Accession PF01370 (see the Pfam website, available online through Washington University in Saint Louis). A search was performed against the HMM database resulting in the identification of an NAD-dependent epimerase/dehydratase domain in the amino acid sequence of human DHDR-3 (SEQ ID NO:8) at about residues 12-365 of SEQ ID NO:8. The results of the search are set forth in FIGS. 14A-14B.

In another embodiment, a DHDR molecule of the present invention is identified based on the presence of a "3-beta hydroxysteroid dehydrogenase domain" in the protein or corresponding nucleic acid molecule. As used herein, the term "3-beta hydroxysteroid dehydrogenase domain" includes a protein domain having an amino acid sequence of about 250-450 amino acid residues and having a bit score for the alignment of the sequence to the 3-beta hydroxysteroid dehydrogenase domain of at least 395-676.9. Preferably, a 3-beta hydroxysteroid dehydrogenase domain includes at least about 300-400, or more preferably about 352-365 amino acid residues, and has a bit score for the alignment of the sequence to the 3-beta hydroxysteroid dehydrogenase domain of at least 300, 325, 350, 375, 400, 425, 450, 475, 500, 525, 550, 575, 600, 625, 650, 675, 700, 725, 750, 775, 800, 825 or higher. The 3-beta hydroxysteroid dehydrogenase domain has been assigned ProDom entry 1280. To identify the presence of a 3-beta hydroxysteroid dehydrogenase domain in a DHDR protein, and to make the determination that a protein of interest has a particular profile, the amino acid sequence of the protein is searched against a database of known protein domains (e.g., the ProDom database) using the default parameters (available online through the ProDom website). A search was performed against the ProDom database resulting in the identification of a 3-beta hydroxysteroid dehydrogenase domain in the amino acid sequence of human DHDR-3 (SEQ ID NO:8) at about residues 11-362 of SEQ ID NO:8. The results of the search are set forth in FIG. 15. A search was also performed against the HMM database resulting in the identification of a 3-beta hydroxysteroid dehydrogenase domain (PFAM accession PF01073, see the Pfam website, available online through Washington University in Saint Louis) in the amino acid sequence of human DHDR-3 (SEQ ID NO:8) at about residues 1-365 of SEQ ID NO:8. The results of the search are set forth in FIGS. 14A-14B.

In another embodiment, a DHDR molecule of the present invention is identified based on the presence of a "short-chain dehydrogenase/reductase domain" in the protein or corresponding nucleic acid molecule. As used herein, the term "short-chain dehydrogenase/reductase domain" includes a protein domain having an amino acid sequence of about 10-100 amino acid residues, and a bit score of at least 47.2. Preferably, a short-chain dehydrogenase/reductase domain includes at least about 20-75, or more preferably about 31 amino acid residues, and has a bit score of at least 5, 10, 15, 20, 25, 30, 35, 40, 45, 50, 55, 60, 65, 70, 75, 80, 85, 90, 95 or more. To identify the presence of a short-chain dehydrogenase/reductase domain in a DHDR protein, and to make the determination that a protein of interest has a particular profile, the amino acid sequence of the protein is searched against a database of known protein domains (e.g., the HMM database). The short-chain dehydrogenase/reductase domain (HMM) has been assigned the PFAM Accession PF00678 (see the Pfam website, available online through Washington University in Saint Louis). A search was performed against the HMM database resulting in the identification of a short-chain dehydrogenase/reductase domain in the amino acid sequence of human DHDR-4 (SEQ ID NO:11) at about residues 250-280 of SEQ ID NO:11. The results of the search are set forth in FIG. 20.

In another embodiment, a DHDR molecule of the present invention is identified based on the presence of a "shikimate 5-dehydrogenase domain" in the protein or corresponding nucleic acid molecule. As used herein, the term "shikimate 5-dehydrogenase domain" includes a protein domain having an amino acid sequence of about 10-100 amino acid residues and having a bit score for the alignment of the sequence to the shikimate 5-dehydrogenase domain of at least 86. Preferably, a shikimate 5-dehydrogenase domain includes at least about 25-75, or more preferably about 48 amino acid residues, and has a bit score for the alignment of the sequence to the shikimate 5-dehydrogenase domain of at least 20, 25, 30, 35, 40, 45, 50, 55, 60, 65, 70, 75, 80 or higher. The shikimate 5-dehydrogenase domain has been assigned ProDom entry 95301. To identify the presence of a shikimate 5-dehydrogenase domain in a DHDR protein, and to make the determination that a protein of interest has a particular profile, the amino acid sequence of the protein is searched against a database of known protein domains (e.g., the ProDom database) using the default parameters (available online through the ProDom website). A search was performed against the ProDom database resulting in the identification of a shikimate 5-dehydrogenase domain in the amino acid sequence of human DHDR-4 (SEQ ID NO:11) at about residues 35-82 of SEQ ID NO:11. The results of the search are set forth in FIGS. 21A-21B.

In another embodiment, a DHDR molecule of the present invention is identified based on the presence of a "dehydrogenase domain" in the protein or corresponding nucleic acid molecule. As used herein, the term "dehydrogenase domain" includes a protein domain having an amino acid sequence of about 10-100 amino acid residues and having a bit score for the alignment of the sequence to the dehydrogenase domain of at least 84. Preferably, a dehydrogenase domain includes at least about 25-75, or more preferably about 50 amino acid residues, and has a bit score for the alignment of the sequence to the dehydrogenase domain of at least 20, 25, 30, 35, 40, 45, 50, 55, 60, 65, 70, 75, 80 or higher. The dehydrogenase domain has been assigned ProDom entry 73753. To identify the presence of a dehydrogenase domain in a DHDR protein, and to make the determination that a protein of interest has a particular profile, the amino acid sequence of the protein is searched against a database of known protein domains (e.g., the ProDom database) using the default parameters (available online through the ProDom website). A search was performed against the ProDom database resulting in the identification of a dehydrogenase domain in the amino acid sequence of human DHDR-4 (SEQ ID NO:11) at about residues 237-286 of SEQ ID NO:11. The results of the search are set forth in FIGS. 21A-21B.

In another embodiment, a DHDR molecule of the present invention is identified based on the presence of a "glucose-1-dehydrogenase domain" in the protein or corresponding nucleic acid molecule. As used herein, the term "glucose-1-dehydrogenase domain" includes a protein domain having an amino acid sequence of about 10-100 amino acid residues and having a bit score for the alignment of the sequence to the glucose-1-dehydrogenase domain of at least 92. Preferably, a dehydrogenase domain includes at least about 25-75, or more preferably about 45 amino acid residues, and has a bit score for the alignment of the sequence to the dehydrogenase domain of at least 20, 25, 30, 35, 40, 45, 50, 55, 60, 65, 70, 75, 80, 85, 90 or higher. The glucose-1-dehydrogenase domain has been assigned ProDom entry 77223. To identify the presence of a glucose-1-dehydrogenase domain in a DHDR protein, and to make the determination that a protein of interest has a particular profile, the amino acid sequence of the protein is searched against a database of known protein domains (e.g., the ProDom database) using the default parameters (available online through the ProDom website). A search was performed against the ProDom database resulting in the identification of a dehydrogenase domain in the amino acid sequence of human DHDR-4 (SEQ ID NO:11) at about residues 243-287 of SEQ ID NO:11. The results of the search are set forth in FIGS. 21A-21B.

In a preferred embodiment, the DHDR molecules of the invention include at least one or more of the following domains: a transmembrane domain, a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, and a glucose-1-dehydrogenase domain.

Isolated proteins of the present invention, preferably DHDR proteins, have an amino acid sequence sufficiently identical to the amino acid sequence of SEQ ID NO:2, 5, 8, 11, or 15, or are encoded by a nucleotide sequence sufficiently identical to SEQ ID NO:1, 3, 4, 6, 7, 9, 10, 12, 14, or 16. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70%-80%, or 90-95% homology and share a common functional activity are defined herein as sufficiently identical.

As used interchangeably herein, an "DHDR activity", "biological activity of DHDR" or "functional activity of DHDR", refers to an activity exerted by a DHDR protein, polypeptide or nucleic acid molecule on a DHDR responsive cell or tissue, or on a DHDR protein substrate, as determined in vivo, or in vitro, according to standard techniques. In one embodiment, a DHDR activity is a direct activity, such as an association with a DHDR-target molecule. As used herein, a "target molecule" or "binding partner" is a molecule with which a DHDR protein binds or interacts in nature, such that DHDR-mediated function is achieved. A DHDR target molecule can be a non-DHDR molecule or a DHDR protein or polypeptide of the present invention (e.g., NAD+, NADP+, or other cofactor). In an exemplary embodiment, a DHDR target molecule is a DHDR ligand (e.g., an alcohol, an aldehyde, a lipid, or a steroid (e.g., a glucocorticoid)). Alternatively, a DHDR activity is an indirect activity, such as a cellular signaling activity mediated by interaction of the DHDR protein with a DHDR ligand. The biological activities of DHDR are described herein. For example, the DHDR proteins of the present invention can have one or more of the following activities: 1) modulate metabolism and catabolism of biochemical-molecules necessary for energy production or storage, 2) modulate intra- or inter-cellular signaling, 3) modulate metabolism or catabolism of metabolically important biomolecules (e.g., glucocorticoids), 4) modulate detoxification of potentially harmful compounds, 5) modulate viral infection (e.g., by modulating viral gene expression), 6) act as a transcriptional cofactor for viral gene activation, 7) modulate viral activity, and/or 8) modulate cellular proliferation.

Accordingly, another embodiment of the invention features isolated DHDR proteins and polypeptides having a DHDR activity. Other preferred proteins are DHDR proteins having one or more of the following domains: a transmembrane domain, a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, or a glucose-1-dehydrogenase domain and, preferably, a DHDR activity.

Additional preferred proteins have at least one transmembrane domain, and one or more of a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, or a glucose-1-dehydrogenase domain, and are, preferably, encoded by a nucleic acid molecule having a nucleotide sequence which hybridizes under stringent hybridization conditions to a complement of a nucleic acid molecule comprising the nucleotide sequence of SEQ ID NO:1, 3, 4, 6, 7, 9, 10, 12, 14, or 16.

The nucleotide sequence of the isolated human DHDR-1 cDNA and the predicted amino acid sequence of the human DHDR-1 polypeptide are shown in FIGS. 1A-1C and in SEQ ID NOs:1 and 2, respectively. The nucleotide sequence of the isolated human DHDR-2 cDNA and the predicted amino acid sequence of the human DHDR-2 polypeptide are shown in FIGS. 6A-6B and in SEQ ID NOs:4 and 5, respectively. The nucleotide sequence of the isolated human DHDR-3 cDNA and the predicted amino acid sequence of the human DHDR-3 polypeptide are shown in FIGS. 11A-11B and in SEQ ID NOs:7 and 8 respectively. The nucleotide sequence of the isolated human DHDR-4 cDNA and the predicted amino acid sequence of the human DHDR-4 polypeptide are shown in FIG. 16 and in SEQ ID NOs:10 and 11, respectively. The nucleotide sequence of the isolated mouse DHDR-2 and the predicted amino acid sequence of the mouse DHDR-2 polypeptide are shown in FIGS. 31A and 31B, respectively, and in SEQ ID NOs:14 and 15, respectively.

The human DHDR-1 gene, which is approximately 2660 nucleotides in length, encodes a protein having a molecular weight of approximately 88.0 kD and which is approximately 802 amino acid residues in length. The human DHDR-2 gene, which is approximately 1379 nucleotides in length, encodes a protein having a molecular weight of approximately 34.2 kD and which is approximately 311 amino acid residues in length. The human DHDR-3 gene, which is approximately 1725 nucleotides in length, encodes a protein having a molecular weight of approximately 40.5 kD and which is approximately 369 amino acid residues in length. The human DHDR-4 gene, which is approximately 1209 nucleotides in length, encodes a protein having a molecular weight of approximately 35.4 kD and which is approximately 322 amino acid residues in length. The mouse DHDR-2 gene, which is approximately 1108 nucleotides in length, encodes a protein having a molecular weight of approximately 34.2 kD and which is approximately 311 amino acid residues in length.

Various aspects of the invention are described in further detail in the following subsections:

I. Isolated Nucleic Acid Molecules

One aspect of the invention pertains to isolated nucleic acid molecules that encode DHDR proteins or biologically active portions thereof, as well as nucleic acid fragments sufficient for use as hybridization probes to identify DHDR-encoding nucleic acid molecules (e.g., DHDR mRNA) and fragments for use as PCR primers for the amplification or mutation of DHDR nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated DHDR nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, 6, 7, 9, 10, 12, 14, or 16, or the nucleotide sequence of the DNA insert of the plasmid deposited with ATCC as Accession Number PTA-1845, or a portion thereof, can be isolated using standard molecular biology techniques and the sequence information provided herein. Using all or portion of the nucleic acid sequence of SEQ ID NO:1, 3, 4, 6, 7, 9, 10, 12, 14, or 16, or the nucleotide sequence of the DNA insert of the plasmid deposited with ATCC as Accession Number PTA-1845, as a hybridization probe, DHDR nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 3, 4, 6, 7, 9, 10, 12, 14, or 16, or the nucleotide sequence of the DNA insert of the plasmid deposited with ATCC as Accession Number PTA-1845 can be isolated by the polymerase chain reaction (PCR) using synthetic oligonucleotide primers designed based upon the sequence of SEQ ID NO:1, 3, 4, 6, 7, 9, 10, 12, 14, or 16, or the nucleotide sequence of the DNA insert of the plasmid deposited with ATCC as Accession Number PTA-1845.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to DHDR nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, 3, 4, 6, 7, 9, 10, 12, 14, or 16. This cDNA may comprise sequences encoding the human DHDR-1 protein (i.e., "the coding region", from nucleotides 63-2468), as well as 5' untranslated sequences (nucleotides 1-62) and 3' untranslated sequences (nucleotides 2469-2660) of SEQ ID NO:1. This cDNA may comprise sequences encoding the human DHDR-2 protein (i.e., "the coding region", from nucleotides 331-1263), as well as 5' untranslated sequences (nucleotides 1-330) and 3' untranslated sequences (nucleotides 1264-1379) of SEQ ID NO:4. This cDNA may comprise sequences encoding the human DHDR-3 protein (i.e., "the coding region", from nucleotides 281-1387), as well as 5' untranslated sequences (nucleotides 1-280) and 3' untranslated sequences (nucleotides 1388-1725) of SEQ ID NO:7. This cDNA may comprise sequences encoding the human DHDR-4 protein (i.e., "the coding region", from nucleotides 61-1026), as well as 5' untranslated sequences (nucleotides 1-60) and 3' untranslated sequences (nucleotides 1027-1209) of SEQ ID NO:10. This cDNA may comprise sequences encoding the mouse DHDR-2 protein (i.e., "the coding region", from nucleotides 102-1034), as well as 5' untranslated sequences (nucleotides 1-101) and 3' untranslated sequences (nucleotides 1035-1108) of SEQ ID NO:14. Alternatively, the nucleic acid molecule can comprise only the coding region of SEQ ID NO:1 (e.g., nucleotides 63-2468, corresponding to SEQ ID NO:3), only the coding region of SEQ ID NO:4 (e.g., nucleotides 331-1263, corresponding to SEQ ID NO:6), only the coding region of SEQ ID NO:7 (e.g., nucleotides 281-1387, corresponding to SEQ ID NO:9), only the coding region of SEQ ID NO:10 (e.g., nucleotides 61-1026, corresponding to SEQ ID NO:12), or only the coding region of SEQ ID NO:14 (e.g., nucleotides 102-1034, corresponding to SEQ ID NO:16).

In another preferred embodiment, an isolated nucleic acid molecule of the invention comprises a nucleic acid molecule which is a complement of the nucleotide sequence shown in SEQ ID NO:1, 3, 4, 6, 7, 9, 10, 12, 14, or 16, or the nucleotide sequence of the DNA insert of the plasmid deposited with ATCC as Accession Number PTA-1845 or a portion of any of these nucleotide sequences. A nucleic acid molecule which is complementary to the nucleotide sequence shown in SEQ ID NO:1, 3, 4, 6, 7, 9, 10, 12, 14, or 16, or the nucleotide sequence of the DNA insert of the plasmid deposited with ATCC as Accession Number PTA-1845 is one which is sufficiently complementary to the nucleotide sequence shown in SEQ ID NO:1, 3, 4, 6, 7, 9, 10, 12, 14, or 16, or the nucleotide sequence of the DNA insert of the plasmid deposited with ATCC as Accession Number PTA-1845 such that it can hybridize to the nucleotide sequence shown in SEQ ID NO:1, 3, 4, 6, 7, 9, 10, 12, 14, or 16, or the nucleotide sequence of the DNA insert of the plasmid deposited with ATCC as Accession Number PTA-1845 respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 89%, 90%, 95%, 96%, 97%, 98%, 99%, 99.1%, 99.2%, 99.3%, 99.4%, 99.5%, 99.6%, 99.7%, 99.8%, 99.9%, 99.99% or more identical to the entire length of the nucleotide sequence shown in SEQ ID NO:1, 3, 4, 6, 7, 9, 10, 12, 14, or 16, or the entire length of the nucleotide sequence of the DNA insert of the plasmid deposited with ATCC as Accession Number PTA-1845, or a portion of any of these nucleotide sequences.

Moreover, the nucleic acid molecule of the invention can comprise only a portion of the nucleic acid sequence of SEQ ID NO:1, 3, 4, 6, 7, 9, 10, 12, 14, or 16, or the nucleotide sequence of the DNA insert of the plasmid deposited with ATCC as Accession Number PTA-1845, for example, a fragment which can be used as a probe or primer or a fragment encoding a portion of a DHDR protein, e.g., a biologically active portion of a DHDR protein. The nucleotide sequences determined from the cloning of the DHDR-1, DHDR-2, DHDR-3, and DHDR-4 genes allow for the generation of probes and primers designed for use in identifying and/or cloning other DHDR family members, as well as DHDR homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 4, 6, 7, 9, 10, 12, 14, or 16, or the nucleotide sequence of the DNA insert of the plasmid deposited with ATCC as Accession Number PTA-1845, of an anti-sense sequence of SEQ ID NO:1, 3, 4, 6, 7, 9, 10, 12, 14, or 16, or the nucleotide sequence of the DNA insert of the plasmid deposited with ATCC as Accession Number PTA-1845, or of a naturally occurring allelic variant or mutant of SEQ ID NO:1, 3, 4, 6, 7, 9, 10, 12, 14, or 16, or the nucleotide sequence of the DNA insert of the plasmid deposited with ATCC as Accession Number PTA-1845. In one embodiment, a nucleic acid molecule of the present invention comprises a nucleotide sequence which is greater than 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000 or more nucleotides in length and hybridizes under stringent hybridization conditions to a nucleic acid molecule of SEQ ID NO:1, 3, 4, 6, 7, 9, 10, 12, 14, or 16, or the nucleotide sequence of the DNA insert of the plasmid deposited with ATCC as Accession Number PTA-1845.

Probes based on the DHDR nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a DHDR protein, such as by measuring a level of a DHDR-encoding nucleic acid in a sample of cells from a subject e.g., detecting DHDR mRNA levels or determining whether a genomic DHDR gene has been mutated or deleted.

A nucleic acid fragment encoding a "biologically active portion of a DHDR protein" can be prepared by isolating a portion of the nucleotide sequence of SEQ ID NO:1, 3, 4, 6, 7, 9, 10, 12, 14, or 16, or the nucleotide sequence of the DNA insert of the plasmid deposited with ATCC as Accession Number PTA-1845, which encodes a polypeptide having a DHDR biological activity (the biological activities of the DHDR proteins are described herein), expressing the encoded portion of the DHDR protein (e.g., by recombinant expression in vitro) and assessing the activity of the encoded portion of the DHDR protein.

The invention further encompasses nucleic acid molecules that differ from the nucleotide sequence shown in SEQ ID NO:1, 3, 4, 6, 7, 9, 10, 12, 14, or 16, or the nucleotide sequence of the DNA insert of the plasmid deposited with ATCC as Accession Number PTA-1845, due to degeneracy of the genetic code and thus encode the same DHDR proteins as those encoded by the nucleotide sequence shown in SEQ ID NO:1, 3, 4, 6, 7, 9, 10, 12, 14, or 16, or the nucleotide sequence of the DNA insert of the plasmid deposited with ATCC as Accession Number PTA-1845. In another embodiment, an isolated nucleic acid molecule of the invention has a nucleotide sequence encoding a protein having an amino acid sequence shown in SEQ ID NO:2, 5, 8, 11, or 15.

In addition to the DHDR nucleotide sequences shown in SEQ ID NO:1, 3, 4, 6, 7, 9, 10, 12, 14, or 16, or the nucleotide sequence of the DNA insert of the plasmid deposited with ATCC as Accession Number PTA-1845, it will be appreciated by those skilled in the art that DNA sequence polymorphisms that lead to changes in the amino acid sequences of the DHDR proteins may exist within a population (e.g., the human population). Such genetic polymorphism in the DHDR genes may exist among individuals within a population due to natural allelic variation. As used herein, the terms "gene" and "recombinant gene" refer to nucleic acid molecules which include an open reading frame encoding a DHDR protein, preferably a mammalian DHDR protein, and can further include non-coding regulatory sequences, and introns.

Allelic variants of DHDR include both functional and non-functional DHDR proteins. Functional allelic variants are naturally occurring amino acid sequence variants of the human DHDR protein that maintain the ability to bind a DHDR ligand or substrate and/or modulate cell proliferation and/or migration mechanisms. Functional allelic variants will typically contain only conservative substitution of one or more amino acids of SEQ ID NO:2, 5, 8, 11, or 15, or substitution, deletion or insertion of non-critical residues in non-critical regions of the protein.

Non-functional allelic variants are naturally occurring amino acid sequence variants of the human DHDR protein that do not have the ability to either bind a DHDR ligand and/or modulate any of the DHDR activities described herein. Non-functional allelic variants will typically contain a non-conservative substitution, a deletion, or insertion or premature truncation of the amino acid sequence of SEQ ID NO:2, 5, 8, 11, or 15, or a substitution, insertion or deletion in critical residues or critical regions of the protein.

The present invention further provides non-human orthologues of the human DHDR proteins. Orthologues of the human DHDR protein are proteins that are isolated from non-human organisms and possess the same DHDR ligand binding and/or modulation of membrane excitability activities of the human DHDR protein. Orthologues of the human DHDR protein can readily be identified as comprising an amino acid sequence that is substantially identical to SEQ ID NO:2, 5, 8, or 11 (e.g., the mouse DHDR-2 of SEQ ID NO:15).

Moreover, nucleic acid molecules encoding other DHDR family members and, thus, which have a nucleotide sequence which differs from the DHDR sequences of SEQ ID NO:1, 3, 4, 6, 7, 9, 10, 12, 14, or 16, or the nucleotide sequence of the DNA insert of the plasmid deposited with ATCC as Accession Number PTA-1845 are intended to be within the scope of the invention. For example, another DHDR cDNA can be identified based on the nucleotide sequence of human or mouse DHDR. Moreover, nucleic acid molecules encoding DHDR proteins from different species, and which, thus, have a nucleotide sequence which differs from the DHDR sequences of SEQ ID NO:1, 3, 4, 6, 7, 9, 10, 12, 14, or 16, or the nucleotide sequence of the DNA insert of the plasmid deposited with ATCC as Accession Number PTA-1845 are intended to be within the scope of the invention. For example, a mouse DHDR cDNA can be identified based on the nucleotide sequence of a human DHDR.

Nucleic acid molecules corresponding to natural allelic variants and homologues of the DHDR cDNAs of the invention can be isolated based on their homology to the DHDR nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the DHDR cDNAs of the invention can further be isolated by mapping to the same chromosome or locus as the DHDR gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 4, 6, 7, 9, 10, 12, 14, or 16, or the nucleotide sequence of the DNA insert of the plasmid deposited with ATCC as Accession Number PTA-1845. In other embodiment, the nucleic acid is at least 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.) = 2(\# \text{ of A+T bases}) + 4(\# \text{ of G+C bases})$. For hybrids between 18 and 49 base pairs in length, $T_m(° C.) = 81.5 + 16.6(\log_{10}[Na^+]) + 0.41(\% \text{ G+C}) - (600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81: 1991-1995), or alternatively 0.2×SSC, 1% SDS.

Preferably, an isolated nucleic acid molecule of the invention that hybridizes under stringent conditions to the sequence of SEQ ID NO:1, 3, 4, 6, 7, 9, 10, 12, 14, or 16, and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the DHDR sequences that may exist in the population, the skilled artisan will further appreciate that changes can be introduced by mutation into the nucleotide sequences of SEQ ID NO:1, 3, 4, 6, 7, 9, 10, 12, 14 or 16, or the nucleotide sequence of the DNA insert of the plasmid deposited with ATCC as Accession Number PTA-1845, thereby leading to changes in the amino acid sequence of the encoded DHDR proteins, without altering the functional ability of the DHDR proteins. For example, nucleotide substitutions leading to amino acid substitutions at "non-essential" amino acid residues can be made in the sequence of SEQ ID NO:1, 3, 4, 6, 7, 9, 10, 12, 14, or 16, or the nucleotide sequence of the DNA insert of the plasmid deposited with ATCC as Accession Number PTA-1845. A "non-essential" amino acid residue is a residue that can be altered from the wild-type sequence of DHDR (e.g., the sequence of SEQ ID NO:2, 5, 8, 11, or 15) without altering the biological activity, whereas an "essential" amino acid residue is required for biological activity. For example, amino acid residues that are conserved among the DHDR proteins of the present invention, e.g., those present in a transmembrane domain, are predicted to be particularly unamenable to alteration. Furthermore, additional amino acid residues that are conserved between the DHDR proteins of the present invention and other members of the DHDR family are not likely to be amenable to alteration.

Accordingly, another aspect of the invention pertains to nucleic acid molecules encoding DHDR proteins that contain changes in amino acid residues that are not essential for activity. Such DHDR proteins differ in amino acid sequence from SEQ ID NO:2, 5, 8, 11, or 15, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 89%, 90%, 95%, 96%, 97%, 98%, 99%, 99.1%, 92%, 99.2%, 99.3%, 99.4%, 99.5%, 99.6%, 99.7%, 99.8%, 99.9%, 99.99% or more identical to SEQ ID NO:2, 5, 8, 11, or 15.

An isolated nucleic acid molecule encoding a DHDR protein identical to the protein of SEQ ID NO:2, 5, 8, 11, or 15 can be created by introducing one or more nucleotide substitutions, additions or deletions into the nucleotide sequence of SEQ ID NO:1, 3, 4, 6, 7, 9, 10, 12, 14, or 16, or the nucleotide sequence of the DNA insert of the plasmid deposited with ATCC as Accession Number PTA-1845, such that one or more amino acid substitutions, additions or deletions are introduced into the encoded protein. Mutations can be introduced into SEQ ID NO:1, 3, 4, 6, 7, 9, 10, 12, 14, or 16, or the nucleotide sequence of the DNA insert of the plasmid deposited with ATCC as Accession Number PTA-1845 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a DHDR protein is preferably replaced with another amino acid residue from the same side chain family. Alternatively, in another embodiment, mutations can be introduced randomly along all or part of a DHDR coding sequence, such as by saturation mutagenesis, and the resultant mutants can be screened for DHDR biological activity to identify mutants that retain activity. Following mutagenesis of SEQ ID NO:1, 3, 4, 6, 7, 9, 10, 12, 14, or 16, or the nucleotide sequence of the DNA insert of the plasmid deposited with ATCC as Accession Number PTA-1845, the encoded protein can be expressed recombinantly and the activity of the protein can be determined.

In a preferred embodiment, a mutant DHDR protein can be assayed for the ability to metabolize or catabolize biochemical molecules necessary for energy production or storage, permit intra- or inter-cellular signaling, metabolize or catabolize metabolically important biomolecules, and to detoxify potentially harmful compounds.

In addition to the nucleic acid molecules encoding DHDR proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire DHDR coding strand, or to only a portion thereof. In one embodiment, an antisense nucleic acid molecule is antisense to a "coding region" of the coding strand of a nucleotide sequence encoding a DHDR. The term "coding region" refers to the region of the nucleotide sequence comprising codons which are translated into amino acid residues (e.g., the coding region of human DHDR corresponds to SEQ ID NO:3, 6, 9 or 12, and the coding region of mouse DHDR corresponds to SEQ ID NO:16). The coding region may or may not include a stop codon. In another embodiment, the antisense nucleic acid molecule is antisense to a "noncoding region" of the coding strand of a nucleotide sequence encoding DHDR. The term "noncoding region" refers to 5' and 3' sequences which flank the coding region that are not translated into amino acids (i.e., also referred to as 5' and 3' untranslated regions).

Given the coding strand sequences encoding DHDR disclosed herein (e.g., SEQ ID NO:3, 6, 9, 12, or 16), antisense nucleic acids of the invention can be designed according to the rules of Watson and Crick base pairing. The antisense nucleic acid molecule can be complementary to the entire coding region of DHDR mRNA, but more preferably is an oligonucleotide which is antisense to only a portion of the coding or noncoding region of DHDR mRNA. For example, the antisense oligonucleotide can be complementary to the region surrounding the translation start site of DHDR mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DHDR protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585-591)) can be used to catalytically cleave DHDR mRNA transcripts to thereby inhibit translation of DHDR mRNA. A ribozyme having specificity for a DHDR-encoding nucleic acid can be designed based upon the nucleotide sequence of a DHDR cDNA disclosed herein (i.e., SEQ ID NO:1, 3, 4, 6, 7, 9, 10, 12, 14, or 16, or the nucleotide sequence of the DNA insert of the plasmid deposited with ATCC as Accession Number PTA-1845). For example, a derivative of a *Tetrahymena* L-19 IVS RNA can be constructed in which the nucleotide sequence of the active site is complementary to the nucleotide sequence to be cleaved in a DHDR-encoding mRNA. See, e.g., Cech et al. U.S. Pat. No. 4,987,071; and Cech et al. U.S. Pat. No. 5,116, 742. Alternatively, DHDR mRNA can be used to select a catalytic RNA having a specific ribonuclease activity from a pool of RNA molecules. See, e.g., Bartel, D. and Szostak, J. W. (1993) *Science* 261:1411-1418.

Alternatively, DHDR gene expression can be inhibited by targeting nucleotide sequences complementary to the regulatory region of the DHDR (e.g., the DHDR promoter and/or enhancers; e.g., nucleotides 1-62 of SEQ ID NO:1, nucleotides 1-330 of SEQ ID NO:4, nucleotides 1-280 of SEQ ID NO:7, nucleotides 1-60 of SEQ ID NO:10, or nucleotides 1-101 of SEQ ID NO:14) to form triple helical structures that prevent transcription of the DHDR gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioessays* 14(12):807-15.

In yet another embodiment, the DHDR nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem.* 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670-675.

PNAs of DHDR nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of DHDR nucleic acid molecules can also be used in the analysis of single base pair mutations in a gene, (e.g., by PNA-directed PCR clamping); as 'artificial restriction enzymes' when used in combination with other enzymes, (e.g., Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of DHDR can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of DHDR nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) *Nucleic Acids Res.* 24 (17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acids Res.* 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Biotechniques* 6:958-976) or intercalating agents (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous DHDR gene within a cell line or microorganism may be modified by inserting a heterologous DNA regulatory element into the genome of a stable cell line or cloned microorganism such that the inserted regulatory element is operatively linked with the endogenous DHDR gene. For example, an endogenous DHDR gene which is normally "transcriptionally silent", i.e., a DHDR gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous DHDR gene may be activated by insertion of a promiscuous regulatory element that works across cell types.

A heterologous regulatory element may be inserted into a stable cell line or cloned microorganism, such that it is operatively linked with an endogenous DHDR gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated DHDR Proteins and Anti-DHDR Antibodies

One aspect of the invention pertains to isolated DHDR proteins, and biologically active portions thereof, as well as polypeptide fragments suitable for use as immunogens to raise anti-DHDR antibodies. In one embodiment, native DHDR proteins can be isolated from cells or tissue sources by an appropriate purification scheme using standard protein purification techniques. In another embodiment, DHDR proteins are produced by recombinant DNA techniques. Alternative to recombinant expression, a DHDR protein or polypeptide can be synthesized chemically using standard peptide synthesis techniques.

An "isolated" or "purified" protein or biologically active portion thereof is substantially free of cellular material or other contaminating proteins from the cell or tissue source from which the DHDR protein is derived, or substantially free from chemical precursors or other chemicals when chemically synthesized. The language "substantially free of cellular material" includes preparations of DHDR protein in which the protein is separated from cellular components of the cells from which it is isolated or recombinantly produced. In one embodiment, the language "substantially free of cellular material" includes preparations of DHDR protein having less than about 30% (by dry weight) of non-DHDR protein (also referred to herein as a "contaminating protein"), more preferably less than about 20% of non-DHDR protein, still more preferably less than about 10% of non-DHDR protein, and most preferably less than about 5% non-DHDR protein. When the DHDR protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of DHDR protein in which the protein is separated from chemical precursors or other chemicals which are involved in the synthesis of the protein. In one embodiment, the language "substantially free of chemical precursors or other chemicals" includes preparations of DHDR protein having less than about 30% (by dry weight) of chemical precursors or non-DHDR chemicals, more preferably less than about 20% chemical precursors or non-DHDR chemicals, still more preferably less than about 10% chemical precursors or non-DHDR chemicals, and most preferably less than about 5% chemical precursors or non-DHDR chemicals.

As used herein, a "biologically active portion" of a DHDR protein includes a fragment of a DHDR protein which participates in an interaction between a DHDR molecule and a non-DHDR molecule. Biologically active portions of a DHDR protein include peptides comprising amino acid sequences sufficiently identical to or derived from the amino acid sequence of the DHDR protein, e.g., the amino acid sequence shown in SEQ ID NO:2, 5, 8, 11, or 15, which include less amino acids than the full length DHDR proteins, and exhibit at least one activity of a DHDR protein. Typically, biologically active portions comprise a domain or motif with at least one activity of the DHDR protein, e.g., modulating membrane excitability. A biologically active portion of a DHDR protein can be a polypeptide which is, for example, 25, 50, 75, 100, 125, 150, 175, 200, 250, 300, 350, 400, 450, 500, 550, 600, 650, 700, 750, 800 or more amino acids in length. Biologically active portions of a DHDR protein can be used as targets for developing agents which modulate a DHDR mediated activity, e.g., a proliferative response.

In one embodiment, a biologically active portion of a DHDR protein comprises at least one transmembrane domain. It is to be understood that a preferred biologically active portion of a DHDR protein of the present invention may contain at least one transmembrane domain and one or more of the following domains: a signal peptide domain, an aldehyde dehydrogenase oxidoreductase domain, an aldehyde dehydrogenase family domain, a short chain dehydrogenase domain, an oxidoreductase protein dehydrogenase domain, a 3-beta hydroxysteroid dehydrogenase domain, a NAD-dependent epimerase/dehydratase domain, a short chain dehydrogenase/reductase domain, a shikimate 5-dehydrogenase domain, a dehydrogenase domain, or a glucose-1-dehydrogenase domain. Moreover, other biologically active portions, in which other regions of the protein are deleted, can be prepared by recombinant techniques and evaluated for one or more of the functional activities of a native DHDR protein.

In a preferred embodiment, the DHDR protein has an amino acid sequence shown in SEQ ID NO:2, 5, 8, 11, or 15. In other embodiments, the DHDR protein is substantially identical to SEQ ID NO:2, 5, 8, 11, or 15, and retains the functional activity of the protein of SEQ ID NO:2, 5, 8, 11, or 15, yet differs in amino acid sequence due to natural allelic variation or mutagenesis, as described in detail in subsection I above. Accordingly, in another embodiment, the DHDR protein is a protein which comprises an amino acid sequence at least about 50%, 55%, 60%, 65%, 70%, 75%, 80%, 85%, 90%, 92%, 95%, 96%, 97%, 98%, 99%, 99.1%, 99.2%, 99.3%, 99.4%, 99.5%, 99.6%, 99.7%, 99.8%, 99.9%, 99.99% or more identical to SEQ ID NO:2, 5, 8, 11, or 15.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the DHDR amino acid sequence of SEQ ID NO:2, 5, 8, 11, or 15 having, e.g., 400 amino acid residues, at least 120, preferably at least 160, more preferably at least 200, even more preferably at least 240, and even more preferably at least 270, 320, 360 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available online through the website of the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the website of the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11-17 (1988)) which has been incorporated into the ALIGN program (version 2.0 or 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to DHDR nucleic acid molecules of the invention. BLAST protein searches can be performed with the XBLAST program, score=100, wordlength=3 to obtain amino acid sequences homologous to DHDR protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. See the website of the National Center for Biotechnology Information.

The invention also provides DHDR chimeric or fusion proteins. As used herein, a DHDR "chimeric protein" or "fusion protein" comprises a DHDR polypeptide operatively linked to a non-DHDR polypeptide. An "DHDR polypeptide" refers to a polypeptide having an amino acid sequence corresponding to a DHDR molecule, whereas a "non-DHDR polypeptide" refers to a polypeptide having an amino acid sequence corresponding to a protein which is not substantially homologous to the DHDR protein, e.g., a protein which is different from the DHDR protein and which is derived from the same or a different organism. Within a DHDR fusion protein the DHDR polypeptide can correspond to all or a portion of a DHDR protein. In a preferred embodiment, a DHDR fusion protein comprises at least one biologically active portion of a DHDR protein. In another preferred embodiment, a DHDR fusion protein comprises at least two biologically active portions of a DHDR protein. Within the fusion protein, the term "operatively linked" is intended to indicate that the DHDR polypeptide and the non-DHDR polypeptide are fused in-frame to each other. The non-DHDR polypeptide can be fused to the N-terminus or C-terminus of the DHDR polypeptide.

For example, in one embodiment, the fusion protein is a GST-DHDR fusion protein in which the DHDR sequences are fused to the C-terminus of the GST sequences. Such fusion proteins can facilitate the purification of recombinant DHDR.

In another embodiment, the fusion protein is a DHDR protein containing a heterologous signal sequence at its N-terminus. In certain host cells (e.g., mammalian host cells), expression and/or secretion of DHDR can be increased through use of a heterologous signal sequence.

The DHDR fusion proteins of the invention can be incorporated into pharmaceutical compositions and administered to a subject in vivo. The DHDR fusion proteins can be used to affect the bioavailability of a DHDR substrate. Use of DHDR fusion proteins may be useful therapeutically for the treatment of disorders caused by, for example, (i) aberrant modification or mutation of a gene encoding a DHDR protein; (ii) mis-regulation of the DHDR gene; and (iii) aberrant post-translational modification of a DHDR protein.

Moreover, the DHDR-fusion proteins of the invention can be used as immunogens to produce anti-DHDR antibodies in a subject, to purify DHDR ligands and in screening assays to identify molecules which inhibit the interaction of DHDR with a DHDR substrate.

Preferably, a DHDR chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A DHDR-encoding nucleic acid can be cloned into such an expression vector such that the fusion moiety is linked in-frame to the DHDR protein.

The present invention also pertains to variants of the DHDR proteins which function as either DHDR agonists (mimetics) or as DHDR antagonists. Variants of the DHDR proteins can be generated by mutagenesis, e.g., discrete point mutation or truncation of a DHDR protein. An agonist of the DHDR proteins can retain substantially the same, or a subset, of the biological activities of the naturally occurring form of a DHDR protein. An antagonist of a DHDR protein can inhibit one or more of the activities of the naturally occurring form of the DHDR protein by, for example, competitively modulating a DHDR-mediated activity of a DHDR protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the DHDR protein.

In one embodiment, variants of a DHDR protein which function as either DHDR agonists (mimetics) or as DHDR antagonists can be identified by screening combinatorial libraries of mutants, e.g., truncation mutants, of a DHDR protein for DHDR protein agonist or antagonist activity. In one embodiment, a variegated library of DHDR variants is generated by combinatorial mutagenesis at the nucleic acid level and is encoded by a variegated gene library. A variegated library of DHDR variants can be produced by, for example, enzymatically ligating a mixture of synthetic oligonucleotides into gene sequences such that a degenerate set of potential DHDR sequences is expressible as individual polypeptides, or alternatively, as a set of larger fusion proteins (e.g., for phage display) containing the set of DHDR sequences therein. There are a variety of methods which can be used to produce libraries of potential DHDR variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DHDR sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477.

In addition, libraries of fragments of a DHDR protein coding sequence can be used to generate a variegated population of DHDR fragments for screening and subsequent selection of variants of a DHDR protein. In one embodiment, a library of coding sequence fragments can be generated by treating a double stranded PCR fragment of a DHDR coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the DHDR protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of DHDR proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify DHDR variants (Arkin and Youvan (1992) *Proc. Natl. Acad. Sci. USA* 89:7811-7815; Delagrave et al. (1993) *Protein Eng.* 6(3):327-331).

In one embodiment, cell based assays can be exploited to analyze a variegated DHDR library. For example, a library of expression vectors can be transfected into a cell line, e.g., a neuronal cell line, which ordinarily responds to a DHDR ligand in a particular DHDR ligand-dependent manner. The transfected cells are then contacted with a DHDR ligand and the effect of expression of the mutant on, e.g., membrane excitability of DHDR can be detected. Plasmid DNA can then be recovered from the cells which score for inhibition, or alternatively, potentiation of signaling by the DHDR ligand, and the individual clones further characterized.

An isolated DHDR protein, or a portion or fragment thereof, can be used as an immunogen to generate antibodies that bind DHDR using standard techniques for polyclonal and monoclonal antibody preparation. A full-length DHDR protein can be used or, alternatively, the invention provides antigenic peptide fragments of DHDR for use as immunogens. The antigenic peptide of DHDR comprises at least 8 amino acid residues of the amino acid sequence shown in SEQ ID NO:2, 5, 8, 11, or 15 and encompasses an epitope of DHDR such that an antibody raised against the peptide forms a specific immune complex with the DHDR protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of DHDR that are located on the surface of the protein, e.g., hydrophilic regions, as well as regions with high antigenicity (see, for example, FIGS. 2, 7, 12, and 18).

A DHDR immunogen typically is used to prepare antibodies by immunizing a suitable subject, (e.g., rabbit, goat, mouse or other mammal) with the immunogen. An appropriate immunogenic preparation can contain, for example, recombinantly expressed DHDR protein or a chemically synthesized DHDR polypeptide. The preparation can further include an adjuvant, such as Freund's complete or incomplete adjuvant, or similar immunostimulatory agent. Immunization of a suitable subject with an immunogenic DHDR preparation induces a polyclonal anti-DHDR antibody response.

Accordingly, another aspect of the invention pertains to anti-DHDR antibodies. The term "antibody" as used herein refers to immunoglobulin molecules and immunologically active portions of immunoglobulin molecules, i.e., molecules that contain an antigen binding site which specifically binds (immunoreacts with) an antigen, such as a DHDR. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind DHDR molecules. The term "monoclonal antibody" or "monoclonal antibody composition", as used herein, refers to a population of antibody molecules that contain only one species of an antigen binding site capable of immunoreacting with a particular epitope of DHDR. A monoclonal antibody composition thus typically displays a single binding affinity for a particular DHDR protein with which it immunoreacts.

Polyclonal anti-DHDR antibodies can be prepared as described above by immunizing a suitable subject with a DHDR immunogen. The anti-DHDR antibody titer in the immunized subject can be monitored over time by standard techniques, such as with an enzyme linked immunosorbent assay (ELISA) using immobilized DHDR. If desired, the antibody molecules directed against DHDR can be isolated from the mammal (e.g., from the blood) and further purified by well known techniques, such as protein A chromatography to obtain the IgG fraction. At an appropriate time after immunization, e.g., when the anti-DHDR antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol.*

Today 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a DHDR immunogen as described above, and the culture supernatants of the resulting hybridoma cells are screened to identify a hybridoma producing a monoclonal antibody that binds DHDR.

Any of the many well known protocols used for fusing lymphocytes and immortalized cell lines can be applied for the purpose of generating an anti-DHDR monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind DHDR, e.g., using a standard ELISA assay.

Alternative to preparing monoclonal antibody-secreting hybridomas, a monoclonal anti-DHDR antibody can be identified and isolated by screening a recombinant combinatorial immunoglobulin library (e.g., an antibody phage display library) with DHDR to thereby isolate immunoglobulin library members that bind DHDR. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-DHDR antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyen et al. (1988) *Science* 239:1534; and Beidler et al. (1988) *J. Immunol.* 141:4053-4060.

An anti-DHDR antibody (e.g., monoclonal antibody) can be used to isolate DHDR by standard techniques, such as affinity chromatography or immunoprecipitation. An anti-DHDR antibody can facilitate the purification of natural DHDR from cells and of recombinantly produced DHDR expressed in host cells. Moreover, an anti-DHDR antibody can be used to detect DHDR protein (e.g., in a cellular lysate or cell supernatant) in order to evaluate the abundance and pattern of expression of the DHDR protein. Anti-DHDR antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

II. Recombinant Expression Vectors and Host Cells

Another aspect of the invention pertains to vectors, preferably expression vectors, containing a nucleic acid encoding a DHDR protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., DHDR proteins, mutant forms of DHDR proteins, fusion proteins, and the like).

The recombinant expression vectors of the invention can be designed for expression of DHDR proteins in prokaryotic or eukaryotic cells. For example, DHDR proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in DHDR activity assays, (e.g., direct assays or competitive assays described in detail below), or to generate antibodies specific for DHDR proteins, for example. In a preferred embodiment, a DHDR fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al. (1990) *Methods Enzymol.* 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the DHDR expression vector is a yeast expression vector. Examples of vectors for expression in yeast *S. cerevisiae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (Invitrogen Corp, San Diego, Calif.).

Alternatively, DHDR proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to DHDR mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a DHDR nucleic acid molecule of the invention is introduced, e.g., a DHDR nucleic acid molecule within a recombinant expression vector or a DHDR nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a DHDR protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a DHDR protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a DHDR protein. Accordingly, the invention further provides methods for producing a DHDR protein using the host cells of the invention. In one embodiment, the method comprises culturing the host cell of the invention (into which a recombinant expression vector encoding a DHDR protein has been introduced) in a suitable medium such that a DHDR protein is produced. In another embodiment, the method further comprises isolating a DHDR protein from the medium or the host cell.

The host cells of the invention can also be used to produce non-human transgenic animals. For example, in one embodiment, a host cell of the invention is a fertilized oocyte or an embryonic stem cell into which DHDR-coding sequences have been introduced. Such host cells can then be used to create non-human transgenic animals in which exogenous DHDR sequences have been introduced into their genome or homologous recombinant animals in which endogenous DHDR sequences have been altered. Such animals are useful for studying the function and/or activity of a DHDR and for identifying and/or evaluating modulators of DHDR activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous DHDR gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a DHDR-encoding nucleic acid into the male pronuclei of a fertilized oocyte, e.g., by microinjection, retroviral infection, and allowing the oocyte to develop in a pseudopregnant female foster animal. The DHDR cDNA sequence of SEQ ID NO:1, SEQ ID NO:4, SEQ ID NO:7, SEQ ID NO:9, or SEQ ID NO:14 can be introduced as a transgene into the genome of a non-human animal. Alternatively, a nonhuman homologue of a human DHDR gene, such as a mouse or rat DHDR gene, can be used as a transgene. Alternatively, a DHDR gene homologue, such as another DHDR family member, can be isolated based on hybridization to the DHDR cDNA sequences of SEQ ID NO:1 or 3, SEQ ID NO:4 or 6, SEQ ID NO:7 or 9, SEQ ID NO:10 or 12, or SEQ ID NO:14 or 16, or the DNA insert of the plasmid deposited with ATCC as Accession Number PTA-1845 (described further in subsection I above) and used as a transgene. Intronic sequences and polyadenylation signals can also be included in the transgene to increase the efficiency of expression of the transgene. A tissue-specific regulatory sequence(s) can be operably linked to a DHDR transgene to direct expression of a DHDR protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a DHDR transgene in its genome and/or expression of DHDR mRNA in tissues or cells of the animals. A transgenic founder animal can then be used to breed additional animals carrying the transgene. Moreover, transgenic animals carrying a transgene encoding a DHDR protein can further be bred to other transgenic animals carrying other transgenes.

To create a homologous recombinant animal, a vector is prepared which contains at least a portion of a DHDR gene into which a deletion, addition or substitution has been introduced to thereby alter, e.g., functionally disrupt, the DHDR gene. The DHDR gene can be a human gene (e.g., the cDNA of SEQ ID NO:3, SEQ ID NO:6, SEQ ID NO:9 or SEQ ID NO:12), but more preferably, is a non-human homologue of a human DHDR gene (e.g., SEQ ID NO:16, or a cDNA isolated by stringent hybridization with the nucleotide sequence of SEQ ID NO:1, SEQ ID NO:4, SEQ ID NO:7 or SEQ ID NO:10). For example, a mouse DHDR gene can be used to construct a homologous recombination nucleic acid molecule, e.g., a vector, suitable for altering an endogenous DHDR gene in the mouse genome. In a preferred embodiment, the homologous recombination nucleic acid molecule is designed such that, upon homologous recombination, the endogenous DHDR gene is functionally disrupted (i.e., no longer encodes a functional protein; also referred to as a "knock out" vector). Alternatively, the homologous recombination nucleic acid molecule can be designed such that, upon homologous recombination, the endogenous DHDR gene is mutated or otherwise altered but still encodes functional protein (e.g., the upstream regulatory region can be altered to thereby alter the expression of the endogenous DHDR protein). In the homologous recombination nucleic acid molecule, the altered portion of the DHDR gene is flanked at its 5' and 3' ends by additional nucleic acid sequence of the DHDR gene to allow for homologous recombination to occur between the exogenous DHDR gene carried by the homologous recombination nucleic acid molecule and an endogenous DHDR gene in a cell, e.g., an embryonic stem cell. The additional flanking DHDR nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced DHDR gene has homologously recombined with the endogenous DHDR gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Curr. Opin. Biotechnol.* 2:823-829 and in PCT International Publication Nos. WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The DHDR nucleic acid molecules, fragments of DHDR proteins, and anti-DHDR antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a DHDR protein or an anti-DHDR antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating-plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention:

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of DHDR activity is administered in combination with other agents (e.g., a small molecule), or in conjunction with another, complementary treatment regime. For example, in one embodiment, a modulator of DHDR activity is used to treat DHDR associated disorder. Accordingly, modulation of DHDR activity may be used in conjunction with, for example, another agent used to treat the disorder (e.g., another agent used to treat a viral or cellular proliferation disorder).

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.* 62:119-58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a DHDR protein of the invention has one or more of the following activities: 1) it modulates metabolism or catabolism of biochemical molecules necessary for energy production or storage, 2) it modulates intra- or inter-cellular signaling, 3) it modulates metabolism or catabolism of metabolically important biomolecules (e.g., glucocorticoids), 4) it modulates detoxification of potentially harmful compounds, 5) it modulates viral infection (e.g., by modulating viral gene expression), 6) it acts as a transcriptional cofactor for viral gene activation, and/or 7) it modulates viral activity, 8) it modulates cellular proliferation.

The isolated nucleic acid molecules of the invention can be used, for example, to express DHDR protein (e.g., via a recombinant expression vector in a host cell in gene therapy applications), to detect DHDR mRNA (e.g., in a biological sample) or a genetic alteration in a DHDR gene, and to modulate DHDR activity, as described further below. The DHDR proteins can be used to treat disorders characterized by insufficient or excessive production of a DHDR substrate or production of DHDR inhibitors. In addition, the DHDR proteins can be used to screen for naturally occurring DHDR substrates, to screen for drugs or compounds which modulate DHDR activity, as well as to treat disorders characterized by insufficient or excessive production of DHDR protein or production of DHDR protein forms which have decreased, aberrant or unwanted activity compared to DHDR wild type protein (e.g., dehydrogenase-associated disorders, such as CNS disorders; cardiac disorders; muscular disorders; cellular growth, differentiation, or migration disorders; neurological disorders; immune disorders; hormonal disorders; and viral disorders. Moreover, the anti-DHDR antibodies of the invention can be used to detect and isolate DHDR proteins, regulate the bioavailability of DHDR proteins, and modulate DHDR activity.

A. Screening Assays:

The invention provides a method (also referred to herein as a "screening assay") for identifying modulators, e.g., candidate or test compounds or agents (e.g., peptides, peptidomimetics, small molecules or other drugs) which bind to DHDR proteins, have a stimulatory or inhibitory effect on, for example, DHDR expression or DHDR activity, or have a stimulatory or inhibitory effect on, for example, the expression or activity of DHDR substrate.

In one embodiment, the invention provides assays for screening candidate or test compounds which are substrates of a DHDR protein or polypeptide or biologically active portion thereof (e.g., aldehydes, alcohols, or steroids (e.g., glucocorticoids)). In another embodiment, the invention provides assays for screening candidate or test compounds which bind to or modulate the activity of a DHDR protein or polypeptide or biologically active portion thereof (e.g., cofactor or coenzyme analogs, or inhibitory molecules). The test compounds of the present invention can be obtained using any of the numerous approaches in combinatorial library methods known in the art, including: biological libraries; spatially addressable parallel solid phase or solution phase libraries;

synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.).

In one embodiment, an assay is a cell-based assay in which a cell which expresses a DHDR protein or biologically active portion thereof is contacted with a test compound and the ability of the test compound to modulate DHDR activity is determined. Determining the ability of the test compound to modulate DHDR activity can be accomplished by monitoring, for example, the production of one or more specific metabolites in a cell which expresses DHDR (see, e.g., Saada et al. (2000) *Biochem. Biophys. Res. Commun.* 269: 382-386). The cell, for example, can be of mammalian origin, e.g., a liver cell, a neuronal cell, or a thymus cell.

The ability of the test compound to modulate DHDR binding to a substrate (e.g., an alcohol, an aldehyde, or a steroid (e.g., a glucocorticoid)) or to bind to DHDR can also be determined. Determining the ability of the test compound to modulate DHDR binding to a substrate can be accomplished, for example, by coupling the DHDR substrate with a radioisotope or enzymatic label such that binding of the DHDR substrate to DHDR can be determined by detecting the labeled DHDR substrate in a complex. Alternatively, DHDR could be coupled with a radioisotope or enzymatic label to monitor the ability of a test compound to modulate DHDR binding to a DHDR substrate in a complex. Determining the ability of the test compound to bind DHDR can be accomplished, for example, by coupling the compound with a radioisotope or enzymatic label such that binding of the compound to DHDR can be determined by detecting the labeled DHDR compound in a complex. For example, compounds (e.g., DHDR substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a DHDR substrate) to interact with DHDR without the labeling of any of the interactants. For example, a microphysiometer can be used to detect the interaction of a compound with DHDR without the labeling of either the compound or the DHDR. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and DHDR.

In another embodiment, an assay is a cell-based assay comprising contacting a cell expressing a DHDR target molecule (e.g., a DHDR substrate) with a test compound and determining the ability of the test compound to modulate (e.g., stimulate or inhibit) the activity of the DHDR target molecule. Determining the ability of the test compound to modulate the activity of a DHDR target molecule can be accomplished, for example, by determining the ability of the DHDR protein to bind to or interact with the DHDR target molecule.

Determining the ability of the DHDR protein, or a biologically active fragment thereof, to bind to or interact with a DHDR target molecule can be accomplished by one of the methods described above for determining direct binding. In a preferred embodiment, determining the ability of the DHDR protein to bind to or interact with a DHDR target molecule can be accomplished by determining the activity of the target molecule. For example, the activity of the target molecule can be determined by detecting induction of a cellular response (i.e., changes in intracellular $K^+$ levels or induction of viral gene expression), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a DHDR protein or biologically active portion thereof is contacted with a test compound and the ability of the test compound to bind to the DHDR protein or biologically active portion thereof is determined. Preferred biologically active portions of the DHDR proteins to be used in assays of the present invention include fragments which participate in interactions with non-DHDR molecules, e.g., fragments with high surface probability scores (see, for example, FIGS. 2, 7, 12, and 18). Binding of the test compound to the DHDR protein can be determined either directly or indirectly as described above. In a preferred embodiment, the assay includes contacting the DHDR protein or biologically active portion thereof with a known compound which binds DHDR to form an assay mixture, contacting the assay mixture with a test compound, and determining the ability of the test compound to interact with a DHDR protein, wherein determining the ability of the test compound to interact with a DHDR protein comprises determining the ability of the test compound to preferentially bind to DHDR or biologically active portion thereof as compared to the known compound.

In another embodiment, the assay is a cell-free assay in which a DHDR protein or biologically active portion thereof is contacted with a test compound and the ability of the test compound to modulate (e.g., stimulate or inhibit) the activity of the DHDR protein or biologically active portion thereof is determined. Determining the ability of the test compound to modulate the activity of a DHDR protein can be accomplished, for example, by determining the ability of the DHDR protein to bind to a DHDR target molecule by one of the methods described above for determining direct binding. Determining the ability of the DHDR protein to bind to a DHDR target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr.*

*Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a DHDR protein can be accomplished by determining the ability of the DHDR protein to further modulate the activity of a downstream effector of a DHDR target molecule. For example, the activity of the effector molecule on an appropriate target can be determined or the binding of the effector to an appropriate target can be determined as previously described.

In yet another embodiment, the cell-free assay involves contacting a DHDR protein or biologically active portion thereof with a known compound which binds the DHDR protein to form an assay mixture, contacting the assay mixture with a test compound, and determining the ability of the test compound to interact with the DHDR protein, wherein determining the ability of the test compound to interact with the DHDR protein comprises determining the ability of the DHDR protein to preferentially bind to or catalyze the transfer of a hydride moiety to or from the target substrate.

In more than one embodiment of the above assay methods of the present invention, it may be desirable to immobilize either DHDR or its target molecule to facilitate separation of complexed from uncomplexed forms of one or both of the proteins, as well as to accommodate automation of the assay. Binding of a test compound to a DHDR protein, or interaction of a DHDR protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/DHDR fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or DHDR protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of DHDR binding or activity determined using standard techniques.

Other techniques for immobilizing proteins on matrices can also be used in the screening assays of the invention. For example, either a DHDR protein or a DHDR target molecule can be immobilized utilizing conjugation of biotin and streptavidin. Biotinylated DHDR protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with DHDR protein or target molecules but which do not interfere with binding of the DHDR protein to its target molecule can be derivatized to the wells of the plate, and unbound target or DHDR protein trapped in the wells by antibody conjugation. Methods for detecting such complexes, in addition to those described above for the GST-immobilized complexes, include immunodetection of complexes using antibodies reactive with the DHDR protein or target molecule, as well as enzyme-linked assays which rely on detecting an enzymatic activity associated with the DHDR protein or target molecule.

In another embodiment, modulators of DHDR expression are identified in a method wherein a cell is contacted with a candidate compound and the expression of DHDR mRNA or protein in the cell is determined. The level of expression of DHDR mRNA or protein in the presence of the candidate compound is compared to the level of expression of DHDR mRNA or protein in the absence of the candidate compound. The candidate compound can then be identified as a modulator of DHDR expression based on this comparison. For example, when expression of DHDR mRNA or protein is greater (statistically significantly greater) in the presence of the candidate compound than in its absence, the candidate compound is identified as a stimulator of DHDR mRNA or protein expression. Alternatively, when expression of DHDR mRNA or protein is less (statistically significantly less) in the presence of the candidate compound than in its absence, the candidate compound is identified as an inhibitor of DHDR mRNA or protein expression. The level of DHDR mRNA or protein expression in the cells can be determined by methods described herein for detecting DHDR mRNA or protein.

In yet another aspect of the invention, the DHDR proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with DHDR ("DHDR-binding proteins" or "DHDR-6-bp") and are involved in DHDR activity. Such DHDR-binding proteins are also likely to be involved in the propagation of signals by the DHDR proteins or DHDR targets as, for example, downstream elements of a DHDR-mediated signaling pathway. Alternatively, such DHDR-binding proteins are likely to be DHDR inhibitors.

The two-hybrid system is based on the modular nature of most transcription factors, which consist of separable DNA-binding and activation domains. Briefly, the assay utilizes two different DNA constructs. In one construct, the gene that codes for a DHDR protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a DHDR-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the DHDR protein.

In another aspect, the invention pertains to a combination of two or more of the assays described herein. For example, a modulating agent can be identified using a cell-based or a cell free assay, and the ability of the agent to modulate the activity of a DHDR protein can be confirmed in vivo, e.g., in an animal such as an animal model for cellular transformation and/or tumorigenesis or an animal model for viral infection.

There are many animal models for viral infection known in the art. For example, a transgenic mouse model for hepatitis B virus infection (HBV) (Guidotti, L. G. et al. (1995) *J. Virol.* 69:6158-6169) may be used. High-level viral gene expression is present in the liver and kidney tissues of these mice, and the hepatocytes of the mice replicate the virus at levels comparable to those in the infected livers of patients with chronic hepatitis.

Another mouse model for HBV infection that may be used includes the mouse model made by transplanting primary human hepatocytes into mice in a matrix under the kidney capsule along with administration of an agonistic antibody against c-Met (Ohashi, K. et al. (2000) *Nat. Med.* 6:327-331). These mice are susceptible to HBV infection. Additionally, they are susceptible to super-infection with hepatitis delta virus (HDV).

Other mouse models for HBV infection that may be used include the mice described in Babinet, C. et al. (1985) *Science* 230:1160-3; Lee, T.-H. et al. (1990) *J. Virol.* 64:5939-5947; Madden, C. R. et al. (2000) *J. Virol.* 74:5266-5272; Brown, J. J. et al. (2000) *Hepatology* 31:173-181; Larkin, J. (1999) *Nat. Med.* 5:907-912; and Araki, K. et al. (1989) *Proc. Natl. Acad. Sci. USA* 86:207-11.

Chronic HBV infection is a major risk factor for hepatocellular carcinoma (Beasley, R. P. (1988) *Cancer* 61:1942-1956; Slagle, B. et al. (1994) In *Viruses and cancer*, Minson, A. et al., eds., University of Cambridge, Cambridge, England 51:149-171), and mice transgenic for the HBV X gene have increased sensitivity to hepatocarcinogens (Slagle, B. L. et al. (1996) *Mol. Carcinog.* 15:261-269). The double transgenic mouse strain described in Madden et al. (supra) can be used to study the effects of test compounds identified by the screening methods of the invention in modulating HBV X-mediated hepatocarcinogen sensitivity. For example, the mice can be treated with a hepatocarcinogen and a test compound, and the effect of the test compound on the hepatocarcinogen-mediated mutation rate of the host DNA can be assayed by functional analysis of a bacteriophage lambda transgene. Briefly, DNA isolated from the livers of such treated mice can be packaged into lambda phage particles and used to infect *E. coli* bacteria. Mutation rates of the lambda particles (methods for determination of which are known in the art) are directly related to the HBV X-mediated host DNA mutation rates in response to the hepatorcarcinogen in the treated mice.

Other mouse models for HBV infection and HBV immunity that may be used include those made by transplanting human peripheral blood mononuclear cells (PBMC) from chronic HBV carriers and HBV-immunized donors, respectively, into lethally-irradiated Balb/c mice (Böcher, W. O. et al. (2000) *Hepatology* 31:480-487; Ilhan, E. et al. (1999) *Hepatology* 29:553-562). Such human/mouse radiation chimeras, called Trimera mice, may be used to study the effects of test compounds identified by the screening methods of the invention on human antibody and T cell responses to HBV infection in vivo (Marcus, H. et al. (1995) *Blood* 86:398-406; Reisner, Y. et al. (1998) *Trends Biotechnol.* 16:242-246; Segall, H. et al. (1996) *Blood* 88:721-730; Böcher, W. O. et al. (1999) *Immunology* 96:634-641).

The effects of a modulating agent on HBV infection can also be studied in other hepadnavirus animal models: the woodchuck hepatitis virus (WHV) model (Korba, B. E. et al. (2000) *Hepatology* 31:1165-1175; Cote, P. J. et al. (2000) *Hepatology* 31:190-200), the duck hepatitis B virus (DHBV) model (Le Guerhier, F. et al. (2000) *Antimicrob. Agents Chemother.* 44:111-122; Vickery, K. et al. (1999) *J. Med. Virol.* 58:19-25), and the chimpanzee and ground and tree squirrel models (Caselmann, W. H. (1994) *Antiviral Res.* 24:121-129).

While an animal model for hepatitis C virus (HCV) infection that adequately reproduces the characteristics of HCV infection in humans does not yet exist, there is an HCV Trimera mouse model (Dekel, B. et al. (1995) *J. Infect. Dis.* 172:25-30), and there are some mouse strains that are transgenic for certain HCV proteins, and thus, may be useful for testing compounds that can modulate DHDR activity in vivo (Pasquinelli, C. et al. (1997) *Hepatology* 25:719-727).

Other animal models for viral infection are also known in the art and may be used in the screening assays of the present invention. For example, there are many animal models for Epstein-Barr virus (EBV) associated lymphoproliferative disease. Such models have been made in rabbits, common marmosets (*Callithrix jacchus*), cottontop tamarins (*Saguinus oedipus oedipus*), rhesus monkeys, and the severe combined immunodeficient (SCID) mouse (Johannessen, I. and Crawford, D. H. (1999) *Rev. Med. Virol.* 9:263-77; Hayashi, K. and Akagi, T. (2000) *Path. Intenational* 50:85-97). The mouse γ-herpesvirus 68 infection model (Speck, S. H. and Virgin, H. W. (1999) *Curr. Opin. Microbiol.* 2:403-9; Virgin, H. W. and Speck, S. H. (1999) *Curr. Opin. Immunol.* 11:371-379) and the cotton rat model for measles virus infection (Niewiesk, S. (1999) *Immunol. Lett.* 65:47-50) present other examples of animal models that may be used in the methods of the invention. Macaques infected with live attenuated simian immunodeficiency virus (SIV) (Geretti, A. M. (1999) *Rev. Med. Virol.* 9:57-67; Almond, N. and Stott, J. (1999) *Immunol. Lett.* 66:167-170) as well as the chimpanzee HIV model (Murthy, K. K. et al. (1998) *AIDS Res. Hum. Retroviruses* 14 Suppl 3:S271-6) can be used as models for human immunodeficiency virus (HIV) infection.

Other examples of animal models that may be used in the methods of the invention include the transgenic mouse model for an AIDS-like disease (Renkema, H. G. and Saksela, K. (2000) *Front. Biosci.* 5:D268-83); the chicken model for lymphoma-inducing herpesviruses (Schat, K. A. and Xing, Z. (2000) *Dev. Comp. Immunol.* 24:201-21); and the mouse model of cytomegalovirus infection (Sweet, C. (1999) *FEMS Microbiol. Rev.* 23:457-82).

In another embodiment of the invention, the ability of the agent to modulate the activity of a DHDR protein can be tested in an animal such as an animal model for a cellular proliferation disorder, e.g., tumorigenesis. Animal based models for studying tumorigenesis in vivo are well known in the art (reviewed in Animal Models of Cancer Predisposition Syndromes, Hiai, H. and Hino, 0. (eds.) 1999, *Progress in Experimental Tumor Research*, Vol. 35; Clarke, A. R. (2000) *Carcinogenesis* 21:435-41) and include, for example, carcinogen-induced tumors (Rithidech, K. et al. (1999) *Mutat. Res.* 428:33-39; Miller, M. L. et al. (2000) *Environ. Mol. Mutagen.* 35:319-327), injection and/or transplantation of tumor cells into an animal, as well as animals bearing mutations in growth regulatory genes, for example, oncogenes (e.g., ras) (Arbeit, J. M. et al. (1993) *Am. J. Pathol.* 142:1187-1197; Sinn, E. et al. (1987) *Cell* 49:465-475; Thorgeirsson, SS et al. *Toxicol Lett* (2000) 112-113:553-555) and tumor suppressor genes (e.g., p53) (Vooijs, M. et al. (1999) *Oncogene* 18:5293-5303; Clark A. R. (1995) *Cancer Metast. Rev.* 14:125-148; Kumar, T. R. et al. (1995) *J. Intern. Med.* 238: 233-238; Donehower, L. A. et al. (1992) *Nature* 356215-221). Furthermore, experimental model systems are available for the study of, for example, ovarian cancer (Hamilton, T. C. et al. (1984) *Semin. Oncol.* 11:285-298; Rahman, N. A. et al. (1998) *Mol. Cell. Endocrinol.* 145:167-174; Beamer, W. G. et al. (1998) *Toxicol. Pathol.* 26:704-710), gastric cancer (Thompson, J. et al. (2000) *Int. J. Cancer* 86:863-869; Fodde, R. et al. (1999) *Cytogenet. Cell Genet.* 86:105-111), breast cancer (Li, M. et al. (2000) *Oncogene* 19:1010-1019; Green, J. E. et al. (2000) *Oncogene* 19:1020-1027), melanoma (Satyamoorthy, K. et al. (1999) *Cancer Metast. Rev.* 18:401-405), and prostate cancer (Shirai, T. et al. (2000) *Mutat. Res.* 462:219-226; Bostwick, D. G. et al. (2000) *Prostate* 43:286-294).

This invention further pertains to novel agents identified by the above-described screening assays. Accordingly, it is within the scope of this invention to further use an agent identified as described herein in an appropriate animal model, as described above. For example, an agent identified as described herein (e.g., a DHDR modulating agent, an antisense DHDR nucleic acid molecule, a DHDR-specific antibody, or a DHDR-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the DHDR nucleotide sequences, described herein, can be used to map the location of the DHDR genes on a chromosome. The mapping of the DHDR sequences to chromosomes is an important first step in correlating these sequences with genes associated with disease.

Briefly, DHDR genes can be mapped to chromosomes by preparing PCR primers (preferably 15-25 bp in length) from the DHDR nucleotide sequences. Computer analysis of the DHDR sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the DHDR sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the DHDR nucleotide sequences to design oligonucleotide primers, sublocalization can be achieved with panels of fragments from specific chromosomes. Other mapping strategies which can similarly be used to map a DHDR sequence to its chromosome include in situ hybridization (described in Fan, Y. et al. (1990) *Proc. Natl. Acad. Sci. USA* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the DHDR gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DHDR sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the DHDR nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The DHDR nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, or SEQ ID NO:10 can comfortably provide positive individual identification with a panel of perhaps 10 to 1,000 primers which each yield a noncoding amplified sequence of 100 bases. If predicted coding sequences, such as those in SEQ ID NO:3, 6, 9, or 12 are used, a more appropriate number of primers for positive individual identification would be 500-2,000.

If a panel of reagents from DHDR nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of DHDR Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, SEQ ID NO:7 or SEQ ID NO:10 are particularly appropriate for this use as greater numbers of polymorphisms occur in the noncoding regions, making it easier to differentiate individuals using this technique. Examples of polynucleotide reagents include the DHDR nucleotide sequences or portions thereof, e.g., fragments derived from the noncoding regions of SEQ ID NO:1, SEQ ID NO:4, SEQ ID NO:7 or SEQ ID NO:10 having a length of at least 20 bases, preferably at least 30 bases.

The DHDR nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such DHDR probes can be used to identify tissue by species and/or by organ type.

In a similar fashion, these reagents, e.g., DHDR primers or probes can be used to screen tissue culture for contamination (i.e., screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining DHDR protein and/or nucleic acid expression as well as DHDR activity, in the context of a biological sample (e.g., blood, serum, cells, tissue) to thereby determine whether an individual is afflicted with a disease or disorder, or is at risk of developing a disorder, associated with aberrant or unwanted DHDR expression or activity. The invention also provides for prognostic (or predictive) assays for determining whether an individual is at risk of developing a disorder associated with DHDR protein, nucleic acid expression or activity. For example, mutations in a DHDR gene can be assayed in a biological sample. Such assays can be used for prognostic or predictive purpose to thereby prophylactically treat an individual prior to the onset of a disorder characterized by or associated with DHDR protein, nucleic acid expression or activity.

Another aspect of the invention pertains to monitoring the influence of agents (e.g., drugs, compounds) on the expression or activity of DHDR in clinical trials.

These and other agents are described in further detail in the following sections.

1. Diagnostic Assays

An exemplary method for detecting the presence or absence of DHDR protein or nucleic acid in a biological sample involves obtaining a biological sample from a test subject and contacting the biological sample with a compound or an agent capable of detecting DHDR protein or nucleic acid (e.g., mRNA, or genomic DNA) that encodes DHDR protein such that the presence of DHDR protein or nucleic acid is detected in the biological sample. A preferred agent for detecting DHDR mRNA or genomic DNA is a labeled nucleic acid probe capable of hybridizing to DHDR mRNA or genomic DNA. The nucleic acid probe can be, for example, the DHDR nucleic acid set forth in SEQ ID NO:1, 3, 4, 6, 7, 9, 10, 12, 14, or 16, or the DNA insert of the plasmid deposited with ATCC as Accession Number PTA-1845, or a portion thereof, such as an oligonucleotide of at least 15, 30, 50, 100, 250 or 500 nucleotides in length and sufficient to specifically hybridize under stringent conditions to DHDR mRNA or genomic DNA. Other suitable probes for use in the diagnostic assays of the invention are described herein.

A preferred agent for detecting DHDR protein is an antibody capable of binding to DHDR protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect DHDR mRNA, protein, or genomic DNA in a biological sample in vitro as well as in vivo. For example, in vitro techniques for detection of DHDR mRNA include Northern hybridizations and in situ hybridizations. In vitro techniques for detection of DHDR protein include enzyme linked immunosorbent assays (ELISAs), Western blots, immunoprecipitations and immunofluorescence. In vitro techniques for detection of DHDR genomic DNA include Southern hybridizations. Furthermore, in vivo techniques for detection of DHDR protein include introducing into a subject a labeled anti-DHDR antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting DHDR protein, mRNA, or genomic DNA, such that the presence of DHDR protein, mRNA or genomic DNA is detected in the biological sample, and comparing the presence of DHDR protein, mRNA or genomic DNA in the control sample with the presence of DHDR protein, mRNA or genomic DNA in the test sample.

The invention also encompasses kits for detecting the presence of DHDR in a biological sample. For example, the kit can comprise a labeled compound or agent capable of detecting DHDR protein or mRNA in a biological sample; means for determining the amount of DHDR in the sample; and means for comparing the amount of DHDR in the sample with a standard. The compound or agent can be packaged in a suitable container. The kit can further comprise instructions for using the kit to detect DHDR protein or nucleic acid.

2. Prognostic Assays

The diagnostic methods described herein can furthermore be utilized to identify subjects having or at risk of developing a disease or disorder associated with aberrant or unwanted DHDR expression or activity. As used herein, the term "aberrant" includes a DHDR expression or activity which deviates from the wild type DHDR expression or activity. Aberrant expression or activity includes increased or decreased expression or activity, as well as expression or activity which does not follow the wild type developmental pattern of expression or the subcellular pattern of expression. For example, aberrant DHDR expression or activity is intended to include the cases in which a mutation in the DHDR gene causes the DHDR gene to be under-expressed or over-expressed and situations in which such mutations result in a non-functional DHDR protein or a protein which does not function in a wild-type fashion, e.g., a protein which does not interact with a DHDR substrate, or one which interacts with a non-DHDR substrate. As used herein, the term "unwanted" includes an unwanted phenomenon involved in a biological response such as cellular proliferation. For example, the term unwanted includes a DHDR expression or activity which is undesirable in a subject.

The assays described herein, such as the preceding diagnostic assays or the following assays, can be utilized to identify a subject having or at risk of developing a disorder associated with a misregulation in DHDR protein activity or nucleic acid expression, such as a CNS disorder (e.g., a cognitive or neurodegenerative disorder), a cellular proliferation, growth, differentiation, or migration disorder, a cardiovascular disorder, musculoskeletal disorder, an immune disorder, a viral disorder, or a hormonal disorder. Alternatively, the prognostic assays can be utilized to identify a subject having or at risk for developing a disorder associated with a misregulation in DHDR protein activity or nucleic acid expression, such as a CNS disorder, a cellular proliferation, growth, differentiation, or migration disorder, a musculoskeletal disorder, a cardiovascular disorder, an immune disorder, a viral disorder, or a hormonal disorder. Thus, the present invention provides a method for identifying a disease or disorder associated with aberrant or unwanted DHDR expression or activity in which a test sample is obtained from a subject and DHDR protein or nucleic acid (e.g., mRNA or genomic DNA) is detected, wherein the presence of DHDR protein or nucleic acid is diagnostic for a subject having or at risk of developing a disease or disorder associated with aberrant or unwanted DHDR expression or activity. As used herein, a "test sample" refers to a biological sample obtained from a subject of interest. For example, a test sample can be a biological fluid (e.g., cerebrospinal fluid or serum), cell sample, or tissue sample (e.g., a liver sample).

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted DHDR expression or activity. For example, such methods can be used to determine whether a subject can be effectively treated with an agent for a CNS disorder, a muscular disorder, a cellular proliferation, growth, differentiation, or migration disorder, an immune disorder, a viral disorder, or a hormonal disorder. Thus, the present invention provides methods for determining whether a subject can be effectively treated with an agent for a disorder associated with aberrant or unwanted DHDR expression or activity in which a test sample is obtained and DHDR protein or nucleic acid expression or activity is detected (e.g., wherein the abundance of DHDR protein or nucleic acid expression or activity is diagnostic for a subject that can be administered the agent to treat a disorder associated with aberrant or unwanted DHDR expression or activity).

The methods of the invention can also be used to detect genetic alterations in a DHDR gene, thereby determining if a subject with the altered gene is at risk for a disorder characterized by misregulation in DHDR protein activity or nucleic acid expression, such as a CNS disorder, a musculoskeletal disorder, a cellular proliferation, growth, differentiation, or migration disorder, a cardiovascular disorder, an immune disorder, a viral disorder, or a hormonal disorder. In preferred embodiments, the methods include detecting, in a sample of cells from the subject, the presence or absence of a genetic alteration characterized by at least one of an alteration affecting the integrity of a gene encoding a DHDR-protein, or the mis-expression of the DHDR gene. For example, such genetic alterations can be detected by ascertaining the existence of at least one of 1) a deletion of one or more nucleotides from a DHDR gene; 2) an addition of one or more nucleotides to a DHDR gene; 3) a substitution of one or more nucleotides of a DHDR gene, 4) a chromosomal rearrangement of a DHDR gene; 5) an alteration in the level of a messenger RNA transcript of a DHDR gene, 6) aberrant modification of a DHDR gene, such as of the methylation pattern of the genomic DNA, 7) the presence of a non-wild type splicing pattern of a messenger RNA transcript of a DHDR gene, 8) a non-wild type level of a DHDR-protein, 9) allelic loss of a DHDR gene, and 10) inappropriate post-translational modification of a DHDR-protein. As described herein, there are a large number of assays known in the art which can be used for detecting alterations in a DHDR gene. A preferred biological sample is a tissue (e.g., a liver sample) or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in a DHDR gene (see Abravaya et al. (1995) *Nucleic Acids Res.* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a DHDR gene under conditions such that hybridization and amplification of the DHDR gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DHDR gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in DHDR can be identified by hybridizing a sample and control nucleic acids, e.g., DNA or RNA, to high density arrays containing hundreds or thousands of oligonucleotides probes (Cronin, M. T. et al. (1996) *Hum. Mutat.* 7:244-255; Kozal, M. J. et al. (1996) *Nat. Med.* 2:753-759). For example, genetic mutations in DHDR can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DHDR gene and detect mutations by comparing the sequence of the sample DHDR with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the DHDR gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type DHDR sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA*

85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in DHDR cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a DHDR sequence, e.g., a wild-type DHDR sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in DHDR genes. For example, single strand conformation polymorphism (SSCP) may be used to detect differences in electrophoretic mobility between mutant and wild type nucleic acids (Orita et al. (1989) *Proc Natl. Acad. Sci USA*:86:2766, see also Cotton (1993) *Mutat. Res.* 285:125-144; and Hayashi (1992) *Genet. Anal. Tech. Appl.* 9:73-79). Single-stranded DNA fragments of sample and control DHDR nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DHDR gene.

Furthermore, any cell type or tissue in which DHDR is expressed may be utilized in the prognostic assays described herein.

3. Monitoring of Effects During Clinical Trials

Monitoring the influence of agents (e.g., drugs) on the expression or activity of a DHDR protein (e.g., the modulation of a virus activity and/or the modulation of cell proliferation and/or migration) can be applied not only in basic drug screening, but also in clinical trials. For example, the effectiveness of an agent determined by a screening assay as described herein to increase DHDR gene expression, protein levels, or upregulate DHDR activity, can be monitored in clinical trials of subjects exhibiting decreased DHDR gene expression, protein levels, or downregulated DHDR activity. Alternatively, the effectiveness of an agent determined by a screening assay to decrease DHDR gene expression, protein levels, or downregulate DHDR activity, can be monitored in clinical trials of subjects exhibiting increased DHDR gene expression, protein levels, or upregulated DHDR activity. In such clinical trials, the expression or activity of a DHDR gene, and preferably, other genes that have been implicated in, for example, a DHDR-associated disorder can be used as a "read out" or markers of the phenotype of a particular cell.

For example, and not by way of limitation, genes, including DHDR, that are modulated in cells by treatment with an agent (e.g., compound, drug or small molecule) which modulates DHDR activity (e.g., identified in a screening assay as described herein) can be identified. Thus, to study the effect of agents on DHDR-associated disorders (e.g., disorders characterized by viral infection and/or deregulated cell proliferation and/or migration), for example, in a clinical trial, cells can be isolated and RNA prepared and analyzed for the levels of expression of DHDR and other genes implicated in the DHDR-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of DHDR or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug-candidate identified by the screening assays described herein) including the steps of (i) obtaining a pre-administration sample from a subject prior to administration of the agent; (ii) detecting the level of expression of a DHDR protein, mRNA, or genomic DNA in the preadministration sample; (iii) obtaining one or more post-administration samples from the subject; (iv) detecting the level of expression or activity of the DHDR protein, mRNA, or genomic DNA in the post-administration samples; (v) comparing the level of expression or activity of the DHDR protein, mRNA, or genomic DNA in the pre-administration sample with the DHDR protein, mRNA, or genomic DNA in the post administration sample or samples; and (vi) altering the administration of the agent to the subject accordingly. For example, increased administration of the agent may be desirable to increase the expression or activity of DHDR to higher levels than detected, i.e., to increase the effectiveness of the agent. Alternatively, decreased administration of the agent may be desirable to decrease expression or activity of DHDR to lower levels than detected, i.e., to decrease the effectiveness of the agent. According to such an embodiment, DHDR expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted DHDR expression or activity, e.g., a dehydrogenase-associated disorder such as a CNS disorder; a cellular proliferation, growth, differentiation, or migration disorder; a, musculoskeletal disorder; a cardiovascular disorder; an immune disorder; a viral disorder; or a hormonal disorder. As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the DHDR molecules of the present invention or DHDR modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted DHDR expression or activity, by administering to the subject a DHDR or an agent which modulates DHDR expression or at least one DHDR activity. Subjects at risk for a disease which is caused or contributed to by aberrant or unwanted DHDR expression or activity can be identified by, for example, any or a combination of diagnostic or prognostic assays as described herein. Administration of a prophylactic agent can occur prior to the manifestation of symptoms characteristic of the DHDR aberrancy, such that a disease or disorder is prevented or, alternatively, delayed in its progression. Depending on the type of DHDR aberrancy, for example, a DHDR, DHDR agonist or DHDR antagonist agent can be used for treating the subject. The appropriate agent can be determined based on screening assays described herein.

2. Therapeutic Methods

Another aspect of the invention pertains to methods of modulating DHDR expression or activity for therapeutic purposes. Accordingly, in an exemplary embodiment, the modulatory method of the invention involves contacting a cell with a DHDR or agent that modulates one or more of the activities of DHDR protein activity associated with the cell. An agent that modulates DHDR protein activity can be an agent as described herein, such as a nucleic acid or a protein, a naturally-occurring target molecule of a DHDR protein (e.g., a DHDR substrate), a DHDR antibody, a DHDR agonist or antagonist, a peptidomimetic of a DHDR agonist or antagonist, or other small molecule. In one embodiment, the agent stimulates one or more DHDR activities. Examples of such stimulatory agents include active DHDR protein and a nucleic acid molecule encoding DHDR that has been introduced into the cell. In another embodiment, the agent inhibits one or more DHDR activities. Examples of such inhibitory agents include antisense DHDR nucleic acid molecules, anti-DHDR antibodies, and DHDR inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a DHDR protein or nucleic acid molecule. In one embodiment, the method involves administering an agent (e.g., an agent identified by a screening assay described herein), or combination of agents that modulates (e.g., upregulates or downregulates) DHDR expression or activity. In another embodiment, the method involves administering a DHDR protein or nucleic acid molecule as therapy to compensate for reduced, aberrant, or unwanted DHDR expression or activity.

Stimulation of DHDR activity is desirable in situations in which DHDR is abnormally downregulated and/or in which increased DHDR activity is likely to have a beneficial effect. Likewise, inhibition of DHDR activity is desirable in situations in which DHDR is abnormally upregulated and/or in which decreased DHDR activity is likely to have a beneficial effect.

3. Pharmacogenomics

The DHDR molecules of the present invention, as well as agents, or modulators which have a stimulatory or inhibitory effect on DHDR activity (e.g., DHDR gene expression) as identified by a screening assay described herein can be administered to individuals to treat (prophylactically or therapeutically) DHDR-associated disorders (e.g., proliferative disorders, CNS disorders, cardiac disorders, metabolic disorders, or muscular disorders) associated with aberrant or unwanted DHDR activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a DHDR molecule or DHDR modulator as well as tailoring the dosage and/or therapeutic regimen of treatment with a DHDR molecule or DHDR modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11):983-985 and Linder, M. W. et al. (1997) Clin. Chem. 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a DHDR protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a DHDR molecule or DHDR modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a DHDR molecule or DHDR modulator, such as a modulator identified by one of the exemplary screening assays described herein.

E. Electronic Apparatus Readable Media and Arrays

Electronic apparatus readable media comprising DHDR sequence information is also provided. As used herein, "DHDR sequence information" refers to any nucleotide and/or amino acid sequence information particular to the DHDR molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said DHDR sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding, or containing data or information that can be read and accessed directly by an electronic apparatus. Such media can include, but are not limited to: magnetic storage media, such as floppy discs, hard disc storage medium, and magnetic tape; optical storage media such as compact discs; electronic storage media such as RAM, ROM, EPROM, EEPROM and the like; and general hard disks and hybrids of these categories such as magnetic/optical storage media. The medium is adapted or configured for having recorded thereon DHDR sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatuses; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the DHDR sequence information.

A variety of software programs and formats can be used to store the sequence information on the electronic apparatus readable medium. For example, the sequence information can be represented in a word processing text file, formatted in commercially-available software such as WordPerfect and Microsoft Word, represented in the form of an ASCII file, or stored in a database application, such as DB2, Sybase, Oracle, or the like, as well as in other forms. Any number of dataprocessor structuring formats (e.g., text file or database) may be employed in order to obtain or create a medium having recorded thereon the DHDR sequence information.

By providing DHDR sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a DHDR associated disease or disorder or a pre-disposition to a DHDR associated disease or disorder, wherein the method comprises the steps of determining DHDR sequence information associated with the subject and based on the DHDR sequence information, determining whether the subject has a DHDR associated disease or disorder or a pre-disposition to a DHDR associated disease or disorder, and/or recommending a particular treatment for the disease, disorder, or pre-disease condition.

The present invention further provides in an electronic system and/or in a network, a method for determining whether a subject has a DHDR associated disease or disorder or a pre-disposition to a disease associated with DHDR wherein the method comprises the steps of determining DHDR sequence information associated with the subject, and based on the DHDR sequence information, determining whether the subject has a DHDR associated disease or disorder or a pre-disposition to a DHDR associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a DHDR associated disease or disorder or a pre-disposition to a DHDR associated disease or disorder associated with DHDR, said method comprising the steps of receiving DHDR sequence information from the subject and/or information related thereto, receiving phenotypic information associated with the subject, acquiring information from the network corresponding to DHDR and/or a DHDR associated disease or disorder, and based on one or more of the phenotypic information, the DHDR information (e.g., sequence information and/or information related thereto), and the acquired information, determining whether the subject has a DHDR associated disease or disorder or a pre-disposition to a DHDR associated disease or disorder. The method may further comprise the step of recommending a particular treatment for the disease, disorder or pre-disease condition.

The present invention also provides a business method for determining whether a subject has a DHDR associated disease or disorder or a pre-disposition to a DHDR associated disease or disorder, said method comprising the steps of receiving information related to DHDR (e.g., sequence information and/or information related thereto), receiving phenotypic information associated with the subject, acquiring information from the network related to DHDR and/or related to a DHDR associated disease or disorder, and based on one or more of the phenotypic information, the DHDR information, and the acquired information, determining whether the subject has a DHDR associated disease or disorder or a pre-disposition to a DHDR associated disease or disorder. The method may further comprise the step of recommending a particular treatment for the disease, disorder or pre-disease condition.

The invention also includes an array comprising a DHDR sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be DHDR. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a DHDR associated disease or disorder, progression of DHDR associated disease or disorder, and processes, such a cellular transformation associated with the DHDR associated disease or disorder.

The array is also useful for ascertaining the effect of the expression of a gene on the expression of other genes in the same cell or in different cells (e.g., ascertaining the effect of DHDR expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including DHDR) that could serve as a molecular target for diagnosis or therapeutic intervention.

This invention is further illustrated by the following examples which should not be construed as limiting. The contents of all references, patents, and published patent applications cited throughout this application, as well as the figures and the sequence listing, are incorporated herein by reference.

EXAMPLES

Example 1

Identification and Characterization of Human and Mouse DHDR cDNA

In this example, the identification and characterization of the genes encoding human DHDR-1 (clone Fbh32142), DHDR-2 (clone Fbh21481), DHDR-3 (clone Fbh25964), and DHDR-4 (clone Fbh21686), and mouse DHDR-2 (clone m21481) is described.

Isolation of the DHDR cDNA

The invention is based, at least in part, on the discovery of several human and mouse genes encoding novel proteins, referred to herein as DHDR-1, DHDR-2, DHDR-3 and DHDR-4. The entire sequences of human clones Fbh32142, Fbh21481, Fbh25964, and Fbh21686, and mouse clone m21481 were determined and found to contain open reading frames termed human "DHDR-1", "DHDR-2", "DHDR-3", and "DHDR-4", and mouse "DHDR-2", respectively, set forth in FIGS. 1A-1C, 6A-6B, 11A-11B, 16, and 31A, respectively. The amino acid sequences of these human and mouse DHDR expression products are set forth in FIGS. 1A-1C, 6A-6B, 11A-11B, 16, and 31B, respectively. The human DHDR-1 protein sequence set forth in SEQ ID NO:2 comprises about 802 amino acid residues and is shown in FIGS. 1A-1C. The human DHDR-2 protein sequence set forth in SEQ ID NO:5 comprises about 311 amino acid residues and is shown in FIGS. 6A-6B. The human DHDR-3 protein sequence set forth in SEQ ID NO:8 comprises about 369 amino acid residues and is shown in FIGS. 11A-11B. The human DHDR-4 protein sequence set forth in SEQ ID NO:11 comprises about 322 amino acid residues and is shown in FIG. 16. The mouse DHDR-2 protein set forth in SEQ ID NO:15 comprises about 311 amino acid residues and is shown in FIG. 31B. The coding regions (open reading frames) of SEQ ID NOs:1, 4, 7, 10, and 14 are set forth as SEQ ID NOs:3, 6, 9, 12, and 16.

Analysis of the Human and Mouse DHDR Molecules

The amino acid sequences of human DHDR-1, DHDR-2, DHDR-3, and DHDR-4 were analyzed using the program PSORT (available online through the PSORT server website) to predict the localization of the proteins within the cell. This program assesses the presence of different targeting and localization amino acid sequences within the query sequence. The results of the analyses show that human DHDR-1 (SEQ ID NO:2) may be localized to the mitochondrion, to the endoplasmic reticulum, to the nucleus, or to secretory vesicles. The results of the analyses further show that human DHDR-2 (SEQ ID NO:5) may be localized to the mitochondrion, to the cytoplasm, to extracellular spaces or the cell wall, to vacuoles, to the nucleus, or to the endoplasmic reticulum. The results of the analyses further show that human DHDR-3 (SEQ ID NO:8) may be localized to the cytoplasm, to the mitochondrion, to the Golgi, to the endoplasmic reticulum, to the extracellular space or cell wall, to vacuoles, to the nucleus, or to secretory vesicles. The results of the analyses further show that human DHDR-4 (SEQ ID NO:11) may be localized to the nucleus, the cytoplasm, to the Golgi, to the mitochondrion, to peroxisomes, to the endoplasmic reticulum, or to secretory vesicles.

An alignment of the human DHDR-4 amino acid sequence with the amino acid sequence of *Rattus norvegicus* putative short-chain dehydrogenase/reductase (Accession Number AF099742) using the CLUSTAL W (1.74) multiple sequence alignment program is set forth in FIG. 17.

Each of the amino acid sequences of human DHDR-1, DHDR-2, DHDR-3, and DHDR-4 were analyzed by the SignalP program (Henrik et al. (1997) Prot. Eng. 10:1-6) for the presence of a signal peptide. These analyses revealed the presence of a signal peptide in the amino acid sequence of human DHDR-2 from residues 1-18 (FIG. 8). These analyses further revealed the possible presence of a signal peptide in the amino acid sequence of human DHDR-4, from residues 1-19 (FIG. 19).

Searches of each of the amino acid sequences of human DHDR-1, DHDR-2, DHDR-3, and DHDR-4 were performed against the Memsat database (FIGS. 3, 8, 13, and 19). These searches resulted in the identification of one transmembrane domain in the amino acid sequence of human DHDR-1 (SEQ ID NO:2) at about residues 159-175, and one transmembrane domain in the amino acid sequence of human DHDR-2 (SEQ ID NO:5) at about residues 7-23 in the native molecule, or about residues 265-283 of the predicted mature protein. These searches further identified four transmembrane domains in the amino acid sequence of human DHDR-3 (SEQ ID NO:8) at about residues 10-26, 73-90, 289-305, and 312-333, and four transmembrane domains in the amino acid sequence of human DHDR-4 (SEQ ID NO:11) at about residues 29-50, 170-188, 208-224, and 258-275 of the native molecule, and at about residues 10-31, 151-169, 189-205, and 239-256 of the predicted mature protein.

Searches of each of the amino acid sequences of human DHDR-1, DHDR-2, DHDR-3, and DHDR-4 were also performed against the HMM database (FIGS. 4, 9, 14, and 20). These searches resulted in the identification of an "aldehyde dehydrogenase family domain" in the amino acid sequence of human DHDR-1 (SEQ ID NO:2) at about residues 47-494 (score=149.8) (FIG. 4); the identification of a "short-chain dehydrogenase domain" in the amino acid sequence of human DHDR-2 (SEQ ID NO:5) at about residues 38-227 (score=120.0) (FIG. 9), and the identification of a "3-beta hydroxysteroid dehydrogenase domain" at about residues 1-365 (score=676.9), a "short chain dehydrogenase domain" at about residues 10-197, and a "NAD-dependent epimerase/ dehydratase domain" at about residues 12-365 of the amino acid sequence of human DHDR-3 (SEQ ID NO:8) (FIGS. 14A-14B). These searches further resulted in the identification of a "short chain dehydrogenase domain" at about residues 38-226 (score=162.5), and a "short chain dehydrogenase/reductase domain" at about residues 250-280 (score=47.2) of the amino acid sequence of human DHDR-4 (SEQ ID NO:11) (FIG. 20).

Searches of each of the amino acid sequences of human DHDR-1, DHDR-2, DHDR-3, and DHDR-4 were also performed against the ProDom database (FIGS. 5, 10, 15, and 21). These searches resulted in the identification of an "aldehyde dehydrogenase oxidoreductase domain" in the amino acid sequence of human DHDR-1 (SEQ ID NO:2) at about residues 101-770 (score=280) (FIGS. 5A-5B), and the identification of an "oxidoreductase protein dehydrogenase domain" in the amino acid sequence of human DHDR-2 (SEQ ID NO:5) at about residues 99-219 (score=113) (FIG. 10). These searches further resulted in the identification of a "3-beta hydroxysteroid dehydrogenase domain" in the amino acid sequence of human DHDR-3 (SEQ ID NO:8) at about residues 11-362 (score=395) (FIG. 15). These searches further resulted in the identification of an "oxidoreductase protein dehydrogenase domain" at about residues 37-231 (score=157), a "shikimate 5-dehydrogenase domain" at about residues 35-82 (score=86), a "dehydrogenase domain" at about residues 237-286 (score=84), and a "glucose-1dehydrogenase domain" at about residues 243-287 (score=92) of the amino acid sequence of human DHDR-4 (SEQ ID NO:11) (FIGS. 21A-21B).

The nucleotide sequences of the mouse and human DHDR-2 genes (SEQ ID NOs:14 and 4, respectively) were aligned using the GAP program in the GCG software package (nwsgapdna.cmp matrix) with a gap weight of 12 and a length weight of 4. The results are shown in FIGS. 32A-32B. As shown in the alignment, the mouse and human DHDR-2 nucleotide sequences are about 88.1% identical.

The amino acid sequences of the mouse and human DHDR-2 genes (SEQ ID NOs:15 and 5, respectively) were aligned FIG. 33 depicts an alignment of the mouse DHDR-2 amino acid sequence using the GAP program in the GCG software package (Blosum 62 matrix) with a gap weight of 12 and a length weight of 4. The results are shown in FIG. 33. As shown in the alignment, the mouse and human DHDR-2 amino acid sequences are about 91.3% identical.

Analysis of DHDR mRNA Expression

This example describes the expression of human DHDR mRNA in various tissues, cell lines, and disease models, as determined using the TaqMan™ procedure and ill situ hybridization analysis.

The Taqman™ procedure is a quantitative, real-time PCR-based approach to detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest and served as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe included an oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separated the reporter dye and the quencher dye, resulting in increased fluorescence of the reporter. Accumulation of PCR products was detected directly by monitoring the increase in fluorescence of the reporter dye. When the probe was intact, the proximity of the reporter dye to the quencher dye resulted in suppression of the reporter fluorescence. During PCR, if the target of interest was present, the probe specifically annealed between the forward and reverse primer sites. The 5'-3' nucleolytic activity of the AmpliTaq™ Gold DNA Polymerase cleaved the probe between the reporter and the quencher only if the probe hybridized to the target. The probe fragments were then displaced from the target, and polymerization of the strand continued. The 3' end of the probe was blocked to prevent extension of the probe during PCR. This process occurred in every cycle and did not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control GAPDH or β-actin gene confirming efficient removal of genomic DNA contamination.

For in situ analysis, various tissues, e.g., tissues obtained from liver or colon, were first frozen on dry ice. Ten-micrometer-thick sections of the tissues were postfixed with 4% formaldehyde in DEPC treated 1× phosphate-buffered saline (PBS) at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissues were then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Human DHDR-1

Figure 2:
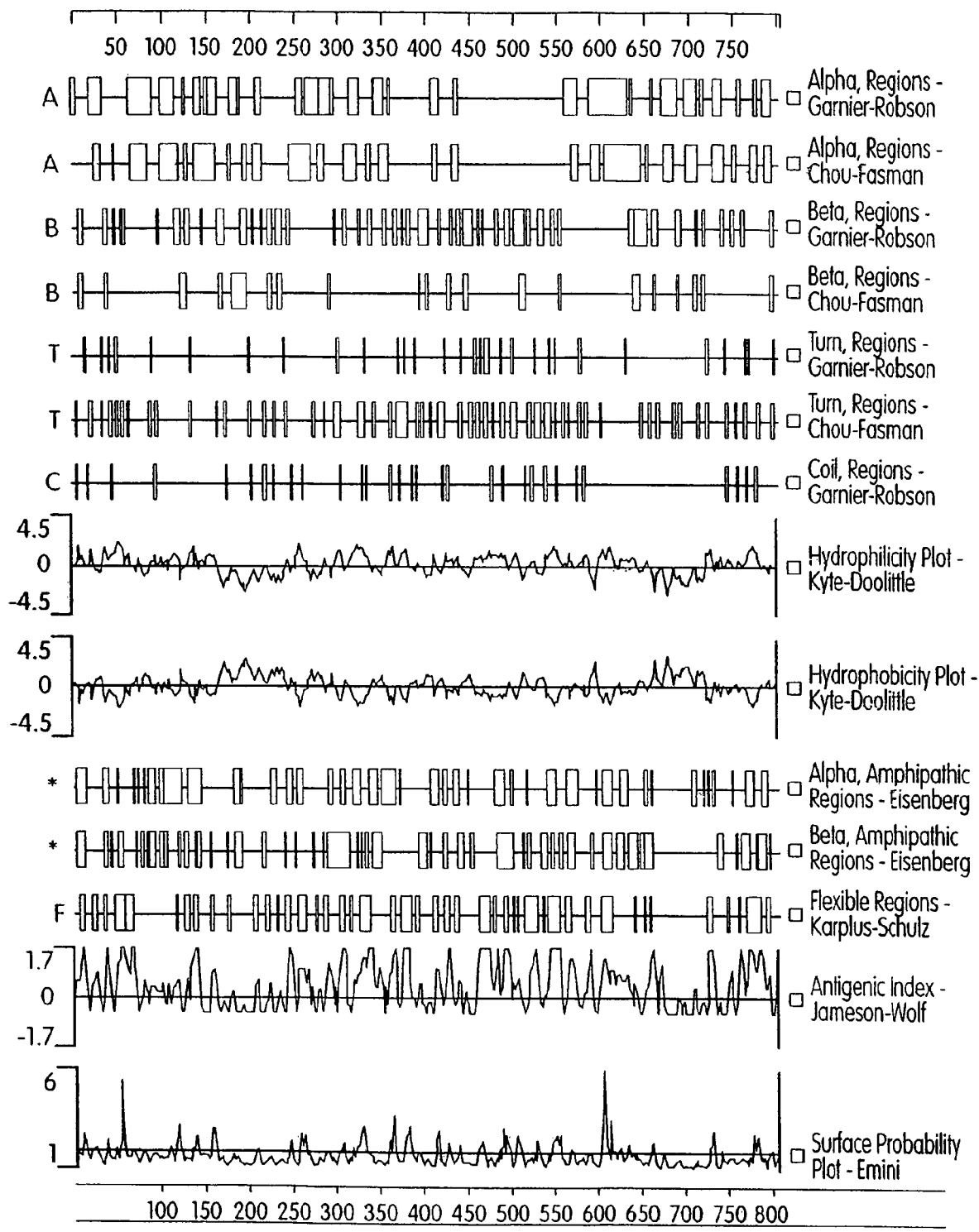
FIG. 2 depicts a structural, hydrophobicity, and antigenicity analysis of the human DHDR-1 protein.
Figure 7:
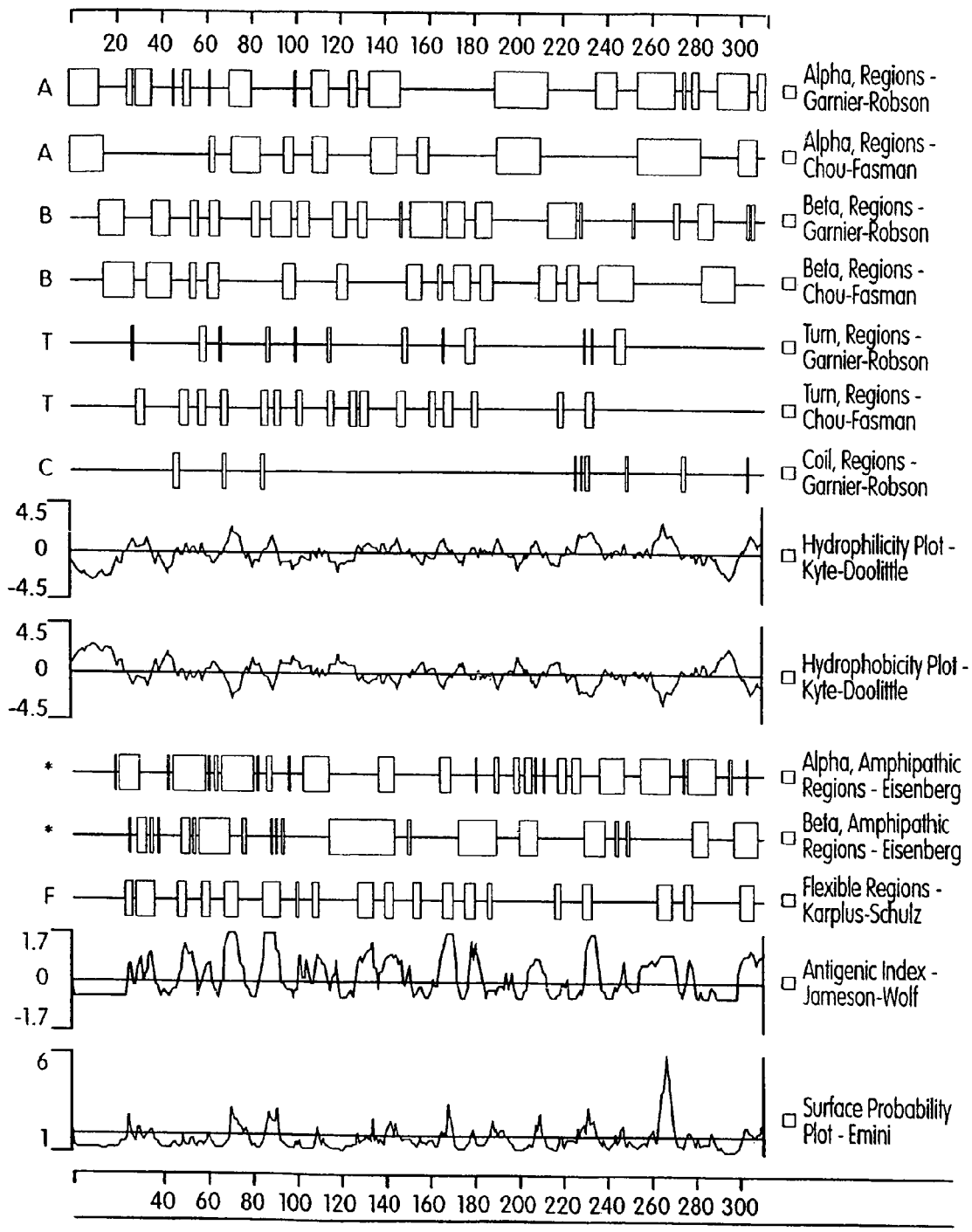
FIG. 7 depicts a structural, hydrophobicity, and antigenicity analysis of the human DHDR-2 protein.
Figure 12:
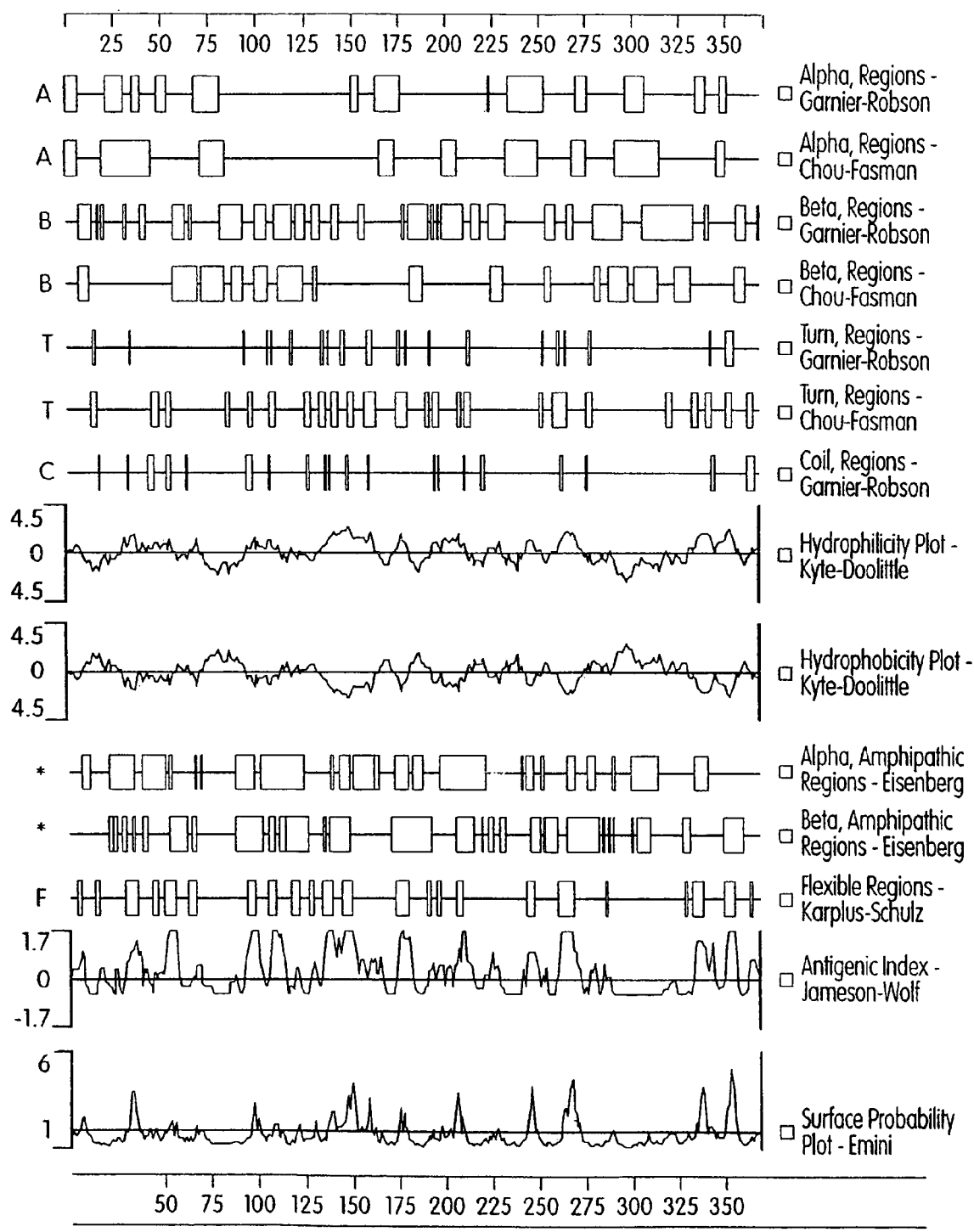
FIG. 12 depicts a structural, hydrophobicity, and antigenicity analysis of the human DHDR-3 protein.
Figure 18:
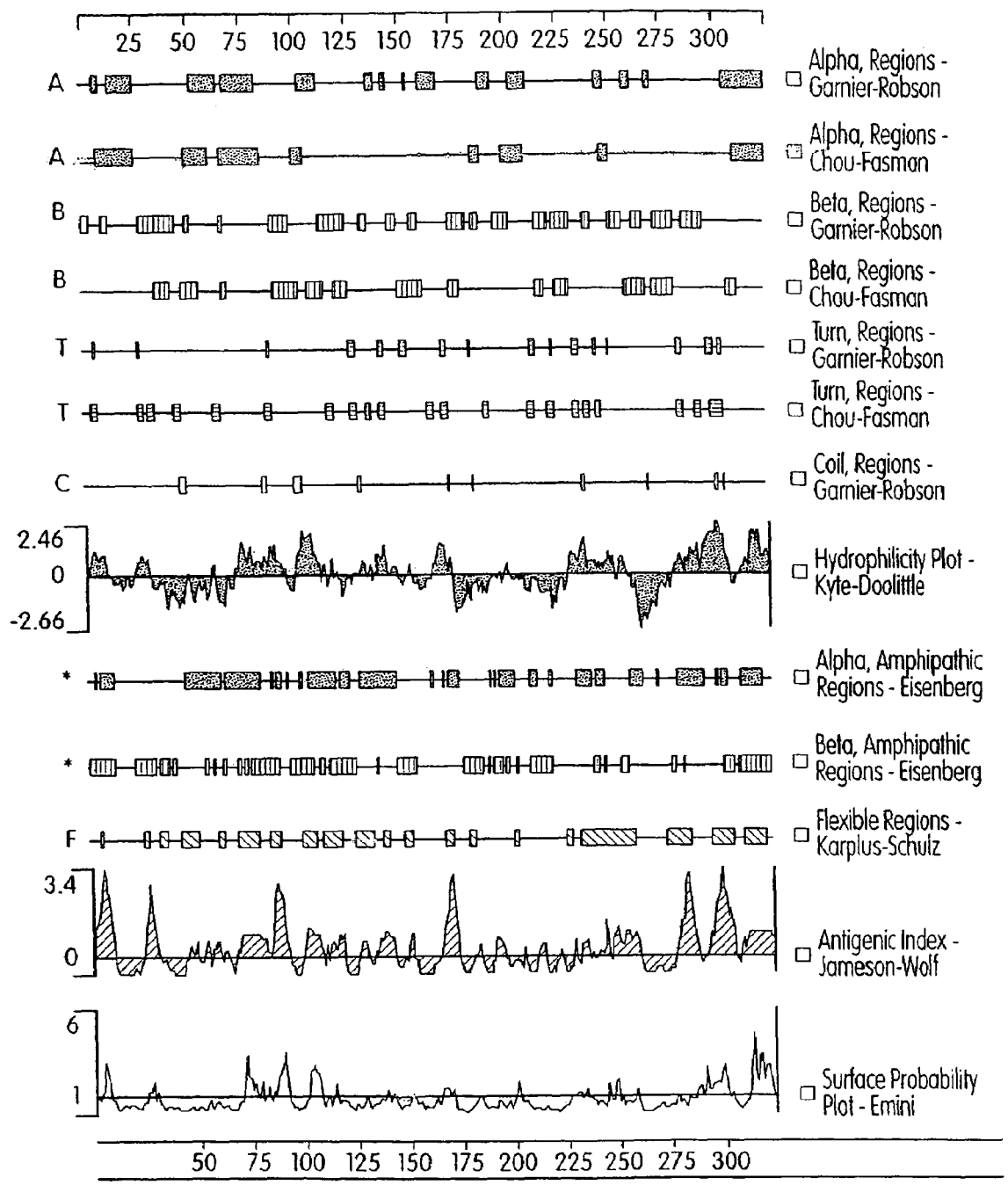
FIG. 18 depicts a structural, hydrophobicity, and antigenicity analysis of the human DHDR-4 protein.
Figure 22:
FIG. 22 depicts the expression levels of human DHDR-1 mRNA in various human cell types and tissues, as determined by Taqman analysis. Samples: (1) normal artery; (2) normal vein; (3) aortic smooth muscle cells—early; (4) coronary smooth muscle cells; (5) human microvascular endothelial cells (HMVECs)—static; (6) human microvascular endothelial cells (HMVECs)—shear; (7) normal heart; (8) heart—congestive heart failure (CHF); (9) kidney; (10) skeletal muscle; (11) normal adipose tissue; (12) pancreas; (13) primary osteoblasts; (14) differentiated osteoclasts; (15) normal skin; (16) normal spinal cord; (17) normal brain cortex; (18) brain—hypothalamus; (19) nerve; (20) dorsal root ganglion (DRG); (21) resting peripheral blood mononuclear cells (PBMCs); (22) glioblastoma; (23) normal breast; (24) breast tumor; (25) normal ovary; (26) ovary tumor; (27) normal prostate; (28) prostate tumor; (29) epithelial cells (prostate); (30) normal colon; (31) colon tumor; (32) normal lung; (33)

The human DHDR-1 gene is highly expressed in coronary smooth muscle cells (SMCs), human umbilical vein endothelial cells (HUVECs), kidney, skeletal muscle, adipose tissue, pancreas, skin, brain (cortex and hypothalamus), dorsal root ganglion (DRG), breast, ovary, prostate, prostate epithelial cells, colon, fibrotic liver, tonsil, and decubitus skin (see FIG. 22). The human DHDR-1 gene is expressed at lower levels in a number of other tissues (see FIG. 22).

The human DHDR-1 gene is also expressed in a number of tumorigenic cell lines, including MCF-7 (breast tumor), ZR75 (breast tumor), T47D (breast tumor), MDA 231 (breast tumor), MDA 435 (breast tumor), SKBr3 (breast tumor), DLD 1 (colon tumor—stage C), SW620 (colon tumor—stage C), HCT116 (colon tumor), HT29 (colon tumor), Colo 205, NCIH125, NCIH322, NCIH460, A549, NHBE, SKOV-3 (ovary tumor), and OVCAR-3 (ovary tumor).

Expression of the human DHDR-1 gene is upregulated in 3/5 ovary tumors (FIG. 23), as compared to normal ovary. In situ hybridization experiments also showed an upregulation of human DHDR-2 in 1 borderline ovary tumor and 2/2 invasive ovary tumors.

Expression of the human DHDR-1 gene is upregulated in 6/7 lung tumors (FIG. 23), as compared to normal lung. In situ hybridization experiments also showed an upregulation in 1/2 lung tumors.

Expression of the human DHDR-1 gene is upregulated in 6/15 hyperplastic/dysplastic lesions in the colon (FIG. 24), 3/4 colon tumors (FIG. 23), and 12/13 colon tumor metastases to the liver (FIGS. 23 and 24), as compared to the expression in normal colon and liver. In situ hybridization experiments also showed a marked elevation of expression as early as hyperplasia/dysplasia (1/1 hyperplastic/dysplastic lesions), which is maintained in primary tumors (5/5 tumors) and metastases (3/3 metastases to the liver).

Expression of the human DHDR-1 gene is upregulated in NOC synchronized HCT116 cells (colon tumor derived cell line) at the time point t=24 after entry into the cell cycle (FIG. 25). The time point t=0 signifies the G2/M border.

Human DHDR-2

Expression of the human DHDR-2 gene is downregulated in 7/7 breast tumors (FIG. 26), as compared to the expression in normal breast; downregulated in 6/6 colon tumors and 4/4 colon tumor metastases to the liver (FIG. 26), as compared to the expression in normal colon and liver; and downregulated in 3/3 glioblastoma brain tumors (FIG. 26).

Human DHDR-4

The human DHDR-4 gene is highly expressed in liver, kidney, brain, skin, prostate epithelial cells, primary osteoblasts, pituitary, CaCO cells, keratinocytes, aortic endothelial cells, fetal kidney, fetal lung, mammary epithelium, fetal spleen, fetal liver, umbilical smooth muscle, RAII Burkitt Lymphoma cells, lung, prostate, K53 red blood cells, fetal dorsal spinal cord, insulinoma cells, normal breast and ovarian epithelia, retina, HMC-1 mast cells, ovarian ascites, d8 dendritic cells, megakaryocytes, human mobilized bone marrow, mammary carcinoma, in melanoma cells, lymph, vein, U937/A70p B cells, A549con cells, WT LN Cap testosterone cells, and esophagus. Significant expression of DHDR-4 was also observed in aorta, breast, liver, lung, small intestine, glial cells, and thymus. Some expression of DHDR-4 was observed in brain, cervix, colon, heart, kidney, muscle, ovary, placenta, testes, and thyroid.

Human DHDR-4 is also greatly induced in situations of hepatitis B virus (HBV) infection (FIG. 28). Human DHDR-4 is expressed at 4-18 fold higher levels in HBV-infected liver than in normal liver. The upregulation in HBV infected liver is specific to HBV; no upregulation of human DHDR-4 is seen in hepatitis C virus (HCV) infected liver (FIG. 28). Human DHDR-4 expression levels are 12-25 fold higher in HBV-expressing HepG2.2.15 cells than in HepG2 control cells (FIG. 28). Treatment of HepG2 cells with Bayer compound IC50 or IC100 results in a strong induction of human DHDR-4 expression, while treatment of HBV-expressing HepG2.2.15 cells with Bayer compound IC50 or IC100results in a strong decrease in expression of human DHDR-4. Transfection of the HBV X transcription factor alone can induce a 5-fold increase in DHDR-4 expression (FIG. 28). In situ hybridization analysis also revealed that human DHDR-4 is expressed at a much higher level in HBV positive liver than in normal liver.

The human DHDR-4 gene is expressed in a number of tumorigenic cell lines, including MCF-7 (breast tumor), ZR75 (breast tumor), T47D (breast tumor), MDA 231 (breast tumor), MDA 435 (breast tumor), DLD 1 (colon tumor—stage C), SW 480, SW 620 (colon tumor—stage C), HCT 116 (colon tumor), HT 29 (colon tumor), Colo 205, NCIH 125, NCIH 67, NCIH 322, and A549.

Expression of human DHDR-4 is downregulated in 6/6 glioblastoma brain tumors (FIG. 29), as compared to normal brain. Expression of human DHDR-4 is downregulated in 6/6 breast tumors, as compared to normal breast (FIG. 30).

Expression of human DHDR-4 is upregulated in 6/8 lung tumors, as compared to normal lung (FIG. 30). In situ data confirmed that human DHDR-4 is upregulated in poorly differentiated non-small cell carcinoma of the lung (PD NSCCL).

Expression of human DHDR-4 is downregulated in synchronized A549 cells at the time point t=6 after entering the cell cycle, and upregulated at t=12 (FIG. 30). The time point t=0 signifies the G2/M border.

Example 2

Expression of Recombinant DHDR Protein in Bacterial Cells

In this example, DHDR is expressed as a recombinant glutathione-S-transferase (GST) fusion polypeptide in *E. coli* and the fusion polypeptide is isolated and characterized. Specifically, DHDR is fused to GST and this fusion polypeptide is expressed in *E. coli*, e.g., strain PEB199. Expression of the GST-DHDR fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant DHDR Protein in COS Cells

To express the DHDR gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire DHDR protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the DHDR DNA sequence is amplified by PCR using two primers. The 5' primer contains the restriction site of interest followed by approximately twenty nucleotides of the DHDR coding sequence starting from the initiation codon; the 3' end sequence contains complementary sequences to the other restriction site of interest, a translation stop codon, the HA tag or FLAG tag and the last 20 nucleotides of the DHDR coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the DHDR gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the DHDR-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the DHDR polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the DHDR coding sequence is cloned directly into the polylinker of the pCDNA/Amp vector using the appropriate restriction sites. The resulting plasmid is transfected into COS cells in the manner described above, and the expression of the DHDR polypeptide is detected by radiolabeling and immunoprecipitation using a DHDR specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide selected from the group consisting of:
   a) a polypeptide which is encoded by a nucleic acid comprising the nucleotide sequence of SEQ ID NO:10 or SEQ ID NO:12; and
   b) a polypeptide comprising the amino acid sequence of SEQ ID NO:11.

2. The polypeptide of claim 1, wherein the polypeptide is encoded by a nucleic acid comprising the nucleotide sequence of SEQ ID NO:10 or SEQ ID NO:12.

3. The polypeptide of claim 1, wherein the polypeptide comprises the amino acid sequence of SEQ ID NO:11.

4. The polypeptide of claim 1, wherein the polypeptide is encoded by a nucleic acid consisting of the nucleotide sequence of SEQ ID NO:10 or SEQ ID NO:12.

5. The polypeptide of claim 1, wherein the polypeptide consists of the amino acid sequence of SEQ ID NO:11.

6. A fusion protein comprising the polypeptide of claim 1, wherein the fusion protein has dehydrogenase activity.

7. A fusion protein comprising the polypeptide of claim 2, wherein the fusion protein has dehydrogenase activity.

8. A fusion protein comprising the polypeptide of claim 3, wherein the fusion protein has dehydrogenase activity.

9. A fusion protein comprising the polypeptide of claim 4, wherein the fusion protein has dehydrogenase activity.

10. A fusion protein comprising the polypeptide of claim 5, wherein the fusion protein has dehydrogenase activity.

* * * * *

SEQUENCE LISTING

```
<160> NUMBER OF SEQ ID NOS: 34

<210> SEQ ID NO 1
<211> LENGTH: 2660
<212> TYPE: DNA
<213> ORGANISM: Homo sapiens
<220> FEATURE:
<221> NAME/KEY: CDS
<222> LOCATION: (63)...(2468)
<220> FEATURE:
<221> NAME/KEY: misc_feature
<222> LOCATION: 6, 8
<223> OTHER INFORMATION: n = A,T,C or G

<400> SEQUENCE: 1
cctttntnrc cacgcgtccg agagcgcccc gcagtcttcg cggaaagcgt tcggggtagg        60 cg atg gct gcg acg cgt gca ggg ccc cgc gcc cgc gag atc ttc acc        107
   Met Ala Ala Thr Arg Ala Gly Pro Arg Ala Arg Glu Ile Phe Thr
   1               5                  10                  15 tcg ctg gag tac gga ccg gtg ccg gag agc cac gca tgc gca ctg gcc        155
Ser Leu Glu Tyr Gly Pro Val Pro Glu Ser His Ala Cys Ala Leu Ala
                20                  25                  30 tgg ctg gac acc cag gac cgg tgc ttg ggc cac tat gtg aat ggg aag        203
Trp Leu Asp Thr Gln Asp Arg Cys Leu Gly His Tyr Val Asn Gly Lys
            35                  40                  45 tgg tta aag cct gaa cac aga aat tca gtg cct tgc cag gat ccc atc        251
Trp Leu Lys Pro Glu His Arg Asn Ser Val Pro Cys Gln Asp Pro Ile
        50                  55                  60 aca gga gag aac ttg gcc agt tgc ctg cag gca cag gcc gag gat gtg        299
Thr Gly Glu Asn Leu Ala Ser Cys Leu Gln Ala Gln Ala Glu Asp Val
    65                  70                  75 gct gca gcc gtg gag gca gcc agg atg gca ttt aag ggc tgg agt gcg        347
Ala Ala Ala Val Glu Ala Ala Arg Met Ala Phe Lys Gly Trp Ser Ala
80                  85                  90                  95
```

```
cac ccc ggc gtc gtc cgg gcc cag cac ctg acc agg ctg gcc gag gtg        395
His Pro Gly Val Val Arg Ala Gln His Leu Thr Arg Leu Ala Glu Val
            100                 105                 110 atc cag aag cac cag cgg ctg ctg tgg acc ctg gaa tcc ctg gtg act        443
Ile Gln Lys His Gln Arg Leu Leu Trp Thr Leu Glu Ser Leu Val Thr
        115                 120                 125 ggg cgg gct gtt cga gag gtt cga gac ggg gac gtc cag ctg gcc cag        491
Gly Arg Ala Val Arg Glu Val Arg Asp Gly Asp Val Gln Leu Ala Gln
    130                 135                 140 cag ctg ctc cac tac cat gca atc cag gca tcc acc cag gag gag gca        539
Gln Leu Leu His Tyr His Ala Ile Gln Ala Ser Thr Gln Glu Glu Ala
145                 150                 155 ctg gca ggc tgg gag ccc atg gga gta att ggc ctc atc ctg cca ccc        587
Leu Ala Gly Trp Glu Pro Met Gly Val Ile Gly Leu Ile Leu Pro Pro
160                 165                 170                 175 aca ttc tcc ttc ctt gag atg atg tgg agg att tgc cct gcc ctg gct        635
Thr Phe Ser Phe Leu Glu Met Met Trp Arg Ile Cys Pro Ala Leu Ala
                180                 185                 190 gtg ggc tgc acc gtg gtg gcc ctc gtg ccc ccg gcc tcc ccg gcg ccc        683
Val Gly Cys Thr Val Val Ala Leu Val Pro Pro Ala Ser Pro Ala Pro
                195                 200                 205 ctc ctc ctg gcc cag ctg gcg ggg gag ctg ggc ccc ttc ccg gga atc        731
Leu Leu Leu Ala Gln Leu Ala Gly Glu Leu Gly Pro Phe Pro Gly Ile
            210                 215                 220 ctg aat gtc gtc agt ggc cct gcg tcc ctg gtg ccc atc ctg gcc tcc        779
Leu Asn Val Val Ser Gly Pro Ala Ser Leu Val Pro Ile Leu Ala Ser
        225                 230                 235 cag cct gga atc cgg aag gtg gcc ttc tgc gga gcc ccg gag gaa ggg        827
Gln Pro Gly Ile Arg Lys Val Ala Phe Cys Gly Ala Pro Glu Glu Gly
240                 245                 250                 255 cgt gcc ctt cga cgg agc ctg gcg gga gag tgt gcg gag ctg ggc ctg        875
Arg Ala Leu Arg Arg Ser Leu Ala Gly Glu Cys Ala Glu Leu Gly Leu
                260                 265                 270 gcg ctg ggg acg gag tcg ctg ctg ctg acg gac acg gcg gac gta            923
Ala Leu Gly Thr Glu Ser Leu Leu Leu Thr Asp Thr Ala Asp Val
                275                 280                 285 gac tcg gcc gtg gag ggt gtc gtg gac gcc gcc tgg tcc gac cgc ggc        971
Asp Ser Ala Val Glu Gly Val Val Asp Ala Ala Trp Ser Asp Arg Gly
            290                 295                 300 ccg ggt ggc ctc agg ctc ctc atc cag gag tct gtg tgg gat gaa gcc       1019
Pro Gly Gly Leu Arg Leu Leu Ile Gln Glu Ser Val Trp Asp Glu Ala
        305                 310                 315 atg aga cgg ctg cag gag cgg atg ggg cgg ctt cgg agt ggc cga ggg       1067
Met Arg Arg Leu Gln Glu Arg Met Gly Arg Leu Arg Ser Gly Arg Gly
320                 325                 330                 335 ctg gat ggg gcc gtg gac atg ggg gcc cgg ggg gct gcc gca tgt gac       1115
Leu Asp Gly Ala Val Asp Met Gly Ala Arg Gly Ala Ala Ala Cys Asp
                340                 345                 350 ctg gtc cag cgc ttt gtg cgt gag gcc cag agc cag ggt gca cag gtg       1163
Leu Val Gln Arg Phe Val Arg Glu Ala Gln Ser Gln Gly Ala Gln Val
            355                 360                 365 ttc cag gct ggt gat gtg cct tcg gaa cgc cca ttc tat ccc cca acc       1211
Phe Gln Ala Gly Asp Val Pro Ser Glu Arg Pro Phe Tyr Pro Pro Thr
        370                 375                 380 ttg gtc tcc aac ctg ccc cca gcc tcc cca tgt gcc cag gtg gag gtg       1259
Leu Val Ser Asn Leu Pro Pro Ala Ser Pro Cys Ala Gln Val Glu Val
385                 390                 395 ccg tgg cct gtg gtc gtg gcc tcc ccc ttc cgc aca gcc aag gag gca       1307
Pro Trp Pro Val Val Val Ala Ser Pro Phe Arg Thr Ala Lys Glu Ala
400                 405                 410                 415
```

|  |  |
|---|---|
| ctg ttg gtg gcc aac ggg acg ccc cgc ggg ggc agc gcc agt gtg tgg<br>Leu Leu Val Ala Asn Gly Thr Pro Arg Gly Gly Ser Ala Ser Val Trp<br>420                   425                   430 | 1355 |
| agc gag agg ctg ggg cag gcg ctg gag ctg ggc tat ggg ctc cag gtg<br>Ser Glu Arg Leu Gly Gln Ala Leu Glu Leu Gly Tyr Gly Leu Gln Val<br>            435                   440                   445 | 1403 |
| ggc act gtc tgg atc aac gcc cac ggc ctc aga gac cct tcg gtg ccc<br>Gly Thr Val Trp Ile Asn Ala His Gly Leu Arg Asp Pro Ser Val Pro<br>              450                   455                 460 | 1451 |
| aca ggc ggc tgc aag gag agt ggg tgt tcc tgg cac ggg ggc cca gac<br>Thr Gly Gly Cys Lys Glu Ser Gly Cys Ser Trp His Gly Gly Pro Asp<br>465                   470                   475 | 1499 |
| ggg ctg tat gag tat ctg cgg ccc tca ggg acc cct gcc cgg ctg tcc<br>Gly Leu Tyr Glu Tyr Leu Arg Pro Ser Gly Thr Pro Ala Arg Leu Ser<br>480                   485                   490                 495 | 1547 |
| tgc ctc tcc aag aac ctg aac tat gac acc ttt ggc ctc gct gtg ccc<br>Cys Leu Ser Lys Asn Leu Asn Tyr Asp Thr Phe Gly Leu Ala Val Pro<br>            500                   505                   510 | 1595 |
| tca acc ctg ccg gct ggg cct gaa ata ggg ccc agc cca gca ccc ccc<br>Ser Thr Leu Pro Ala Gly Pro Glu Ile Gly Pro Ser Pro Ala Pro Pro<br>              515                   520                 525 | 1643 |
| tat ggg ctc ttc gtt ggg ggc cgt ttc cag gct cct ggg gcc cga agc<br>Tyr Gly Leu Phe Val Gly Gly Arg Phe Gln Ala Pro Gly Ala Arg Ser<br>530                   535                   540 | 1691 |
| tcc agg ccc atc cgg gat tcg tct ggc aat ctc cat ggc tac gtg gct<br>Ser Arg Pro Ile Arg Asp Ser Ser Gly Asn Leu His Gly Tyr Val Ala<br>545                   550                   555 | 1739 |
| gag ggt gga gcc aag gac atc cga ggt gct gtg gag gcc gct cac cag<br>Glu Gly Gly Ala Lys Asp Ile Arg Gly Ala Val Glu Ala Ala His Gln<br>560                   565                   570                 575 | 1787 |
| gct ttc cct ggc tgg gcg ggc cag tcc cca gga gcc cgg gca gcc ctg<br>Ala Phe Pro Gly Trp Ala Gly Gln Ser Pro Gly Ala Arg Ala Ala Leu<br>                   580                   585                 590 | 1835 |
| ctg tgg gcc ctg gcg gct gca ctg gag cgc cgg aag tct acc ctg gcc<br>Leu Trp Ala Leu Ala Ala Ala Leu Glu Arg Arg Lys Ser Thr Leu Ala<br>              595                   600                 605 | 1883 |
| tca agg ctg gag agg cag gga gcg gag ctc aag gct gcg gag gcg gag<br>Ser Arg Leu Glu Arg Gln Gly Ala Glu Leu Lys Ala Ala Glu Ala Glu<br>610                   615                   620 | 1931 |
| gtg gag ctg agc gca aga cga ctt cgg gcg tgg ggg gcc cgg gtg cag<br>Val Glu Leu Ser Ala Arg Arg Leu Arg Ala Trp Gly Ala Arg Val Gln<br>            625                   630                 635 | 1979 |
| gcc caa ggc cac acc ctg cag gta gcc ggg ctg aga ggc cct gtg ctg<br>Ala Gln Gly His Thr Leu Gln Val Ala Gly Leu Arg Gly Pro Val Leu<br>640                     645                   650                 655 | 2027 |
| cgc ctg cgg gag ccg ctg ggt gtg ctg gct gtg gtg tgt ccg gac gag<br>Arg Leu Arg Glu Pro Leu Gly Val Leu Ala Val Val Cys Pro Asp Glu<br>                   660                   665                 670 | 2075 |
| tgg ccc ctg ctt gcc ttc gtg tcc ctg ctg gct ccc gcc ctg gcc tac<br>Trp Pro Leu Leu Ala Phe Val Ser Leu Leu Ala Pro Ala Leu Ala Tyr<br>            675                   680                 685 | 2123 |
| ggc aac act gtg gtc atg gtg ccc agt gcg gcc tgt cct ctg ctg gcc<br>Gly Asn Thr Val Val Met Val Pro Ser Ala Ala Cys Pro Leu Leu Ala<br>              690                   695                 700 | 2171 |
| ctg gag gtc tgc cag gac atg gcc acc gtg ttc cca gca ggc ctg gcc<br>Leu Glu Val Cys Gln Asp Met Ala Thr Val Phe Pro Ala Gly Leu Ala<br>705                   710                   715 | 2219 |
| aac gtg gtg aca gga gac cgg gac cat ctg acc cgc tgc ctg gcc ttg<br>Asn Val Val Thr Gly Asp Arg Asp His Leu Thr Arg Cys Leu Ala Leu | 2267 |

-continued

```
                720                 725                 730                 735
cac caa gac gtc cag gcc atg tgg tat ttc gga tca gcc cag ggt tcc        2315
His Gln Asp Val Gln Ala Met Trp Tyr Phe Gly Ser Ala Gln Gly Ser
                740                 745                 750 cag ttt gtc gag tgg gcc tcg gca gga aac ctc aaa ccg gtg tgg gcg        2363
Gln Phe Val Glu Trp Ala Ser Ala Gly Asn Leu Lys Pro Val Trp Ala
            755                 760                 765 agc agg ggc tgc ccg cgg gcc tgg gac cag gag gcc gag ggg gca ggc        2411
Ser Arg Gly Cys Pro Arg Ala Trp Asp Gln Glu Ala Glu Gly Ala Gly
        770                 775                 780 cca gag ctg ggg ctg cga gtg gcg cgg acc aag gcc ctg tgg ctg cct        2459
Pro Glu Leu Gly Leu Arg Val Ala Arg Thr Lys Ala Leu Trp Leu Pro
    785                 790                 795 atg ggg gac tgatgcctga gcgccaccta ctgcattttg gacacctcac                2508
Met Gly Asp
800 accaagggga gatgcacccc acagacacct gggactttcc ccttctggtt cctgtgtctc       2568 ccaataaact ctctgaccaa ccctaaaaaa aaaaaaaaaa aaaaaaaaaa rwarmaactt       2628 ctggcagata tgaggctttt ttcttttttt tt                                     2660

<210> SEQ ID NO 2
<211> LENGTH: 802
<212> TYPE: PRT
<213> ORGANISM: Homo sapiens

<400> SEQUENCE: 2

Met Ala Ala Thr Arg Ala Gly Pro Arg Ala Arg Glu Ile Phe Thr Ser
1               5                   10                  15

Leu Glu Tyr Gly Pro Val Pro Glu Ser His Ala Cys Ala Leu Ala Trp
            20                  25                  30

Leu Asp Thr Gln Asp Arg Cys Leu Gly His Tyr Val Asn Gly Lys Trp
        35                  40                  45

Leu Lys Pro Glu His Arg Asn Ser Val Pro Cys Gln Asp Pro Ile Thr
    50                  55                  60

Gly Glu Asn Leu Ala Ser Cys Leu Gln Ala Gln Ala Glu Asp Val Ala
65                  70                  75                  80

Ala Ala Val Glu Ala Ala Arg Met Ala Phe Lys Gly Trp Ser Ala His
                85                  90                  95

Pro Gly Val Val Arg Ala Gln His Leu Thr Arg Leu Ala Glu Val Ile
            100                 105                 110

Gln Lys His Gln Arg Leu Leu Trp Thr Leu Glu Ser Leu Val Thr Gly
        115                 120                 125

Arg Ala Val Arg Glu Val Arg Asp Gly Asp Val Gln Leu Ala Gln Gln
    130                 135                 140

Leu Leu His Tyr His Ala Ile Gln Ala Ser Thr Gln Glu Glu Ala Leu
145                 150                 155                 160

Ala Gly Trp Glu Pro Met Gly Val Ile Gly Leu Ile Leu Pro Pro Thr
                165                 170                 175

Phe Ser Phe Leu Glu Met Met Trp Arg Ile Cys Pro Ala Leu Ala Val
            180                 185                 190

Gly Cys Thr Val Val Ala Leu Val Pro Pro Ala Ser Pro Ala Pro Leu
        195                 200                 205

Leu Leu Ala Gln Leu Ala Gly Glu Leu Gly Pro Phe Pro Gly Ile Leu
    210                 215                 220

Asn Val Val Ser Gly Pro Ala Ser Leu Val Pro Ile Leu Ala Ser Gln
```

-continued

```
            225                 230                 235                 240

Pro Gly Ile Arg Lys Val Ala Phe Cys Gly Ala Pro Glu Glu Gly Arg
                245                 250                 255

Ala Leu Arg Arg Ser Leu Ala Gly Glu Cys Ala Glu Leu Gly Leu Ala
            260                 265                 270

Leu Gly Thr Glu Ser Leu Leu Leu Thr Asp Thr Ala Asp Val Asp
        275                 280                 285

Ser Ala Val Glu Gly Val Val Asp Ala Ala Trp Ser Asp Arg Gly Pro
        290                 295                 300

Gly Gly Leu Arg Leu Leu Ile Gln Glu Ser Val Trp Asp Glu Ala Met
305                 310                 315                 320

Arg Arg Leu Gln Glu Arg Met Gly Arg Leu Arg Ser Gly Arg Gly Leu
                325                 330                 335

Asp Gly Ala Val Asp Met Gly Ala Arg Gly Ala Ala Ala Cys Asp Leu
            340                 345                 350

Val Gln Arg Phe Val Arg Glu Ala Gln Ser Gln Gly Ala Gln Val Phe
        355                 360                 365

Gln Ala Gly Asp Val Pro Ser Glu Arg Pro Phe Tyr Pro Pro Thr Leu
    370                 375                 380

Val Ser Asn Leu Pro Pro Ala Ser Pro Cys Ala Gln Val Glu Val Pro
385                 390                 395                 400

Trp Pro Val Val Ala Ser Pro Phe Arg Thr Ala Lys Glu Ala Leu
                405                 410                 415

Leu Val Ala Asn Gly Thr Pro Arg Gly Gly Ser Ala Ser Val Trp Ser
            420                 425                 430

Glu Arg Leu Gly Gln Ala Leu Glu Leu Gly Tyr Gly Leu Gln Val Gly
        435                 440                 445

Thr Val Trp Ile Asn Ala His Gly Leu Arg Asp Pro Ser Val Pro Thr
    450                 455                 460

Gly Gly Cys Lys Glu Ser Gly Cys Ser Trp His Gly Gly Pro Asp Gly
465                 470                 475                 480

Leu Tyr Glu Tyr Leu Arg Pro Ser Gly Thr Pro Ala Arg Leu Ser Cys
                485                 490                 495

Leu Ser Lys Asn Leu Asn Tyr Asp Thr Phe Gly Leu Ala Val Pro Ser
            500                 505                 510

Thr Leu Pro Ala Gly Pro Glu Ile Gly Pro Ser Pro Ala Pro Pro Tyr
        515                 520                 525

Gly Leu Phe Val Gly Gly Arg Phe Gln Ala Pro Gly Ala Arg Ser Ser
    530                 535                 540

Arg Pro Ile Arg Asp Ser Ser Gly Asn Leu His Gly Tyr Val Ala Glu
545                 550                 555                 560

Gly Gly Ala Lys Asp Ile Arg Gly Ala Val Glu Ala Ala His Gln Ala
                565                 570                 575

Phe Pro Gly Trp Ala Gly Gln Ser Pro Gly Ala Arg Ala Ala Leu Leu
            580                 585                 590

Trp Ala Leu Ala Ala Leu Glu Arg Arg Lys Ser Thr Leu Ala Ser
        595                 600                 605

Arg Leu Glu Arg Gln Gly Ala Glu Leu Lys Ala Glu Ala Glu Val
    610                 615                 620

Glu Leu Ser Ala Arg Arg Leu Arg Ala Trp Gly Ala Arg Val Gln Ala
625                 630                 635                 640

Gln Gly His Thr Leu Gln Val Ala Gly Leu Arg Gly Pro Val Leu Arg
                645                 650                 655
```

```
Leu Arg Glu Pro Leu Gly Val Leu Ala Val Val Cys Pro Asp Glu Trp
            660                 665                 670

Pro Leu Leu Ala Phe Val Ser Leu Leu Ala Pro Ala Leu Ala Tyr Gly
            675                 680                 685

Asn Thr Val Val Met Val Pro Ser Ala Ala Cys Pro Leu Leu Ala Leu
            690                 695                 700

Glu Val Cys Gln Asp Met Ala Thr Val Phe Pro Ala Gly Leu Ala Asn
705                 710                 715                 720

Val Val Thr Gly Asp Arg Asp His Leu Thr Arg Cys Leu Ala Leu His
            725                 730                 735

Gln Asp Val Gln Ala Met Trp Tyr Phe Gly Ser Ala Gln Gly Ser Gln
            740                 745                 750

Phe Val Glu Trp Ala Ser Ala Gly Asn Leu Lys Pro Val Trp Ala Ser
            755                 760                 765

Arg Gly Cys Pro Arg Ala Trp Asp Gln Glu Ala Glu Gly Ala Gly Pro
            770                 775                 780

Glu Leu Gly Leu Arg Val Ala Arg Thr Lys Ala Leu Trp Leu Pro Met
785                 790                 795                 800

Gly Asp

<210> SEQ ID NO 3
<211> LENGTH: 2406
<212> TYPE: DNA
<213> ORGANISM: Homo sapiens
<220> FEATURE:
<221> NAME/KEY: CDS
<222> LOCATION: (1)...(2406)

<400> SEQUENCE: 3 atg gct gcg acg cgt gca ggg ccc cgc gcc cgc gag atc ttc acc tcg      48
Met Ala Ala Thr Arg Ala Gly Pro Arg Ala Arg Glu Ile Phe Thr Ser
1               5                   10                  15 ctg gag tac gga ccg gtg ccg gag agc cac gca tgc gca ctg gcc tgg      96
Leu Glu Tyr Gly Pro Val Pro Glu Ser His Ala Cys Ala Leu Ala Trp
            20                  25                  30 ctg gac acc cag gac cgg tgc ttg ggc cac tat gtg aat ggg aag tgg     144
Leu Asp Thr Gln Asp Arg Cys Leu Gly His Tyr Val Asn Gly Lys Trp
        35                  40                  45 tta aag cct gaa cac aga aat tca gtg cct tgc cag gat ccc atc aca     192
Leu Lys Pro Glu His Arg Asn Ser Val Pro Cys Gln Asp Pro Ile Thr
    50                  55                  60 gga gag aac ttg gcc agt tgc ctg cag gca cag gcc gag gat gtg gct     240
Gly Glu Asn Leu Ala Ser Cys Leu Gln Ala Gln Ala Glu Asp Val Ala
65                  70                  75                  80 gca gcc gtg gag gca gcc agg atg gca ttt aag ggc tgg agt gcg cac     288
Ala Ala Val Glu Ala Ala Arg Met Ala Phe Lys Gly Trp Ser Ala His
                85                  90                  95 ccc ggc gtc gtc cgg gcc cag cac ctg acc agg ctg gcc gag gtg atc     336
Pro Gly Val Val Arg Ala Gln His Leu Thr Arg Leu Ala Glu Val Ile
            100                 105                 110 cag aag cac cag cgg ctg ctg tgg acc ctg gaa tcc ctg gtg act ggg     384
Gln Lys His Gln Arg Leu Leu Trp Thr Leu Glu Ser Leu Val Thr Gly
        115                 120                 125 cgg gct gtt cga gag gtt cga gac ggg gac gtc cag ctg gcc cag cag     432
Arg Ala Val Arg Glu Val Arg Asp Gly Asp Val Gln Leu Ala Gln Gln
    130                 135                 140 ctg ctc cac tac cat gca atc cag gca tcc acc cag gag gag gca ctg     480
Leu Leu His Tyr His Ala Ile Gln Ala Ser Thr Gln Glu Glu Ala Leu
```

-continued

```
                145                 150                 155                 160
gca ggc tgg gag ccc atg gga gta att ggc ctc atc ctg cca ccc aca    528
Ala Gly Trp Glu Pro Met Gly Val Ile Gly Leu Ile Leu Pro Pro Thr
                165                 170                 175 ttc tcc ttc ctt gag atg atg tgg agg att tgc cct gcc ctg gct gtg    576
Phe Ser Phe Leu Glu Met Met Trp Arg Ile Cys Pro Ala Leu Ala Val
            180                 185                 190 ggc tgc acc gtg gtg gcc ctc gtg ccc ccg gcc tcc ccg gcg ccc ctc    624
Gly Cys Thr Val Val Ala Leu Val Pro Pro Ala Ser Pro Ala Pro Leu
        195                 200                 205 ctc ctg gcc cag ctg gcg ggg gag ctg ggc ccc ttc ccg gga atc ctg    672
Leu Leu Ala Gln Leu Ala Gly Glu Leu Gly Pro Phe Pro Gly Ile Leu
    210                 215                 220 aat gtc gtc agt ggc cct gcg tcc ctg gtg ccc atc ctg gcc tcc cag    720
Asn Val Val Ser Gly Pro Ala Ser Leu Val Pro Ile Leu Ala Ser Gln
225                 230                 235                 240 cct gga atc cgg aag gtg gcc ttc tgc gga gcc ccg gag gaa ggg cgt    768
Pro Gly Ile Arg Lys Val Ala Phe Cys Gly Ala Pro Glu Glu Gly Arg
                245                 250                 255 gcc ctt cga cgg agc ctg gcg gga gag tgt gcg gag ctg ggc ctg gcg    816
Ala Leu Arg Arg Ser Leu Ala Gly Glu Cys Ala Glu Leu Gly Leu Ala
            260                 265                 270 ctg ggg acg gag tcg ctg ctg ctg acg gac acg gcg gac gta gac        864
Leu Gly Thr Glu Ser Leu Leu Leu Thr Asp Thr Ala Asp Val Asp
        275                 280                 285 tcg gcc gtg gag ggt gtc gtg gac gcc gcc tgg tcc gac cgc ggc ccg    912
Ser Ala Val Glu Gly Val Val Asp Ala Ala Trp Ser Asp Arg Gly Pro
    290                 295                 300 ggt ggc ctc agg ctc ctc atc cag gag tct gtg tgg gat gaa gcc atg    960
Gly Gly Leu Arg Leu Leu Ile Gln Glu Ser Val Trp Asp Glu Ala Met
305                 310                 315                 320 aga cgg ctg cag gag cgg atg ggg cgg ctt cgg agt ggc cga ggg ctg   1008
Arg Arg Leu Gln Glu Arg Met Gly Arg Leu Arg Ser Gly Arg Gly Leu
                325                 330                 335 gat ggg gcc gtg gac atg ggg gcc cgg ggg gct gcc gca tgt gac ctg   1056
Asp Gly Ala Val Asp Met Gly Ala Arg Gly Ala Ala Ala Cys Asp Leu
            340                 345                 350 gtc cag cgc ttt gtg cgt gag gcc cag agc cag ggt gca cag gtg ttc   1104
Val Gln Arg Phe Val Arg Glu Ala Gln Ser Gln Gly Ala Gln Val Phe
        355                 360                 365 cag gct ggt gat gtg cct tcg gaa cgc cca ttc tat ccc cca acc ttg   1152
Gln Ala Gly Asp Val Pro Ser Glu Arg Pro Phe Tyr Pro Pro Thr Leu
    370                 375                 380 gtc tcc aac ctg ccc cca gcc tcc cca tgt gcc cag gtg gag gtg ccg   1200
Val Ser Asn Leu Pro Pro Ala Ser Pro Cys Ala Gln Val Glu Val Pro
385                 390                 395                 400 tgg cct gtg gtc gtg gcc tcc ccc ttc cgc aca gcc aag gag gca ctg   1248
Trp Pro Val Val Val Ala Ser Pro Phe Arg Thr Ala Lys Glu Ala Leu
                405                 410                 415 ttg gtg gcc aac ggg acg ccc cgc ggg ggc agc gcc agt gtg tgg agc   1296
Leu Val Ala Asn Gly Thr Pro Arg Gly Gly Ser Ala Ser Val Trp Ser
            420                 425                 430 gag agg ctg ggg cag gcg ctg gag ctg ggc tat ggg ctc cag gtg ggc   1344
Glu Arg Leu Gly Gln Ala Leu Glu Leu Gly Tyr Gly Leu Gln Val Gly
        435                 440                 445 act gtc tgg atc aac gcc cac ggc ctc aga gac cct tcg gtg ccc aca   1392
Thr Val Trp Ile Asn Ala His Gly Leu Arg Asp Pro Ser Val Pro Thr
    450                 455                 460 ggc ggc tgc aag gag agt ggg tgt tcc tgg cac ggg ggc cca gac ggg   1440
Gly Gly Cys Lys Glu Ser Gly Cys Ser Trp His Gly Gly Pro Asp Gly
```

```
Gly Gly Cys Lys Glu Ser Gly Cys Ser Trp His Gly Gly Pro Asp Gly
465                 470                 475                 480 ctg tat gag tat ctg cgg ccc tca ggg acc cct gcc cgg ctg tcc tgc   1488
Leu Tyr Glu Tyr Leu Arg Pro Ser Gly Thr Pro Ala Arg Leu Ser Cys
                485                 490                 495 ctc tcc aag aac ctg aac tat gac acc ttt ggc ctc gct gtg ccc tca   1536
Leu Ser Lys Asn Leu Asn Tyr Asp Thr Phe Gly Leu Ala Val Pro Ser
            500                 505                 510 acc ctg ccg gct ggg cct gaa ata ggg ccc agc cca gca ccc ccc tat   1584
Thr Leu Pro Ala Gly Pro Glu Ile Gly Pro Ser Pro Ala Pro Pro Tyr
        515                 520                 525 ggg ctc ttc gtt ggg ggc cgt ttc cag gct cct ggg gcc cga agc tcc   1632
Gly Leu Phe Val Gly Gly Arg Phe Gln Ala Pro Gly Ala Arg Ser Ser
    530                 535                 540 agg ccc atc cgg gat tcg tct ggc aat ctc cat ggc tac gtg gct gag   1680
Arg Pro Ile Arg Asp Ser Ser Gly Asn Leu His Gly Tyr Val Ala Glu
545                 550                 555                 560 ggt gga gcc aag gac atc cga ggt gct gtg gag gcc gct cac cag gct   1728
Gly Gly Ala Lys Asp Ile Arg Gly Ala Val Glu Ala Ala His Gln Ala
                565                 570                 575 ttc cct ggc tgg gcg ggc cag tcc cca gga gcc cgg gca gcc ctg ctg   1776
Phe Pro Gly Trp Ala Gly Gln Ser Pro Gly Ala Arg Ala Ala Leu Leu
            580                 585                 590 tgg gcc ctg gcg gct gca ctg gag cgc cgg aag tct acc ctg gcc tca   1824
Trp Ala Leu Ala Ala Ala Leu Glu Arg Arg Lys Ser Thr Leu Ala Ser
        595                 600                 605 agg ctg gag agg cag gga gcg gag ctc aag gct gcg gag gcg gag gtg   1872
Arg Leu Glu Arg Gln Gly Ala Glu Leu Lys Ala Ala Glu Ala Glu Val
    610                 615                 620 gag ctg agc gca aga cga ctt cgg gcg tgg ggg gcc cgg gtg cag gcc   1920
Glu Leu Ser Ala Arg Arg Leu Arg Ala Trp Gly Ala Arg Val Gln Ala
625                 630                 635                 640 caa ggc cac acc ctg cag gta gcc ggg ctg aga ggc cct gtg ctg cgc   1968
Gln Gly His Thr Leu Gln Val Ala Gly Leu Arg Gly Pro Val Leu Arg
                645                 650                 655 ctg cgg gag ccg ctg ggt gtg ctg gct gtg gtg tgt ccg gac gag tgg   2016
Leu Arg Glu Pro Leu Gly Val Leu Ala Val Val Cys Pro Asp Glu Trp
            660                 665                 670 ccc ctg ctt gcc ttc gtg tcc ctg ctg gct ccc gcc ctg gcc tac ggc   2064
Pro Leu Leu Ala Phe Val Ser Leu Leu Ala Pro Ala Leu Ala Tyr Gly
        675                 680                 685 aac act gtg gtc atg gtg ccc agt gcg gcc tgt cct ctg ctg gcc ctg   2112
Asn Thr Val Val Met Val Pro Ser Ala Ala Cys Pro Leu Leu Ala Leu
    690                 695                 700 gag gtc tgc cag gac atg gcc acc gtg ttc cca gca ggc ctg gcc aac   2160
Glu Val Cys Gln Asp Met Ala Thr Val Phe Pro Ala Gly Leu Ala Asn
705                 710                 715                 720 gtg gtg aca gga gac cgg gac cat ctg acc cgc tgc ctg gcc ttg cac   2208
Val Val Thr Gly Asp Arg Asp His Leu Thr Arg Cys Leu Ala Leu His
                725                 730                 735 caa gac gtc cag gcc atg tgg tat ttc gga tca gcc cag ggt tcc cag   2256
Gln Asp Val Gln Ala Met Trp Tyr Phe Gly Ser Ala Gln Gly Ser Gln
            740                 745                 750 ttt gtc gag tgg gcc tcg gca gga aac ctc aaa ccg gtg tgg gcg agc   2304
Phe Val Glu Trp Ala Ser Ala Gly Asn Leu Lys Pro Val Trp Ala Ser
        755                 760                 765 agg ggc tgc ccg cgg gcc tgg gac cag gag gcc gag ggg gca ggc cca   2352
Arg Gly Cys Pro Arg Ala Trp Asp Gln Glu Ala Glu Gly Ala Gly Pro
    770                 775                 780
```

-continued

```
gag ctg ggg ctg cga gtg gcg cgg acc aag gcc ctg tgg ctg cct atg      2400
Glu Leu Gly Leu Arg Val Ala Arg Thr Lys Ala Leu Trp Leu Pro Met
785                 790                 795                 800 ggg gac                                                               2406
Gly Asp <210> SEQ ID NO 4
<211> LENGTH: 1379
<212> TYPE: DNA
<213> ORGANISM: Homo sapiens
<220> FEATURE:
<221> NAME/KEY: CDS
<222> LOCATION: (331)...(1263)
<220> FEATURE:
<221> NAME/KEY: misc_feature
<222> LOCATION: 1337
<223> OTHER INFORMATION: n = A,T,C or G

<400> SEQUENCE: 4
tttggccctc gaggccaaga attcggcacg aggagcaagt ggccttaaca catggatttt     60
cttccaaaaa tgcagaccca ttttaattaa gtttgtaatt aaccactggg gagggcaggc    120
cccctggatt cggtctgctt tcggagacac tgtgagtaac ttcctatttg ttgaacattt    180
ggggattagc acgcccactg ggtgttcagc ttggaggctt gcacagagct gagctccctg    240
cagccttggg cctcccc ctg ccctgggagt cctgatcagc gtctctttgc aaagccaatc    300
cccttttact ccgttgtccc ccagaacaag atg gga gtc atg gcc atg ctg atg     354
                                   Met Gly Val Met Ala Met Leu Met
                                   1               5 ctc ccc ctg ctg ctg ctg gga atc agc ggc ctc ctc ttc att tac caa      402
Leu Pro Leu Leu Leu Leu Gly Ile Ser Gly Leu Leu Phe Ile Tyr Gln
        10                  15                  20 gag gtg tcc agg ctg tgg tca aag tca gct gtg cag aac aaa gtg gtg      450
Glu Val Ser Arg Leu Trp Ser Lys Ser Ala Val Gln Asn Lys Val Val
25                  30                  35                  40 gtg atc acc gat gcc atc tca gga ctg ggc aag gag tgt gct cgg gtg      498
Val Ile Thr Asp Ala Ile Ser Gly Leu Gly Lys Glu Cys Ala Arg Val
                45                  50                  55 ttc cac aca ggt ggg gca agg ctg gtg ctg tgt gga aag aac tgg gag      546
Phe His Thr Gly Gly Ala Arg Leu Val Leu Cys Gly Lys Asn Trp Glu
            60                  65                  70 agg cta gag aac cta tat gat gcc ttg atc agc gtg gct gac ccc agc      594
Arg Leu Glu Asn Leu Tyr Asp Ala Leu Ile Ser Val Ala Asp Pro Ser
        75                  80                  85 aag aca ttc acc cca aag ctg gtc ctg ttg gac ctc tca gac atc agc      642
Lys Thr Phe Thr Pro Lys Leu Val Leu Leu Asp Leu Ser Asp Ile Ser
    90                  95                  100 tgt gtc cca gat gtg gca aaa gaa gtc ctg gat tgc tat ggc tgt gtg      690
Cys Val Pro Asp Val Ala Lys Glu Val Leu Asp Cys Tyr Gly Cys Val
105                 110                 115                 120 gac atc ctc atc aac aat gcc agt gtg aag gtg aag ggg cct gcc cat      738
Asp Ile Leu Ile Asn Asn Ala Ser Val Lys Val Lys Gly Pro Ala His
                125                 130                 135 aag att tct ctg gag ctc gac aaa aag atc atg gat gcc aat tac ttt      786
Lys Ile Ser Leu Glu Leu Asp Lys Lys Ile Met Asp Ala Asn Tyr Phe
            140                 145                 150 ggc ccc atc aca ttg acg aaa gcc ctg ctt ccc aac atg atc tcc cgg      834
Gly Pro Ile Thr Leu Thr Lys Ala Leu Leu Pro Asn Met Ile Ser Arg
        155                 160                 165 aga aca ggc caa atc gtg tta gtg aat aat atc caa ggg aag ttt gga      882
Arg Thr Gly Gln Ile Val Leu Val Asn Asn Ile Gln Gly Lys Phe Gly
    170                 175                 180
```

-continued

```
atc ccg ttc cgt acg act tac gct gcc tcc aag cac gca gcc ctg ggc        930
Ile Pro Phe Arg Thr Thr Tyr Ala Ala Ser Lys His Ala Ala Leu Gly
185             190                 195                 200 ttc ttt gac tgc ctc cga gcc gaa gtg gag gaa tac gat gtt gtc atc        978
Phe Phe Asp Cys Leu Arg Ala Glu Val Glu Glu Tyr Asp Val Val Ile
                205                 210                 215 agc acc gtg agc ccg act ttc atc cgg tcg tac cac gtg tat cca gag       1026
Ser Thr Val Ser Pro Thr Phe Ile Arg Ser Tyr His Val Tyr Pro Glu
    220                 225                 230 caa gga aac tgg gaa gct tcc att tgg aaa ttc ttt ttc agg aag ctg       1074
Gln Gly Asn Trp Glu Ala Ser Ile Trp Lys Phe Phe Phe Arg Lys Leu
        235                 240                 245 acc tac ggc gtg cac cca gta gag gtg gcg gag gag gtg atg cgc acc       1122
Thr Tyr Gly Val His Pro Val Glu Val Ala Glu Glu Val Met Arg Thr
            250                 255                 260 gtg cgg agg aag aag caa gag gtg ttt atg gcc aac ccc atc ccc aag       1170
Val Arg Arg Lys Lys Gln Glu Val Phe Met Ala Asn Pro Ile Pro Lys
265                 270                 275                 280 gcc gcc gtg tac gtc cgc acc ttc ttc ccg gag ttc ttt ttc gcc gtg       1218
Ala Ala Val Tyr Val Arg Thr Phe Phe Pro Glu Phe Phe Phe Ala Val
                285                 290                 295 gtg gcc tgt ggg gtg aag gag aag ctc aat gtc ccg gag gag ggg           1263
Val Ala Cys Gly Val Lys Glu Lys Leu Asn Val Pro Glu Glu Gly
                300                 305                 310 taactgcagg aggccaaatg ggccacccct tggaaataaa ggttttctg gcaaaaaaaa       1323 aaaaaaaaaa aaantttgcg gccgcaagct tattccttt agggagggtt aatttt          1379

<210> SEQ ID NO 5
<211> LENGTH: 311
<212> TYPE: PRT
<213> ORGANISM: Homo sapiens

<400> SEQUENCE: 5

Met Gly Val Met Ala Met Leu Met Leu Pro Leu Leu Leu Gly Ile
  1               5                  10                  15

Ser Gly Leu Leu Phe Ile Tyr Gln Glu Val Ser Arg Leu Trp Ser Lys
                20                  25                  30

Ser Ala Val Gln Asn Lys Val Val Ile Thr Asp Ala Ile Ser Gly
        35                  40                  45

Leu Gly Lys Glu Cys Ala Arg Val Phe His Thr Gly Gly Ala Arg Leu
    50                  55                  60

Val Leu Cys Gly Lys Asn Trp Glu Arg Leu Glu Asn Leu Tyr Asp Ala
65                  70                  75                  80

Leu Ile Ser Val Ala Asp Pro Ser Lys Thr Phe Thr Pro Lys Leu Val
                85                  90                  95

Leu Leu Asp Leu Ser Asp Ile Ser Cys Val Pro Asp Val Ala Lys Glu
                100                 105                 110

Val Leu Asp Cys Tyr Gly Cys Val Asp Ile Leu Ile Asn Asn Ala Ser
            115                 120                 125

Val Lys Val Lys Gly Pro Ala His Lys Ile Ser Leu Glu Leu Asp Lys
        130                 135                 140

Lys Ile Met Asp Ala Asn Tyr Phe Gly Pro Ile Thr Leu Thr Lys Ala
145                 150                 155                 160

Leu Leu Pro Asn Met Ile Ser Arg Arg Thr Gly Gln Ile Val Leu Val
                165                 170                 175

Asn Asn Ile Gln Gly Lys Phe Gly Ile Pro Phe Arg Thr Thr Tyr Ala
```

```
                    180                 185                 190
Ala Ser Lys His Ala Ala Leu Gly Phe Phe Asp Cys Leu Arg Ala Glu
        195                 200                 205

Val Glu Glu Tyr Asp Val Val Ile Ser Thr Val Ser Pro Thr Phe Ile
    210                 215                 220

Arg Ser Tyr His Val Tyr Pro Glu Gln Gly Asn Trp Glu Ala Ser Ile
225                 230                 235                 240

Trp Lys Phe Phe Phe Arg Lys Leu Thr Tyr Gly Val His Pro Val Glu
            245                 250                 255

Val Ala Glu Glu Val Met Arg Thr Val Arg Arg Lys Lys Gln Glu Val
        260                 265                 270

Phe Met Ala Asn Pro Ile Pro Lys Ala Ala Val Tyr Val Arg Thr Phe
    275                 280                 285

Phe Pro Glu Phe Phe Phe Ala Val Val Ala Cys Gly Val Lys Glu Lys
290                 295                 300

Leu Asn Val Pro Glu Glu Gly
305                 310

<210> SEQ ID NO 6
<211> LENGTH: 933
<212> TYPE: DNA
<213> ORGANISM: Homo sapiens
<220> FEATURE:
<221> NAME/KEY: CDS
<222> LOCATION: (1)...(933)

<400> SEQUENCE: 6 atg gga gtc atg gcc atg ctg atg ctc ccc ctg ctg ctg ctg gga atc      48
Met Gly Val Met Ala Met Leu Met Leu Pro Leu Leu Leu Leu Gly Ile
1               5                   10                  15 agc ggc ctc ctc ttc att tac caa gag gtg tcc agg ctg tgg tca aag      96
Ser Gly Leu Leu Phe Ile Tyr Gln Glu Val Ser Arg Leu Trp Ser Lys
            20                  25                  30 tca gct gtg cag aac aaa gtg gtg gtg atc acc gat gcc atc tca gga     144
Ser Ala Val Gln Asn Lys Val Val Val Ile Thr Asp Ala Ile Ser Gly
        35                  40                  45 ctg ggc aag gag tgt gct cgg gtg ttc cac aca ggt ggg gca agg ctg     192
Leu Gly Lys Glu Cys Ala Arg Val Phe His Thr Gly Gly Ala Arg Leu
    50                  55                  60 gtg ctg tgt gga aag aac tgg gag agg cta gag aac cta tat gat gcc     240
Val Leu Cys Gly Lys Asn Trp Glu Arg Leu Glu Asn Leu Tyr Asp Ala
65                  70                  75                  80 ttg atc agc gtg gct gac ccc agc aag aca ttc acc cca aag ctg gtc     288
Leu Ile Ser Val Ala Asp Pro Ser Lys Thr Phe Thr Pro Lys Leu Val
                85                  90                  95 ctg ttg gac ctc tca gac atc agc tgt gtc cca gat gtg gca aaa gaa     336
Leu Leu Asp Leu Ser Asp Ile Ser Cys Val Pro Asp Val Ala Lys Glu
            100                 105                 110 gtc ctg gat tgc tat ggc tgt gtg gac atc ctc atc aac aat gcc agt     384
Val Leu Asp Cys Tyr Gly Cys Val Asp Ile Leu Ile Asn Asn Ala Ser
        115                 120                 125 gtg aag gtg aag ggg cct gcc cat aag att tct ctg gag ctc gac aaa     432
Val Lys Val Lys Gly Pro Ala His Lys Ile Ser Leu Glu Leu Asp Lys
    130                 135                 140 aag atc atg gat gcc aat tac ttt ggc ccc atc aca ttg acg aaa gcc     480
Lys Ile Met Asp Ala Asn Tyr Phe Gly Pro Ile Thr Leu Thr Lys Ala
145                 150                 155                 160 ctg ctt ccc aac atg atc tcc cgg aga aca ggc caa atc gtg tta gtg     528
Leu Leu Pro Asn Met Ile Ser Arg Arg Thr Gly Gln Ile Val Leu Val
```

```
aat aat atc caa ggg aag ttt gga atc ccg ttc cgt acg act tac gct    576
Asn Asn Ile Gln Gly Lys Phe Gly Ile Pro Phe Arg Thr Thr Tyr Ala
            180                 185                 190 gcc tcc aag cac gca gcc ctg ggc ttc ttt gac tgc ctc cga gcc gaa    624
Ala Ser Lys His Ala Ala Leu Gly Phe Phe Asp Cys Leu Arg Ala Glu
        195                 200                 205 gtg gag gaa tac gat gtt gtc atc agc acc gtg agc ccg act ttc atc    672
Val Glu Glu Tyr Asp Val Val Ile Ser Thr Val Ser Pro Thr Phe Ile
    210                 215                 220 cgg tcg tac cac gtg tat cca gag caa gga aac tgg gaa gct tcc att    720
Arg Ser Tyr His Val Tyr Pro Glu Gln Gly Asn Trp Glu Ala Ser Ile
225                 230                 235                 240 tgg aaa ttc ttt ttc agg aag ctg acc tac ggc gtg cac cca gta gag    768
Trp Lys Phe Phe Phe Arg Lys Leu Thr Tyr Gly Val His Pro Val Glu
                245                 250                 255 gtg gcg gag gag gtg atg cgc acc gtg cgg agg aag aag caa gag gtg    816
Val Ala Glu Glu Val Met Arg Thr Val Arg Arg Lys Lys Gln Glu Val
            260                 265                 270 ttt atg gcc aac ccc atc ccc aag gcc gcc gtg tac gtc cgc acc ttc    864
Phe Met Ala Asn Pro Ile Pro Lys Ala Ala Val Tyr Val Arg Thr Phe
        275                 280                 285 ttc ccg gag ttc ttt ttc gcc gtg gtg gcc tgt ggg gtg aag gag aag    912
Phe Pro Glu Phe Phe Phe Ala Val Val Ala Cys Gly Val Lys Glu Lys
    290                 295                 300 ctc aat gtc ccg gag gag ggg                                        933
Leu Asn Val Pro Glu Glu Gly
305                 310

<210> SEQ ID NO 7
<211> LENGTH: 1725
<212> TYPE: DNA
<213> ORGANISM: Homo sapiens
<220> FEATURE:
<221> NAME/KEY: CDS
<222> LOCATION: (281)...(1387)
<220> FEATURE:
<221> NAME/KEY: misc_feature
<222> LOCATION: 1606, 1620, 1631, 1655, 1658, 1666, 1673, 1688, 1705,
       1711
<223> OTHER INFORMATION: n = A,T,C or G

<400> SEQUENCE: 7
gagaaggagg agccagcgga aggacggtgt gcgggccggc cagccctgga cgaaagaaga    60
gggcccctcc aggccagtct gggcaccctg ggatagcggc tgcagccatc agcagggggca   120 gacggcaggt ggcctggttg ctgcagctcc caggatcagc tctgccctcc ccgcaaacgc   180
cagcctcgtc accgctccag ggcacctcca gcagtaacag gtggttgcag caggtggcag   240
ccagcccctg gatgagccaa ggtctcttcc ccagccaggc atg gcc gac tct gca    295
                                              Met Ala Asp Ser Ala
                                                1               5 cag gcc cag aag ctg gtg tac ctg gtc aca ggg ggc tgt ggc ttc ctg    343
Gln Ala Gln Lys Leu Val Tyr Leu Val Thr Gly Gly Cys Gly Phe Leu
            10                  15                  20 gga gag cac gtg gtg cga atg ctg ctg cag cgg gag ccc cgg ctc ggg    391
Gly Glu His Val Val Arg Met Leu Leu Gln Arg Glu Pro Arg Leu Gly
        25                  30                  35 gag ctg cgg gtc ttt gac caa cac ctg ggt ccc tgg ctg gag gag ctg    439
Glu Leu Arg Val Phe Asp Gln His Leu Gly Pro Trp Leu Glu Glu Leu
    40                  45                  50 aag aca ggg cct gtg agg gtg act gcc atc cag ggg gac gtg acc cag    487
```

-continued

```
Lys Thr Gly Pro Val Arg Val Thr Ala Ile Gln Gly Asp Val Thr Gln
 55                  60                  65 gcc cat gag gtg gca gca gct gtg gcc gga gcc cat gtg gtc atc cac        535
Ala His Glu Val Ala Ala Ala Val Ala Gly Ala His Val Val Ile His
 70                  75                  80                  85 acg gct ggg ctg gta gac gtg ttt ggc agg gcc agt ccc aag acc atc        583
Thr Ala Gly Leu Val Asp Val Phe Gly Arg Ala Ser Pro Lys Thr Ile
                 90                  95                 100 cat gag gtc aac gtg cag ggt acc cgg aac gtg atc gag gct tgt gtg        631
His Glu Val Asn Val Gln Gly Thr Arg Asn Val Ile Glu Ala Cys Val
                    105                 110                 115 cag acc gga aca cgg ttc ctg gtc tac acc agc agc atg gaa gtt gtg        679
Gln Thr Gly Thr Arg Phe Leu Val Tyr Thr Ser Ser Met Glu Val Val
                120                 125                 130 ggg cct aac acc aaa ggt cac ccc ttc tac agg ggc aac gaa gac acc        727
Gly Pro Asn Thr Lys Gly His Pro Phe Tyr Arg Gly Asn Glu Asp Thr
135                 140                 145 cca tac gaa gca gtg cac agg cac ccc tat cct tgc agc aag gcc ctg        775
Pro Tyr Glu Ala Val His Arg His Pro Tyr Pro Cys Ser Lys Ala Leu
150                 155                 160                 165 gcc gag tgg ctg gtc ctg gag gcc aac ggg agg aag gtc cgt ggg ggg        823
Ala Glu Trp Leu Val Leu Glu Ala Asn Gly Arg Lys Val Arg Gly Gly
                170                 175                 180 ctc ccc ctg gtg acg tgt gcc ctt cgt ccc acg ggc atc tac ggt gaa        871
Leu Pro Leu Val Thr Cys Ala Leu Arg Pro Thr Gly Ile Tyr Gly Glu
                185                 190                 195 ggc cac cag atc atg agg gac ttc tac cgc cag ggc ctg cgc ctg gga        919
Gly His Gln Ile Met Arg Asp Phe Tyr Arg Gln Gly Leu Arg Leu Gly
                200                 205                 210 ggt tgg ctc ttc cgg gcc atc ccg gcc tct gtg gag cat ggc cgg gtc        967
Gly Trp Leu Phe Arg Ala Ile Pro Ala Ser Val Glu His Gly Arg Val
215                 220                 225 tat gtg ggc aat gtt gcc tgg atg cac gtg ctg gca gcc cgg gag ctg       1015
Tyr Val Gly Asn Val Ala Trp Met His Val Leu Ala Ala Arg Glu Leu
230                 235                 240                 245 gag cag cgg gca gcc ctg atg ggc ggc cag gta tac ttc tgc tac gat       1063
Glu Gln Arg Ala Ala Leu Met Gly Gly Gln Val Tyr Phe Cys Tyr Asp
                250                 255                 260 gga tca ccc tac agg agc tac gag gat ttc aac atg gag ttc ctg ggc       1111
Gly Ser Pro Tyr Arg Ser Tyr Glu Asp Phe Asn Met Glu Phe Leu Gly
                265                 270                 275 ccc tgc gga ctg cgg ctg gtg ggc gcc cgc cca ttg ctg ccc tac tgg       1159
Pro Cys Gly Leu Arg Leu Val Gly Ala Arg Pro Leu Leu Pro Tyr Trp
                280                 285                 290 ctg ctg gtg ttc ctg gct gcc ctc aat gcc ctg ctg cag tgg ctg ctg       1207
Leu Leu Val Phe Leu Ala Ala Leu Asn Ala Leu Leu Gln Trp Leu Leu
                295                 300                 305 cgg cca ctg gtg ctc tac gca ccc ctg ctg aac ccc tac acg ctg gcc       1255
Arg Pro Leu Val Leu Tyr Ala Pro Leu Leu Asn Pro Tyr Thr Leu Ala
310                 315                 320                 325 gtg gcc aac acc acc ttc acc gtc agc acc gac aag gct cag cgc cat       1303
Val Ala Asn Thr Thr Phe Thr Val Ser Thr Asp Lys Ala Gln Arg His
                330                 335                 340 ttc ggc tat gag ccc ctg ttc tcg tgg gag gat agc cgg acc cgc acc       1351
Phe Gly Tyr Glu Pro Leu Phe Ser Trp Glu Asp Ser Arg Thr Arg Thr
                345                 350                 355 att ctc tgg gta cag gcc gct acg ggt tca gcc cag tgacggtggg           1397
Ile Leu Trp Val Gln Ala Ala Thr Gly Ser Ala Gln
                360                 365
```

```
gctgggcct ggaggcccag atacagcaca tccacccagg tcccgagccc tcacaccctg   1457
gacgggaagg gacagctgca ttccagagca ggaggcaggg ctctgggcc agaatggctg    1517 tccttgtcgt agagccctcc acattttctt tttcttttt gagacagggt cttgctctgt    1577
cacccagact ggaatgcaag tggtgtgant cataagctca ctngmaccct yaanccttct   1637
gggttcaagc aatccttnct ngcctyaanc cttctngaac aagcttggga nccacaggtg   1697
cacgccancc acanccctggc ttttttt                                     1725
```

<210> SEQ ID NO 8
<211> LENGTH: 369
<212> TYPE: PRT
<213> ORGANISM: Homo sapiens

<400> SEQUENCE: 8

```
Met Ala Asp Ser Ala Gln Ala Gln Lys Leu Val Tyr Leu Val Thr Gly
 1               5                  10                  15

Gly Cys Gly Phe Leu Gly Glu His Val Val Arg Met Leu Leu Gln Arg
                20                  25                  30

Glu Pro Arg Leu Gly Glu Leu Arg Val Phe Asp Gln His Leu Gly Pro
            35                  40                  45

Trp Leu Glu Glu Leu Lys Thr Gly Pro Val Arg Val Thr Ala Ile Gln
 50                  55                  60

Gly Asp Val Thr Gln Ala His Glu Val Ala Ala Val Ala Gly Ala
65                  70                  75                  80

His Val Val Ile His Thr Ala Gly Leu Val Asp Val Phe Gly Arg Ala
                85                  90                  95

Ser Pro Lys Thr Ile His Glu Val Asn Val Gln Gly Thr Arg Asn Val
            100                 105                 110

Ile Glu Ala Cys Val Gln Thr Gly Thr Arg Phe Leu Val Tyr Thr Ser
        115                 120                 125

Ser Met Glu Val Val Gly Pro Asn Thr Lys Gly His Pro Phe Tyr Arg
130                 135                 140

Gly Asn Glu Asp Thr Pro Tyr Glu Ala Val His Arg His Pro Tyr Pro
145                 150                 155                 160

Cys Ser Lys Ala Leu Ala Glu Trp Leu Val Leu Glu Ala Asn Gly Arg
                165                 170                 175

Lys Val Arg Gly Gly Leu Pro Leu Val Thr Cys Ala Leu Arg Pro Thr
            180                 185                 190

Gly Ile Tyr Gly Glu Gly His Gln Ile Met Arg Asp Phe Tyr Arg Gln
        195                 200                 205

Gly Leu Arg Leu Gly Gly Trp Leu Phe Arg Ala Ile Pro Ala Ser Val
210                 215                 220

Glu His Gly Arg Val Tyr Val Gly Asn Val Ala Trp Met His Val Leu
225                 230                 235                 240

Ala Ala Arg Glu Leu Glu Gln Arg Ala Ala Leu Met Gly Gly Gln Val
                245                 250                 255

Tyr Phe Cys Tyr Asp Gly Ser Pro Tyr Arg Ser Tyr Glu Asp Phe Asn
            260                 265                 270

Met Glu Phe Leu Gly Pro Cys Gly Leu Arg Leu Val Gly Ala Arg Pro
        275                 280                 285

Leu Leu Pro Tyr Trp Leu Leu Val Phe Leu Ala Ala Leu Asn Ala Leu
290                 295                 300

Leu Gln Trp Leu Leu Arg Pro Leu Val Leu Tyr Ala Pro Leu Leu Asn
305                 310                 315                 320
```

```
Pro Tyr Thr Leu Ala Val Ala Asn Thr Thr Phe Thr Val Ser Thr Asp
            325                 330                 335

Lys Ala Gln Arg His Phe Gly Tyr Glu Pro Leu Phe Ser Trp Glu Asp
            340                 345                 350

Ser Arg Thr Arg Thr Ile Leu Trp Val Gln Ala Ala Thr Gly Ser Ala
            355                 360                 365

Gln

<210> SEQ ID NO 9
<211> LENGTH: 1107
<212> TYPE: DNA
<213> ORGANISM: Homo sapiens
<220> FEATURE:
<221> NAME/KEY: CDS
<222> LOCATION: (1)...(1107)

<400> SEQUENCE: 9 atg gcc gac tct gca cag gcc cag aag ctg gtg tac ctg gtc aca ggg      48
Met Ala Asp Ser Ala Gln Ala Gln Lys Leu Val Tyr Leu Val Thr Gly
 1               5                  10                  15 ggc tgt ggc ttc ctg gga gag cac gtg gtg cga atg ctg ctg cag cgg      96
Gly Cys Gly Phe Leu Gly Glu His Val Val Arg Met Leu Leu Gln Arg
             20                  25                  30 gag ccc cgg ctc ggg gag ctg cgg gtc ttt gac caa cac ctg ggt ccc     144
Glu Pro Arg Leu Gly Glu Leu Arg Val Phe Asp Gln His Leu Gly Pro
         35                  40                  45 tgg ctg gag gag ctg aag aca ggg cct gtg agg gtg act gcc atc cag     192
Trp Leu Glu Glu Leu Lys Thr Gly Pro Val Arg Val Thr Ala Ile Gln
     50                  55                  60 ggg gac gtg acc cag gcc cat gag gtg gca gca gct gtg gcc gga gcc     240
Gly Asp Val Thr Gln Ala His Glu Val Ala Ala Ala Val Ala Gly Ala
 65                  70                  75                  80 cat gtg gtc atc cac acg gct ggg ctg gta gac gtg ttt ggc agg gcc     288
His Val Val Ile His Thr Ala Gly Leu Val Asp Val Phe Gly Arg Ala
                 85                  90                  95 agt ccc aag acc atc cat gag gtc aac gtg cag ggt acc cgg aac gtg     336
Ser Pro Lys Thr Ile His Glu Val Asn Val Gln Gly Thr Arg Asn Val
            100                 105                 110 atc gag gct tgt gtg cag acc gga aca cgg ttc ctg gtc tac acc agc     384
Ile Glu Ala Cys Val Gln Thr Gly Thr Arg Phe Leu Val Tyr Thr Ser
        115                 120                 125 agc atg gaa gtt gtg ggg cct aac acc aaa ggt cac ccc ttc tac agg     432
Ser Met Glu Val Val Gly Pro Asn Thr Lys Gly His Pro Phe Tyr Arg
    130                 135                 140 ggc aac gaa gac acc cca tac gaa gca gtg cac agg cac ccc tat cct     480
Gly Asn Glu Asp Thr Pro Tyr Glu Ala Val His Arg His Pro Tyr Pro
145                 150                 155                 160 tgc agc aag gcc ctg gcc gag tgg ctg gtc ctg gag gcc aac ggg agg     528
Cys Ser Lys Ala Leu Ala Glu Trp Leu Val Leu Glu Ala Asn Gly Arg
                165                 170                 175 aag gtc cgt ggg ggg ctg ccc ctg gtg acg tgt gcc ctt cgt ccc acg     576
Lys Val Arg Gly Gly Leu Pro Leu Val Thr Cys Ala Leu Arg Pro Thr
            180                 185                 190 ggc atc tac ggt gaa ggc cac cag atc atg agg gac ttc tac cgc cag     624
Gly Ile Tyr Gly Glu Gly His Gln Ile Met Arg Asp Phe Tyr Arg Gln
        195                 200                 205 ggc ctg cgc ctg gga ggt tgg ctc ttc cgg gcc atc ccg gcc tct gtg     672
Gly Leu Arg Leu Gly Gly Trp Leu Phe Arg Ala Ile Pro Ala Ser Val
    210                 215                 220
```

-continued

| | | |
|---|---|---|
| gag cat ggc cgg gtc tat gtg ggc aat gtt gcc tgg atg cac gtg ctg<br>Glu His Gly Arg Val Tyr Val Gly Asn Val Ala Trp Met His Val Leu<br>225                           230                       235                    240 | 720 | |
| gca gcc cgg gag ctg gag cag cgg gca gcc ctg atg ggc ggc cag gta<br>Ala Ala Arg Glu Leu Glu Gln Arg Ala Ala Leu Met Gly Gly Gln Val<br>                    245                       250                      255 | 768 | |
| tac ttc tgc tac gat gga tca ccc tac agg agc tac gag gat ttc aac<br>Tyr Phe Cys Tyr Asp Gly Ser Pro Tyr Arg Ser Tyr Glu Asp Phe Asn<br>260                         265                       270 | 816 | |
| atg gag ttc ctg ggc ccc tgc gga ctg cgg ctg gtg ggc gcc cgc cca<br>Met Glu Phe Leu Gly Pro Cys Gly Leu Arg Leu Val Gly Ala Arg Pro<br>               275                       280                       285 | 864 | |
| ttg ctg ccc tac tgg ctg ctg gtg ttc ctg gct gcc ctc aat gcc ctg<br>Leu Leu Pro Tyr Trp Leu Leu Val Phe Leu Ala Ala Leu Asn Ala Leu<br>290                         295                       300 | 912 | |
| ctg cag tgg ctg ctg cgg cca ctg gtg ctc tac gca ccc ctg ctg aac<br>Leu Gln Trp Leu Leu Arg Pro Leu Val Leu Tyr Ala Pro Leu Leu Asn<br>305                           310                       315                    320 | 960 | |
| ccc tac acg ctg gcc gtg gcc aac acc acc ttc acc gtc agc acc gac<br>Pro Tyr Thr Leu Ala Val Ala Asn Thr Thr Phe Thr Val Ser Thr Asp<br>                    325                       330                      335 | 1008 | |
| aag gct cag cgc cat ttc ggc tat gag ccc ctg ttc tcg tgg gag gat<br>Lys Ala Gln Arg His Phe Gly Tyr Glu Pro Leu Phe Ser Trp Glu Asp<br>340                         345                       350 | 1056 | |
| agc cgg acc cgc acc att ctc tgg gta cag gcc gct acg ggt tca gcc<br>Ser Arg Thr Arg Thr Ile Leu Trp Val Gln Ala Ala Thr Gly Ser Ala<br>               355                       360                       365 | 1104 | |
| cag<br>Gln | 1107 | |

```
<210> SEQ ID NO 10
<211> LENGTH: 1209
<212> TYPE: DNA
<213> ORGANISM: Homo sapiens
<220> FEATURE:
<221> NAME/KEY: CDS
<222> LOCATION: (61)...(1026)

<400> SEQUENCE: 10
```

| | | |
|---|---|---|
| cccacgcgtc cgcccacgcg tccgcggacg cgtgggcgga cgcgtggcg cccgcctcga | 60 | |
| atg tcc ctg aga ccc aga agg gcc tgc gct cag ctg ctc tgg cac ccc<br>Met Ser Leu Arg Pro Arg Arg Ala Cys Ala Gln Leu Leu Trp His Pro<br>1                     5                      10                       15 | 108 | |
| gct gca ggg atg gcc tcc tgg gct aag ggc agg agc tac ctg gcg cct<br>Ala Ala Gly Met Ala Ser Trp Ala Lys Gly Arg Ser Tyr Leu Ala Pro<br>                   20                       25                       30 | 156 | |
| ggt ttg ctg cag ggc caa gtg gcc atc gtc acc ggc ggg gcc acg ggc<br>Gly Leu Leu Gln Gly Gln Val Ala Ile Val Thr Gly Gly Ala Thr Gly<br>35                         40                       45 | 204 | |
| atc gga aaa gcc atc gtg aag gag ctc ctg gag ctg ggg agt aat gtg<br>Ile Gly Lys Ala Ile Val Lys Glu Leu Leu Glu Leu Gly Ser Asn Val<br>               50                       55                       60 | 252 | |
| gtc att gca tcc cgt aag ttg gag aga ttg aag tct gcg gca gat gaa<br>Val Ile Ala Ser Arg Lys Leu Glu Arg Leu Lys Ser Ala Ala Asp Glu<br>65                         70                       75                    80 | 300 | |
| ctg cag gcc aac cta cct ccc aca aag cag gca cga gtc att ccc ata<br>Leu Gln Ala Asn Leu Pro Pro Thr Lys Gln Ala Arg Val Ile Pro Ile<br>                   85                       90                       95 | 348 | |
| caa tgc aac atc cgg aat gag gag gag gtg aat aat ttg gtc aaa tct<br>Gln Cys Asn Ile Arg Asn Glu Glu Glu Val Asn Asn Leu Val Lys Ser<br>100                         105                       110 | 396 | |

```
acc tta gat act ttt ggt aag atc aat ttc ttg gtg aac aat gga gga      444
Thr Leu Asp Thr Phe Gly Lys Ile Asn Phe Leu Val Asn Asn Gly Gly
        115                 120                 125 ggc cag ttt ctt tcc cct gct gaa cac atc agt tct aag gga tgg cac      492
Gly Gln Phe Leu Ser Pro Ala Glu His Ile Ser Ser Lys Gly Trp His
130                 135                 140 gct gtg ctt gag acc aac ctg acg ggt acc ttc tac atg tgc aaa gca      540
Ala Val Leu Glu Thr Asn Leu Thr Gly Thr Phe Tyr Met Cys Lys Ala
145                 150                 155                 160 gtt tac agc tcc tgg atg aaa gag cat gga gga tct atc gtc aat atc      588
Val Tyr Ser Ser Trp Met Lys Glu His Gly Gly Ser Ile Val Asn Ile
                165                 170                 175 att gtc cct act aaa gct gga ttt cca tta gct gtg cat tct gga gct      636
Ile Val Pro Thr Lys Ala Gly Phe Pro Leu Ala Val His Ser Gly Ala
            180                 185                 190 gca aga gca ggt gtt tac aac ctc acc aaa tct tta gct ttg gaa tgg      684
Ala Arg Ala Gly Val Tyr Asn Leu Thr Lys Ser Leu Ala Leu Glu Trp
        195                 200                 205 gcc tgc agt gga ata cgg atc aat tgt gtt gcc cct gga gtt att tat      732
Ala Cys Ser Gly Ile Arg Ile Asn Cys Val Ala Pro Gly Val Ile Tyr
210                 215                 220 tcc cag act gct gtg gag aac tat ggt tcc tgg gga caa agc ttc ttt      780
Ser Gln Thr Ala Val Glu Asn Tyr Gly Ser Trp Gly Gln Ser Phe Phe
225                 230                 235                 240 gaa ggg tct ttt cag aaa atc ccc gct aaa cga att ggt gtt cct gag      828
Glu Gly Ser Phe Gln Lys Ile Pro Ala Lys Arg Ile Gly Val Pro Glu
                245                 250                 255 gag gtc tcc tct gtg gtc tgc ttc cta ctg tct cct gca gct tcc ttc      876
Glu Val Ser Ser Val Val Cys Phe Leu Leu Ser Pro Ala Ala Ser Phe
            260                 265                 270 atc act gga cag tcg gtg gat gtg gat ggg ggc cgg agt ctc tat act      924
Ile Thr Gly Gln Ser Val Asp Val Asp Gly Gly Arg Ser Leu Tyr Thr
        275                 280                 285 cac tcg tat gag gta cca gat cat gac aac tgg ccc aag gga gca ggg      972
His Ser Tyr Glu Val Pro Asp His Asp Asn Trp Pro Lys Gly Ala Gly
290                 295                 300 gac ctt tct gtt gtc aaa aag atg aag gag acc tta aag gag aaa gct     1020
Asp Leu Ser Val Val Lys Lys Met Lys Glu Thr Leu Lys Glu Lys Ala
305                 310                 315                 320 aag ctc tgagctgagg aaacaaggtg tcctccatcc ccagtgcctt cacatcttga      1076
Lys Leu ggatatgctt ctgtactttt taaaagctta tagttggtat ggaaaacatt tttcttattt      1136
ttaagtgtta ttaattatat ctatggaaaa actattcctg aaatatatac agtcttatgt      1196
cccaaaaaaa aaa                                                         1209

<210> SEQ ID NO 11
<211> LENGTH: 322
<212> TYPE: PRT
<213> ORGANISM: Homo sapiens

<400> SEQUENCE: 11

Met Ser Leu Arg Pro Arg Arg Ala Cys Ala Gln Leu Leu Trp His Pro
1               5                   10                  15

Ala Ala Gly Met Ala Ser Trp Ala Lys Gly Arg Ser Tyr Leu Ala Pro
            20                  25                  30

Gly Leu Leu Gln Gly Gln Val Ala Ile Val Thr Gly Gly Ala Thr Gly
        35                  40                  45
```

-continued

```
Ile Gly Lys Ala Ile Val Lys Glu Leu Leu Glu Leu Gly Ser Asn Val
 50                  55                  60

Val Ile Ala Ser Arg Lys Leu Glu Arg Leu Lys Ser Ala Ala Asp Glu
 65                  70                  75                  80

Leu Gln Ala Asn Leu Pro Pro Thr Lys Gln Ala Arg Val Ile Pro Ile
                 85                  90                  95

Gln Cys Asn Ile Arg Asn Glu Glu Val Asn Asn Leu Val Lys Ser
                100                 105                 110

Thr Leu Asp Thr Phe Gly Lys Ile Asn Phe Leu Val Asn Asn Gly Gly
            115                 120                 125

Gly Gln Phe Leu Ser Pro Ala Glu His Ile Ser Ser Lys Gly Trp His
130                 135                 140

Ala Val Leu Glu Thr Asn Leu Thr Gly Thr Phe Tyr Met Cys Lys Ala
145                 150                 155                 160

Val Tyr Ser Ser Trp Met Lys Glu His Gly Gly Ser Ile Val Asn Ile
                165                 170                 175

Ile Val Pro Thr Lys Ala Gly Phe Pro Leu Ala Val His Ser Gly Ala
                180                 185                 190

Ala Arg Ala Gly Val Tyr Asn Leu Thr Lys Ser Leu Ala Leu Glu Trp
            195                 200                 205

Ala Cys Ser Gly Ile Arg Ile Asn Cys Val Ala Pro Gly Val Ile Tyr
210                 215                 220

Ser Gln Thr Ala Val Glu Asn Tyr Gly Ser Trp Gly Gln Ser Phe Phe
225                 230                 235                 240

Glu Gly Ser Phe Gln Lys Ile Pro Ala Lys Arg Ile Gly Val Pro Glu
                245                 250                 255

Glu Val Ser Ser Val Val Cys Phe Leu Leu Ser Pro Ala Ala Ser Phe
                260                 265                 270

Ile Thr Gly Gln Ser Val Asp Val Asp Gly Gly Arg Ser Leu Tyr Thr
            275                 280                 285

His Ser Tyr Glu Val Pro Asp His Asp Asn Trp Pro Lys Gly Ala Gly
290                 295                 300

Asp Leu Ser Val Val Lys Lys Met Lys Glu Thr Leu Lys Glu Lys Ala
305                 310                 315                 320

Lys Leu
```

<210> SEQ ID NO 12
<211> LENGTH: 966
<212> TYPE: DNA
<213> ORGANISM: Homo sapiens
<220> FEATURE:
<221> NAME/KEY: CDS
<222> LOCATION: (1)...(966)

<400> SEQUENCE: 12

```
atg tcc ctg aga ccc aga agg gcc tgc gct cag ctg ctc tgg cac ccc      48
Met Ser Leu Arg Pro Arg Arg Ala Cys Ala Gln Leu Leu Trp His Pro
 1               5                  10                  15 gct gca ggg atg gcc tcc tgg gct aag ggc agg agc tac ctg gcg cct      96
Ala Ala Gly Met Ala Ser Trp Ala Lys Gly Arg Ser Tyr Leu Ala Pro
                20                  25                  30 ggt ttg ctg cag ggc caa gtg gcc atc gtc acc ggc ggg gcc acg ggc     144
Gly Leu Leu Gln Gly Gln Val Ala Ile Val Thr Gly Gly Ala Thr Gly
            35                  40                  45 atc gga aaa gcc atc gtg aag gag ctc ctg gag ctg ggg agt aat gtg     192
Ile Gly Lys Ala Ile Val Lys Glu Leu Leu Glu Leu Gly Ser Asn Val
 50                  55                  60
```

| | | | | | | | | | | | | | | | | |
|---|---|---|---|---|---|---|---|---|---|---|---|---|---|---|---|---|
| gtc | att | gca | tcc | cgt | aag | ttg | gag | aga | ttg | aag | tct | gcg | gca | gat | gaa | 240 |
| Val | Ile | Ala | Ser | Arg | Lys | Leu | Glu | Arg | Leu | Lys | Ser | Ala | Ala | Asp | Glu | |
| 65 | | | | 70 | | | | | 75 | | | | | 80 | | |
| ctg | cag | gcc | aac | cta | cct | ccc | aca | aag | cag | gca | cga | gtc | att | ccc | ata | 288 |
| Leu | Gln | Ala | Asn | Leu | Pro | Pro | Thr | Lys | Gln | Ala | Arg | Val | Ile | Pro | Ile | |
| | | | | 85 | | | | | 90 | | | | | 95 | | |
| caa | tgc | aac | atc | cgg | aat | gag | gag | gag | gtg | aat | aat | ttg | gtc | aaa | tct | 336 |
| Gln | Cys | Asn | Ile | Arg | Asn | Glu | Glu | Glu | Val | Asn | Asn | Leu | Val | Lys | Ser | |
| | | | 100 | | | | | 105 | | | | | 110 | | | |
| acc | tta | gat | act | ttt | ggt | aag | atc | aat | ttc | ttg | gtg | aac | aat | gga | gga | 384 |
| Thr | Leu | Asp | Thr | Phe | Gly | Lys | Ile | Asn | Phe | Leu | Val | Asn | Asn | Gly | Gly | |
| | | | 115 | | | | | 120 | | | | | 125 | | | |
| ggc | cag | ttt | ctt | tcc | cct | gct | gaa | cac | atc | agt | tct | aag | gga | tgg | cac | 432 |
| Gly | Gln | Phe | Leu | Ser | Pro | Ala | Glu | His | Ile | Ser | Ser | Lys | Gly | Trp | His | |
| | 130 | | | | | 135 | | | | | 140 | | | | | |
| gct | gtg | ctt | gag | acc | aac | ctg | acg | ggt | acc | ttc | tac | atg | tgc | aaa | gca | 480 |
| Ala | Val | Leu | Glu | Thr | Asn | Leu | Thr | Gly | Thr | Phe | Tyr | Met | Cys | Lys | Ala | |
| 145 | | | | | 150 | | | | | 155 | | | | | 160 | |
| gtt | tac | agc | tcc | tgg | atg | aaa | gag | cat | gga | gga | tct | atc | gtc | aat | atc | 528 |
| Val | Tyr | Ser | Ser | Trp | Met | Lys | Glu | His | Gly | Gly | Ser | Ile | Val | Asn | Ile | |
| | | | | 165 | | | | | 170 | | | | | 175 | | |
| att | gtc | cct | act | aaa | gct | gga | ttt | cca | tta | gct | gtg | cat | tct | gga | gct | 576 |
| Ile | Val | Pro | Thr | Lys | Ala | Gly | Phe | Pro | Leu | Ala | Val | His | Ser | Gly | Ala | |
| | | | 180 | | | | | 185 | | | | | 190 | | | |
| gca | aga | gca | ggt | gtt | tac | aac | ctc | acc | aaa | tct | tta | gct | ttg | gaa | tgg | 624 |
| Ala | Arg | Ala | Gly | Val | Tyr | Asn | Leu | Thr | Lys | Ser | Leu | Ala | Leu | Glu | Trp | |
| | | 195 | | | | | 200 | | | | | 205 | | | | |
| gcc | tgc | agt | gga | ata | cgg | atc | aat | tgt | gtt | gcc | cct | gga | gtt | att | tat | 672 |
| Ala | Cys | Ser | Gly | Ile | Arg | Ile | Asn | Cys | Val | Ala | Pro | Gly | Val | Ile | Tyr | |
| | 210 | | | | | 215 | | | | | 220 | | | | | |
| tcc | cag | act | gct | gtg | gag | aac | tat | ggt | tcc | tgg | gga | caa | agc | ttc | ttt | 720 |
| Ser | Gln | Thr | Ala | Val | Glu | Asn | Tyr | Gly | Ser | Trp | Gly | Gln | Ser | Phe | Phe | |
| 225 | | | | | 230 | | | | | 235 | | | | | 240 | |
| gaa | ggg | tct | ttt | cag | aaa | atc | ccc | gct | aaa | cga | att | ggt | gtt | cct | gag | 768 |
| Glu | Gly | Ser | Phe | Gln | Lys | Ile | Pro | Ala | Lys | Arg | Ile | Gly | Val | Pro | Glu | |
| | | | | 245 | | | | | 250 | | | | | 255 | | |
| gag | gtc | tcc | tct | gtg | gtc | tgc | ttc | cta | ctg | tct | cct | gca | gct | tcc | ttc | 816 |
| Glu | Val | Ser | Ser | Val | Val | Cys | Phe | Leu | Leu | Ser | Pro | Ala | Ala | Ser | Phe | |
| | | | 260 | | | | | 265 | | | | | 270 | | | |
| atc | act | gga | cag | tcg | gtg | gat | gtg | gat | ggg | ggc | cgg | agt | ctc | tat | act | 864 |
| Ile | Thr | Gly | Gln | Ser | Val | Asp | Val | Asp | Gly | Gly | Arg | Ser | Leu | Tyr | Thr | |
| | | 275 | | | | | 280 | | | | | 285 | | | | |
| cac | tcg | tat | gag | gta | cca | gat | cat | gac | aac | tgg | ccc | aag | gga | gca | ggg | 912 |
| His | Ser | Tyr | Glu | Val | Pro | Asp | His | Asp | Asn | Trp | Pro | Lys | Gly | Ala | Gly | |
| | 290 | | | | | 295 | | | | | 300 | | | | | |
| gac | ctt | tct | gtt | gtc | aaa | aag | atg | aag | gag | acc | tta | aag | gag | aaa | gct | 960 |
| Asp | Leu | Ser | Val | Val | Lys | Lys | Met | Lys | Glu | Thr | Leu | Lys | Glu | Lys | Ala | |
| 305 | | | | | 310 | | | | | 315 | | | | | 320 | |
| aag | ctc | | | | | | | | | | | | | | | 966 |
| Lys | Leu | | | | | | | | | | | | | | | |

<210> SEQ ID NO 13
<211> LENGTH: 303
<212> TYPE: PRT
<213> ORGANISM: Rattus norvegicus

<400> SEQUENCE: 13

| | | | | | | | | | | | | | | | |
|---|---|---|---|---|---|---|---|---|---|---|---|---|---|---|---|
| Met | Gly | Ser | Trp | Lys | Ser | Gly | Gln | Ser | Tyr | Leu | Ala | Ala | Gly | Leu | Leu |
| 1 | | | | 5 | | | | | 10 | | | | | 15 | |

```
Gln Asn Gln Val Ala Val Val Thr Gly Gly Ala Thr Gly Ile Gly Lys
            20                  25                  30

Ala Ile Ser Arg Glu Leu Leu His Leu Gly Cys Asn Val Val Ile Ala
        35                  40                  45

Ser Arg Lys Leu Asp Arg Leu Thr Ala Ala Val Asp Glu Leu Arg Ala
    50                  55                  60

Ser Gln Pro Pro Ser Ser Thr Gln Val Thr Ala Ile Gln Cys Asn
65                  70                  75                  80

Ile Arg Lys Glu Glu Glu Val Asn Asn Leu Val Lys Ser Thr Leu Ala
                85                  90                  95

Lys Tyr Gly Lys Ile Asn Phe Leu Val Asn Asn Ala Gly Gln Phe
            100                 105                 110

Met Ala Pro Ala Glu Asp Ile Thr Ala Lys Gly Trp Gln Ala Val Ile
            115                 120                 125

Glu Thr Asn Leu Thr Gly Thr Phe Tyr Met Cys Lys Ala Val Tyr Asn
130                 135                 140

Ser Trp Met Lys Asp His Gly Gly Ser Ile Val Asn Ile Ile Val Leu
145                 150                 155                 160

Leu Asn Asn Gly Phe Pro Thr Ala Ala His Ser Gly Ala Ala Arg Ala
                165                 170                 175

Gly Val Tyr Asn Leu Thr Lys Thr Met Ala Leu Thr Trp Ala Ser Ser
            180                 185                 190

Gly Val Arg Ile Asn Cys Val Ala Pro Gly Thr Ile Tyr Ser Gln Thr
        195                 200                 205

Ala Val Asp Asn Tyr Gly Glu Leu Gly Gln Thr Met Phe Glu Met Ala
    210                 215                 220

Phe Glu Asn Ile Pro Ala Lys Arg Val Gly Leu Pro Glu Glu Ile Ser
225                 230                 235                 240

Pro Leu Val Cys Phe Leu Leu Ser Pro Ala Ala Ser Phe Ile Thr Gly
                245                 250                 255

Gln Leu Ile Asn Val Asp Gly Gly Gln Ala Leu Tyr Thr Arg Asn Phe
            260                 265                 270

Thr Ile Pro Asp His Asp Asn Trp Pro Val Gly Ala Gly Asp Ser Ser
        275                 280                 285

Phe Ile Lys Lys Val Lys Glu Ser Leu Lys Lys Gln Ala Arg Leu
    290                 295                 300

<210> SEQ ID NO 14
<211> LENGTH: 1108
<212> TYPE: DNA
<213> ORGANISM: Mus musculus
<220> FEATURE:
<221> NAME/KEY: CDS
<222> LOCATION: (102)...(1034)

<400> SEQUENCE: 14
ggaatggatg ctgttggctt aaacctcccc ctgccctggg ggttgcaacc agggtctctg      60
caaagccaat cctttgtcat cccgctgtcc tgcagagcaa g atg ggg ctc atg gct    116
                                             Met Gly Leu Met Ala
                                               1               5 gtc ctg atg cta ccc ctg ctg ctg gga atc agc ggc ctc ctc ttc          164
Val Leu Met Leu Pro Leu Leu Leu Gly Ile Ser Gly Leu Leu Phe
             10                  15                  20 att tac cag gag gca tcc agg ctg tgg tcg aag tct gcc gtg cag aac      212
Ile Tyr Gln Glu Ala Ser Arg Leu Trp Ser Lys Ser Ala Val Gln Asn
         25                  30                  35
```

```
aaa gtg gtg gtc atc aca gat gcc atc tca gga ctg gga aag gag tgt          260
Lys Val Val Val Ile Thr Asp Ala Ile Ser Gly Leu Gly Lys Glu Cys
        40                  45                  50 gct cgg gtg ttc cat gca ggt ggg gca agg ctg gtg ctg tgt gga aag          308
Ala Arg Val Phe His Ala Gly Gly Ala Arg Leu Val Leu Cys Gly Lys
    55                  60                  65 aac tgg gag gga ctg gag agc ctc tat gcc acc ttg acc agt gtg gct          356
Asn Trp Glu Gly Leu Glu Ser Leu Tyr Ala Thr Leu Thr Ser Val Ala
70                  75                  80                  85 gac ccc agc aag aca ttc acc ccc aag ctg gtc ctg gat ctc tca              404
Asp Pro Ser Lys Thr Phe Thr Pro Lys Leu Val Leu Asp Leu Ser
                90                  95                 100 gac att agc tgt gtt caa gat gtg gcc aaa gag gtc ctg gac tgc tac          452
Asp Ile Ser Cys Val Gln Asp Val Ala Lys Glu Val Leu Asp Cys Tyr
            105                 110                 115 ggc tgt gtg gac atc ctc atc aac aat gcc agc gtg aaa gtg aag ggg          500
Gly Cys Val Asp Ile Leu Ile Asn Asn Ala Ser Val Lys Val Lys Gly
        120                 125                 130 cct gcc cac aag att tcc ctg gag ctt gac aaa aag atc atg gat gcc          548
Pro Ala His Lys Ile Ser Leu Glu Leu Asp Lys Lys Ile Met Asp Ala
    135                 140                 145 aac tac ttc gga ccc atc act tta acc aaa gtt ctg ctt ccc aac atg          596
Asn Tyr Phe Gly Pro Ile Thr Leu Thr Lys Val Leu Leu Pro Asn Met
150                 155                 160                 165 atc tcc agg aga aca ggc cag att gtg tta gtg aac aac atc caa gcg          644
Ile Ser Arg Arg Thr Gly Gln Ile Val Leu Val Asn Asn Ile Gln Ala
                170                 175                 180 aag ttt gga atc ccg ttc cgc aca gct tat gca gcc tct aag cat gcc          692
Lys Phe Gly Ile Pro Phe Arg Thr Ala Tyr Ala Ala Ser Lys His Ala
            185                 190                 195 gtc atg ggc ttc ttt gac tgc ctc cga gcc gag gtt gag gaa tac gat          740
Val Met Gly Phe Phe Asp Cys Leu Arg Ala Glu Val Glu Glu Tyr Asp
        200                 205                 210 gtt gtg gtc agc acc gtg agc cca act ttc atc cgc tcc tac cgt gct          788
Val Val Val Ser Thr Val Ser Pro Thr Phe Ile Arg Ser Tyr Arg Ala
    215                 220                 225 tcc cct gag caa aga aac tgg gag aca tcc att tgt aaa ttc ttc tgc          836
Ser Pro Glu Gln Arg Asn Trp Glu Thr Ser Ile Cys Lys Phe Phe Cys
230                 235                 240                 245 agg aag cta gcc tat ggc gtg cac ccg gtg gag gtg gct gag gaa gtg          884
Arg Lys Leu Ala Tyr Gly Val His Pro Val Glu Val Ala Glu Glu Val
                250                 255                 260 atg cgc aca gta cgg agg aag aag caa gag gtg ttc atg gcc aac ccg          932
Met Arg Thr Val Arg Arg Lys Lys Gln Glu Val Phe Met Ala Asn Pro
            265                 270                 275 gtt cct aag gct gcc gtg ttc atc cgc acc ttc ttc cct gag ttc ttc          980
Val Pro Lys Ala Ala Val Phe Ile Arg Thr Phe Phe Pro Glu Phe Phe
        280                 285                 290 ttc gct gtg gtg gcc tgt ggg gtg aag gag aag ctc aat gtc cca gaa         1028
Phe Ala Val Val Ala Cys Gly Val Lys Glu Lys Leu Asn Val Pro Glu
    295                 300                 305 gag ggt taacctcgtg gccaaggggg tcactcaagg ggaataaagg ctttcctaga          1084
Glu Gly
310 gaaaaaaaaa aaaaaaaaaa aaaa                                              1108

<210> SEQ ID NO 15
<211> LENGTH: 311
<212> TYPE: PRT
<213> ORGANISM: Mus musculus
```

<400> SEQUENCE: 15

| | | | | | | | | | | | | | | | |
|---|---|---|---|---|---|---|---|---|---|---|---|---|---|---|---|
| Met | Gly | Leu | Met | Ala | Val | Leu | Met | Leu | Pro | Leu | Leu | Leu | Leu | Gly | Ile |
| 1 | | | | 5 | | | | | 10 | | | | | 15 | |
| Ser | Gly | Leu | Leu | Phe | Ile | Tyr | Gln | Glu | Ala | Ser | Arg | Leu | Trp | Ser | Lys |
| | | | 20 | | | | | 25 | | | | | 30 | | |
| Ser | Ala | Val | Gln | Asn | Lys | Val | Val | Ile | Thr | Asp | Ala | Ile | Ser | Gly | |
| | | 35 | | | | | 40 | | | | | 45 | | | |
| Leu | Gly | Lys | Glu | Cys | Ala | Arg | Val | Phe | His | Ala | Gly | Ala | Arg | Leu | |
| | 50 | | | | | 55 | | | | | 60 | | | | |
| Val | Leu | Cys | Gly | Lys | Asn | Trp | Glu | Gly | Leu | Glu | Ser | Leu | Tyr | Ala | Thr |
| 65 | | | | | 70 | | | | | 75 | | | | | 80 |
| Leu | Thr | Ser | Val | Ala | Asp | Pro | Ser | Lys | Thr | Phe | Thr | Pro | Lys | Leu | Val |
| | | | | 85 | | | | | 90 | | | | | 95 | |
| Leu | Leu | Asp | Leu | Ser | Asp | Ile | Ser | Cys | Val | Gln | Asp | Val | Ala | Lys | Glu |
| | | | 100 | | | | | 105 | | | | | 110 | | |
| Val | Leu | Asp | Cys | Tyr | Gly | Cys | Val | Asp | Ile | Leu | Ile | Asn | Asn | Ala | Ser |
| | | 115 | | | | | 120 | | | | | 125 | | | |
| Val | Lys | Val | Lys | Gly | Pro | Ala | His | Lys | Ile | Ser | Leu | Glu | Leu | Asp | Lys |
| | 130 | | | | | 135 | | | | | 140 | | | | |
| Lys | Ile | Met | Asp | Ala | Asn | Tyr | Phe | Gly | Pro | Ile | Thr | Leu | Thr | Lys | Val |
| 145 | | | | | 150 | | | | | 155 | | | | | 160 |
| Leu | Leu | Pro | Asn | Met | Ile | Ser | Arg | Arg | Thr | Gly | Gln | Ile | Val | Leu | Val |
| | | | | 165 | | | | | 170 | | | | | 175 | |
| Asn | Asn | Ile | Gln | Ala | Lys | Phe | Gly | Ile | Pro | Phe | Arg | Thr | Ala | Tyr | Ala |
| | | | 180 | | | | | 185 | | | | | 190 | | |
| Ala | Ser | Lys | His | Ala | Val | Met | Gly | Phe | Phe | Asp | Cys | Leu | Arg | Ala | Glu |
| | | 195 | | | | | 200 | | | | | 205 | | | |
| Val | Glu | Glu | Tyr | Asp | Val | Val | Ser | Thr | Val | Ser | Pro | Thr | Phe | Ile | |
| | 210 | | | | | 215 | | | | | 220 | | | | |
| Arg | Ser | Tyr | Arg | Ala | Ser | Pro | Glu | Gln | Arg | Asn | Trp | Glu | Thr | Ser | Ile |
| 225 | | | | | 230 | | | | | 235 | | | | | 240 |
| Cys | Lys | Phe | Phe | Cys | Arg | Lys | Leu | Ala | Tyr | Gly | Val | His | Pro | Val | Glu |
| | | | | 245 | | | | | 250 | | | | | 255 | |
| Val | Ala | Glu | Glu | Val | Met | Arg | Thr | Val | Arg | Arg | Lys | Lys | Gln | Glu | Val |
| | | | 260 | | | | | 265 | | | | | 270 | | |
| Phe | Met | Ala | Asn | Pro | Val | Pro | Lys | Ala | Ala | Val | Phe | Ile | Arg | Thr | Phe |
| | | 275 | | | | | 280 | | | | | 285 | | | |
| Phe | Pro | Glu | Phe | Phe | Phe | Ala | Val | Val | Ala | Cys | Gly | Val | Lys | Glu | Lys |
| | 290 | | | | | 295 | | | | | 300 | | | | |
| Leu | Asn | Val | Pro | Glu | Glu | Gly | | | | | | | | | |
| 305 | | | | | 310 | | | | | | | | | | |

<210> SEQ ID NO 16
<211> LENGTH: 933
<212> TYPE: DNA
<213> ORGANISM: Mus musculus
<220> FEATURE:
<221> NAME/KEY: CDS
<222> LOCATION: (1)...(933)

<400> SEQUENCE: 16

| atg | ggg | ctc | atg | gct | gtc | ctg | atg | cta | ccc | ctg | ctg | ctg | gga | atc | | 48 |
|---|---|---|---|---|---|---|---|---|---|---|---|---|---|---|---|---|
| Met | Gly | Leu | Met | Ala | Val | Leu | Met | Leu | Pro | Leu | Leu | Leu | Gly | Ile | | |
| 1 | | | | 5 | | | | | 10 | | | | | 15 | | |

| agc | ggc | ctc | ctc | ttc | att | tac | cag | gag | gca | tcc | agg | ctg | tgg | tcg | aag | 96 |

```
Ser Gly Leu Leu Phe Ile Tyr Gln Glu Ala Ser Arg Leu Trp Ser Lys
         20                  25                  30 tct gcc gtg cag aac aaa gtg gtg gtc atc aca gat gcc atc tca gga      144
Ser Ala Val Gln Asn Lys Val Val Val Ile Thr Asp Ala Ile Ser Gly
         35                  40                  45 ctg gga aag gag tgt gct cgg gtg ttc cat gca ggt ggg gca agg ctg      192
Leu Gly Lys Glu Cys Ala Arg Val Phe His Ala Gly Gly Ala Arg Leu
 50                  55                  60 gtg ctg tgt gga aag aac tgg gag gga ctg gag agc ctc tat gcc acc      240
Val Leu Cys Gly Lys Asn Trp Glu Gly Leu Glu Ser Leu Tyr Ala Thr
 65                  70                  75                  80 ttg acc agt gtg gct gac ccc agc aag aca ttc acc ccc aag ctg gtc      288
Leu Thr Ser Val Ala Asp Pro Ser Lys Thr Phe Thr Pro Lys Leu Val
                 85                  90                  95 ctc ctg gat ctc tca gac att agc tgt gtt caa gat gtg gcc aaa gag      336
Leu Leu Asp Leu Ser Asp Ile Ser Cys Val Gln Asp Val Ala Lys Glu
                 100                 105                 110 gtc ctg gac tgc tac ggc tgt gtg gac atc ctc atc aac aat gcc agc      384
Val Leu Asp Cys Tyr Gly Cys Val Asp Ile Leu Ile Asn Asn Ala Ser
             115                 120                 125 gtg aaa gtg aag ggg cct gcc cac aag att tcc ctg gag ctt gac aaa      432
Val Lys Val Lys Gly Pro Ala His Lys Ile Ser Leu Glu Leu Asp Lys
         130                 135                 140 aag atc atg gat gcc aac tac ttc gga ccc atc act tta acc aaa gtt      480
Lys Ile Met Asp Ala Asn Tyr Phe Gly Pro Ile Thr Leu Thr Lys Val
145                 150                 155                 160 ctg ctt ccc aac atg atc tcc agg aga aca ggc cag att gtg tta gtg      528
Leu Leu Pro Asn Met Ile Ser Arg Arg Thr Gly Gln Ile Val Leu Val
                 165                 170                 175 aac aac atc caa gcg aag ttt gga atc ccg ttc cgc aca gct tat gca      576
Asn Asn Ile Gln Ala Lys Phe Gly Ile Pro Phe Arg Thr Ala Tyr Ala
             180                 185                 190 gcc tct aag cat gcc gtc atg ggc ttc ttt gac tgc ctc cga gcc gag      624
Ala Ser Lys His Ala Val Met Gly Phe Phe Asp Cys Leu Arg Ala Glu
         195                 200                 205 gtt gag gaa tac gat gtt gtg gtc agc acc gtg agc cca act ttc atc      672
Val Glu Glu Tyr Asp Val Val Val Ser Thr Val Ser Pro Thr Phe Ile
 210                 215                 220 cgc tcc tac cgt gct tcc cct gag caa aga aac tgg gag aca tcc att      720
Arg Ser Tyr Arg Ala Ser Pro Glu Gln Arg Asn Trp Glu Thr Ser Ile
225                 230                 235                 240 tgt aaa ttc ttc tgc agg aag cta gcc tat ggc gtg cac ccg gtg gag      768
Cys Lys Phe Phe Cys Arg Lys Leu Ala Tyr Gly Val His Pro Val Glu
                 245                 250                 255 gtg gct gag gaa gtg atg cgc aca gta cgg agg aag aag caa gag gtg      816
Val Ala Glu Glu Val Met Arg Thr Val Arg Arg Lys Lys Gln Glu Val
             260                 265                 270 ttc atg gcc aac ccg gtt cct aag gct gcc gtg ttc atc cgc acc ttc      864
Phe Met Ala Asn Pro Val Pro Lys Ala Ala Val Phe Ile Arg Thr Phe
         275                 280                 285 ttc cct gag ttc ttc ttc gct gtg gtg gcc tgt ggg gtg aag gag aag      912
Phe Pro Glu Phe Phe Phe Ala Val Val Ala Cys Gly Val Lys Glu Lys
 290                 295                 300 ctc aat gtc cca gaa gag ggt                                          933
Leu Asn Val Pro Glu Glu Gly
305                 310

<210> SEQ ID NO 17
<211> LENGTH: 491
<212> TYPE: PRT
```

<213> ORGANISM: Artificial Sequence
<220> FEATURE:
<223> OTHER INFORMATION: aldehyde dehydrogenase domain

<400> SEQUENCE: 17

```
Glu Trp Val Asp Ser Ala Ser Gly Lys Thr Phe Glu Val Val Asn Pro
  1               5                  10                  15

Ala Asn Lys Gly Glu Val Ile Gly Arg Val Pro Glu Ala Thr Ala Glu
             20                  25                  30

Asp Val Asp Ala Ala Val Lys Ala Ala Lys Glu Ala Phe Lys Ser Gly
         35                  40                  45

Pro Trp Trp Ala Lys Val Pro Ala Ser Glu Arg Ala Arg Ile Leu Arg
 50                  55                  60

Lys Leu Ala Asp Leu Ile Glu Glu Arg Glu Asp Glu Leu Ala Ala Leu
 65                  70                  75                  80

Glu Thr Leu Asp Leu Gly Lys Pro Leu Ala Glu Ala Lys Gly Asp Thr
                 85                  90                  95

Glu Val Gly Arg Ala Ile Asp Glu Ile Arg Tyr Tyr Ala Gly Trp Ala
                100                 105                 110

Arg Lys Leu Met Gly Glu Arg Val Ile Pro Ser Leu Ala Thr Asp
             115                 120                 125

Gly Asp Glu Glu Leu Asn Tyr Thr Arg Arg Glu Pro Leu Gly Val Val
         130                 135                 140

Gly Val Ile Ser Pro Trp Asn Phe Pro Leu Leu Leu Ala Leu Trp Lys
145                 150                 155                 160

Leu Ala Pro Ala Leu Ala Ala Gly Asn Thr Val Val Leu Lys Pro Ser
                165                 170                 175

Glu Gln Thr Pro Leu Thr Ala Leu Leu Leu Ala Glu Leu Ile Glu Glu
             180                 185                 190

Ala Gly Ala Asn Asn Leu Pro Lys Gly Val Val Asn Val Pro Gly
         195                 200                 205

Phe Gly Ala Glu Val Gly Gln Ala Leu Leu Ser His Pro Asp Ile Asp
210                 215                 220

Lys Ile Ser Phe Thr Gly Ser Thr Glu Val Gly Lys Leu Ile Met Glu
225                 230                 235                 240

Ala Ala Ala Ala Lys Asn Leu Lys Lys Val Thr Leu Glu Leu Gly Gly
                245                 250                 255

Lys Ser Pro Val Ile Val Phe Asp Asp Ala Asp Leu Asp Lys Ala Val
             260                 265                 270

Glu Arg Ile Val Phe Gly Ala Phe Gly Asn Ala Gly Gln Val Cys Ile
         275                 280                 285

Ala Pro Ser Arg Leu Leu Val His Glu Ser Ile Tyr Asp Glu Phe Val
290                 295                 300

Glu Lys Leu Lys Glu Arg Val Lys Lys Leu Lys Leu Ile Gly Asp Pro
305                 310                 315                 320

Leu Asp Ser Asp Thr Asn Ile Tyr Gly Pro Leu Ile Ser Glu Gln Gln
                325                 330                 335

Phe Asp Arg Val Leu Ser Tyr Ile Glu Asp Gly Lys Glu Glu Gly Ala
             340                 345                 350

Lys Val Leu Cys Gly Gly Glu Arg Asp Glu Ser Lys Glu Tyr Leu Gly
         355                 360                 365

Gly Gly Tyr Tyr Val Gln Pro Thr Ile Phe Thr Asp Val Thr Pro Asp
370                 375                 380

Met Lys Ile Met Lys Glu Glu Ile Phe Gly Pro Val Leu Pro Ile Ile
```

```
385                 390                 395                 400

Lys Phe Asp Leu Asp Glu Ala Ile Glu Leu Ala Asn Asp Thr Glu Tyr
                405                 410                 415

Gly Leu Ala Ala Tyr Val Phe Thr Lys Asp Ile Leu Ala Arg Ala Phe
                420                 425                 430

Arg Val Ala Lys Ala Leu Glu Ala Gly Ile Val Trp Val Asn Asp Val
                435                 440                 445

Cys Val His Ala Ala Glu Pro Gln Leu Pro Phe Gly Gly Val His Gln
            450                 455                 460

Ser Ser Gly Ile Gly Arg Glu His Gly Gly Lys Tyr Gly Leu Glu Glu
465                 470                 475                 480

Tyr Thr Glu Ile Lys Thr Val Thr Ile Arg Leu
                485                 490

<210> SEQ ID NO 18
<211> LENGTH: 671
<212> TYPE: PRT
<213> ORGANISM: Artificial Sequence
<220> FEATURE:
<223> OTHER INFORMATION: aldehyde dehydrogenase oxidoreductase domain
<220> FEATURE:
<221> NAME/KEY: VARIANT
<222> LOCATION: 96, 97, 98, 99, 100, 101, 102, 103, 104, 105, 106, 107,
      108, 109, 110, 111, 112, 113, 114, 162, 163, 164, 165, 166, 167,
      168, 169, 170, 171, 172, 173, 174, 175, 176, 177, 178, 179,
      180, 181, 182, 385, 386, 387, 388, 389, 390, 391
<223> OTHER INFORMATION: Xaa = Any Amino Acid
<220> FEATURE:
<221> NAME/KEY: VARIANT
<222> LOCATION: 392, 393, 394, 395, 396, 397, 398, 399, 400, 401, 402,
      403, 404, 405, 406, 407, 408, 409, 410, 411, 412, 413, 414, 415,
      416, 417, 418, 419, 420, 421, 422, 423, 424, 425, 426, 427,
      428, 429, 430, 431, 432, 433, 434, 435, 436, 437, 438
<223> OTHER INFORMATION: Xaa = Any Amino Acid
<220> FEATURE:
<221> NAME/KEY: VARIANT
<222> LOCATION: 439, 440, 441, 442, 443, 444, 445, 446, 447, 448, 449,
      450, 488, 489, 490, 491, 492, 493, 494, 495, 496, 497, 498, 499,
      500, 516, 517, 518, 519, 520, 521, 522, 523, 524, 525, 526,
      527, 528, 529
<223> OTHER INFORMATION: Xaa = Any Amino Acid

<400> SEQUENCE: 18

Arg Ala Gln His Leu Thr Arg Leu Ala Glu Val Ile Gln Lys His Gln
1               5                   10                  15

Arg Leu Leu Trp Thr Leu Glu Ser Leu Val Thr Gly Arg Ala Val Arg
                20                  25                  30

Glu Val Arg Asp Gly Asp Val Gln Leu Ala Gln Gln Leu Leu His Tyr
            35                  40                  45

His Ala Ile Gln Ala Ser Thr Gln Glu Glu Ala Leu Ala Gly Trp Glu
        50                  55                  60

Pro Met Gly Val Ile Gly Leu Ile Leu Pro Thr Phe Ser Phe Leu
65                  70                  75                  80

Glu Met Met Trp Arg Ile Cys Pro Ala Leu Ala Val Gly Val Thr Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Gly Glu Leu Gly Pro Phe Pro Gly Ile Leu Asn Val Val Ser
            115                 120                 125

Gly Pro Ala Ser Leu Val Pro Ile Leu Ala Ser Gln Pro Gly Ile Arg
        130                 135                 140

Lys Val Ala Phe Cys Gly Ala Pro Glu Glu Gly Arg Ala Leu Arg Arg
```

```
                145                 150                 155                 160
Ser Xaa Xaa Xaa Xaa Xaa Xaa Xaa Xaa Xaa Xaa Xaa Xaa Xaa
                    165                 170                 175
Xaa Xaa Xaa Xaa Xaa Xaa Asp Thr Ala Asp Val Asp Ser Ala Val Glu
                180                 185                 190
Gly Val Val Asp Ala Ala Trp Ser Asp Pro Gly Pro Gly Gly Leu Arg
                195                 200                 205
Leu Leu Ile Gln Glu Ser Val Trp Asp Glu Ala Met Arg Arg Leu Gln
            210                 215                 220
Glu Arg Met Gly Arg Leu Arg Ser Gly Arg Gly Leu Asp Gly Ala Val
225                 230                 235                 240
Asp Met Gly Ala Arg Gly Ala Ala Cys Asp Leu Val Gln Arg Phe
                    245                 250                 255
Val Arg Glu Ala Gln Ser Gln Gly Ala Gln Val Phe Gln Ala Gly Asp
                260                 265                 270
Val Pro Ser Glu Arg Pro Phe Tyr Pro Pro Thr Leu Val Ser Asn Leu
            275                 280                 285
Pro Pro Ala Ser Pro Cys Ala Gln Val Glu Val Pro Trp Pro Val Val
            290                 295                 300
Val Ala Ser Pro Phe Arg Thr Ala Lys Glu Ala Leu Leu Val Ala Asn
305                 310                 315                 320
Gly Thr Pro Arg Gly Gly Ser Ala Ser Val Trp Ser Glu Arg Leu Gly
                    325                 330                 335
Gln Ala Leu Glu Leu Gly Tyr Gly Leu Gln Val Gly Thr Val Trp Ile
                340                 345                 350
Asn Ala His Gly Leu Arg Asp Pro Ser Val Pro Thr Gly Gly Cys Lys
                355                 360                 365
Glu Ser Gly Cys Ser Trp His Gly Gly Pro Asp Gly Leu Tyr Glu Tyr
            370                 375                 380
Xaa Xaa Xaa Xaa Xaa Xaa Xaa Xaa Xaa Xaa Xaa Xaa Xaa Xaa Xaa Xaa
385                 390                 395                 400
Xaa Xaa Xaa Xaa Xaa Xaa Xaa Xaa Xaa Xaa Xaa Xaa Xaa Xaa Xaa
                    405                 410                 415
Xaa Xaa Xaa Xaa Xaa Xaa Xaa Xaa Xaa Xaa Xaa Xaa Xaa Xaa Xaa
                420                 425                 430
Xaa Xaa Xaa Xaa Xaa Xaa Xaa Xaa Xaa Xaa Xaa Xaa Xaa Xaa Xaa
                435                 440                 445
Xaa Xaa Ser Ser Gly Asn Leu His Gly Tyr Val Ala Glu Gly Gly Ala
            450                 455                 460
Lys Asp Ile Arg Gly Ala Val Glu Ala Ala His Gln Ala Phe Pro Gly
465                 470                 475                 480
Trp Ala Gly Gln Ser Pro Gly Xaa Xaa Xaa Xaa Xaa Xaa Xaa Xaa
                    485                 490                 495
Xaa Xaa Xaa Xaa Glu Arg Arg Lys Ser Thr Leu Ala Ser Arg Leu Glu
                500                 505                 510
Arg Gln Gly Xaa Xaa Xaa Xaa Xaa Xaa Xaa Xaa Xaa Xaa Xaa Xaa
            515                 520                 525
Xaa Arg Arg Leu Arg Ala Trp Gly Ala Arg Val Gln Ala Gln Gly His
            530                 535                 540
Thr Leu Gln Val Ala Gly Leu Arg Gly Pro Val Leu Arg Leu Arg Glu
545                 550                 555                 560
Pro Leu Gly Val Leu Ala Val Val Cys Pro Asp Glu Trp Pro Leu Leu
                565                 570                 575
```

```
Ala Phe Val Ser Leu Leu Ala Pro Ala Leu Ala Thr Gly Asn Thr Val
            580                 585                 590

Val Met Val Pro Ser Ala Ala Cys Pro Leu Leu Ala Leu Glu Val Cys
        595                 600                 605

Gln Asp Met Ala Thr Val Phe Pro Ala Gly Leu Ala Asn Val Val Thr
    610                 615                 620

Gly Asp Arg Asp His Leu Thr Arg Cys Leu Ala Leu His Gln Asp Val
625                 630                 635                 640

Gln Ala Met Trp Tyr Phe Gly Ser Ala Gln Gly Ser Gln Phe Val Glu
                645                 650                 655

Trp Ala Ser Ala Gly Asn Leu Lys Pro Val Trp Ala Ser Arg Gly
            660                 665                 670

<210> SEQ ID NO 19
<211> LENGTH: 203
<212> TYPE: PRT
<213> ORGANISM: Artificial Sequence
<220> FEATURE:
<223> OTHER INFORMATION: short chain dehydrogenase domain

<400> SEQUENCE: 19

Lys Val Ala Leu Val Thr Gly Ala Ser Ser Gly Ile Gly Leu Ala Ile
1               5                   10                  15

Ala Lys Arg Leu Ala Lys Glu Gly Ala Lys Val Val Ala Asp Arg
            20                  25                  30

Asn Glu Glu Lys Leu Glu Lys Gly Ala Val Ala Lys Glu Leu Lys Glu
        35                  40                  45

Leu Gly Gly Asn Asp Lys Asp Arg Ala Leu Ala Ile Gln Leu Asp Val
    50                  55                  60

Thr Asp Glu Glu Ser Val Ala Ala Val Glu Gln Ala Val Glu Arg Leu
65                  70                  75                  80

Gly Arg Leu Asp Val Leu Val Asn Asn Ala Gly Ile Ile Leu Leu
                85                  90                  95

Arg Pro Gly Pro Phe Ala Glu Leu Ser Arg Thr Met Glu Glu Asp Trp
            100                 105                 110

Asp Arg Val Ile Asp Val Asn Leu Thr Gly Val Phe Leu Leu Thr Arg
        115                 120                 125

Ala Val Leu Pro Leu Met Ala Met Lys Lys Arg Gly Gly Arg Ile
    130                 135                 140

Val Asn Ile Ser Ser Val Ala Gly Arg Lys Glu Gly Gly Leu Val Gly
145                 150                 155                 160

Val Pro Gly Gly Ser Ala Tyr Ser Ala Ser Lys Ala Ala Val Ile Gly
                165                 170                 175

Leu Thr Arg Ser Leu Ala Leu Glu Leu Ala Pro His Gly Ile Arg Val
            180                 185                 190

Asn Ala Val Ala Pro Gly Gly Val Asp Thr Asp
        195                 200

<210> SEQ ID NO 20
<211> LENGTH: 14
<212> TYPE: PRT
<213> ORGANISM: Artificial Sequence
<220> FEATURE:
<223> OTHER INFORMATION: alpha2 macroglobulin family domain

<400> SEQUENCE: 20

Ile Asp Glu Asp Asp Ile Thr Ile Arg Ser Tyr Phe Pro Glu
```

```
<210> SEQ ID NO 21
<211> LENGTH: 127
<212> TYPE: PRT
<213> ORGANISM: Artificial Sequence
<220> FEATURE:
<223> OTHER INFORMATION: oxidoreductase protein dehydrogenase

<400> SEQUENCE: 21

Asp Leu Ser Asp Ile Ser Cys Val Pro Asp Val Ala Lys Glu Val Leu
 1               5                  10                  15

Asp Cys Tyr Gly Cys Val Asp Ile Leu Ile Asn Asn Ala Ser Val Lys
             20                  25                  30

Val Lys Gly Pro Ala His Lys Ile Ser Leu Glu Leu Asp Lys Lys Ile
         35                  40                  45

Met Asp Ala Asn Tyr Phe Gly Pro Ile Leu Thr Leu Thr Lys Ala Leu
 50                  55                  60

Leu Pro Asn Met Ile Ser Arg Arg Thr Gly Gln Ile Val Leu Val Asn
65                  70                  75                  80

Asn Ile Gln Gly Lys Phe Gly Ile Pro Phe Arg Thr Thr Tyr Ala Ala
                 85                  90                  95

Ser Lys His Ala Ala Ser Lys His Ala Ala Leu Gly Phe Phe Asp Cys
            100                 105                 110

Leu Arg Ala Glu Val Glu Glu Tyr Asp Val Val Ile Ser Thr Val
        115                 120                 125

<210> SEQ ID NO 22
<211> LENGTH: 12
<212> TYPE: PRT
<213> ORGANISM: Artificial Sequence
<220> FEATURE:
<223> OTHER INFORMATION: S-adenosylmethionine synthetase domain

<400> SEQUENCE: 22

His Phe Gly Arg Glu Glu Val Asp Phe Pro Trp Glu
 1               5                  10

<210> SEQ ID NO 23
<211> LENGTH: 424
<212> TYPE: PRT
<213> ORGANISM: Artificial Sequence
<220> FEATURE:
<223> OTHER INFORMATION: 3-beta hydroxysteroid dehydrogenase domain

<400> SEQUENCE: 23

Glu Leu Ser Glu Ser Leu Asp Met Ala Gly Leu Ser Cys Leu Val Thr
 1               5                  10                  15

Gly Gly Gly Gly Phe Leu Gly Arg His Ile Val Arg Glu Leu Leu Arg
             20                  25                  30

Glu Gly Glu Ser Leu Gln Glu Val Arg Val Phe Asp Leu Arg Phe Ser
         35                  40                  45

Pro Glu Leu Asp Glu Asp Ser Ser Lys Leu Gln Val Ile Thr Lys Ile
 50                  55                  60

Lys Tyr Ile Glu Gly Asp Val Thr Asp Lys Gln Asp Leu Ala Ala Ala
65                  70                  75                  80

Leu Gln Gly Ile Ser Cys Cys Thr Leu Leu Asp Met Thr Leu Met Asp
                 85                  90                  95

Asp Val Val Ile His Thr Ala Ala Ile Ile Asp Val Phe Gly Glu Leu
            100                 105                 110
```

```
Arg Val Ser Gly Ser Asp Leu Ser Phe Gly Val Thr Val Leu Phe Leu
            115                 120                 125

Ala Val Thr Glu Gly Ser Tyr Val Phe Tyr Met Gly Ala Thr Asp
        130                 135                 140

Leu Arg Lys Ala Ser Arg Asp Arg Ile Met Lys Val Asn Val Lys Gly
145                 150                 155                 160

Thr Gln Asn Val Leu Asp Ala Cys Val Glu Ala Gly Val Arg Val Leu
                165                 170                 175

Val Tyr Thr Ser Ser Met Glu Val Val Gly Pro Asn Ser Arg Gly Gln
            180                 185                 190

Pro Ile Val Asn Gly Asp Glu Thr Thr Pro Tyr Glu Ser Thr Asp Asp
            195                 200                 205

His Gln Asp Ala Tyr Pro Glu Ser Lys Ala Leu Ala Glu Lys Leu Val
            210                 215                 220

Leu Lys Ala Asn Gly Ser Met Leu Lys Asn Gly Gly Arg Leu Tyr Thr
225                 230                 235                 240

Cys Ala Leu Arg Pro Ala Gly Ile Phe Glu Gly Asp Gln Phe Leu Val
                245                 250                 255

Pro Phe Leu Arg Gln Leu Val Lys Asn Gly Leu Ala Lys Phe Arg Ile
                260                 265                 270

Gly Asp Lys Asn Ala Leu Ser Asp Arg Val Tyr Val Gly Asn Val Ala
            275                 280                 285

Trp Ala His Ile Leu Ala Ala Arg Ala Leu Gln Asp Pro Lys Lys Gly
            290                 295                 300

Arg Glu Gly Ala Ser Ser Ile Ala Gly Gln Ala Tyr Phe Ile Ser Asp
305                 310                 315                 320

Asp Ser Pro Val Asn Ser Tyr Asp Asp Phe Asn Arg Thr Leu Leu Lys
                325                 330                 335

Ala Leu Gly Leu Arg Leu Pro Ser Thr Trp Arg Leu Pro Leu Pro Leu
                340                 345                 350

Leu Tyr Val Leu Ala Tyr Leu Asn Glu Leu Leu Ser Trp Leu Leu Arg
            355                 360                 365

Lys Leu Ala Leu Arg Tyr Thr Pro Leu Leu Asn Pro Tyr Thr Val Thr
370                 375                 380

Leu Ala Asn Thr Thr Phe Thr Phe Ser Thr Asn Lys Ala Lys Lys Asp
385                 390                 395                 400

Leu Gly Tyr Glu Pro Leu Val Thr Trp Glu Glu Ala Arg Ala Lys Thr
                405                 410                 415

Ile Glu Trp Ile Gln Glu Leu Glu
            420

<210> SEQ ID NO 24
<211> LENGTH: 359
<212> TYPE: PRT
<213> ORGANISM: Artificial Sequence
<220> FEATURE:
<223> OTHER INFORMATION: NAD dependent epimerase/dehydratase domain

<400> SEQUENCE: 24

Ile Leu Val Thr Gly Gly Ala Gly Phe Ile Gly Ser His Leu Val Arg
1               5                   10                  15

Glu Leu Leu Asn Asn Tyr Gly Asp Asp Lys Val Val Val Leu Asp Asn
                20                  25                  30

Leu Thr Asp Tyr Tyr Gln Tyr Ala Gly Asn Glu Ala Arg Leu Glu Val
            35                  40                  45
```

-continued

```
Val Glu Gly Asn Pro Arg Tyr Thr Phe Val Lys Gly Asp Ile Cys Asp
 50                  55                  60

Arg Asp Leu Leu Asp Lys Val Phe Ala Glu His Gln Pro Asp Ala Val
 65                  70                  75                  80

Ile His Phe Ala Ala Glu Ser His Val Asp Arg Ser Ile Glu Lys Pro
                 85                  90                  95

Leu Ala Tyr Ile Asp Thr Asn Val Val Gly Thr Leu Thr Leu Leu Glu
            100                 105                 110

Ala Ala Arg Asn Tyr Trp Ser Ala Leu Asp Glu Thr Lys Ala Gly Val
        115                 120                 125

Lys Lys Phe Val Phe Ser Ser Thr Asp Glu Val Tyr Gly Asp Leu Glu
130                 135                 140

Ser Ile Pro Ile Ser Ala Phe Thr Glu Asp Thr Pro Tyr Asn Pro Ser
145                 150                 155                 160

Ser Pro Tyr Gly Ala Ser Lys Ala Ser Ser Glu Leu Leu Val Arg Ala
                165                 170                 175

Tyr His Arg Ala Tyr Gly Leu Pro Ala Ile Ile Leu Arg Tyr Phe Asn
            180                 185                 190

Val Tyr Gly Pro Tyr Gln Ser Gly Arg Ile Gly Glu Asp Pro Asn Gly
        195                 200                 205

Phe Pro Glu Lys Leu Ile Pro Leu Ile Ile Gln Asn Ala Leu Gly Lys
210                 215                 220

Gly Glu Pro Leu Pro Val Tyr Gly Asp Gly Tyr Pro Thr Pro Asp Gly
225                 230                 235                 240

Thr Gln Val Arg Asp Trp Ile His Val Glu Asp His Ala Arg Ala Asn
                245                 250                 255

His Leu Leu Ala Leu Thr Lys Gly Arg Ala Gly Lys Gly Ser Glu Val
            260                 265                 270

Tyr Asn Ile Gly Gly Gly Asn Glu Tyr Ser Asn Leu Glu Val Val Glu
        275                 280                 285

Ala Ile Glu Lys Leu Leu Gly Glu Leu Ala Pro Glu Lys Pro His Val
290                 295                 300

Lys Ala Lys Glu Asp Pro Ala Thr Phe Val Asp Asp Arg Pro Gly Asp
305                 310                 315                 320

Asp Ala Arg Tyr Ala Ala Asp Ala Ser Lys Ile Lys Arg Glu Leu Gly
                325                 330                 335

Trp Lys Pro Glu Val Thr Asn Leu Glu Glu Gly Leu Ala Asp Thr Val
            340                 345                 350

Asn Trp Tyr Leu Glu Asn Glu
        355

<210> SEQ ID NO 25
<211> LENGTH: 260
<212> TYPE: PRT
<213> ORGANISM: Artificial Sequence
<220> FEATURE:
<223> OTHER INFORMATION: 3-beta hydroxysteroid dehydrogenase delta5
      domain
<220> FEATURE:
<221> NAME/KEY: VARIANT
<222> LOCATION: 139, 140, 141, 142, 143, 144, 145, 146, 147, 148, 149,
      150, 192, 193, 194, 195, 196, 197, 198, 199, 200, 201, 202, 203,
      204, 205, 206, 207, 208, 209, 210, 211, 212, 213, 214, 215,
      216, 217
<223> OTHER INFORMATION: Xaa = Any Amino Acid

<400> SEQUENCE: 25
```

```
His Glu Val Asn Val Gln Gly Thr Arg Asn Val Ile Glu Ala Cys Val
1               5                   10                  15

Gln Thr Gly Thr Arg Phe Leu Val Tyr Thr Ser Met Glu Val Val
            20                  25                  30

Gly Pro Asn Thr Lys Gly His Pro Phe Tyr Arg Gly Asn Glu Asp Thr
            35                  40                  45

Pro Tyr Glu Ala Val His Arg His Pro Tyr Pro Cys Ser Lys Ala Leu
50                  55                  60

Ala Glu Trp Leu Val Leu Glu Ala Asn Gly Arg Lys Val Arg Gly Gly
65                  70                  75                  80

Leu Pro Leu Val Thr Cys Ala Leu Arg Pro Thr Gly Ile Tyr Gly Glu
                85                  90                  95

Gly His Gln Ile Met Arg Asp Phe Tyr Arg Gln Gly Leu Arg Leu Gly
                100                 105                 110

Gly Trp Leu Phe Arg Ala Ile Pro Ala Ser Val Glu His Gly Arg Val
            115                 120                 125

Tyr Val Gly Asn Val Ala Trp Met His Val Xaa Xaa Xaa Xaa Xaa Xaa
130                 135                 140

Xaa Xaa Xaa Xaa Xaa Xaa Met Gly Gly Val Tyr Phe Cys Tyr Asp Gly
145                 150                 155                 160

Ser Pro Tyr Arg Ser Tyr Glu Asp Phe Asn Met Glu Phe Leu Gly Pro
                165                 170                 175

Cys Gly Leu Arg Leu Val Gly Ala Arg Pro Leu Leu Pro Tyr Trp Xaa
                180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Asn Pro Tyr Thr Leu Ala Val
            210                 215                 220

Ala Asn Thr Thr Phe Thr Val Ser Thr Asp Lys Ala Gln Arg His Phe
225                 230                 235                 240

Gly Tyr Glu Pro Leu Phe Ser Trp Glu Asp Ser Arg Thr Arg Thr Ile
                245                 250                 255

Leu Trp Val Gln
            260
```

<210> SEQ ID NO 26
<211> LENGTH: 23
<212> TYPE: PRT
<213> ORGANISM: Artificial Sequence
<220> FEATURE:
<223> OTHER INFORMATION: 3-beta hydroxysteroid dehydrogenase delta5
      domain

<400> SEQUENCE: 26

```
Val Tyr Leu Val Thr Gly Gly Cys Gly Phe Leu Gly Glu His Val Val
1               5                   10                  15

Arg Met Leu Leu Gln Arg Glu
            20
```

<210> SEQ ID NO 27
<211> LENGTH: 35
<212> TYPE: PRT
<213> ORGANISM: Artificial Sequence
<220> FEATURE:
<223> OTHER INFORMATION: short chain dehydrogenase/reductase C2 domain

<400> SEQUENCE: 27

```
Gly Arg Leu Gly Glu Pro Glu Glu Ile Ala Asn Ala Val Val Phe Leu
```

```
                1               5                   10                  15
Ala Ser Asp Ala Ala Ser Asp Ala Ala Ser Tyr Ile Thr Gly Gln Thr
            20                  25                  30

Leu Val Val
        35

<210> SEQ ID NO 28
<211> LENGTH: 181
<212> TYPE: PRT
<213> ORGANISM: Artificial Sequence
<220> FEATURE:
<223> OTHER INFORMATION: oxidoreductase protein dehydrogenase NAD
      reductase domain

<400> SEQUENCE: 28

Lys Ala Ile Val Lys Glu Leu Leu Glu Leu Gly Ser Asn Val Val Ile
 1               5                   10                  15

Ala Lys Arg Lys Leu Glu Arg Leu Lys Ser Ala Ala Asp Glu Leu Gln
            20                  25                  30

Ala Asn Leu Pro Pro Thr Lys Gln Ala Arg Val Ile Pro Ile Gln Cys
        35                  40                  45

Asn Ile Arg Asn Glu Glu Glu Val Asn Asn Leu Val Lys Ser Thr Leu
    50                  55                  60

Asp Thr Phe Gly Lys Ile Asn Phe Leu Cys Asn Asn Gly Gly Gly Gln
65                  70                  75                  80

Phe Leu Ser Pro Ala Glu His Ile Ser Ser Lys Gly Trp His Ala Val
                85                  90                  95

Leu Glu Thr Asn Leu Thr Gly Thr Phe Tyr Met Cys Lys Ala Val Tyr
            100                 105                 110

Ser Ser Trp Met Lys Glu His Gly Gly Ser Ile Val Asn Ile Ile Val
        115                 120                 125

Pro Thr Lys Ala Gly Phe Pro Leu Ala Val His Ser Gly Ala Ala Arg
    130                 135                 140

Ala Gly Val Tyr Asn Leu Thr Lys Ser Leu Ala Leu Glu Trp Ala Cys
145                 150                 155                 160

Ser Gly Ile Arg Ile Asn Cys Val Ala Pro Gly Val Ile Tyr Ser Gln
                165                 170                 175

Thr Ala Val Glu Asn
            180

<210> SEQ ID NO 29
<211> LENGTH: 85
<212> TYPE: PRT
<213> ORGANISM: Artificial Sequence
<220> FEATURE:
<223> OTHER INFORMATION: oxidoreductase protein dehydrogenase NAD
      reductase domain

<400> SEQUENCE: 29

Gly Gln Val Ala Ile Val Thr Gly Gly Ala Thr Gly Ile Gly Lys Ala
 1               5                   10                  15

Ile Val Lys Glu Leu Leu Glu Leu Gly Ser Asn Val Val Ile Ala Ser
            20                  25                  30

Arg Lys Leu Glu Arg Leu Lys Ser Ala Ala Asp Glu Leu Gln Ala Asn
        35                  40                  45

Leu Pro Pro Thr Lys Gln Ala Arg Val Ile Pro Ile Gln Cys Asn Ile
    50                  55                  60

Arg Asn Glu Glu Glu Val Asn Asn Leu Val Lys Ser Thr Leu Asp Thr
```

```
65                  70                  75                  80
Phe Gly Lys Ile Asn
                85
```

<210> SEQ ID NO 30
<211> LENGTH: 23
<212> TYPE: PRT
<213> ORGANISM: Artificial Sequence
<220> FEATURE:
<223> OTHER INFORMATION: oxidoreductase protein dehydrogenase NAD
      reductase domain

<400> SEQUENCE: 30

```
Ala Leu Glu Trp Ala Cys Ser Gly Ile Arg Ile Asn Cys Val Ala Pro
 1               5                  10                  15

Gly Val Ile Tyr Ser Gln Thr
            20
```

<210> SEQ ID NO 31
<211> LENGTH: 45
<212> TYPE: PRT
<213> ORGANISM: Artificial Sequence
<220> FEATURE:
<223> OTHER INFORMATION: glucose-1 dehydrogenase domain

<400> SEQUENCE: 31

```
Ser Phe Gln Lys Ile Pro Ala Lys Arg Ile Gly Val Pro Glu Glu Val
 1               5                  10                  15

Ser Ser Val Val Cys Phe Leu Leu Ser Pro Ala Ala Ser Phe Ile Thr
            20                  25                  30

Gly Gln Ser Cys Asp Cys Asp Gly Gly Arg Ser Leu Tyr
        35                  40                  45
```

<210> SEQ ID NO 32
<211> LENGTH: 48
<212> TYPE: PRT
<213> ORGANISM: Artificial Sequence
<220> FEATURE:
<223> OTHER INFORMATION: shikimate 5-dehydrogenase domain

<400> SEQUENCE: 32

```
Leu Gln Gly Gln Val Ala Ile Val Thr Gly Gly Ala Thr Gly Ile Gly
 1               5                  10                  15

Lys Ala Ile Val Lys Glu Leu Leu Glu Leu Gly Ser Asn Val Val Ile
            20                  25                  30

Ala Ser Arg Lys Leu Glu Arg Leu Lys Ser Ala Ala Asp Glu Leu Gln
        35                  40                  45
```

<210> SEQ ID NO 33
<211> LENGTH: 50
<212> TYPE: PRT
<213> ORGANISM: Artificial Sequence
<220> FEATURE:
<223> OTHER INFORMATION: dehydrogenase domain

<400> SEQUENCE: 33

```
Gln Ser Phe Phe Glu Gly Ser Phe Gln Lys Ile Pro Ala Lys Arg Ile
 1               5                  10                  15

Gly Val Pro Glu Glu Val Ser Ser Val Val Cys Phe Leu Leu Ser Pro
            20                  25                  30

Ala Ala Ser Phe Ile Thr Gly Gln Ser Val Asp Val Asp Gly Gly Arg
        35                  40                  45
```

```
Ser Leu
    50

<210> SEQ ID NO 34
<211> LENGTH: 52
<212> TYPE: PRT
<213> ORGANISM: Artificial Sequence
<220> FEATURE:
<223> OTHER INFORMATION: hypothetical protein domain

<400> SEQUENCE: 34

Tyr Leu Ala Pro Gly Gln Gly Gln Val Ala Ile Val Thr Gly Gly Ala
  1               5                  10                  15

Thr Gly Ile Gly Lys Ala Ile Val Lys Glu Leu Leu Glu Leu Gly Ser
             20                  25                  30

Asn Val Ile Ala Ser Arg Lys Leu Glu Arg Leu Lys Ser Ala Ala
         35                  40                  45

Asp Glu Leu Gln
    50
```